(12) United States Patent
Mita et al.

(10) Patent No.: US 8,119,671 B2
(45) Date of Patent: Feb. 21, 2012

(54) ISOXAZOLINE-SUBSTITUTED BENZAMIDE COMPOUND AND PEST CONTROL AGENT

(75) Inventors: Takeshi Mita, Funabashi (JP); Yuki Furukawa, Funabashi (JP); Motoyoshi Iwasa, Funabashi (JP); Mitsuaki Komoda, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 4 days.

(21) Appl. No.: 12/449,996

(22) PCT Filed: Mar. 6, 2008

(86) PCT No.: PCT/JP2008/054096
§ 371 (c)(1),
(2), (4) Date: Nov. 30, 2009

(87) PCT Pub. No.: WO2008/108448
PCT Pub. Date: Sep. 12, 2008

(65) Prior Publication Data
US 2010/0144797 A1 Jun. 10, 2010

(30) Foreign Application Priority Data

| Mar. 7, 2007 | (JP) | 2007-057045 |
| Mar. 30, 2007 | (JP) | 2007-091654 |
| Jun. 8, 2007 | (JP) | 2007-152801 |

(51) Int. Cl.
*A01N 43/80* (2006.01)
*C07D 261/04* (2006.01)
(52) U.S. Cl. ........................ 514/378; 548/240
(58) Field of Classification Search ............ 548/240; 514/378
See application file for complete search history.

(56) References Cited

U.S. PATENT DOCUMENTS

| 7,662,972 B2 * | 2/2010 | Mita et al. | 548/240 |
| 7,951,828 B1 * | 5/2011 | Mita et al. | 514/378 |
| 2007/0066617 A1 | 3/2007 | Mita et al. | |
| 2010/0179195 A1 * | 7/2010 | Lahm et al. | 514/340 |

FOREIGN PATENT DOCUMENTS

| WO | WO 01/70673 A2 | 9/2001 |
| WO | WO 2005/085216 A1 | 9/2005 |
| WO | WO 2007/026965 A1 | 3/2007 |
| WO | WO 2007/079162 A1 | 7/2007 |
| WO | WO 2007/125984 A1 | 11/2007 |
| WO | WO 2009/024541 * | 2/2009 |
| WO | WO 2009/049846 A1 | 4/2009 |
| WO | WO 2009/080250 A2 | 7/2009 |

OTHER PUBLICATIONS

Corbet & Mignani, Selected Patented Cross-Coupling Reaction Technologies, 2006, Chem. Rev, 106, p. 2651-2710.*

* cited by examiner

*Primary Examiner* — Andrew D Kosar
*Assistant Examiner* — Karen Cheng
(74) *Attorney, Agent, or Firm* — Oliff & Berridge, PLC

(57) ABSTRACT

Novel pest control agents, particularly insecticides or miticides are provided. Isoxazoline-substituted benzamide compounds of General Formula (1) or a salt thereof:

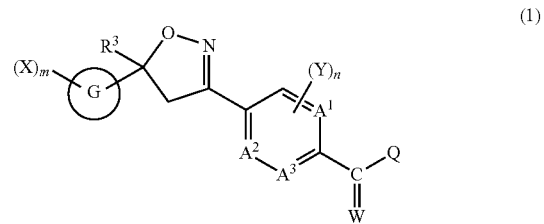

(where $A^1$, $A^2$ and $A^3$ are independently C or N, G is a benzene ring, etc., Q is a structure of Q-1, Q-2 or Q3:

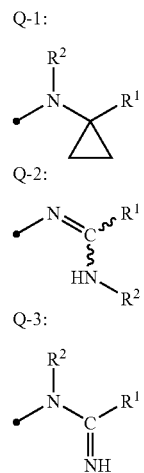

(where, for example, $R^1$ in Q-1 is a $C_1$ to $C_4$ haloalkyl, etc., and $R^2$ is H, etc., $R^1$ in Q-2 is —$OR^{1a}$, etc., $R^{1a}$ is a $C_1$ to $C_4$ alkyl, etc., and $R^2$ is H, etc.), W is O or S, X is a halogen atom, a $C_1$ to $C_2$ haloalkyl, etc., Y is a halogen atom, a $C_1$ to $C_2$ alkyl, etc., $R^3$ is a $C_1$ to $C_2$ haloalkyl, etc., m is an integer of 1-3, etc., and n is an integer of 0 or 1, etc.), and pest control agents containing the compounds.

4 Claims, No Drawings

ISOXAZOLINE-SUBSTITUTED BENZAMIDE COMPOUND AND PEST CONTROL AGENT

TECHNICAL FIELD

The present invention relates to a novel isoxazoline-substituted benzamide compound and salts thereof, and a pest control agent containing the compound as an active ingredient. The pest control agent in the present invention means insect pest control agents aimed at harmful arthropods in the agriculture and horticulture field or in the livestock/sanitation field (control agents against internal or external parasites of the mammal or the bird as domestic animals or pet animals and control agents against insanitary insects or discomfort insects for domestic use or business use). In addition, the agricultural chemical in the present invention means insecticides/miticides, nematicides, herbicides, bactericides and the like in the agricultural and horticultural field.

BACKGROUND ART

Conventionally, it is known that with respect to isoxazoline-substituted benzamide compounds, an N-(2-phenylcyclopropyl)-4-(5-substituted-5-substituted aryl-4,5-dihydroisoxazole-3-yl) benzamide compound exhibits pest control activity, particularly insecticidal/miticidal activity (see Patent Document 1). However, there is disclosed nothing with respect to a specific N-(1-substituted cyclopropyl)-4-(5-substituted-5-substituted aryl-4,5-dihydroisoxazole-3-yl) benzamide compound according to the present invention.

In addition, it is also known that a specific N-(2-(N-hydroxycarbamoyl)cyclopentyl)-4-(5-pyridyl-4,5-dihydroisoxazole-3-yl)benzamide derivative has, for example, inhibitory activity against matrix metalloprotease and TNF-α, and is used as an anti-inflammatory drug or a cartilage protecting drug (see patent Document 2). However, the usefulness of the derivative as a pest control agent is not known at all.

Furthermore, it is known that isoxazoline-substituted benzylurea compounds such as N-(4-(5-substituted-5-substituted aryl-4,5-dihydroisoxazole-3-yl) benzoyl) urea compounds and $N^2$-substituted-$N^1$-(4-(5-substituted-5-substituted aryl-4,5-dihydroisoxazole-3-yl)benzoyl) urea compounds exhibit pest control activity, particularly insecticidal/miticidal activity (see Patent Document 1, Patent Document 3 and Patent Document 4). However, there is disclosed nothing with respect to a specific O-substituted-N-(4-(5-substituted-5-substituted aryl-4,5-dihydroisoxazole-3-yl) benzoyl) isourea compound according to the present invention.
[Patent Document 1]
International Publication No. WO 2005/085216 pamphlet
[Patent Document 2]
International Publication No. WO 01/070673 pamphlet
[Patent Document 3]
US Patent No. 2007/0066617 pamphlet
[Patent Document 4]
International Publication No. WO 2007/026965 pamphlet

DISCLOSURE OF THE INVENTION

Problem to be Solved by the Invention

The development of pest control agents for the purpose of controlling various pests such as agricultural and horticultural pests, forest pests and insanitary pests has been progressed and until today, various agents have been practically applied.

However, due to use of these agents for a long period, recently pests have acquired drug resistance and there has been increased the number of situations in which the control by related art insecticides or bactericides which have been conventionally used is difficult. In addition, a part of the related art pest control agents has high toxicity or some of them remain in the environment for a long period to disturb the ecosystem, which has become a significant problem. Under such a situation, the development of a novel pest control agent having not only high pest control activity, but also low toxicity and low persistency is constantly expected.

Means for Solving the Problem

As a result of assiduous research intended to overcome these disadvantages, the present inventors have found that a novel isoxazoline-substituted benzamide compound represented by the following General Formula (1) and General Formula (2) according to the present invention exhibits excellent pest control activity, particularly excellent insecticidal/miticidal activity and is an extremely useful compound having substantially no adverse effect on non-target organisms such as the mammal, the fish and beneficial insects to complete the present invention.

That is, the present invention relates to [1] to [10].

[1] An isoxazoline-substituted benzamide compound represented by General Formula (1):

[Chemical Formula 1]

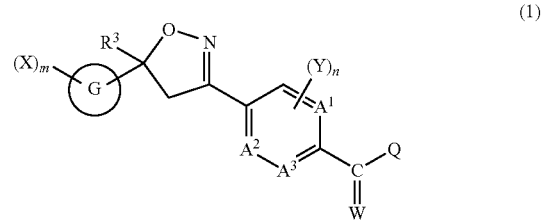

(1)

(where $A^1$, $A^2$ and $A^3$ independently represent a carbon atom or a nitrogen atom, G represents a benzene ring, a nitrogen-containing 6-membered aromatic heterocycle, a furan ring, a thiophene ring or a 5-membered aromatic heterocycle containing two or more hetero atoms selected from an oxygen atom, a sulfur atom and a nitrogen atom, W represents an oxygen atom or a sulfur atom, Q represents a structure represented by Q-1, Q-2 or Q-3:

[Chemical Formula 2]

Q-1:

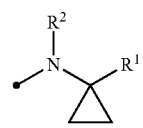

Q-2:

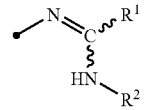

Q-3:

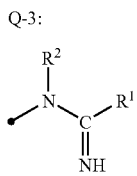

X represents a halogen atom, a cyano, a nitro, —SF$_5$, a C$_1$ to C$_6$ alkyl, a C$_1$ to C$_6$ haloalkyl, a hydroxy(C$_1$ to C$_4$) haloalkyl, a C$_1$ to C$_4$ alkoxy(C$_1$ to C$_4$) haloalkyl, —S(O)$_r$R$^4$ or —NH$_2$, where when m represents an integer of 2 or more, Xs may be the same as or different from each other, Y represents a halogen atom, a cyano, a nitro, a C$_1$ to C$_6$ alkyl, a C$_1$ to C$_6$ haloalkyl, a (C$_1$ to C$_4$) alkyl arbitrarily substituted with R$^5$, a C$_2$ to C$_6$ alkenyl, a C$_2$ to C$_6$ alkynyl, —OR$^4$, —S(O)$_r$R$^4$, —N(R$^7$)R$^6$, —C(S)NH$_2$, D-1 to D-5, D-14, D-24 or D-41, where when n represents an integer of 2 or more, Ys may be the same as or different from each other, when Q represents Q-1, R$^1$ represents a cyano, a C$_1$ to C$_6$ alkyl, a C$_1$ to C$_6$ haloalkyl, a (C$_1$ to C$_4$) alkyl arbitrarily substituted with R$^8$, a C$_3$ to C$_6$ cycloalkyl, E-6, E-7, E-12, E-25, a C$_2$ to C$_6$ alkenyl, a C$_2$ to C$_6$ haloalkenyl, a C$_3$ to C$_6$ alkynyl, —C(O)R$^9$, —C(R$^9$)=NOR$^{10}$, —C(O)OR$^{11}$, —C(O)N(R$^{13}$)R$^{12}$, —C(S)NH$_2$, a phenyl, a phenyl substituted with (Z)$_{p1}$, D-1, D-8, D-11, D-14 to D-17, D-21 to D-24, D-28, D-29, D-34, D-35, D-41, D-52 to D-56, D-58, D-59, a C$_1$ to C$_6$ alkoxy or a C$_1$ to C$_6$ haloalkoxy, R$^2$ represents a hydrogen atom, a C$_1$ to C$_6$ alkyl, a C$_1$ to C$_6$ haloalkyl, a (C$_1$ to C$_4$) alkyl arbitrarily substituted with R$^{14}$, a C$_3$ to C$_6$ cycloalkyl, a C$_3$ to C$_6$ alkenyl, a C$_3$ to C$_6$ alkynyl, —C(O)R$^{15}$, —C(O)OR$^{16}$, a C$_1$ to C$_6$ haloalkylthio or —SN(R$^{18}$)R$^{17}$, when Q represents Q-2 or Q-3, R$^1$ represents —OR$^{1a}$, —SR$^{1a}$ or —N(R$^{1c}$)R$^{1b}$, R$^{1a}$ represents a C$_1$ to C$_6$ alkyl, a C$_1$ to C$_6$ haloalkyl, a (C$_1$ to C$_4$) alkyl arbitrarily substituted with R$^8$, a C$_3$ to C$_6$ cycloalkyl, a C$_3$ to C$_6$ alkenyl or a C$_3$ to C$_6$ alkynyl, R$^{1b}$ represents a cyano, a nitro, a C$_1$ to C$_6$ alkyl, a C$_1$ to C$_6$ haloalkyl, a C$_3$ to C$_6$ cycloalkyl, a C$_3$ to C$_6$ alkenyl, a C$_3$ to C$_6$ alkynyl, a C$_1$ to C$_6$ alkoxy or a C$_1$ to C$_6$ haloalkoxy, R$^{1c}$ represents a hydrogen atom or a C$_1$ to C$_4$ alkyl, R$^2$ represents a hydrogen atom, a C$_1$ to C$_6$ alkyl, a C$_1$ to C$_6$ haloalkyl, a (C$_1$ to C$_4$) alkyl arbitrarily substituted with R$^{14}$, a C$_3$ to C$_6$ cycloalkyl, a C$_3$ to C$_6$ alkenyl, a C$_3$ to C$_6$ alkynyl, a C$_1$ to C$_6$ alkoxy or —N(R$^{20}$)R$^{19}$, R$^3$ represents a C$_1$ to C$_6$ haloalkyl or a C$_3$ to C$_8$ halocycloalkyl, D-1 to D-59 individually represent an aromatic heterocycle represented by Structural Formulae:

[Chemical Formula 3]

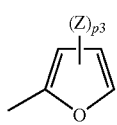
D-1

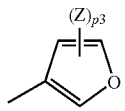
D-2

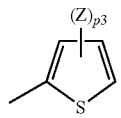
D-3

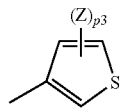
D-4

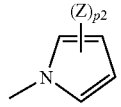
D-5

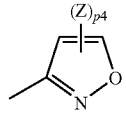
D-8

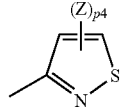
D-11

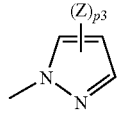
D-14

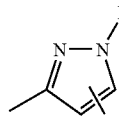
D-15

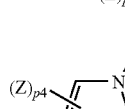
D-16

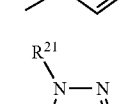
D-17

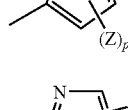
D-21

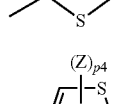
D-22

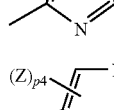
D-23

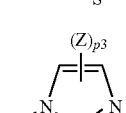
D-24

-continued

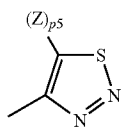
D-28

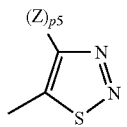
D-29

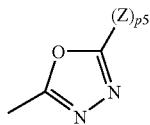
D-34

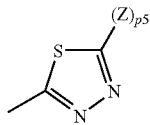
D-35

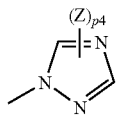
D-41

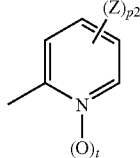
D-52

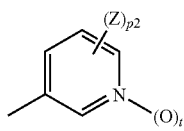
D-53

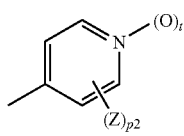
D-54

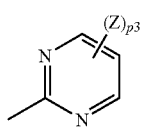
D-55

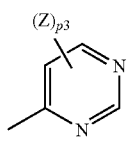
D-56

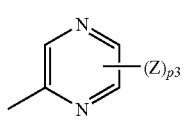
D-58

-continued

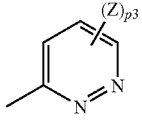
D-59

Z represents a halogen atom, a cyano, a nitro, a $C_1$ to $C_6$ alkyl, a $C_1$ to $C_6$ haloalkyl, a $C_1$ to $C_6$ alkoxy, a $C_1$ to $C_6$ haloalkoxy, a $C_1$ to $C_6$ alkylthio, a $C_1$ to $C_6$ haloalkylthio, a $C_1$ to $C_6$ alkylsulfinyl, a $C_1$ to $C_6$ haloalkylsulfinyl, a $C_1$ to $C_6$ alkylsulfonyl, a $C_1$ to $C_6$ haloalkylsulfonyl or —C(S)NH$_2$, where when p1, p2, p3 or p4 represents an integer of 2 or more, Zs may be the same as or different from each other, E-6 to E-25 individually represent a saturated heterocycle represented by Structural Formulae:

[Chemical Formula 4]

E-6

E-7

E-12

E-25

$R^4$ represents a $C_1$ to $C_4$ alkyl, a $C_1$ to $C_4$ haloalkyl or a $C_1$ to $C_2$ haloalkoxy($C_1$ to $C_2$)haloalkyl, $R^5$ represents —OH, a $C_1$ to $C_4$ alkoxy, a $C_1$ to $C_4$ haloalkoxy, a $C_1$ to $C_4$ alkylthio, a $C_1$ to $C_4$ haloalkylthio, a $C_1$ to $C_4$ alkylsulfinyl, a $C_1$ to $C_4$ haloalkylsulfinyl, a $C_1$ to $C_4$ alkylsulfonyl or a $C_1$ to $C_4$ haloalkylsulfonyl, $R^6$ represents a hydrogen atom, a $C_1$ to $C_6$ alkyl, —CHO, —C(O)R$^{23}$, —C(O)OR$^{23}$, —C(O)SR$^{23}$, —C(S)OR$^{23}$, —C(S)SR$^{23}$ or —S(O)$_2$R$^{23}$, $R^7$ represents a hydrogen atom or a $C_1$ to $C_6$ alkyl, $R^8$ represents a $C_1$ to $C_4$ alkoxy, a $C_1$ to $C_4$ alkylthio, a $C_1$ to $C_4$ alkylsulfinyl or a $C_1$ to $C_4$ alkylsulfonyl, $R^9$ represents a hydrogen atom or a $C_1$ to $C_2$ alkyl, $R^{10}$ represents a hydrogen atom, a $C_1$ to $C_4$ alkyl or a $C_1$ to $C_4$ haloalkyl, $R^{11}$ represents a hydrogen atom, a $C_1$ to $C_2$ alkyl or a $C_1$ to $C_2$ haloalkyl, $R^{12}$ represents a $C_1$ to $C_6$ alkyl, a $C_1$ to $C_6$ haloalkyl, a $C_3$ to $C_6$ cycloalkyl, a $C_3$ to $C_6$ alkenyl, a $C_3$ to $C_6$ alkynyl or a phenyl, $R^{13}$ represents a hydrogen atom or a $C_1$ to $C_4$ alkyl, $R^{14}$ represents a cyano, —OR$^{24}$, —S(O)$_r$R$^{24}$ or —N(R$^{26}$)R$^{25}$, $R^{15}$ represents a $C_1$ to $C_6$ alkyl, a $C_1$ to $C_6$ haloalkyl, a $C_1$ to $C_4$ alkoxy($C_1$ to $C_4$) alkyl, a $C_1$ to $C_4$ alkylthio($C_1$ to $C_4$) alkyl, a $C_1$ to $C_4$ alkylsulfinyl($C_1$ to $C_4$) alkyl, a $C_1$ to $C_4$ alkylsulfonyl($C_1$ to $C_4$) alkyl, a $C_3$ to $C_6$ cycloalkyl, a $C_2$ to $C_6$ alkenyl, a $C_1$ to $C_6$ alkoxycarbonyl, a phenyl, a phenyl substituted with $(Z)_{p1}$ or D-52 to D-54, $R^{16}$ represents a $C_1$ to $C_6$ alkyl, a $C_1$ to $C_6$ haloalkyl, a $C_1$ to $C_4$ alkoxy($C_1$ to $C_4$) alkyl, a $C_3$ to $C_6$ alkenyl or a phenyl, $R^{17}$ represents a $C_1$ to $C_6$ alkyl, a $C_1$ to $C_6$ alkoxycarbonyl($C_1$ to $C_4$) alkyl or a $C_1$ to $C_6$ alkoxycarbonyl, $R^{18}$ represents a $C_1$ to $C_6$ alkyl or a benzyl, $R^{19}$ represents a hydrogen atom, a $C_1$ to $C_4$ alkyl, —CHO, a $C_1$ to $C_4$ alkylcarbonyl or a $C_1$ to $C_4$ alkoxycarbonyl, $R^{20}$ represents a hydrogen atom or a $C_1$ to $C_4$ alkyl, $R^{21}$ represents a $C_1$ to $C_4$ alkyl or a $C_1$ to $C_4$ haloalkyl, $R^{22}$ represents a fluorine atom, a $C_1$ to $C_4$ alkyl or a $C_1$ to $C_4$ haloalkyl, $R^{23}$ represents a $C_1$ to $C_6$ alkyl, a $C_1$ to $C_6$ haloalkyl or a $C_3$ to $C_6$ cycloalkyl, $R^{24}$ represents a $C_1$ to $C_4$ alkyl, a $C_1$ to $C_4$ haloalkyl, a $C_1$ to $C_4$ alkylcarbonyl or a $C_1$ to $C_4$ alkoxycarbonyl, $R^{25}$ represents a $C_1$ to $C_4$ alkoxycarbonyl, $R^{26}$ represents a hydrogen atom or a $C_1$ to $C_4$ alkyl, m represents an integer of 0 to 5, n represents an integer of 0 to 4, p1 represents an integer of 1 to 5, p2 represents an integer of 0 to 4, p3 represents an integer of 0 to 3, p4 represents an integer of 0 to 2, p5 represents an integer of 0 or 1, q2 represents an integer of 0 to 2, q3 represents an integer of 0 to 2, r represents an integer of 0 to 2, and t represents an integer of 0 or 1), or a salt thereof.

[2] The isoxazoline-substituted benzamide compound according to [1], in which $A^1$ represents a carbon atom or a nitrogen atom, each of $A^2$ and $A^3$ represents a carbon atom, G represents a benzene ring, X represents a halogen atom, a cyano, a nitro, —$SF_5$, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m represents 2 or 3, Xs may be the same as or different from each other, Y represents a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkenyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —N($R^7$)$R^6$ or —C(S)NH$_2$, when Q represents Q-1, $R^1$ represents a cyano, a $C_1$ to $C_6$ haloalkyl, a ($C_1$ to $C_4$) alkyl arbitrarily substituted with $R^8$, a $C_3$ to $C_6$ cycloalkyl, E-6, E-7, E-12, a $C_2$ to $C_6$ alkenyl, —C($R^9$)=NOR$^{10}$, —C(O)N($R^{13}$)$R^{12}$, a phenyl, a phenyl substituted with $(Z)_{p1}$, D-16, D-17, D-21, D-22, D-28, D-34, D-41, D-52 or D-55, $R^2$ represents a hydrogen atom, a $C_1$ to $C_4$ alkyl, a ($C_1$ to $C_2$) alkyl arbitrarily substituted with $R^{14}$, a $C_3$ to $C_4$ alkynyl, —C(O)$R^{15}$ or —C(O)OR$^{16}$, when Q represents Q-2, $R^1$ represents —OR$^{1a}$, —SR$^{1a}$ or —N($R^{1c}$)$R^{1b}$, $R^{1a}$ represents a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl, $R^{1b}$ represents a cyano, a nitro, a $C_1$ to $C_4$ alkyl, a $C_1$ to $C_4$ alkoxy or a $C_1$ to $C_4$ haloalkoxy, $R^{1c}$ represents a hydrogen atom or a $C_1$ to $C_2$ alkyl, $R^2$ represents a hydrogen atom, a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl, when Q represents Q-3, $R^1$ represents —OR$^{1a}$ or —SR$^{1a}$, $R^{1a}$ represents a $C_1$ to $C_4$ alkyl, a $C_1$ to $C_4$ haloalkyl or a $C_3$ to $C_4$ alkynyl, $R^2$ represents a hydrogen atom, a $C_1$ to $C_4$ alkyl, a $C_1$ to $C_4$ haloalkyl, a $C_3$ to $C_4$ cycloalkyl or a $C_3$ to $C_4$ alkynyl, $R^3$ represents a $C_1$ to $C_4$ haloalkyl, Z represents a halogen atom, a cyano, a nitro or a $C_1$ to $C_2$ alkoxy, where when p1 or p2 represents an integer of 2 or more, Zs may be the same as or different from each other, $R^6$ represents a hydrogen atom, a $C_1$ to $C_4$ alkyl, —CHO, a $C_1$ to $C_4$ alkylcarbonyl, a $C_1$ to $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, $R^7$ represents a hydrogen atom or a $C_1$ to $C_4$ alkyl, $R^8$ represents a $C_1$ to $C_2$ alkoxy or a $C_1$ to $C_2$ haloalkoxy, $R^9$ represents a hydrogen atom or a methyl, $R^{10}$ represents a $C_1$ to $C_2$ alkyl, $R^{12}$ represents a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl, $R^{13}$ represents a hydrogen atom or a $C_1$ to $C_2$ alkyl, $R^{14}$ represents a cyano, a $C_1$ to $C_2$ alkoxy or a $C_1$ to $C_2$ haloalkoxy, $R^{15}$ represents a $C_1$ to $C_4$ alkyl, a $C_1$ to $C_2$ alkoxy($C_1$ to $C_2$) alkyl, a $C_3$ to $C_4$ cycloalkyl or a $C_2$ to $C_4$ alkenyl, $R^{16}$ represents a $C_1$ to $C_4$ alkyl, $R^{21}$ represents a $C_1$ to $C_2$ alkyl, m represents an integer of 1 to 3, n represents an integer of 0 or 1, p1 represents an integer of 1 to 3, p2 represents an integer of 0 to 2, p3, p4 and p5 represent an integer of 0 or 1, q2 and q3 represent 0, and t represents 0, or a salt thereof.

[3] The isoxazoline-substituted benzamide compound according to [2], in which Q represents Q-1 or Q-2, X represents a halogen atom, a cyano, —$SF_5$, a $C_1$ to $C_2$ haloalkyl, a $C_1$ to $C_2$ haloalkoxy or a $C_1$ to $C_2$ haloalkylthio, where when m represents 2 or 3, Xs may be the same as or different from each other, Y represents a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkenyl, a $C_2$ to $C_3$ alkynyl, a $C_1$ to $C_2$ haloalkoxy, a $C_1$ to $C_2$ haloalkylthio, —N($R^7$)$R^6$ or —C(S)NH$_2$, when Q represents Q-1, $R^1$ represents a $C_1$ to $C_4$ haloalkyl, a $C_1$ to $C_2$ alkoxy($C_1$ to $C_2$) alkyl, a $C_3$ to $C_4$ cycloalkyl, a $C_2$ to $C_4$ alkenyl, —C(O)N($R^{13}$)$R^{12}$, a phenyl substituted with $(Z)_{p1}$, D-22, D-52 or D-55, $R^2$ represents a hydrogen atom, a $C_1$ to $C_2$ alkyl, a cyanomethyl, a $C_1$ to $C_2$ alkoxymethyl, a propargyl, —C(O)$R^{15}$ or —C(O)OR$^{16}$, when Q represents Q-2, $R^1$ represents —OR$^{1a}$ or —N($R^{1c}$)$R^{1b}$, $R^{1a}$ represents a $C_1$ to $C_4$ alkyl, a $C_1$ to $C_4$ haloalkyl or a $C_3$ to $C_4$ alkynyl, $R^{1b}$ represents a cyano, a nitro or a $C_1$ to $C_2$ alkoxy, $R^{1c}$ represents a hydrogen atom or a methyl, $R^2$ represents a hydrogen atom, a $C_1$ to $C_4$ alkyl, a $C_1$ to $C_4$ haloalkyl, a $C_3$ to $C_4$ cycloalkyl or a $C_3$ to $C_4$ alkynyl, $R^3$ represents a $C_1$ to $C_2$ haloalkyl, Z represents a cyano or a nitro, $R^6$ represents a hydrogen atom, a $C_1$ to $C_2$ alkyl or a $C_1$ to $C_2$ alkylcarbonyl, $R^7$ represents a hydrogen atom or a $C_1$ to $C_2$ alkyl, $R^{12}$ represents a $C_1$ to $C_4$ alkyl, a $C_1$ to $C_4$ haloalkyl, a $C_3$ to $C_4$ alkenyl or a $C_3$ to $C_4$ alkynyl, $R^{13}$ represents a hydrogen atom or a methyl, $R^{15}$ represents a $C_1$ to $C_2$ alkyl, a $C_1$ to $C_2$ alkoxymethyl, a cyclopropyl or a vinyl, $R^{16}$ represents a $C_1$ to $C_2$ alkyl, p1 represents 1, and p2 represents an integer of 0 or 1, or a salt thereof.

[4] The isoxazoline-substituted benzamide compound according to [3], in which $A^1$ represents a carbon atom, W represents an oxygen atom, Q represents Q-1, X represents a halogen atom or a trifluoromethyl, where when m represents 2 or 3, Xs may be the same as or different from each other, Y represents a halogen atom, a methyl, an ethyl or a trifluoromethyl, $R^1$ represents a $C_1$ to $C_2$ haloalkyl, —C(O)NHR$^{12}$, D-22 or D-52, $R^2$ represents a hydrogen atom, $R^3$ represents a trifluoromethyl or a chlorodifluoromethyl, $R^{12}$ represents a $C_1$ to $C_2$ haloalkyl, and p2 and p4 represent 0, or a salt thereof.

[5] The isoxazoline-substituted benzamide compound according to [3], in which $A^1$ represents a carbon atom, W represents an oxygen atom, Q represents Q-2, X represents a halogen atom or a trifluoromethyl, where when m represents 2 or 3, Xs may be the same as or different from each other, Y represents a halogen atom, a methyl, an ethyl or a trifluoromethyl, $R^1$ represents —OR$^{1a}$, $R^{1a}$ represents a $C_1$ to $C_2$ alkyl, $R^2$ represents a hydrogen atom or a $C_1$ to $C_2$ alkyl, and $R^3$ represents a trifluoromethyl or a chlorodifluoromethyl, or a salt thereof.

[6] An isoxazoline-substituted benzamide compound represented by General Formula (2):

[Chemical Formula 5]

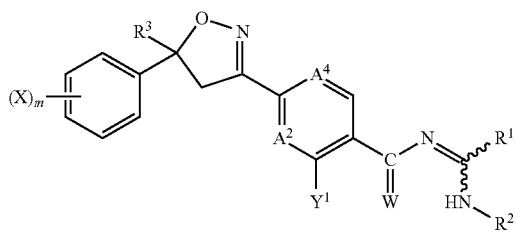

(2)

(where $A^2$ represents C—Y$^2$ or a nitrogen atom, $A^4$ represents CH or a nitrogen atom, W represents an oxygen atom or a sulfur atom, X represents a halogen atom, a cyano, a nitro, —SF$_5$, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio or a $C_1$ to $C_4$ haloalkylthio, where when m represents 2 or 3, Xs may be the same as or different from each other, $Y^1$ represents a hydrogen atom, a halogen atom, a cyano, a nitro, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkenyl, a $C_2$ to $C_4$ alkynyl, a $C_1$ to $C_4$ alkoxy, a $C_1$ to $C_4$ haloalkoxy, a $C_1$ to $C_4$ alkylthio, a $C_1$ to $C_4$ haloalkylthio, —N(R$^7$)R$^6$ or —C(S)NH$_2$, $Y^2$ may form together with $Y^1$, —CH=CHCH=CH—, —CH=CHCH=N—, —CH=CHN=CH—, —CH=NCH=CH— or —N=CHCH=CH— to form together with a carbon atom to which $Y^1$ and $Y^2$ are bonded, a 6-membered ring, $R^1$ represents —OR$^{1a}$, —SR$^{1a}$ or —N(R$^{1c}$)R$^{1b}$, $R^{1a}$ represents a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl, $R^{1b}$ represents a cyano, a nitro, a $C_1$ to $C_4$ alkyl, a $C_1$ to $C_4$ alkoxy or a $C_1$ to $C_4$ haloalkoxy, $R^{1c}$ represents a hydrogen atom or a $C_1$ to $C_2$ alkyl, $R^2$ represents a hydrogen atom, a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl, $R^3$ represents a $C_1$ to $C_4$ haloalkyl, $R^6$ represents a hydrogen atom, a $C_1$ to $C_4$ alkyl, —CHO, a $C_1$ to $C_4$ alkylcarbonyl, a $C_1$ to a $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl, $R^7$ represents a hydrogen atom or a $C_1$ to $C_4$ alkyl, and m represents an integer of 1 to 3), or a salt thereof.

[7] A pest control agent containing one type or two or more types selected from the isoxazoline-substituted benzamide compounds as described in [1] to [6] and salts thereof, as active ingredient(s).

[8] An agricultural chemical containing one type or two or more types selected from the isoxazoline-substituted benzamide compounds as described in [1] to [6] and salts thereof, as active ingredient(s).

[9] A control agent against internal or external parasites of the mammal or the bird containing one type or two or more types selected from the isoxazoline-substituted benzamide compounds as described in [1] to [6] and salts thereof, as active ingredient(s).

[10] An insecticide or a miticide containing one type or two or more types selected from the isoxazoline-substituted benzamide compounds as described in [1] to [6] and salts thereof, as active ingredient(s).

Effects of the Invention

The compound of the present invention has excellent insecticidal/miticidal activity against many types of agricultural insect pests, spider mites, internal or external parasites of the mammal or the bird, and exerts satisfactory controlling effect also against insect pests which have acquired resistance to the related art insecticides. Furthermore, the compound has substantially no adverse effect on the mammal, the fish and beneficial insects and has low persistency, so that the compound has light burden on the environment.

Accordingly, the present invention can provide a useful novel pest control agent.

BEST MODES FOR CARRYING OUT THE INVENTION

With respect to the amide structure of the compound of the present invention represented by General Formula (1) and General Formula (2), it is considered that tautomers represented by the following formulae may exist depending on the type of a substituent and on conditions, however, the present invention encompasses all of such structures.

[Chemical Formula 6]

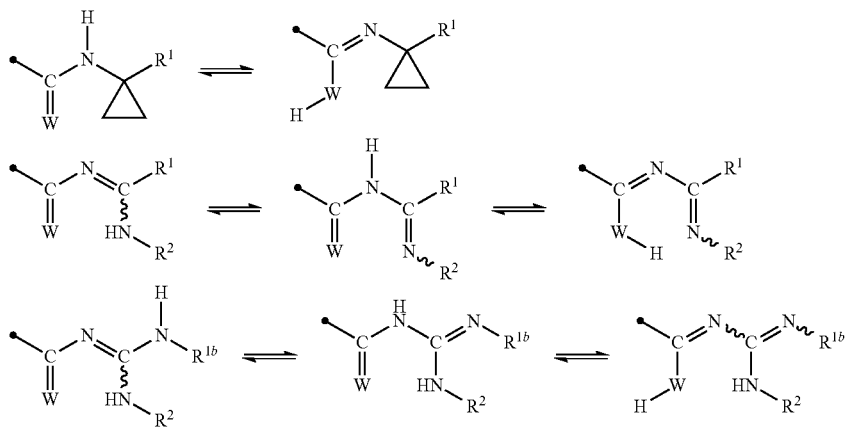

In addition, in the compounds encompassed in the present invention, geometric isomers thereof such as an E-form and a Z-form may exist depending on the type of a substituent, however, the present invention encompasses the E-form, the Z-form and a mixture containing the E-form and the Z-form in any mixing ratio. Furthermore, with respect to the compound encompassed in the present invention, optically active substances due to the presence of one or two or more asymmetric carbon atom(s) exist, however, the present invention encompasses all of such optically active substances or racemic bodies.

Examples of the compound encompassed in the present invention capable of being converted into an acid addition salt by a common method include: salts of halogenated hydrogen acids such as hydrofluoric acid, hydrochloric acid, hydrobromic acid and hydroiodic acid; salts of inorganic acids such as nitric acid, sulfuric acid, phosphoric acid, chloric acid and perchloric acid; salts of sulfonic acids such as methanesulfonic acid, ethanesulfonic acid, trifluoromethanesulfonic acid, benzenesulfonic acid and p-toluenesulfonic acid; salts of carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; or salts of amino acids such as glutamic acid and aspartic acid.

In addition, examples of the compound encompassed in the present invention capable of being converted into a metal salt by a common method include: salts of alkali metals such as lithium, sodium and potassium; salts of alkaline earth metals such as calcium, barium and magnesium; or salts of aluminum.

Next, specific examples of each substituent shown in the present specification are shown below. Here, n-, s- and t- (and tert-) mean normal-, iso-, secondary- and tertiary-, respectively, and Ph- means phenyl.

Examples of the halogen atom in the compound of the present invention include a fluorine atom, a chlorine atom, a bromine atom and an iodine atom. Here, the expression "halo" in the present specification represents these halogen atoms.

The expression "$C_a$ to $C_b$ alkyl" in the present specification represents a straight chain or branched hydrocarbon group having a to b pieces of carbon atoms, and specific examples thereof include a methyl group, an ethyl group, an n-propyl group, an i-propyl group, an n-butyl group, an i-butyl group, an s-butyl group, a tert-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 1,1-dimethylbutyl group, a 1,3-dimethylbutyl group. Each alkyl group of "$C_a$ to $C_b$ alkyl" is selected from within the range of the specified number of carbon atoms.

The expression "$C_a$ to $C_b$ haloalkyl" in the present specification represents a straight chain or branched hydrocarbon group having a to b pieces of carbon atoms in which a hydrogen atom bonded to a carbon atom is optionally replaced by halogen atoms. At this time, when two or more hydrogen atoms are replaced by two or more halogen atoms, these halogen atoms may be the same as or different from each other. Specific examples of the "$C_a$ to $C_b$ haloalkyl" include a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 1,1,2,2-tetrafluoroethyl group, a pentafluoroethyl group, a 2-chloro-1,1,2,2-tetrafluoroethyl group, a 2-bromo-1,1,2,2-tetrafluoroethyl group, a 2-fluoropropyl group, a 2-chloropropyl group, a 2-bromopropyl group, a 2,3-dichloropropyl group, a 2,3-dibromopropyl group, a 3,3,3-trifluoropropyl group, a 3-bromo-3,3-difluoropropyl group, a 2,2,3,3-tetrafluoropropyl group, a 2,2,3,3,3-pentafluoropropyl group, a 1,1,2,3,3,3-hexafluoropropyl group, a heptafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2- tetrafluoro-1-(trifluoromethyl)ethyl group, a 2,2,3,3,4,4-hexafluorobutyl group, a 2,2,3,4,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 2-chloro-1,1-dimethylethyl group, a 2-bromo-1,1-dimethylethyl group, a 5-chloro-2,2,3,4,4,5,5-heptafluoropentyl group and a tridecafluorohexyl group. Each haloalkyl group of "$C_a$ to $C_b$, haloalkyl" is selected from within the range of the specified number of carbon atoms.

The expression "$C_a$ to $C_b$, cycloalkyl" in the present specification represents a cyclic hydrocarbon group having a to b pieces of carbon atoms capable of forming a monocyclic or composite ring structure containing a 3-membered ring to a 6-membered ring. In addition, each ring may be arbitrarily substituted with an alkyl group within the range of a specified number of carbon atoms. Specific examples of the "$C_a$ to $C_b$ cycloalkyl" include a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group and a cyclohexyl group. Each cycloalkyl group of "$C_a$ to $C_b$ cycloalkyl" is selected from within the range of the specified number of carbon atoms.

The expression "$C_a$ to $C_b$ halocycloalkyl" in the present specification represents a cyclic hydrocarbon group having a to b pieces of carbon atoms in which a hydrogen atom bonded to a carbon atom is optionally replaced by halogen atoms and which is capable of forming a monocyclic or composite ring structure containing a 3-membered ring to a 6-membered ring. In addition, each ring may be arbitrarily substituted with an alkyl group within the range of a specified number of carbon atoms and the replacement of hydrogen atoms by halogen atoms may be performed in any one of a ring structure part, a side chain part and both of them. Furthermore, when two or more hydrogen atoms are replaced by two or more halogen atoms, these halogen atoms may be the same as or different from each other. Specific examples of the "$C_a$ to $C_b$ halocycloalkyl" include a 2-fluorocyclopropyl group, a 2-chlorocyclopropyl group, a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group and a 2-chloro-2,3,3-trifluorocyclobutyl group. Each halocycloalkyl group of "$C_a$ to $C_b$ halocycloalkyl" is selected from within the range of the specified number of carbon atoms.

The expression "$C_a$ to $C_b$ alkenyl" in the present specification represents a straight chain or branched unsaturated hydrocarbon group having a to b pieces of carbon atoms and having one or two or more double bond(s) in the molecule thereof, and specific examples thereof include a vinyl group, a 1-propenyl group, a 2-propenyl group, a 1-methylethenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group and a 2-methyl-2-pentenyl group. Each alkenyl group of "$C_a$ to $C_b$ alkenyl" is selected from within the range of the specified number of carbon atoms.

The expression "$C_a$ to $C_b$ haloalkenyl" in the present specification represents a straight chain or branched unsaturated hydrocarbon group having a to b pieces of carbon atoms and having one or two or more double bond(s) in the molecule thereof in which a hydrogen atom bonded to a carbon atom is optionally replaced by a halogen atom. At this time, when two or more hydrogen atoms are replaced by two or more halogen atoms, these halogen atoms may be the same as or different from each other. Specific examples of the "$C_a$ to $C_b$ haloalkenyl" include a 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 1-(trifluoromethyl)ethenyl group, a 3-chloro-2-butenyl group, a 3-bromo-2-butenyl group, a 4,4-difluoro-3-butenyl group, a 3,4,4-trifluoro-3-butenyl group and a 3-chloro-4,4,4-trifluoro-2-butenyl group. Each haloalkenyl group of "$C_a$ to $C_b$ haloalkenyl" is selected from within the range of the specified number of carbon atoms.

The expression "$C_a$ to $C_b$ alkynyl" in the present specification represents a straight chain or branched unsaturated hydrocarbon group having a to b pieces of carbon atoms and having one or two or more triple bond(s) in the molecule thereof, and specific examples thereof include an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group and a 2-hexynyl group. Each alkynyl group of "$C_a$ to $C_b$ alkynyl" is selected from within the range of the specified number of carbon atoms.

The expression "$C_a$ to $C_b$ alkoxy" in the present specification represents an alkyl-O-group as defined above having a to b pieces of carbon atoms and specific examples thereof include a methoxy group, an ethoxy group, an n-propyloxy group, an i-propyloxy group, an n-butyloxy group, an i-butyloxy group, an s-butyloxy group, a tert-butyloxy group, an n-pentyloxy group and an n-hexyloxy group. Each alkoxy group of "$C_a$ to $C_b$ alkoxy" is selected from within the range of the specified number of carbon atoms.

The expression "$C_a$ to $C_b$ haloalkoxy" in the present specification represents a haloalkyl-O— group as defined above having a to b pieces of carbon atoms and specific examples thereof include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a 2-chloro-1,1,2-trifluoroethoxy group, a 2-bromo-1,1,2-trifluoroethoxy group, a pentafluoroethoxy group, a 2-bromo-1,1,2,2-tetrafluoroethoxy group, a 2,2,3,3-tetrafluoropropyloxy group, a 1,1,2,3,3,3-hexafluoropropyloxy group, a 2,2,2-trifluoro-1-(trifluoromethyl)ethoxy group, a heptafluoropropyloxy group and a 2-bromo-1,1,2,3,3,3-hexafluoropropyloxy group. Each haloalkoxy group of "$C_a$ to $C_b$ haloalkoxy" is selected from within the range of the specified number of carbon atoms.

The expression "$C_a$ to $C_b$ alkylthio" in the present specification represents an alkyl-S— group as defined above having a to b pieces of carbon atoms and specific examples thereof include a methylthio group, an ethylthio group, an n-propylthio group, an i-propylthio group, an n-butylthio group, an i-butylthio group, an s-butylthio group, a tert-butylthio group, an n-pentylthio group and an n-hexylthio group. Each alkylthio group of "$C_a$ to $C_b$ alkylthio" is selected from within the range of the specified number of carbon atoms.

The expression "$C_a$ to $C_b$ haloalkylthio" in the present specification represents a haloalkyl-S— group as defined above having a to b pieces of carbon atoms and specific examples thereof include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2- trifluoroethylthio group, a pentafluoroethylthio group, a 2-bromo-1,1,2,2-tetrafluoroethylthio group, a 1,1,2,3,3,3-hexafluoropropylthio group, a heptafluoropropylthio group, a 1,2,2,2-tetrafluoro-1-(trifluoromethyl)ethylthio group and a nonafluorobutylthio group. Each haloalkylthio group of "$C_a$ to $C_b$ haloalkylthio" is selected from within the range of the specified number of carbon atoms.

The expression "$C_a$ to $C_b$ alkylsulfinyl" in the present specification represents an alkyl-S(O)— group as defined above having a to b pieces of carbon atoms and specific examples thereof include a methylsulfinyl group, an ethylsulfinyl group, an n-propylsulfinyl group, an i-propylsulfinyl group, an n-butylsulfinyl group, an i-butylsulfinyl group, an s-butylsulfinyl group and a tert-butylsulfinyl group. Each alkylsulfinyl group of "$C_a$ to $C_b$, alkylsulfinyl" is selected from within the range of the specified number of carbon atoms.

The expression "$C_a$ to $C_b$, haloalkylsulfinyl" in the present specification represents a haloalkyl-S(O)— group as defined above having a to b pieces of carbon atoms and specific examples thereof include a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 2-bromo-1,1,2,2-tetrafluoroethylsulfinyl group, a 1,2,2,2-tetrafluoro-1-(trifluoromethyl)ethylsulfinyl group and a nonafluorobutylsulfinyl group. Each haloalkylsulfinyl group of "$C_a$ to $C_b$ haloalkylsulfinyl" is selected from within the range of the specified number of carbon atoms.

The expression "$C_a$ to $C_b$ alkylsulfonyl" in the present specification represents an alkyl-SO$_2$— group as defined above having a to b pieces of carbon atoms and specific examples thereof include a methylsulfonyl group, an ethylsulfonyl group, an n-propylsulfonyl group, an i-propylsulfonyl group, an n-butylsulfonyl group, an i-butylsulfonyl group, an s-butylsulfonyl group, a tert-butylsulfonyl group, an n-pentylsulfonyl group and an n-hexylsulfonyl group. Each alkylsulfonyl group of "$C_a$ to $C_b$ alkylsulfonyl" is selected from within the range of the specified number of carbon atoms.

The expression "$C_a$ to $C_b$ haloalkylsulfonyl" in the present specification represents a haloalkyl-SO$_2$— group as defined above having a to b pieces of carbon atoms and specific examples thereof include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group, a 2-chloro-1,1,2-trifluoroethylsulfonyl group and a 2-bromo-1,1,2,2-tetrafluoroethylsulfonyl group. Each haloalkylsulfonyl group of "$C_a$ to $C_b$ haloalkylsulfonyl" is selected from within the range of the specified number of carbon atoms.

The expression "$C_a$ to $C_b$ alkylcarbonyl" in the present specification represents an alkyl-C(O)— group as defined above having a to b pieces of carbon atoms and specific examples thereof include an acetyl group, a propionyl group, a butyryl group, an isobutyryl group, a valeryl group, an isovaleryl group, a 2-methylbutanoyl group and a pivaloyl group. Each alkylcarbonyl group of "$C_a$ to $C_b$ alkylcarbonyl" is selected from within the range of the specified number of carbon atoms.

The expression "$C_a$ to $C_b$ haloalkylcarbonyl" in the present specification represents a haloalkyl-C(O)— group as defined above having a to b pieces of carbon atoms and specific examples thereof include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group and a 3-chloro-2,2-dimethylpropanoyl group. Each haloalkylcarbonyl group of "$C_a$ to $C_b$ haloalkylcarbonyl" is selected from within the range of the specified number of carbon atoms.

The expression "$C_a$ to $C_b$ alkoxycarbonyl" in the present specification represents an alkyl-O—C(O)— group as defined above having a to b pieces of carbon atoms and specific examples thereof include a methoxycarbonyl group, an ethoxycarbonyl group, an n-propyloxycarbonyl group, an i-propyloxycarbonyl group, an n-butoxycarbonyl group, an i-butoxycarbonyl group and a tert-butoxycarbonyl group. Each alkoxycarbonyl group of "$C_a$ to $C_b$ alkoxycarbonyl" is selected from within the range of the specified number of carbon atoms.

The expression "$C_a$ to $C_b$ alkylthiocarbonyl" in the present specification represents an alkyl-S—C(O)— group as defined above having a to b pieces of carbon atoms and specific examples thereof include a methylthio-C(O)— group, an ethylthio-C(O)— group, an n-propylthio-C(O)— group, an i-propylthio-C(O)— group, an n-butylthio-C(O)— group, an i-butylthio-C(O)— group and a tert-butylthio-C(O)— group. Each alkylthiocarbonyl group of "$C_a$ to $C_b$ alkylthiocarbonyl" is selected from within the range of the specified number of carbon atoms.

The expression "$C_a$ to $C_b$ alkoxythiocarbonyl" in the present specification represents an alkyl-O—C(S)— group as defined above having a to b pieces of carbon atoms and specific examples thereof include a methoxy-C(S)— group, an ethoxy-C(S)— group, an n-propyloxy-C(S)— group and an i-propyloxy-C(S)— group. Each alkoxythiocarbonyl group of "$C_a$ to $C_b$ alkoxythiocarbonyl" is selected from within the range of the specified number of carbon atoms.

The expression "$C_a$ to $C_b$ alkyldithiocarbonyl" in the present specification represents an alkyl-S—C(S)— group as defined above having a to b pieces of carbon atoms and specific examples thereof include a methylthio-C(S)— group, an ethylthio-C(S)— group, an n-propylthio-C(S)— group and an i-propylthio-C(S)— group. Each alkyldithiocarbonyl group of "$C_a$ to $C_b$ alkyldithiocarbonyl" is selected from within the range of the specified number of carbon atoms.

The expression "$C_a$ to $C_b$ alkoxy($C_d$ to $C_e$) alkyl", "$C_a$ to $C_b$ alkylthio($C_d$ to $C_e$) alkyl", "$C_a$ to $C_b$ alkylsulfinyl($C_d$ to $C_e$) alkyl", "$C_a$ to $C_b$ alkylsulfonyl($C_d$ to $C_e$) alkyl" or "$C_a$ to $C_b$ alkoxycarbonyl($C_d$ to $C_e$) alkyl" in the present specification represents an alkyl group as defined above having d to e pieces of carbon atoms in which a hydrogen atom bonded to a carbon atom is optionally replaced by any of $C_a$ to $C_b$ alkoxy group, $C_a$ to $C_b$ alkylthio group, $C_a$ to $C_b$ alkylsulfinyl group, $C_a$ to $C_b$ alkylsulfonyl group and $C_a$ to $C_b$ alkoxycarbonyl group as defined above. Each of these groups is selected from within the range of the specified number of carbon atoms.

The expression "$C_a$ to $C_b$ alkyl arbitrarily substituted with $R^5$", "$C_a$ to $C_b$ alkyl arbitrarily substituted with $R^8$" or "$C_a$ to $C_b$ alkyl arbitrarily substituted with $R^{14}$" in the present specification represents an alkyl group as defined above having a to b pieces of carbon atoms in which a hydrogen atom bonded to a carbon atom is optionally replaced by any of $R^5$, $R^8$ or $R^{14}$, and each of these groups is selected from within the range of the specified number of carbon atoms. At this time, when a substituent $R^5$, $R^8$ or $R^{14}$ on each ($C_a$ to $C_b$) alkyl group exists in the number of 2 or more, $R^5$s, $R^8$s or $R^{14}$s may be the same as or different from each other.

The expression "hydroxy($C_d$ to CO haloalkyl", "$C_a$ to $C_b$ alkoxy($C_d$ to $C_e$) haloalkyl" or "$C_a$ to $C_b$ haloalkoxy($C_d$ to $C_e$) haloalkyl" in the present specification represents a haloalkyl group as defined above having d to e pieces of carbon atoms in which a hydrogen atom or a halogen atom bonded to a carbon atom is optionally replaced by any of $C_a$ to $C_b$ alkoxy group, $C_a$ to $C_b$ haloalkoxy group as defined above or a hydroxy group. Each of these groups is selected from within the range of the specified number of carbon atoms.

In the compound encompassed in the present invention, examples of the combination of atoms represented by $A^1$, $A^2$, $A^3$ and $A^4$ include the following groups:

A-I: $A^1$, $A^2$ and $A^3$ are carbon atoms,
A-II: $A^1$ is a nitrogen atom, $A^2$ and $A^3$ are carbon atoms,
A-III: $A^2$ is a nitrogen atom, $A^1$ and $A^3$ are carbon atoms,
A-IV: $A^1$ and $A^3$ are nitrogen atoms, $A^2$ is a carbon atom,
A-V: $A^1$ and $A^2$ are nitrogen atoms, $A^3$ is a carbon atom,
A-VI: $A^2$ and $A^3$ are nitrogen atoms, $A^1$ is a carbon atom,
A-VII: $A^2$ is $C-Y^2$, $A^4$ is CH, and
A-VIII: $A^2$ and $A^4$ are nitrogen atoms.

In the compound encompassed in the present invention, examples of the substituent represented by G include aromatic 6-membered rings and aromatic 5-membered rings. Among them, preferred are a benzene ring, a pyridine ring, a thiophene ring, a pyrazole ring and a thiazole ring, and further, particularly preferred is a benzene ring.

In the compound encompassed in the present invention, examples of the substituent represented by W include an oxygen atom or a sulfur atom.

In the compound encompassed in the present invention, examples of the range of the substituent represented by X include the following groups. At this time, in each group, when m represents an integer of 2 or more, Xs may be the same as or different from each other.

X-I: a halogen atom and a trifluoromethyl,
X-II: a halogen atom, a cyano, $-SF_5$, a $C_1$ to $C_2$ haloalkyl, a $C_1$ to $C_2$ haloalkoxy and a $C_1$ to $C_2$ haloalkylthio,
X-III: a halogen atom, $-SF_5$, a $C_1$ to $C_4$ haloalkyl, a $C_1$ to $C_4$ haloalkoxy and a $C_1$ to $C_4$ haloalkylthio,
X-IV: a halogen atom, a cyano, a nitro, a $C_1$ to $C_4$ alkyl, a $C_1$ to $C_4$ haloalkyl, a $C_1$ to $C_4$ alkoxy, a $C_1$ to $C_4$ haloalkoxy, a $C_1$ to $C_4$ alkylthio and a $C_1$ to $C_4$ haloalkylthio,
X-V: a halogen atom, a $C_1$ to $C_4$ alkyl, a $C_1$ to $C_4$ haloalkyl and a $C_1$ to $C_4$ haloalkoxy,
X-VI: a halogen atom, $-SF_5$, a $C_1$ to $C_6$ haloalkyl, a hydroxy($C_1$ to $C_4$) haloalkyl, a $C_1$ to $C_4$ alkoxy($C_1$ to $C_4$) haloalkyl, $-OR^4$ and $-SR^4$ (where $R^4$ represents a $C_1$ to $C_4$ haloalkyl or $C_1$ to $C_2$ haloalkoxy($C_1$ to $C_2$) haloalkyl),
X-VII: a halogen atom, a cyano, a nitro, a $C_1$ to $C_6$ alkyl, a $C_1$ to $C_6$ haloalkyl, $-OR^4$ and $-S(O)_rR^4$ (where $R^4$ represents a $C_1$ to $C_4$ alkyl, a $C_1$ to $C_4$ haloalkyl or a $C_1$ to $C_2$ haloalkoxy($C_1$ to $C_2$) haloalkyl; and r represents an integer of 0 to 2), and
X-VIII: a halogen atom, a $C_1$ to $C_6$ alkyl, a $C_1$ to $C_6$ haloalkyl, $-OR^4$ (where $R^4$ represents a $C_1$ to $C_4$ haloalkyl) and $-NH_2$.

In the compound encompassed in the present invention, examples of m representing the number of substituents represented by X include integers of 0 to 5 and among them, m is preferably 1, 2 and 3.

In the compound encompassed in the present invention, examples of the range of the substituent represented by Y include the following groups. At this time, in each group, when n represents an integer of 2 or more, Ys may be the same as or different from each other.

Y-I: a halogen atom, a methyl, an ethyl and a trifluoromethyl,
Y-II: a halogen atom, a cyano, a nitro, a $C_1$ to $C_2$ alkyl, a $C_1$ to $C_2$ haloalkyl, a $C_1$ to $C_2$ alkoxymethyl, a $C_2$ to $C_3$ alkenyl, a $C_2$ to $C_3$ alkynyl, a $C_1$ to $C_2$ haloalkoxy, a $C_1$ to $C_2$ haloalkylthio, $-N(R^7)R^6$ (where $R^6$ represents a hydrogen atom, a $C_1$ to $C_2$ alkyl or a $C_1$ to $C_2$ alkylcarbonyl; and $R^7$ represents a hydrogen atom or a $C_1$ to $C_2$ alkyl) and $-C(S)NH_2$,
Y-III: a halogen atom, a cyano, a $C_1$ to $C_4$ alkyl, a $C_1$ to $C_4$ haloalkyl, a $C_1$ to $C_2$ alkoxy($C_1$ to $C_2$) alkyl, a $C_2$ to $C_4$ alkenyl, a $C_2$ to $C_4$ alkynyl and $-C(S)NH_2$,
Y-IV: a nitro, a $C_1$ to $C_4$ alkoxy, a $C_1$ to $C_4$ haloalkoxy, a $C_1$ to $C_4$ alkylthio, a $C_1$ to $C_4$ haloalkylthio and $-N(R^7)R^6$ (where $R^6$ represents a hydrogen atom, a $C_1$ to $C_4$ alkyl, $-CHO$, a $C_1$ to $C_4$ alkylcarbonyl, a $C_1$ to $C_4$ haloalkylcarbonyl, a $C_1$ to $C_4$ alkoxycarbonyl, a $C_1$ to $C_4$ alkylthiocarbonyl, a $C_1$ to $C_4$ alkoxythiocarbonyl or a $C_1$ to $C_4$ alkyldithiocarbonyl; and $R^7$ represents a hydrogen atom or a $C_1$ to $C_4$ alkyl),
Y-V: a halogen atom, a cyano, a $C_1$ to $C_6$ alkyl, a $C_1$ to $C_6$ haloalkyl, a ($C_1$ to $C_4$) alkyl arbitrarily substituted with $R^5$ (where $R^5$ represents $-OH$, a $C_1$ to $C_4$ alkoxy, a $C_1$ to $C_4$ haloalkoxy, a $C_1$ to $C_4$ alkylthio, a $C_1$ to $C_4$ haloalkylthio, a $C_1$ to $C_4$ alkylsulfinyl, a $C_1$ to $C_4$ haloalkylsulfinyl, a $C_1$ to $C_4$ alkylsulfonyl or a $C_1$ to $C_4$ haloalkylsulfonyl), a $C_2$ to $C_6$ alkenyl, a $C_2$ to $C_6$ alkynyl and $-C(S)NH_2$,
Y-VI: a nitro, $-OR^4$, $-S(O)_rR^4$ (where $R^4$ represents a $C_1$ to $C_4$ alkyl, a $C_1$ to $C_4$ haloalkyl or a $C_1$ to $C_2$ haloalkoxy($C_1$ to $C_2$) haloalkyl; and r represents an integer of 0 to 2) and $-N(R^7)R^6$ (where $R^6$ represents a hydrogen atom, a $C_1$ to $C_6$ alkyl, $-CHO$, $-C(O)R^{23}$, $-C(O)OR^{23}$, $-C(O)SR^{23}$, $-C(S)OR^{23}$, $-C(S)SR^{23}$ or $-S(O)_2R^{23}$; $R^7$ represents a hydrogen atom or a $C_1$ to $C_6$ alkyl; and $R^{23}$ represents a $C_1$ to $C_6$ alkyl, a $C_1$ to $C_6$ haloalkyl or a $C_3$ to $C_6$ cycloalkyl),
Y-VII: D-1 to D-5, D-14, D-24 and D-41 (where p2, p3 and p4 represents 0), and
Y-VIII: $Y^1$ and $Y^2$ together form $-CH=CHCH=CH-$, $-CH=CHCH=N-$, $-CH=CHN=CH-$, $-CH=NCH=CH-$ or $-N=CHCH=CH-$ to form together with a carbon atom to which $Y^1$ and $Y^2$ are bonded, a 6-membered ring.

In the compound encompassed in the present invention, examples of n representing the number of substituents represented by Y include integers of 0 to 4 and among them, n is preferably 0 and 1.

In the compound encompassed in the present invention, examples of the range of the substituent represented by $R^1$ include the following groups:

$R^1$-I: a $C_1$ to $C_2$ haloalkyl, $-C(O)NHR^{12}$ (where $R^{12}$ represents a $C_1$ to $C_2$ haloalkyl), D-22 and D-52 (where p2 and p4 represent 0 and t represents 0),
$R^1$-II: $-OR^{1a}$ (where $R^{1a}$ represents a $C_1$ to $C_2$ alkyl),
$R^1$-III: a $C_1$ to $C_4$ haloalkyl, a $C_1$ to $C_2$ alkoxy($C_1$ to $C_2$) alkyl, a $C_3$ to $C_4$ cycloalkyl, a $C_2$ to $C_4$ alkenyl, $-C(O)N(R^{13})R^{12}$ (where $R^{12}$ represents a $C_1$ to $C_4$ alkyl, a $C_1$ to $C_4$ haloalkyl, a $C_3$ to $C_4$ alkenyl or a $C_3$ to $C_4$ alkynyl; and $R^{13}$ represents a hydrogen atom or a methyl), a phenyl substituted with $(Z)_{p1}$, D-22, D-52 and D-55 (where Z represents a cyano or a nitro; p1 represents 1; p2, p3 and p4 represent an integer of 0 or 1; and t represents 0),
$R^1$-IV: $-OR^{1a}$ (where $R^{1a}$ represents a $C_1$ to $C_4$ alkyl, a $C_1$ to $C_4$ haloalkyl or a $C_3$ to $C_4$ alkynyl),
$R^1$-V: $-N(R^{1c})R^{1b}$ (where $R^{1b}$ represents a cyano, a nitro or a $C_1$ to $C_2$ alkoxy; and $R^{1C}$ represents a hydrogen atom or a methyl),
$R^1$-VI: a $C_1$ to $C_6$ haloalkyl, a ($C_1$ to $C_4$) alkyl arbitrarily substituted with $R^8$ (where $R^8$ represents a $C_1$ to $C_2$ alkoxy or a $C_1$ to $C_2$ haloalkoxy), a $C_3$ to $C_6$ cycloalkyl, E-6, E-7, E-12 (where q2 and q3 represent 0) and a $C_2$ to $C_6$ alkenyl,
$R^1$-VII: a cyano, $-C(R^9)=NOR^{10}$ (where $R^9$ represents a hydrogen atom or a methyl; and $R^{10}$ represents a $C_1$ to $C_2$ alkyl) and $-C(O)N(R^{13})R^{12}$ (where $R^{12}$ represents a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl; and $R^{13}$ represents a hydrogen atom or a $C_1$ to $C_2$ alkyl), $R^1$-VIII: a phenyl, a phenyl substituted with $(Z)_{p1}$, D-16, D-17, D-21, D-22, D-28, D-34, D-41, D-52 and D-55 (where $R^{21}$ represents a $C_1$ to $C_2$ alkyl; Z represents a halogen atom, a cyano, a nitro or a $C_1$ to $C_2$ alkoxy, where when p1 or p2 represents an integer of 2 or more, Zs may be the same as or different from each other; p1 represents an integer of 1 to 3; p2 represents an integer of 0 to 2; p3, p4 and p5 represent an integer of 0 or 1; and t represents 0), $R^1$-IX: —$OR^{1a}$ (where $R^{1a}$ represents a $C_1$ to $C_6$ alkyl, a $C_1$ to $C_6$ haloalkyl, a $C_3$ to $C_6$ cycloalkyl, a $C_3$ to $C_6$ alkenyl or a $C_3$ to $C_6$ alkynyl) and —$SR^{1a}$ (where $R^{1a}$ represents a $C_1$ to $C_4$ alkyl, a $C_1$ to $C_4$ haloalkyl or a $C_3$ to $C_4$ alkynyl), $R^1$-X: —$N(R^{1c})R^{1b}$ (where $R^{1b}$ represents a cyano, a nitro, a $C_1$ to $C_4$ alkyl, a $C_1$ to $C_4$ alkoxy or a $C_1$ to $C_4$ haloalkoxy; and $R^{1C}$ represents a hydrogen atom or a $C_1$ to $C_2$ alkyl), $R^1$-XI: —$OR^{1a}$ and —$SR^{1a}$ (where $R^{1a}$ represents a $C_1$ to $C_4$ alkyl, a $C_1$ to $C_4$ haloalkyl or a $C_3$ to $C_4$ alkynyl).

In the compound encompassed in the present invention, examples of the range of the substituent represented by $R^2$ include the following groups:

$R^2$-I: a hydrogen atom, $R^2$-II: a $C_1$ to $C_2$ alkyl, $R^2$-III: a $C_1$ to $C_2$ alkyl, a cyanomethyl, a $C_1$ to $C_2$ alkoxymethyl, a propargyl, —$C(O)R^{15}$ (where $R^{15}$ represents a $C_1$ to $C_2$ alkyl, a $C_1$ to $C_2$ alkoxymethyl, a cyclopropyl or a vinyl) and —$C(O)OR^{16}$ (where $R^{16}$ represents a $C_1$ to $C_2$ alkyl), $R^2$-IV: a $C_1$ to $C_4$ alkyl, a $C_1$ to $C_4$ haloalkyl, a $C_3$ to $C_4$ cycloalkyl and a $C_3$ to $C_4$ alkynyl, $R^2$-V: a $C_1$ to $C_4$ alkyl, a ($C_1$ to $C_2$) alkyl arbitrarily substituted with $R^{14}$ (where $R^{14}$ represents a cyano, a $C_1$ to $C_2$ alkoxy or a $C_1$ to $C_2$ haloalkoxy), a $C_3$ to $C_4$ alkynyl, —$C(O)R^{15}$ (where $R^{15}$ represents a $C_1$ to $C_4$ alkyl, a $C_1$ to $C_2$ alkoxy ($C_1$ to $C_2$) alkyl, a $C_3$ to $C_4$ cycloalkyl or a $C_2$ to $C_4$ alkenyl) and —$C(O)OR^{16}$ (where $R^{16}$ represents a $C_1$ to $C_4$ alkyl), $R^2$-VI: a $C_1$ to $C_6$ alkyl, a $C_1$ to $C_6$ haloalkyl, a $C_3$ to $C_6$ cycloalkyl, a $C_3$ to $C_6$ alkenyl and a $C_3$ to $C_6$ alkynyl.

In the compound encompassed in the present invention, examples of the range of the substituent represented by $R^3$ include the following groups:

$R^3$-I: a trifluoromethyl and a chlorodifluoromethyl, $R^3$-II: a difluoromethyl, a trifluoromethyl, a chlorodifluoromethyl, a bromodifluoromethyl and a 1,1,2,2-tetrafluoroethyl, $R^3$-III: a $C_1$ to $C_2$ alkyl arbitrarily substituted with arbitrary two or more pieces of halogen atoms, $R^3$-IV: a $C_1$ to $C_4$ haloalkyl, and $R^3$-V: a $C_1$ to $C_6$ haloalkyl and a $C_3$ to $C_8$ halocycloalkyl.

These groups representing the range of each substituent of the compound encompassed in the present invention may be optionally combined, and each of the combinations represents the range of the compound according to the present invention. Examples of the combination of the ranges of Q, $R^1$ and $R^2$ include combinations shown in Table 1, with proviso that the combinations shown in Table 1 is only for exemplification, so that these examples should not be construed as limiting the scope of the present invention.

TABLE 1

| Q | $R^1$ | $R^2$ |
|---|---|---|
| Q-1 | $R^1$-I | $R^2$-I |
| Q-1 | $R^1$-I | $R^2$-III |
| Q-1 | $R^1$-I | $R^2$-V |
| Q-2 | $R^1$-II | $R^2$-I |
| Q-2 | $R^1$-II | $R^2$-II |
| Q-2 | $R^1$-II | $R^2$-IV |
| Q-2 | $R^1$-II | $R^2$-VI |
| Q-1 | $R^1$-III | $R^2$-I |
| Q-1 | $R^1$-III | $R^2$-III |
| Q-1 | $R^1$-III | $R^2$-V |
| Q-2 | $R^1$-IV | $R^2$-I |
| Q-2 | $R^1$-IV | $R^2$-II |
| Q-2 | $R^1$-IV | $R^2$-IV |
| Q-2 | $R^1$-V | $R^2$-I |
| Q-2 | $R^1$-V | $R^2$-II |
| Q-1 | $R^1$-VI | $R^2$-I |
| Q-1 | $R^1$-VI | $R^2$-III |
| Q-1 | $R^1$-VII | $R^2$-I |
| Q-1 | $R^1$-VII | $R^2$-III |
| Q-1 | $R^1$-VIII | $R^2$-I |
| Q-1 | $R^1$-VIII | $R^2$-III |
| Q-2 | $R^1$-IX | $R^2$-I |
| Q-2 | $R^1$-IX | $R^2$-II |
| Q-2 | $R^1$-X | $R^2$-I |
| Q-3 | $R^1$-XI | $R^2$-II |
| Q-3 | $R^1$-XI | $R^2$-IV |

The compound of the present invention can be produced, for example by the following methods.

Production Method A

[Chemical Formula 7]

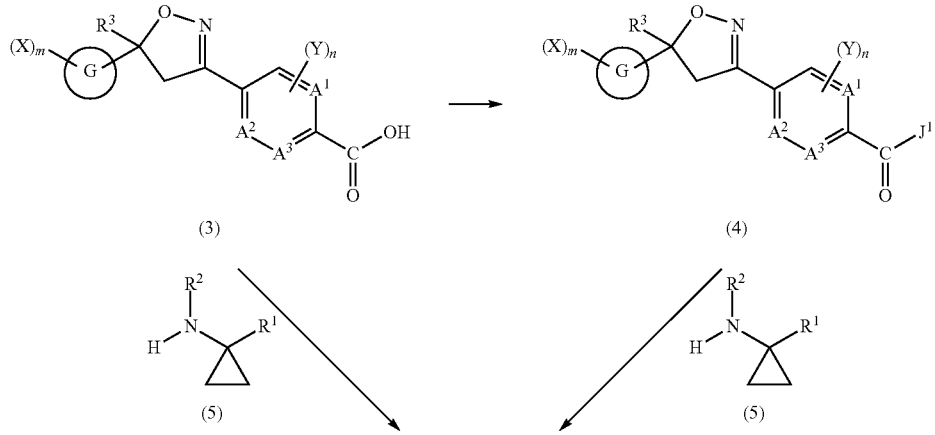

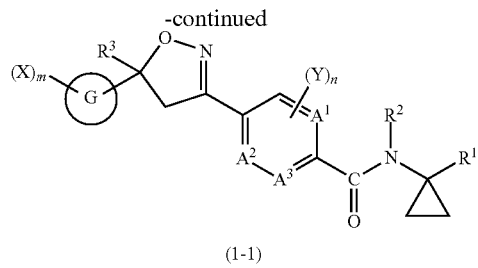

(1-1)

By reacting 1 equivalent of a compound represented by General Formula (4) (where $A^1$, $A^2$, $A^3$, G, X, Y, $R^3$, m and n represent the same as those defined above; and $J^1$ represents a chlorine atom, a bromine atom, a $C_1$ to $C_4$ alkylcarbonyloxy group (such as a pivaloyloxy group), a $C_1$ to $C_4$ alkoxycarbonyloxy group (such as an isobutyloxycarbonyloxy group) or an azolyl group (such as an imidazol-1-yl group)) which can be synthesized from a publicly-known compound represented by General Formula (3) (where $A^1$, $A^2$, $A^3$, G, X, Y, $R^3$, m and n represent the same as those defined above) which is described in International Patent Application Publication (WO 2005/085216) or the like using a publicly-known method described in literatures such as: a method for reacting the compound represented by General Formula (3) with a halogenating agent such as thionyl chloride, phosphorus pentachloride and oxalyl chloride according to a method described in Journal of Medicinal Chemistry (J. Med. Chem.) (1991) Vol. 34, p. 1630; a method for reacting the compound represented by General Formula (3) with a halogenated organic acid such as pivaloyl chloride and isobutyl chloroformate according to a method described in Tetrahedron Letters (Tetrahedron Lett.) (2003) Vol. 44, p. 4819, Journal of Medicinal Chemistry (J. Med. Chem.) (1991) Vol. 34, p. 222, or the like, if necessary in the presence of a base; or a method for reacting the compound represented by General Formula (3) with carbonyldiimidazole or sulfonyldiimidazole and the like, which are described in the Journal of Organic Chemistry (J. Org. Chem.) (1989) Vol. 54, P. 5620, with 1 to 10 equivalent(s) of a compound represented by General Formula (5) (where $R^1$ and $R^2$ represents the same as those defined above) using as a solvent, for example dichloromethane, chloroform, 1,2-dichloroethane, diethyl ether, tert-butyl methyl ether, 1,2-dimethoxyethane, tetrahydrofuran, 1,4-dioxane, ethyl acetate, acetonitrile, water, or a mixture of two or more types of these solvents in an arbitrary mixing ratio, if necessary in the presence of 1 to 2 equivalent(s) of a base such as sodium carbonate, potassium carbonate, triethylamine, pyridine and 4-(dimethylamino) pyridine, at a temperature in the range from 0° C. to a reflux temperature of the above solvent for 10 minutes to 24 hours, a compound of the present invention represented by General Formula (1-1) (where $A^1$, $A^2$, $A^3$, G, X, Y, $R^1$, $R^2$, $R^3$, m and n represent the same as those defined above) which falls under General Formula (1), in which W represents an oxygen atom; and Q represents Q-1, can be synthesized.

In addition, the compound of the present invention represented by General Formula (1-1) can also be obtained by reacting 1 equivalent of the compound represented by General Formula (3) with 1 to 20 equivalent(s) of the compound represented by General Formula (5) using as a solvent, for example dichloromethane, chloroform, 1,2-dichloroethane, diethyl ether, tert-butyl methyl ether, 1,2-dimethoxyethane, tetrahydrofuran or 1,4-dioxane, if necessary in the presence of 1 to 4 equivalent(s) of a base such as sodium carbonate, potassium carbonate, triethylamine, pyridine and 4-(dimethylamino) pyridine using 1 to 4 equivalent(s) of a condensing agent such as DCC (1,3-dicyclohexylcarbodiimide), WSC (1-ethyl-3-(3-dimethylaminopropyl)-carbodiimide hydrochloride), or CDI (carbonyldiimidazole), at a temperature in the range from 0° C. to a reflux temperature of the above solvent for 10 minutes to 24 hours.

Production Method B

[Chemical Formula 8]

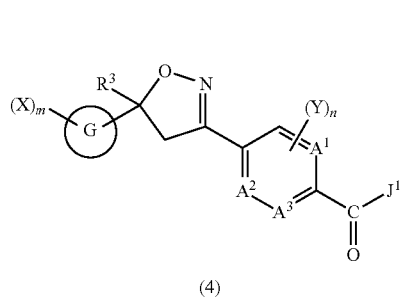 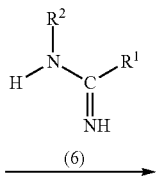

(4)  (6)

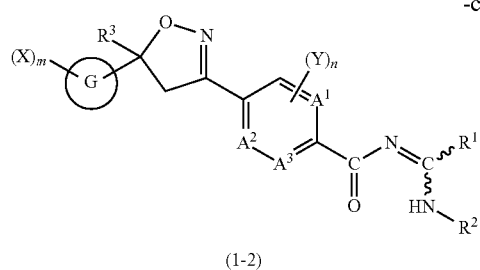

(1-2)    (1-3)

By reacting the compound represented by General Formula (4) (where $A^1$, $A^2$, $A^3$, G, X, Y, $R^3$, m, n and $J^1$ represent the same as those defined above) with a compound represented by General Formula (6) (where $R^1$ and $R^2$ represent the same as those defined above) or salts thereof under substantially the same reaction conditions as in Production Method A, a compound of the present invention represented by General Formula (1-2) (where $A^1$, $A^2$, $A^3$, G, X, Y, $R^1$, $R^2$, $R^3$, m and n represent the same as those defined above) which falls under General Formula (1) (where W represents an oxygen atom; and Q represents Q-2) and/or a compound of the present invention represented by General Formula (1-3) (where $A^1$, $A^2$, $A^3$, G, X, Y, $R^1$, $R^2$, $R^3$, m and n represent the same as those defined above) which falls under General Formula (1) (where W is an oxygen atom; and Q represents Q-3) can be obtained.

Production Method C

[Chemical Formula 9]

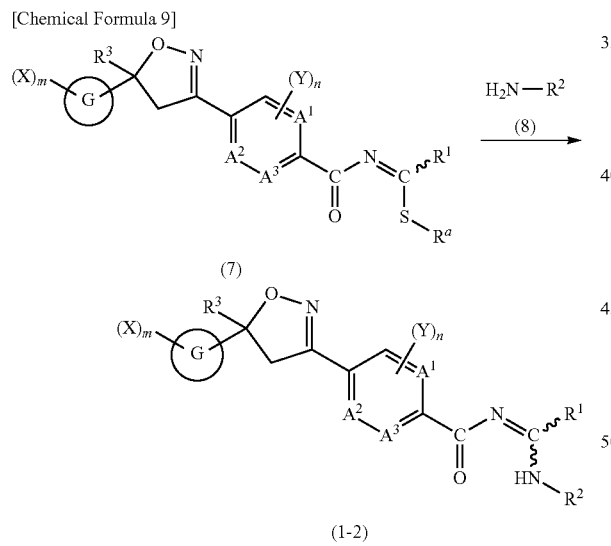

By reacting 1 equivalent of a compound represented by General Formula (7) (where $A^1$, $A^2$, $A^3$, X, Y, $R^1$, $R^3$, m and n represent the same as those defined above; and $R^a$ represents a lower alkyl group such as a methyl and an ethyl) with 1 to 50 equivalent(s) of a compound represented by General Formula (8) (where $R^2$ represent the same as those defined above) or salts thereof using as a solvent, for example toluene, dichloromethane, chloroform, 1,2-dichloroethane, methanol, ethanol, diethyl ether, tert-butyl methyl ether, 1,2-dimethoxyethane, tetrahydrofuran, 1,4-dioxane, ethyl acetate, N,N-dimethylformamide, acetic acid, acetonitrile, water, or a mixture of these solvents in an arbitrary mixing ratio, if necessary in the presence of 1 to 20 equivalent(s) of a base such as potassium carbonate, sodium hydrogen carbonate, triethylamine, diisopropylethylamine and pyridine, at a temperature in the range from 0° C. to a reflux temperature of the above solvent for 5 minutes to 24 hours, the compound of the present invention represented by General $R^3$, m and n represent the same as those defined above) which falls under General Formula (1) (where W represents an oxygen atom; and Q represents Q-2) can be obtained.

Some of the compounds represented by General Formula (8) are publicly known compounds and a part of them is commercially available. In addition, the others can be easily synthesized according to a general synthetic method of primary amines described in literatures.

Production Method D

[Chemical Formula 10]

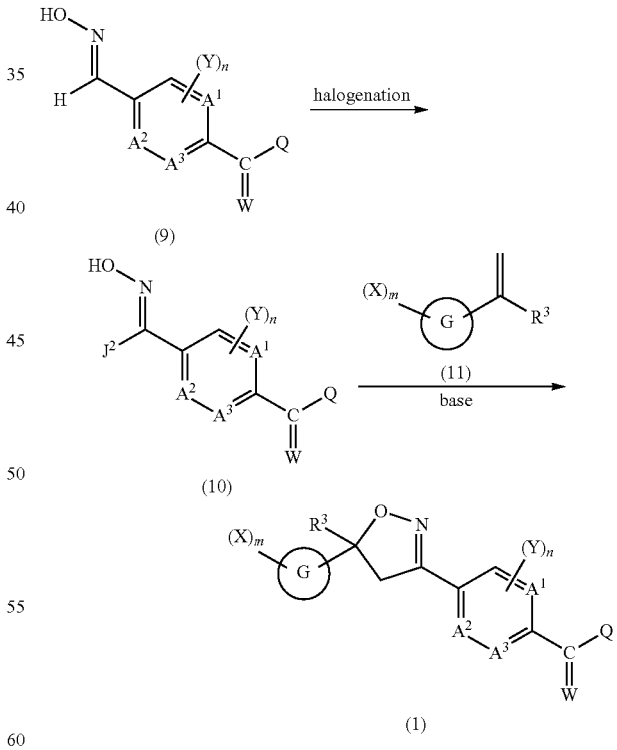

By halogenating a compound represented by General Formula (9) (where $A^1$, $A^2$, $A^3$, W, Y, Q and n represent the same as those defined above) using as a solvent, for example dichloromethane, chloroform, 1,2-dimethoxyethane, tetrahydrofuran, 1,4-dioxane or N,N-dimethylformamide and using a halogenating agent such as N-chlorosuccinimide, a sodium hypochlorite aqueous solution, tert-butyl hypochlorite ester and a chlorine gas in an amount of 1 to 2 equivalent(s) relative to 1 equivalent of a compound represented by General Formula (9) at a temperature in the range from 0° C. to a reflux temperature of the above solvent for 10 minutes to 2 hours, a hydroxamic acid chloride represented by General Formula (10) (where $A^1$, $A^2$, $A^3$, W, Y, Q and n represent the same as those defined above; and $J^2$ represents a halogen atom such as a chlorine atom and a bromine atom) can be obtained.

By reacting 1 equivalent of the thus obtained compound represented by General Formula (10) with 1 to 2 equivalent(s) of a compound represented by General Formula (11) (where G, X, $R^3$ and m represent the same as those defined above) using as a solvent, for example dichloromethane, chloroform, 1,2-dimethoxyethane, tetrahydrofuran, 1,4-dioxane or N,N-dimethylformamide, if necessary in the presence of 1 to 2 equivalent(s) of a base such as sodium carbonate, potassium carbonate, sodium hydrogen carbonate and triethylamine at a temperature in the range from 0° C. to a reflux temperature of the above solvent for 10 minutes to 24 hours, the compound of the present invention represented by General Formula (1) (where $A^1$, $A^2$, $A^3$, G, W, X, Y, Q, $R^3$, m and n represent the same as those defined above) can be obtained.

A compound represented by General Formula (11) used here is a publicly-known compound described in International Patent Application Publication (WO 2005/085216) or the like.

Production Method E

[Chemical Formula 11]

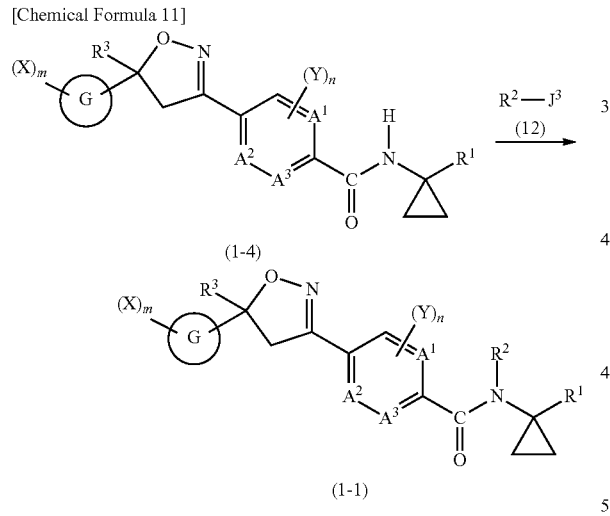

(1-1)

By reacting 1 equivalent of a compound of the present invention represented by General Formula (1-4) (where $A^1$, $A^2$, $A^3$, G, X, Y, $R^1$, $R^3$, m and n represent the same as those defined above) which falls under General Formula (1) (where W is an oxygen atom; Q is Q-1; and $R^2$ is a hydrogen atom) with 1 to 10 equivalent(s) of a compound represented by General Formula (12) (where $R^2$ represents the same as that defined above other than a hydrogen atom; and $J^3$ represents an advantageous leaving group such as a chlorine atom, a bromine atom, an iodine atom, a $C_1$ to $C_4$ alkylcarbonyloxy group (such as a pivaloyloxy group), a $C_1$ to $C_4$ alkylsulfonate group (such as a methanesulfonyloxy group), a $C_1$ to $C_4$ haloalkylsulfonate group (such as a trifluoromethanesulfonyloxy group), an arylsulfonate group (such as a benzenesulfonyloxy group and a p-toluenesulfonyloxy group) and an azolyl group (such as an imidazole-1-yl group)) using as a solvent, for example tert-butyl methyl ether, tetrahydrofuran, 1,4-dioxane, N,N-dimethylformamide or acetonitrile, if necessary in the presence of 1 to 3 equivalent(s) of a base such as sodium hydride, sodium hydroxide, potassium hydroxide, potassium-tert-butoxide, sodium carbonate, potassium carbonate, triethylamine and pyridine at a temperature in the range from 0 to 90° C. for 10 minutes to 24 hours, the compound of the present invention represented by General Formula (1-1) (where $A^1$, $A^2$, $A^3$, G, X, Y, $R^1$, $R^3$, m and n represent the same as those defined above; and $R^2$ represents the same as those defined above other than a hydrogen atom) which falls under General Formula (1) (where W is an oxygen atom; and Q represents Q-1) can be obtained.

Some of the compounds represented by General Formula (12) used here are publicly-known compounds and a part of them is commercially available. In addition, the others can be easily synthesized according to a general synthetic method described in literatures such as methods described in Chemistry Letters (Chem. Lett.) (1976) p. 373; Chemical and Pharmaceutical Bulletin (Chem. Pharm. Bull.) (1986) Vol. 34, p. 540 and (2001) Vol. 49, p. 1102; Journal of the American Chemical Society (J. Am. Chem. Soc.) (1964) Vol. 86, p. 4383; the Journal of Organic Chemistry (J. Org. Chem.) (1976) Vol. 41, p. 4028, (1978) Vol. 43, p. 3244 and (1983) Vol. 48, p. 5280; Organic Synthesis (Org. Synth.) (1988) Collective Vol. 6, p. 101; Synthesis (Synthesis) (1990) p. 1159; Tetrahedron Letters (Tetrahedron Lett.) (1972) p. 4339; Japanese Patent Application Publication (JP 05/125017); UK Patent Publication (GB 2,161,802); and European Patent Publication (EP 0,051,273).

Production Method F

[Chemical Formula 12]

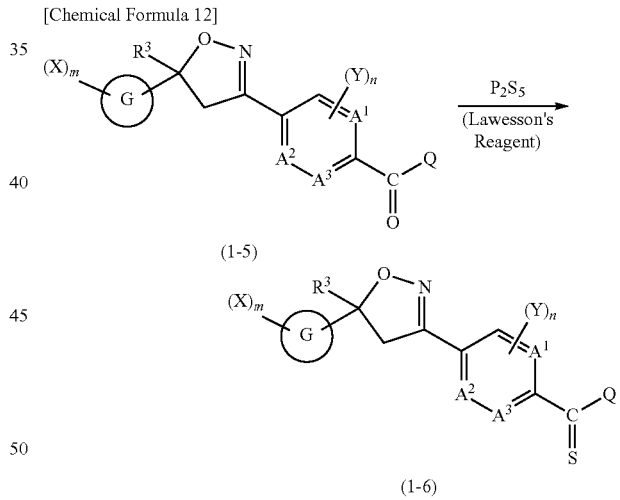

(1-6)

By reacting 1 equivalent of a compound of the present invention represented by General Formula (1-5) (where $A^1$, $A^2$, $A^3$, G, X, Y, Q, $R^3$, m and n represent the same as those defined above) which falls under General Formula (1) (where W is an oxygen atom) with 1 to 10 equivalent(s) of a sulfurizing agent such as di-phosphorus pentasulfide, di-phosphorus pentasulfide-HMDO (hexamethyldisiloxane) and Lawesson's Reagent (2,4-bis(4-methoxyphenyl)-1,3,2,4-dithiadiphosphetane 2,4-disulfide): either if necessary using as a solvent, for example, benzene, toluene, chlorobenzene, dichloromethane, chloroform, 1,2-dichloroethane, tert-butyl methyl ether, 1,2-dimethoxyethane, tetrahydrofuran, 1,4-dioxane or HMPA (hexamethylphosphoric triamide) and if necessary in the presence of 1 to 4 equivalent(s) of a base such as sodium carbonate, potassium carbonate, sodium hydrogen carbonate, triethylamine and pyridine at a temperature in the range from room temperature to a reflux temperature of the reaction mixture for 10 minutes to 50 hours; or using as a solvent, a base such as pyridine at a temperature in the range from 80° C. to a reflux temperature of the reaction mixture for 1 to 3 hour(s), a compound of the present invention represented by General Formula (1-6) (where $A^1$, $A^2$, $A^3$, G, X, Y, Q, $R^3$, m and n represent the same as those defined above) which falls under General Formula (1) (where W is a sulfur atom) can be obtained.

In Production Method A to Production Method F, the objective compound of the present invention can be obtained by subjecting the reaction mixture after the completion of the reaction to a usual post-treatment such as: directly concentrating the reaction mixture; or dissolving the reaction mixture in an organic solvent, cleaning the resultant solution with water and then concentrating the solution; or charging the reaction mixture into ice water, extracting the objective compound with an organic solvent and then concentrating the resultant extract. In addition, when the purification becomes necessary, the objective compound can be isolated/purified by an arbitrary purifying method such as recrystallization, column chromatography, thin-layer chromatography and preparative liquid chromatography.

Some of the compounds represented by General Formula (5) used in Production Method A are publicly-known compounds and a part of them is commercially available. In addition, the others can be synthesized, for example according to Reaction Formula 1 or Reaction Formula 2.

Reaction Formula 1

[Chemical Formula 13]

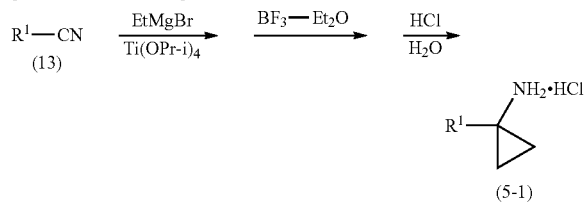

(5-1)

By reacting a compound represented by General Formula (13) (where $R^1$ represents the same as that defined above) with ethyl magnesium bromide according to a publicly-known method described in literatures such as the Journal of Organic Chemistry (J. Org. Chem.) (2002) Vol. 67, p. 3965 in the presence of titanium tetraisopropoxide, 1-substituted cyclopropylamine represented by General Formula (5-1) (where $R^1$ represents the same as that defined above) which falls under General Formula (5) (where $R^2$ is a hydrogen atom) can be obtained.

Some of the compounds represented by General Formula (13) used here are publicly-known compounds and a part of them is commercially available. In addition, the others can be easily synthesized according to a general synthetic method of nitrile derivatives described in literatures.

Reaction Formula 2

[Chemical Formula 14]

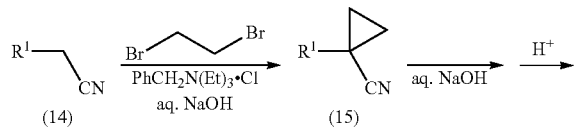

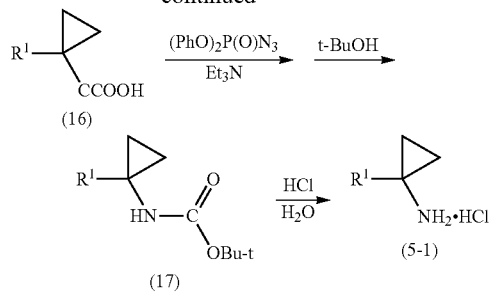

By hydrolyzing using a sodium hydroxide aqueous solution or the like, 1-substituted cyclopropane carbonitrile represented by General Formula (15) (where $R^1$ represents the same as that defined above) which is obtained by reacting a substituted acetonitrile represented by General Formula (14) (where $R^1$ represents the same as that defined above) with 1,2-dibromoethane according to a publicly-known method described in literatures such as International Patent Application Publication (WO 2005/005420) in the presence of a base such as sodium hydroxide, a 1-substituted cyclopropane carboxylic acid represented by General Formula (16) (where $R^1$ represents the same as that defined above) can be obtained. Next, by hydrolyzing under an acidic condition, a compound represented by General Formula (17) (where $R^1$ represents the same as that defined above) which is obtained by subjecting the above compound represented by General Formula (16) to the Curtius rearrangement using diphenylphosphorylazide, 1-substituted cyclopropylamine represented by General Formula (5-1) (where $R^1$ represents the same as that defined above) which falls under General Formula (5) (where $R^2$ is a hydrogen atom) can be obtained.

Some of the compounds represented by General Formula (14) used here are publicly-known compounds and a part of them is commercially available. In addition, the others can be easily synthesized according to a general synthetic method of substituted acetonitrile derivatives described in literatures.

Some of the compounds represented by General Formula (6) used in Production Method B are publicly-known compounds and a part of them is commercially available. In addition, the others can be synthesized, for example according to Reaction Formula 3 or Reaction Formula 4.

Reaction Formula 3

[Chemical Formula 15]

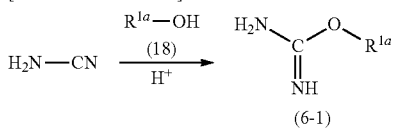

By reacting cyanamide with alcohols represented by General Formula (18) (where $R^{1a}$ represents the same as that defined above) according to a publicly-known method described in literatures such as the Journal of Organic Chemistry (J. Org. Chem.) (2003) Vol. 68, p. 5114 and Tetrahedron Letters (Tetrahedron Lett.) (1987) Vol. 28, p. 1969 in the presence of an acid catalyst such as methanesulfonic acid and p-toluenesulfonic acid, a compound represented by General Formula (6-1) (where $R^{1a}$ represents the same as that defined above) which falls under General Formula (6) (where $R^1$ is —$OR^{1a}$; and $R^2$ is a hydrogen atom) can be obtained.

Some of the alcohols represented by General Formula (18) used here are publicly-known compounds and a part of them is commercially available. In addition, the others can be easily synthesized according to a general synthetic method of alcohols described in literatures.

Reaction Formula 4

[Chemical Formula 16]

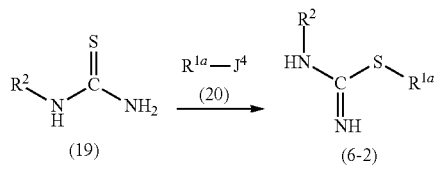

By reacting a thiourea represented by General Formula (19) (where $R^2$ represents the same as that defined above) or an N-substituted thiourea with a compound represented by General Formula (20) (where $R^{1a}$ represents the same as that defined above; and $J^4$ represents an advantageous leaving group such as a chlorine atom, a bromine atom, an iodine atom, a $C_1$ to $C_4$ alkylsulfonate group (such as a methanesulfonyloxy group), a $C_1$ to $C_4$ haloalkylsulfonate group (such as a trifluoromethanesulfonyloxy group) and an arylsulfonate group (such as a benzenesulfonyloxy group and a p-toluenesulfonyloxy group)) according to a publicly-known method described in literatures such as Chemical and Pharmaceutical Bulletin (Chem. Pharm. Bull.) (1989) Vol. 37 p. 1080 and the Journal of Organic Chemistry (J. Org. Chem.) (1976) Vol. 41, p. 2835, a compound represented by General Formula (6-2) (where $R^{1a}$ and $R^2$ represent the same as those defined above) which falls under General Formula (6) (where $R^1$ is $—SR^{1a}$) can be obtained.

Some of the compounds represented by General Formula (19) used here are publicly-known compounds and a part of them is commercially available. In addition, the others can be easily synthesized according to a general synthetic method of thiourea or an N-substituted thiourea described in literatures.

In addition, some of the compounds represented by General Formula (20) used here are publicly-known compounds and a part of them is commercially available. In addition, the others can be easily synthesized in substantially the same manner as in the synthesis of the compound represented by General Formula (12).

A compound represented by General Formula (7) used in Production Method C can be synthesized, for example as follows.

Reaction Formula 5

[Chemical Formula 17]

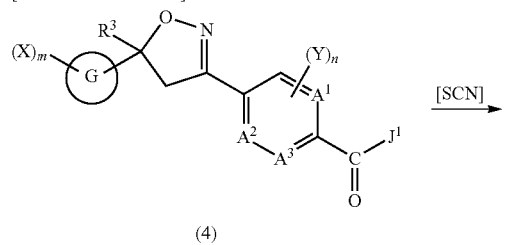

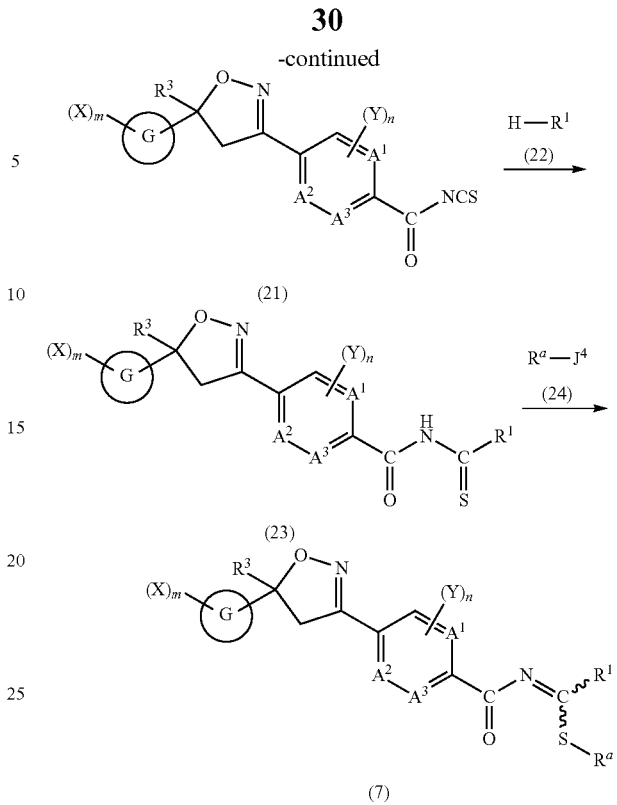

By reacting a compound represented by General Formula (21) (where $A^1$, $A^2$, $A^3$, G, X, Y, $R^3$, m and n represent the same as those defined above) which is obtained by reacting a compound represented by General Formula (4) (where $A^1$, $A^2$, $A^3$, G, X, Y, $R^3$, m, n and $J^1$ represent the same as those defined above) with a thiocyanate such as potassium thiocyanate and ammonium thiocyanate according to a publicly-known method described in literatures such as Journal of Heterocyclic Chemistry (J. Heterocyclic Chem.) (1989) Vol. 26, p. 1331 and Tetrahedron Letters (Tetrahedron Lett.) (2005) Vol. 46, p. 419, with alcohols, mercaptans, amines, hydroxylamines or hydrazines represented by General Formula (22) (where $R^1$ represents the same as that defined above) according to a publicly-known method described in literatures such as Chemical and Pharmaceutical Bulletin (Chem. Pharm. Bull) (2001) Vol. 49, p. 353, Chemistry and Industry (Chemistry & Industry) (1978) p. 92 and Synthesis (Synthesis) (1985) p. 423, a compound represented by General Formula (23) (where $A^1$, $A^2$, $A^3$, G, X, Y, $R^1$, $R^3$, m and n represent the same as those defined above) can be obtained. Next, by alkylating the compound represented by General Formula (23) using a compound represented by General Formula (24) (where $R^a$ and $J^4$ represent the same as those defined above) according to a publicly-known method described in literatures such as Japanese Patent Application Publication (JP 02/229164), a compound represented by General Formula (7) (where $A^1$, $A^2$, $A^3$, G, X, Y, $R^3$, $R^a$, m and n represent the same as those defined above) can be synthesized.

Some of the compounds represented by General Formula (22) used here are publicly-known compounds and a part of them is commercially available. In addition, the others can be easily synthesized according to a general synthetic method of alcohols, mercaptans, amines, hydroxylamines and hydrazines described in literatures.

In addition, some of the compounds represented by General Formula (24) used here are publicly-known compounds and a part of them is commercially available. In addition, the others can be easily synthesized in substantially the same manner as in the synthesis of a compound represented by General Formula (12).

A compound represented by General Formula (9) used in Production Method D can be synthesized, for example as follows.

Reaction Formula 6

[Chemical Formula 18]

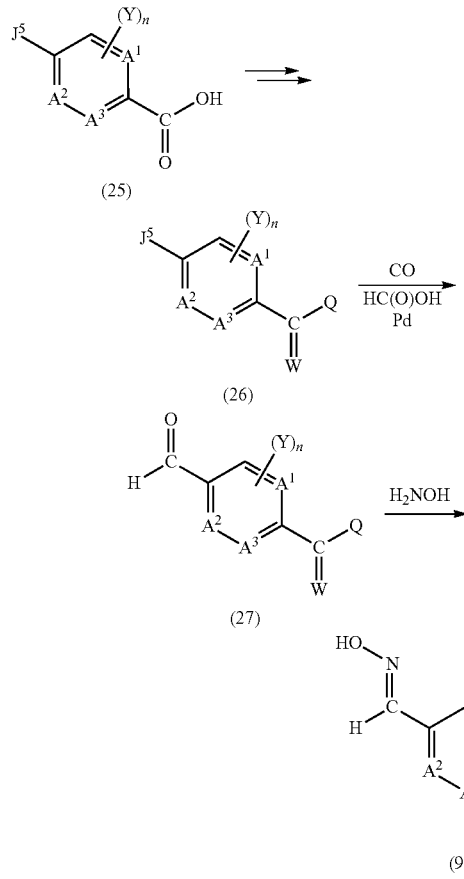

That is, by subjecting a compound represented by General Formula (26) (where $A^1$, $A^2$, $A^3$, W, Y, Q, n and $J^5$ represent the same as those defined above) capable of being synthesized from a compound represented by General Formula (25) (where $A^1$, $A^2$, $A^3$, Y and n represent the same as those defined above; and $J^5$ represents a bromine atom, an iodine atom, a halosulfonyloxy group (such as a fluorosulfonyloxy group), a $C_1$ to $C_4$ haloalkylsulfonyloxy group (such as a trifluoromethanesulfonyloxy group) or an arylsulfonyloxy group (such as a benzenesulfonyloxy group)) in substantially the same manner as in Production Method A, Production Method B, Production Method C, Production Method E and Production Method F, to a CO insertion reaction using a transition metal catalyst such as palladium in the coexistence of a hydride source such as formic acid according to a publicly-known method described in literatures such as Bulletin of the Chemical Society of Japan (Bull. Chem. Soc. Jpn.) (1994) Vol. 67, p. 2329 and Journal of the American Chemical Society (J. Am. Chem. Soc.) (1986) Vol. 108, p. 452, a compound represented by General Formula (27) (where $A^1$, $A^2$, $A^3$, W, Y, Q and n represent the same as those defined above) can be obtained.

By reacting the thus obtained compound represented by General Formula (27) with a hydroxylamine or salts thereof according to a publicly-known method described in literatures such as Journal of Medicinal Chemistry (J. Med. Chem.) (2001) Vol. 44, p. 2308, a compound represented by General Formula (9) (where $A^1$, $A^2$, $A^3$, W, Y, Q and n represent the same as those defined above) can be easily synthesized.

Some of the compounds represented by General Formula (25) used here are publicly-known compounds and a part of them is commercially available. In addition, the others can be easily synthesized according to a general synthetic method of substituted aromatic carboxylic acids described in literatures.

In each of these reactions, after the completion of the reaction, by subjecting the reaction product to a usual post-treatment, production intermediates that are raw material compounds for Production Method A to Production Method D can be obtained.

In addition, the production intermediates produced by the above methods can also be used as they are in a reaction of the next process without isolation/purification.

Specific examples of the compound encompassed in the present invention include the compounds shown in the following Table 2. However, the compounds in Table 2 are only for exemplification and these compounds should not be construed as limiting the scope of the present invention.

Here, an expression Et in Table 2 represents an ethyl group. In the same manner, n-Pr and Pr-n represent an n-propyl group; i-Pr and Pr-i represent an isopropyl group; c-Pr and Pr-c represent a cyclopropyl group; and Ph represents a phenyl group.

Aromatic heterocycles represented by D-1a to D-59a in the table represent the following structures:

[Chemical Formula 19]

D-1a:

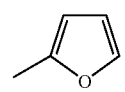

D-8b:

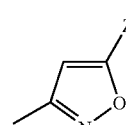

D-11a:

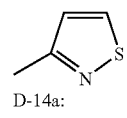

D-14a:

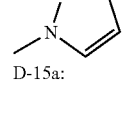

D-15a:

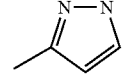

-continued
D-16b:
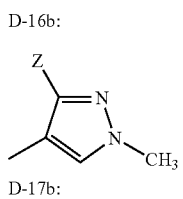
D-17b:
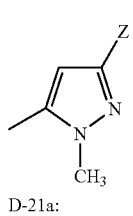
D-21a:
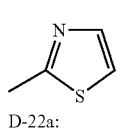
D-22a:
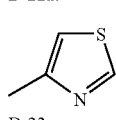
D-23a:
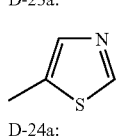
D-24a:
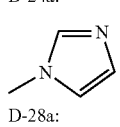
D-28a:
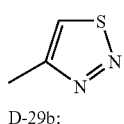
D-29b:
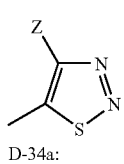
D-34a:
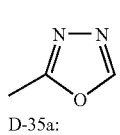
D-35a:
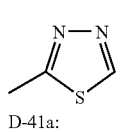
D-41a:
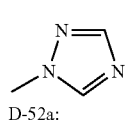
D-52a:
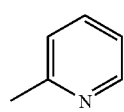
-continued
D-53a:
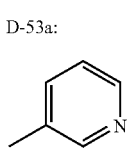
D-54a:
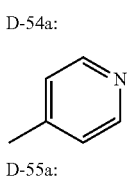
D-55a:
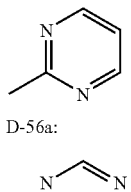
D-56a:
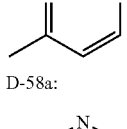
D-58a:
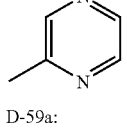
D-59a:
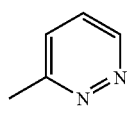
and for example, the expression ((D-17b)Cl) represents a 3-chloro-1-methylpyrazole-5-yl group.
In addition, aliphatic heterocycles represented by E-7a to E-12a in the table represent the following structures:
[Chemical Formula 20]
E-6a:
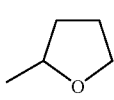
E-7a:
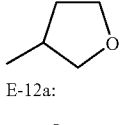
E-12a:
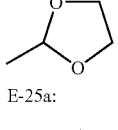
E-25a:
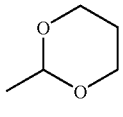

and further, T-3 in the table represents the following structure:

[Chemical Formula 21]

T-3:

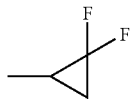

In the following Table 2, the number representing the substituted position of a substituent $(X)_m$ corresponds to the position indicated by the number attached to the following structural formula, and the expression "-" represents "non-substituted".

[Chemical Formula 22]

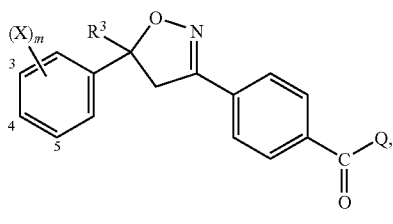

[1]-1

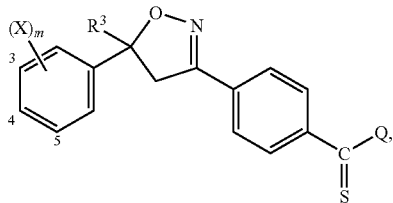

[1]-2

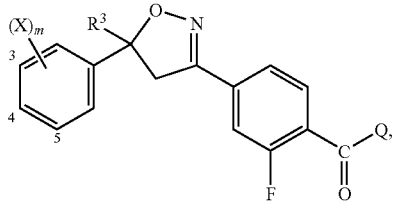

[1]-3

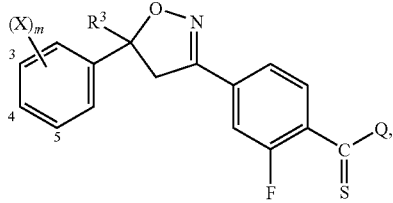

[1]-4

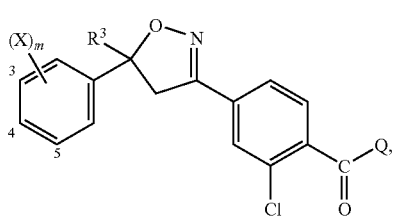

[1]-5

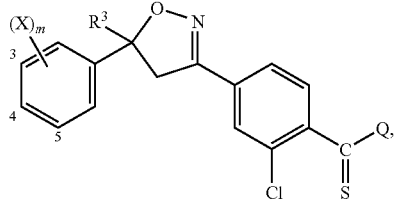

[1]-6

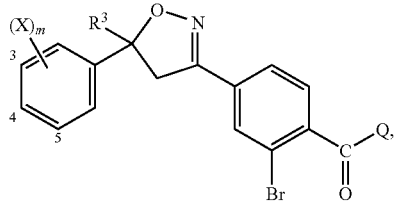

[1]-7

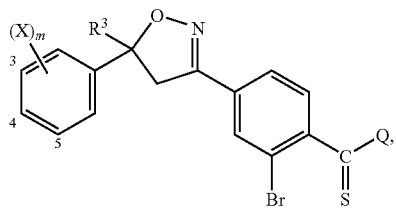

[1]-8

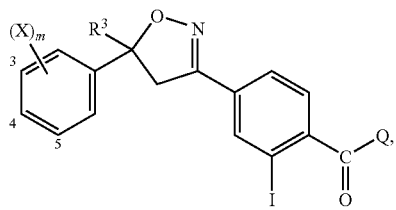

[1]-9

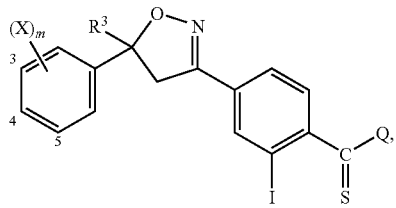

[1]-10

[Chemical Formula 23]

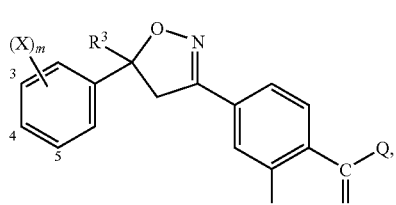

[1]-11

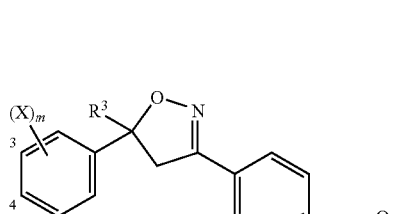

[1]-12

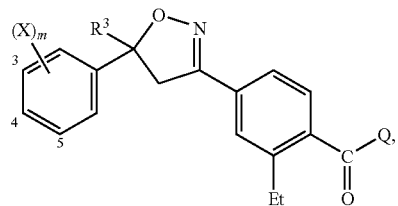 [1]-13
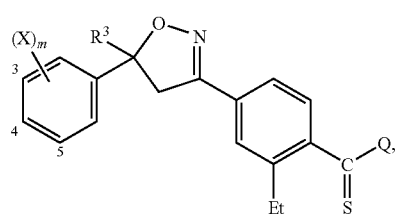 [1]-14
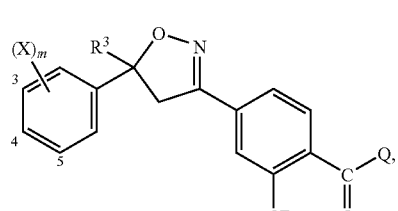 [1]-15
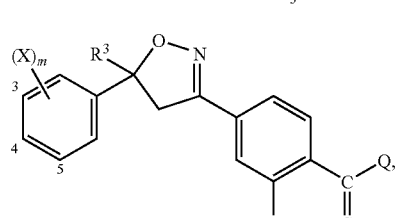 [1]-16
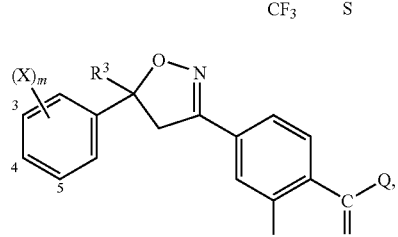 [1]-17
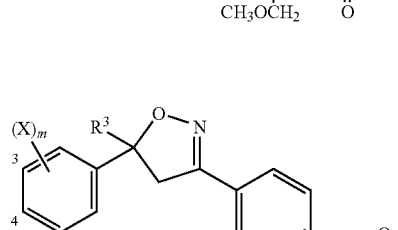 [1]-18
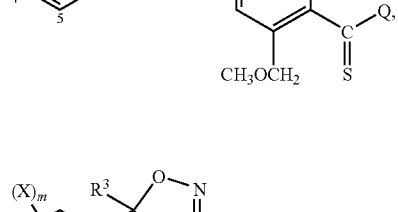 [1]-19
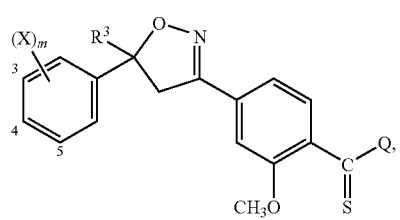 [1]-20
[Chemical Formula 24]
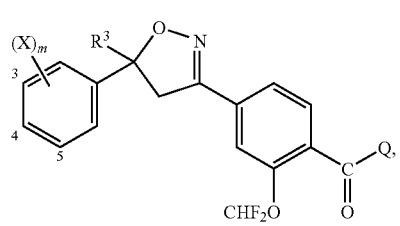 [1]-21
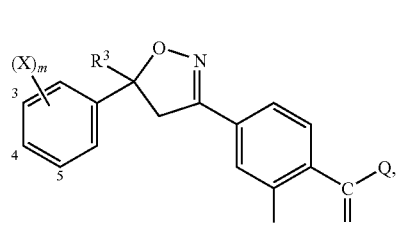 [1]-22
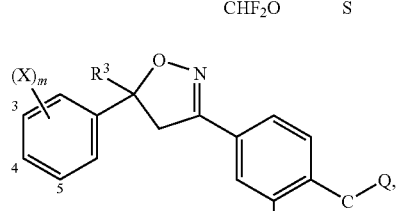 [1]-23
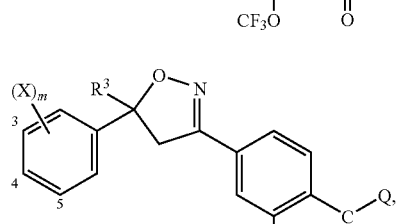 [1]-24
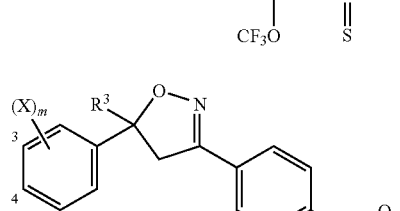 [1]-25
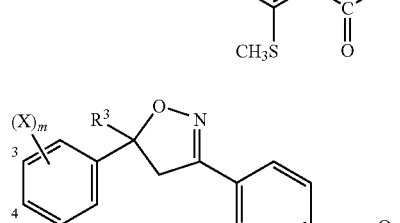 [1]-26

[1]-27 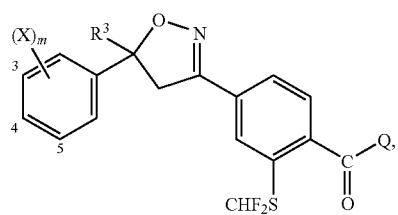
[1]-28 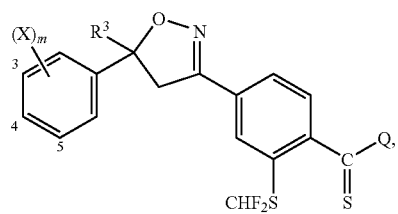
[1]-29 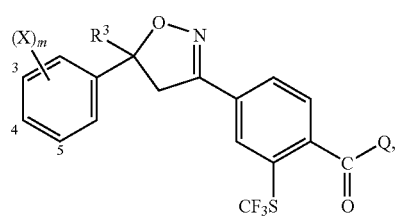
[1]-30 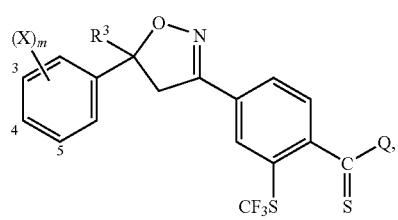
[Chemical Formula 25]
[1]-31 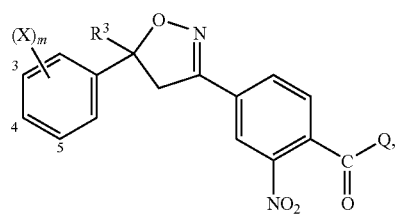
[1]-32 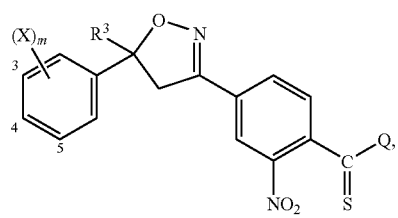
[1]-33 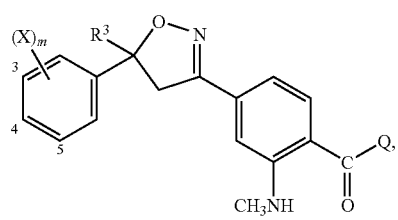
[1]-34 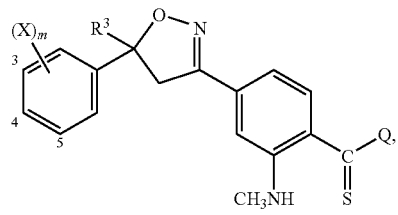
[1]-35 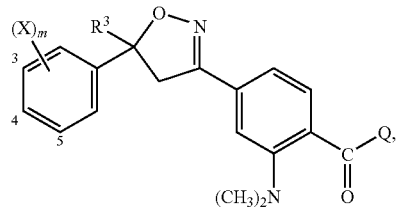
[1]-36 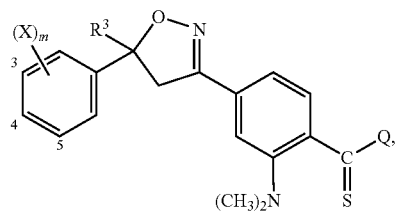
[1]-37 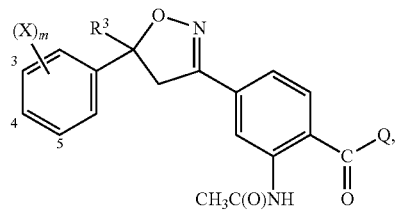
[1]-38 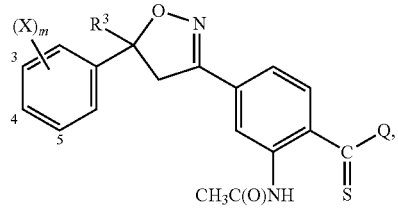
[1]-39 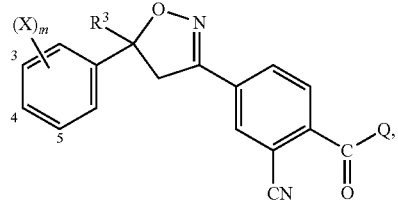
[1]-40 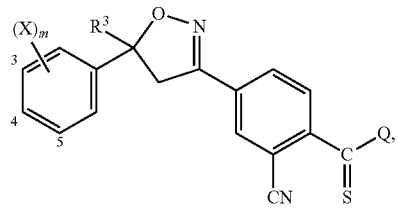

[Chemical Formula 26]
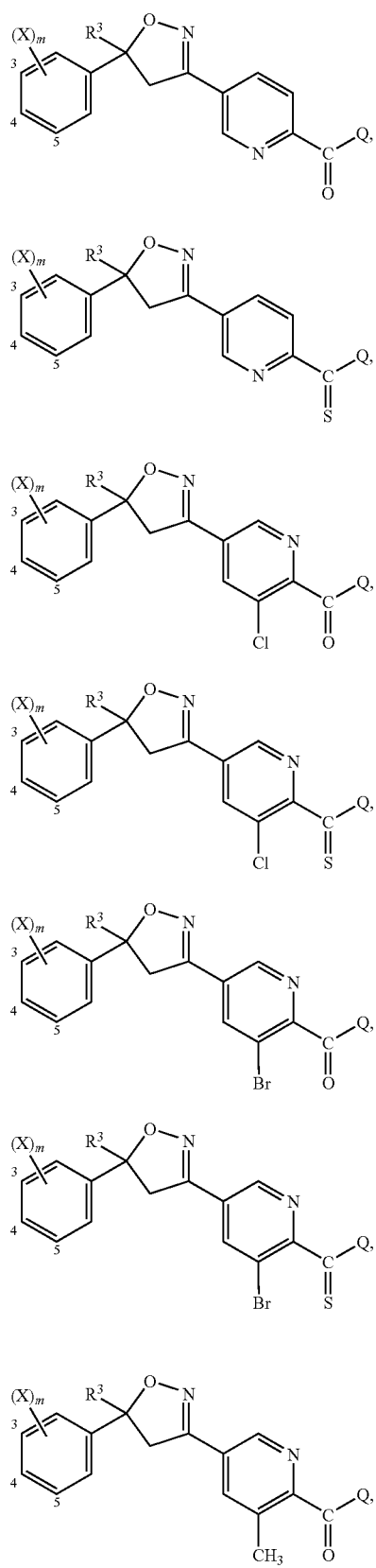
[1]-41
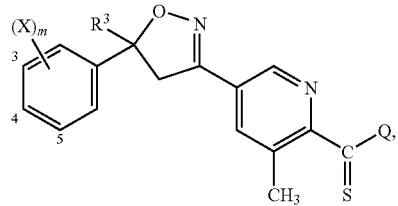
[1]-48
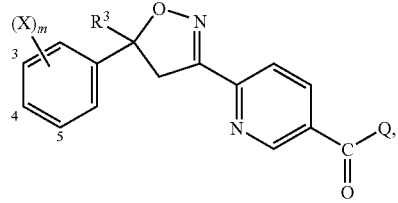
[1]-49
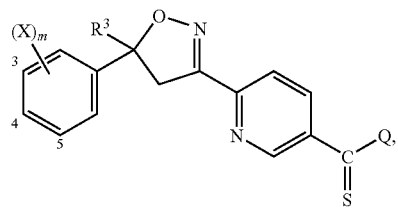
[1]-50
[Chemical Formula 27]
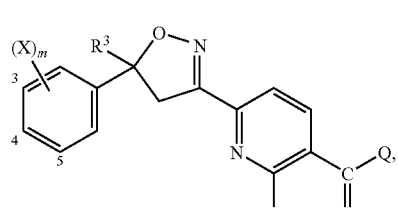
[1]-51
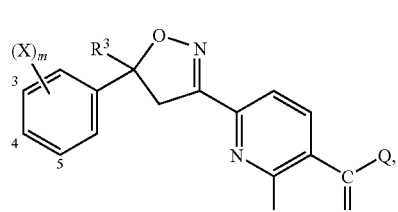
[1]-52
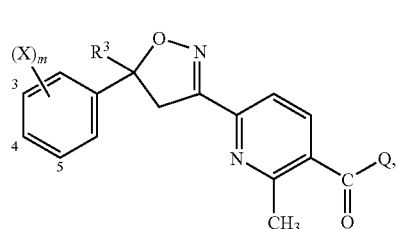
[1]-53
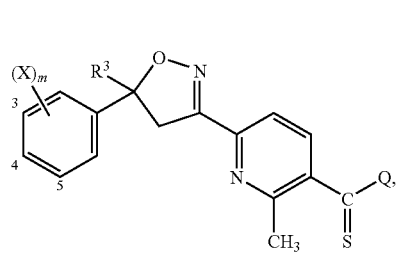
[1]-54

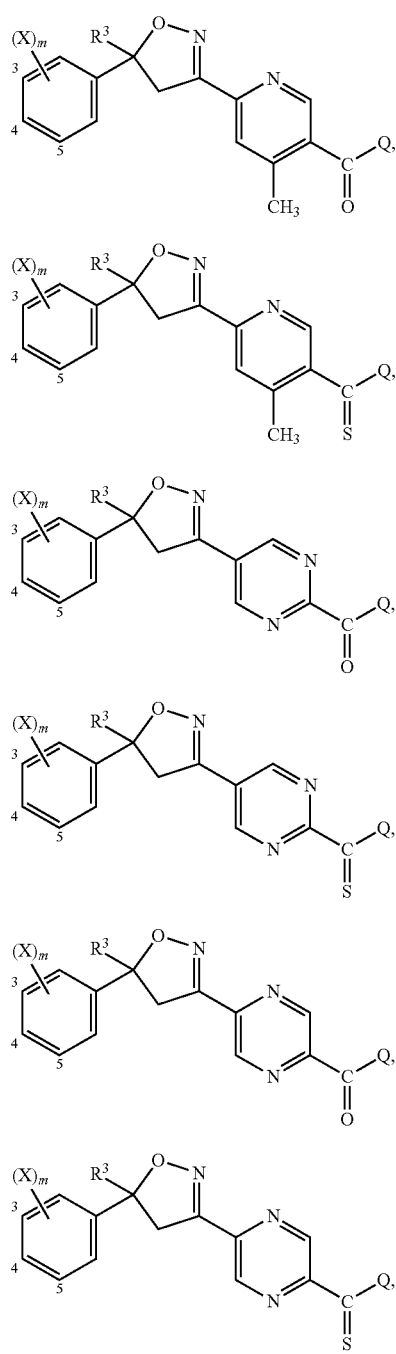

[1]-55

[1]-56

[1]-57

[1]-58

[1]-59

[1]-60

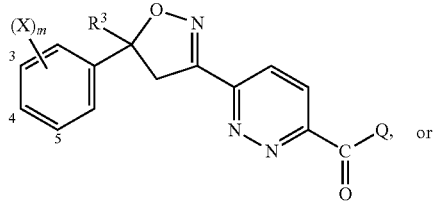

[1]-61

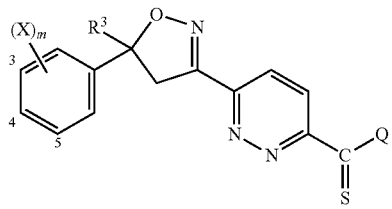

[1]-62

Here, the substituent represented by Q in General Formulae [1]-1 to [1]-62 individually represents a structure represented by the following Q-1 to Q-3:

[Chemical Formula 29]

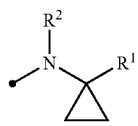

Q-1

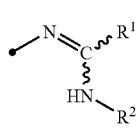

Q-2

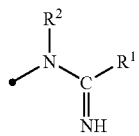

Q-3

TABLE 2

| (X)$_m$ | R$^3$ | Q   | R$^2$    | R$^1$           |
|---------|-------|-----|----------|-----------------|
| 3-F     | CF$_3$ | Q-2 | H        | OCH$_3$         |
| 3-F     | CF$_3$ | Q-2 | H        | OEt             |
| 3-F     | CF$_3$ | Q-2 | CH$_3$   | OCH$_3$         |
| 3-Cl    | CF$_3$ | Q-1 | H        | C(O)NHCH$_2$CF$_3$ |
| 3-Cl    | CF$_3$ | Q-1 | H        | D-52a           |
| 3-Cl    | CF$_3$ | Q-2 | H        | OCH$_3$         |
| 3-Cl    | CF$_3$ | Q-2 | H        | OEt             |
| 3-Cl    | CF$_3$ | Q-2 | CH$_3$   | OCH$_3$         |
| 3-Cl    | CF$_3$ | Q-2 | CH$_3$   | OEt             |
| 3-Cl    | CF$_3$ | Q-2 | Et       | OCH$_3$         |
| 3-Cl    | CF$_3$ | Q-2 | CH$_2$CF$_3$ | OCH$_3$     |

TABLE 2-continued

| (X)$_m$ | R$^3$ | Q | R$^2$ | R$^1$ |
|---|---|---|---|---|
| 3-Br | CF$_3$ | Q-1 | H | C(O)NHCH$_2$CF$_3$ |
| 3-Br | CF$_3$ | Q-1 | H | D-22a |
| 3-Br | CF$_3$ | Q-1 | H | D-52a |
| 3-Br | CF$_3$ | Q-2 | H | OCH$_3$ |
| 3-Br | CF$_3$ | Q-2 | H | OEt |
| 3-Br | CF$_3$ | Q-2 | CH$_3$ | OCH$_3$ |
| 3-Br | CF$_3$ | Q-2 | CH$_3$ | OEt |
| 3-Br | CF$_3$ | Q-2 | Et | OCH$_3$ |
| 3-Br | CF$_3$ | Q-2 | Et | OEt |
| 3-Br | CF$_3$ | Q-2 | CH$_2$CF$_3$ | OCH$_3$ |
| 3-Br | CF$_3$ | Q-2 | CH$_2$C≡CH | OCH$_3$ |
| 3-Br | CF$_2$Cl | Q-2 | H | OCH$_3$ |
| 3-Br | CF$_2$Cl | Q-2 | H | OEt |
| 3-Br | CF$_2$Cl | Q-2 | CH$_3$ | OCH$_3$ |
| 3-I | CF$_3$ | Q-1 | H | CF$_3$ |
| 3-I | CF$_3$ | Q-1 | H | C(O)NHCH$_2$CF$_3$ |
| 3-I | CF$_3$ | Q-1 | H | D-22a |
| 3-I | CF$_3$ | Q-1 | H | D-52a |
| 3-I | CF$_3$ | Q-2 | H | OCH$_3$ |
| 3-I | CF$_3$ | Q-2 | H | OEt |
| 3-I | CF$_3$ | Q-2 | H | OCH$_2$CF$_3$ |
| 3-I | CF$_3$ | Q-2 | H | OCH$_2$C≡CH |
| 3-I | CF$_3$ | Q-2 | CH$_3$ | OCH$_3$ |
| 3-I | CF$_3$ | Q-2 | CH$_3$ | OEt |
| 3-I | CF$_3$ | Q-2 | Et | OCH$_3$ |
| 3-I | CF$_3$ | Q-2 | Et | OEt |
| 3-I | CF$_3$ | Q-2 | n-Pr | OCH$_3$ |
| 3-I | CF$_3$ | Q-2 | i-Pr | OCH$_3$ |
| 3-I | CF$_3$ | Q-2 | CH$_2$CF$_3$ | OCH$_3$ |
| 3-I | CF$_3$ | Q-2 | CH$_2$C≡CH | OCH$_3$ |
| 3-I | CF$_2$Cl | Q-1 | H | C(O)NHCH$_2$CF$_3$ |
| 3-I | CF$_2$Cl | Q-1 | H | D-52a |
| 3-I | CF$_2$Cl | Q-2 | H | OCH$_3$ |
| 3-I | CF$_2$Cl | Q-2 | H | OEt |
| 3-I | CF$_2$Cl | Q-2 | CH$_3$ | OCH$_3$ |
| 3-I | CF$_2$Cl | Q-2 | CH$_3$ | OEt |
| 3-I | CF$_2$Cl | Q-2 | Et | OCH$_3$ |
| 3-I | CF$_2$Cl | Q-2 | CH$_2$CF$_3$ | OCH$_3$ |
| 3-CF$_3$ | CF$_3$ | Q-1 | H | CF$_3$ |
| 3-CF$_3$ | CF$_3$ | Q-1 | H | C(O)NHCH$_2$CF$_3$ |
| 3-CF$_3$ | CF$_3$ | Q-1 | H | D-22a |
| 3-CF$_3$ | CF$_3$ | Q-1 | H | D-52a |
| 3-CF$_3$ | CF$_3$ | Q-2 | H | OCH$_3$ |
| 3-CF$_3$ | CF$_3$ | Q-2 | H | OEt |
| 3-CF$_3$ | CF$_3$ | Q-2 | H | OCH$_2$CF$_3$ |
| 3-CF$_3$ | CF$_3$ | Q-2 | H | OCH$_2$C≡CH |
| 3-CF$_3$ | CF$_3$ | Q-2 | CH$_3$ | OCH$_3$ |
| 3-CF$_3$ | CF$_3$ | Q-2 | CH$_3$ | OEt |
| 3-CF$_3$ | CF$_3$ | Q-2 | Et | OCH$_3$ |
| 3-CF$_3$ | CF$_3$ | Q-2 | Et | OEt |
| 3-CF$_3$ | CF$_3$ | Q-2 | n-Pr | OCH$_3$ |
| 3-CF$_3$ | CF$_3$ | Q-2 | i-Pr | OCH$_3$ |
| 3-CF$_3$ | CF$_3$ | Q-2 | CH$_2$CF$_3$ | OCH$_3$ |
| 3-CF$_3$ | CF$_3$ | Q-2 | CH$_2$C≡CH | OCH$_3$ |
| 3-CF$_3$ | CF$_2$Cl | Q-1 | H | C(O)NHCH$_2$CF$_3$ |
| 3-CF$_3$ | CF$_2$Cl | Q-1 | H | D-52a |
| 3-CF$_3$ | CF$_2$Cl | Q-2 | H | OCH$_3$ |
| 3-CF$_3$ | CF$_2$Cl | Q-2 | H | OEt |
| 3-CF$_3$ | CF$_2$Cl | Q-2 | CH$_3$ | OCH$_3$ |
| 3-CF$_3$ | CF$_2$Cl | Q-2 | CH$_3$ | OEt |
| 3-CF$_3$ | CF$_2$Cl | Q-2 | Et | OCH$_3$ |
| 3-CF$_3$ | CF$_2$Cl | Q-2 | CH$_2$CF$_3$ | OCH$_3$ |
| 3-CF$_2$CF$_3$ | CF$_3$ | Q-1 | H | C(O)NHCH$_2$CF$_3$ |
| 3-CF$_2$CF$_3$ | CF$_3$ | Q-1 | H | D-22a |
| 3-CF$_2$CF$_3$ | CF$_3$ | Q-1 | H | D-52a |
| 3-CF$_2$CF$_3$ | CF$_3$ | Q-2 | H | OCH$_3$ |
| 3-CF$_2$CF$_3$ | CF$_3$ | Q-2 | H | OEt |
| 3-CF$_2$CF$_3$ | CF$_3$ | Q-2 | CH$_3$ | OCH$_3$ |
| 3-CF$_2$CF$_3$ | CF$_3$ | Q-2 | CH$_3$ | OEt |
| 3-CF$_2$CF$_3$ | CF$_3$ | Q-2 | Et | OCH$_3$ |
| 3-CF$_2$CF$_3$ | CF$_3$ | Q-2 | Et | OEt |
| 3-CF$_2$CF$_3$ | CF$_3$ | Q-2 | CH$_2$CF$_3$ | OCH$_3$ |
| 3-CF$_2$CF$_3$ | CF$_3$ | Q-2 | CH$_2$C≡CH | OCH$_3$ |
| 3-CF$_2$CF$_3$ | CF$_2$Cl | Q-2 | H | OCH$_3$ |
| 3-CF$_2$CF$_3$ | CF$_2$Cl | Q-2 | H | OEt |
| 3-CF$_2$CF$_3$ | CF$_2$Cl | Q-2 | CH$_3$ | OCH$_3$ |
| 3-CF$_2$CF$_2$CF$_3$ | CF$_3$ | Q-1 | H | C(O)NHCH$_2$CF$_3$ |
| 3-CF$_2$CF$_2$CF$_3$ | CF$_3$ | Q-1 | H | D-52a |

TABLE 2-continued

| (X)$_m$ | R$^3$ | Q | R$^2$ | R$^1$ |
|---|---|---|---|---|
| 3-CF$_2$CF$_2$CF$_3$ | CF$_3$ | Q-2 | H | OCH$_3$ |
| 3-CF$_2$CF$_2$CF$_3$ | CF$_3$ | Q-2 | H | OEt |
| 3-CF$_2$CF$_2$CF$_3$ | CF$_3$ | Q-2 | CH$_3$ | OCH$_3$ |
| 3-CF$_2$CF$_2$CF$_3$ | CF$_3$ | Q-2 | CH$_3$ | OEt |
| 3-CF$_2$CF$_2$CF$_3$ | CF$_3$ | Q-2 | Et | OCH$_3$ |
| 3-CF$_2$CF$_2$CF$_3$ | CF$_3$ | Q-2 | CH$_2$CF$_3$ | OCH$_3$ |
| 3-CF(CF$_3$)$_2$ | CF$_3$ | Q-1 | H | C(O)NHCH$_2$CF$_3$ |
| 3-CF(CF$_3$)$_2$ | CF$_3$ | Q-1 | H | D-52a |
| 3-CF(CF$_3$)$_2$ | CF$_3$ | Q-2 | H | OCH$_3$ |
| 3-CF(CF$_3$)$_2$ | CF$_3$ | Q-2 | H | OEt |
| 3-CF(CF$_3$)$_2$ | CF$_3$ | Q-2 | CH$_3$ | OCH$_3$ |
| 3-CF(CF$_3$)$_2$ | CF$_3$ | Q-2 | CH$_3$ | OEt |
| 3-CF(CF$_3$)$_2$ | CF$_3$ | Q-2 | Et | OCH$_3$ |
| 3-CF(CF$_3$)$_2$ | CF$_3$ | Q-2 | CH$_2$CF$_3$ | OCH$_3$ |
| 3-CF$_2$CF$_2$CF$_2$CF$_3$ | CF$_3$ | Q-2 | H | OCH$_3$ |
| 3-CF$_2$CF$_2$CF$_2$CF$_3$ | CF$_3$ | Q-2 | H | OEt |
| 3-CF$_2$CF$_2$CF$_2$CF$_3$ | CF$_3$ | Q-2 | CH$_3$ | OCH$_3$ |
| 3-C(CF$_3$)$_2$OH | CF$_3$ | Q-2 | H | OCH$_3$ |
| 3-C(CF$_3$)$_2$OH | CF$_3$ | Q-2 | H | OEt |
| 3-C(CF$_3$)$_2$OH | CF$_3$ | Q-2 | CH$_3$ | OCH$_3$ |
| 3-C(CF$_3$)$_2$OCH$_3$ | CF$_3$ | Q-2 | H | OCH$_3$ |
| 3-C(CF$_3$)$_2$OCH$_3$ | CF$_3$ | Q-2 | H | OEt |
| 3-C(CF$_3$)$_2$OCH$_3$ | CF$_3$ | Q-2 | CH$_3$ | OCH$_3$ |
| 3-OCF$_3$ | CF$_3$ | Q-1 | H | C(O)NHCH$_2$CF$_3$ |
| 3-OCF$_3$ | CF$_3$ | Q-1 | H | D-22a |
| 3-OCF$_3$ | CF$_3$ | Q-1 | H | D-52a |
| 3-OCF$_3$ | CF$_3$ | Q-2 | H | OCH$_3$ |
| 3-OCF$_3$ | CF$_3$ | Q-2 | H | OEt |
| 3-OCF$_3$ | CF$_3$ | Q-2 | CH$_3$ | OCH$_3$ |
| 3-OCF$_3$ | CF$_3$ | Q-2 | CH$_3$ | OEt |
| 3-OCF$_3$ | CF$_3$ | Q-2 | Et | OCH$_3$ |
| 3-OCF$_3$ | CF$_3$ | Q-2 | Et | OEt |
| 3-OCF$_3$ | CF$_3$ | Q-2 | CH$_2$CF$_3$ | OCH$_3$ |
| 3-OCF$_3$ | CF$_3$ | Q-2 | CH$_2$C≡CH | OCH$_3$ |
| 3-OCF$_3$ | CF$_2$Cl | Q-2 | H | OCH$_3$ |
| 3-OCF$_3$ | CF$_2$Cl | Q-2 | H | OEt |
| 3-OCF$_3$ | CF$_2$Cl | Q-2 | CH$_3$ | OCH$_3$ |
| 3-OCF$_2$Br | CF$_3$ | Q-1 | H | C(O)NHCH$_2$CF$_3$ |
| 3-OCF$_2$Br | CF$_3$ | Q-1 | H | D-52a |
| 3-OCF$_2$Br | CF$_3$ | Q-2 | H | OCH$_3$ |
| 3-OCF$_2$Br | CF$_3$ | Q-2 | H | OEt |
| 3-OCF$_2$Br | CF$_3$ | Q-2 | CH$_3$ | OCH$_3$ |
| 3-OCF$_2$Br | CF$_3$ | Q-2 | CH$_3$ | OEt |
| 3-OCF$_2$Br | CF$_3$ | Q-2 | Et | OCH$_3$ |
| 3-OCF$_2$Br | CF$_3$ | Q-2 | CH$_2$CF$_3$ | OCH$_3$ |
| 3-OCF$_2$CHF$_2$ | CF$_3$ | Q-2 | H | OCH$_3$ |
| 3-OCF$_2$CHF$_2$ | CF$_3$ | Q-2 | H | OEt |
| 3-OCF$_2$CHF$_2$ | CF$_3$ | Q-2 | CH$_3$ | OCH$_3$ |
| 3-OCF$_2$CHFCl | CF$_3$ | Q-2 | H | OCH$_3$ |
| 3-OCF$_2$CHFCl | CF$_3$ | Q-2 | H | OEt |
| 3-OCF$_2$CHFCl | CF$_3$ | Q-2 | CH$_3$ | OCH$_3$ |
| 3-OCF$_2$CHFCF$_3$ | CF$_3$ | Q-2 | H | OCH$_3$ |
| 3-OCF$_2$CHFCF$_3$ | CF$_3$ | Q-2 | H | OEt |
| 3-OCF$_2$CHFCF$_3$ | CF$_3$ | Q-2 | CH$_3$ | OCH$_3$ |
| 3-OCF$_2$CHFOCF$_3$ | CF$_3$ | Q-2 | H | OCH$_3$ |
| 3-OCF$_2$CHFOCF$_3$ | CF$_3$ | Q-2 | H | OEt |
| 3-OCF$_2$CHFOCF$_3$ | CF$_3$ | Q-2 | CH$_3$ | OCH$_3$ |
| 3-SCF$_3$ | CF$_3$ | Q-1 | H | C(O)NHCH$_2$CF$_3$ |
| 3-SCF$_3$ | CF$_3$ | Q-1 | H | D-22a |
| 3-SCF$_3$ | CF$_3$ | Q-1 | H | D-52a |
| 3-SCF$_3$ | CF$_3$ | Q-2 | H | OCH$_3$ |
| 3-SCF$_3$ | CF$_3$ | Q-2 | H | OEt |
| 3-SCF$_3$ | CF$_3$ | Q-2 | CH$_3$ | OCH$_3$ |
| 3-SCF$_3$ | CF$_3$ | Q-2 | CH$_3$ | OEt |
| 3-SCF$_3$ | CF$_3$ | Q-2 | Et | OCH$_3$ |
| 3-SCF$_3$ | CF$_3$ | Q-2 | Et | OEt |
| 3-SCF$_3$ | CF$_3$ | Q-2 | CH$_2$CF$_3$ | OCH$_3$ |
| 3-SCF$_3$ | CF$_3$ | Q-2 | CH$_2$C≡CH | OCH$_3$ |
| 3-SCF$_3$ | CF$_2$Cl | Q-2 | H | OCH$_3$ |
| 3-SCF$_3$ | CF$_2$Cl | Q-2 | H | OEt |
| 3-SCF$_3$ | CF$_2$Cl | Q-2 | CH$_3$ | OCH$_3$ |
| 3-SCF$_2$Cl | CF$_3$ | Q-1 | H | C(O)NHCH$_2$CF$_3$ |
| 3-SCF$_2$Cl | CF$_3$ | Q-1 | H | D-52a |
| 3-SCF$_2$Cl | CF$_3$ | Q-2 | H | OCH$_3$ |
| 3-SCF$_2$Cl | CF$_3$ | Q-2 | H | OEt |
| 3-SCF$_2$Cl | CF$_3$ | Q-2 | CH$_3$ | OCH$_3$ |
| 3-SCF$_2$Cl | CF$_3$ | Q-2 | CH$_3$ | OEt |
| 3-SCF$_2$Cl | CF$_3$ | Q-2 | Et | OCH$_3$ |

TABLE 2-continued

| (X)$_m$ | R$^3$ | Q | R$^2$ | R$^1$ |
|---|---|---|---|---|
| 3-SCF$_2$Cl | CF$_3$ | Q-2 | CH$_2$CF$_3$ | OCH$_3$ |
| 3-SCF$_2$Br | CF$_3$ | Q-1 | H | C(O)NHCH$_2$CF$_3$ |
| 3-SCF$_2$Br | CF$_3$ | Q-1 | H | D-52a |
| 3-SCF$_2$Br | CF$_3$ | Q-2 | H | OCH$_3$ |
| 3-SCF$_2$Br | CF$_3$ | Q-2 | H | OEt |
| 3-SCF$_2$Br | CF$_3$ | Q-2 | CH$_3$ | OCH$_3$ |
| 3-SCF$_2$Br | CF$_3$ | Q-2 | CH$_3$ | OEt |
| 3-SCF$_2$Br | CF$_3$ | Q-2 | Et | OCH$_3$ |
| 3-SCF$_2$Br | CF$_3$ | Q-2 | CH$_2$CF$_3$ | OCH$_3$ |
| 3-SF$_5$ | CF$_3$ | Q-1 | H | C(O)NHCH$_2$CF$_3$ |
| 3-SF$_5$ | CF$_3$ | Q-1 | H | D-22a |
| 3-SF$_5$ | CF$_3$ | Q-1 | H | D-52a |
| 3-SF$_5$ | CF$_3$ | Q-2 | H | OCH$_3$ |
| 3-SF$_5$ | CF$_3$ | Q-2 | H | OEt |
| 3-SF$_5$ | CF$_3$ | Q-2 | CH$_3$ | OCH$_3$ |
| 3-SF$_5$ | CF$_3$ | Q-2 | CH$_3$ | OEt |
| 3-SF$_5$ | CF$_3$ | Q-2 | Et | OCH$_3$ |
| 3-SF$_5$ | CF$_3$ | Q-2 | Et | OEt |
| 3-SF$_5$ | CF$_3$ | Q-2 | CH$_2$CF$_3$ | OCH$_3$ |
| 3-SF$_5$ | CF$_3$ | Q-2 | CH$_2$C≡CH | OCH$_3$ |
| 3-SF$_5$ | CF$_2$Cl | Q-2 | H | OCH$_3$ |
| 3-SF$_5$ | CF$_2$Cl | Q-2 | H | OEt |
| 3-SF$_5$ | CF$_2$Cl | Q-2 | CH$_3$ | OCH$_3$ |
| 3,4-F$_2$ | CF$_3$ | Q-2 | H | OCH$_3$ |
| 3,4-F$_2$ | CF$_3$ | Q-2 | H | OEt |
| 3,4-F$_2$ | CF$_3$ | Q-2 | CH$_3$ | OCH$_3$ |
| 3,5-F$_2$ | CF$_3$ | Q-2 | H | OCH$_3$ |
| 3,5-F$_2$ | CF$_3$ | Q-2 | H | OEt |
| 3,5-F$_2$ | CF$_3$ | Q-2 | CH$_3$ | OCH$_3$ |
| 3-Cl-4-F | CF$_3$ | Q-1 | H | CF$_3$ |
| 3-Cl-4-F | CF$_3$ | Q-1 | H | C(O)NHCH$_2$CF$_3$ |
| 3-Cl-4-F | CF$_3$ | Q-1 | H | D-22a |
| 3-Cl-4-F | CF$_3$ | Q-1 | H | D-52a |
| 3-Cl-4-F | CF$_3$ | Q-2 | H | OCH$_3$ |
| 3-Cl-4-F | CF$_3$ | Q-2 | H | OEt |
| 3-Cl-4-F | CF$_3$ | Q-2 | H | OCH$_2$CF$_3$ |
| 3-Cl-4-F | CF$_3$ | Q-2 | H | OCH$_2$C≡CH |
| 3-Cl-4-F | CF$_3$ | Q-2 | CH$_3$ | OCH$_3$ |
| 3-Cl-4-F | CF$_3$ | Q-2 | CH$_3$ | OEt |
| 3-Cl-4-F | CF$_3$ | Q-2 | Et | OCH$_3$ |
| 3-Cl-4-F | CF$_3$ | Q-2 | Et | OEt |
| 3-Cl-4-F | CF$_3$ | Q-2 | n-Pr | OCH$_3$ |
| 3-Cl-4-F | CF$_3$ | Q-2 | i-Pr | OCH$_3$ |
| 3-Cl-4-F | CF$_3$ | Q-2 | CH$_2$CF$_3$ | OCH$_3$ |
| 3-Cl-4-F | CF$_3$ | Q-2 | CH$_2$C≡CH | OCH$_3$ |
| 3-Cl-4-F | CF$_2$Cl | Q-1 | H | C(O)NHCH$_2$CF$_3$ |
| 3-Cl-4-F | CF$_2$Cl | Q-1 | H | D-52a |
| 3-Cl-4-F | CF$_2$Cl | Q-2 | H | OCH$_3$ |
| 3-Cl-4-F | CF$_2$Cl | Q-2 | H | OEt |
| 3-Cl-4-F | CF$_2$Cl | Q-2 | CH$_3$ | OCH$_3$ |
| 3-Cl-4-F | CF$_2$Cl | Q-2 | CH$_3$ | OEt |
| 3-Cl-4-F | CF$_2$Cl | Q-2 | Et | OCH$_3$ |
| 3-Cl-4-F | CF$_2$Cl | Q-2 | CH$_2$CF$_3$ | OCH$_3$ |
| 3-F-5-Cl | CF$_3$ | Q-1 | H | CF$_3$ |
| 3-F-5-Cl | CF$_3$ | Q-1 | H | C(O)NHCH$_2$CF$_3$ |
| 3-F-5-Cl | CF$_3$ | Q-1 | H | D-22a |
| 3-F-5-Cl | CF$_3$ | Q-1 | H | D-52a |
| 3-F-5-Cl | CF$_3$ | Q-2 | H | OCH$_3$ |
| 3-F-5-Cl | CF$_3$ | Q-2 | H | OEt |
| 3-F-5-Cl | CF$_3$ | Q-2 | H | OCH$_2$CF$_3$ |
| 3-F-5-Cl | CF$_3$ | Q-2 | H | OCH$_2$C≡CH |
| 3-F-5-Cl | CF$_3$ | Q-2 | CH$_3$ | OCH$_3$ |
| 3-F-5-Cl | CF$_3$ | Q-2 | CH$_3$ | OEt |
| 3-F-5-Cl | CF$_3$ | Q-2 | Et | OCH$_3$ |
| 3-F-5-Cl | CF$_3$ | Q-2 | Et | OEt |
| 3-F-5-Cl | CF$_3$ | Q-2 | n-Pr | OCH$_3$ |
| 3-F-5-Cl | CF$_3$ | Q-2 | i-Pr | OCH$_3$ |
| 3-F-5-Cl | CF$_3$ | Q-2 | CH$_2$CF$_3$ | OCH$_3$ |
| 3-F-5-Cl | CF$_3$ | Q-2 | CH$_2$C≡CH | OCH$_3$ |
| 3-F-5-Cl | CF$_2$Cl | Q-1 | H | C(O)NHCH$_2$CF$_3$ |
| 3-F-5-Cl | CF$_2$Cl | Q-1 | H | D-52a |
| 3-F-5-Cl | CF$_2$Cl | Q-2 | H | OCH$_3$ |
| 3-F-5-Cl | CF$_2$Cl | Q-2 | H | OEt |
| 3-F-5-Cl | CF$_2$Cl | Q-2 | CH$_3$ | OCH$_3$ |
| 3-F-5-Cl | CF$_2$Cl | Q-2 | CH$_3$ | OEt |
| 3-F-5-Cl | CF$_2$Cl | Q-2 | Et | OCH$_3$ |
| 3-F-5-Cl | CF$_2$Cl | Q-2 | CH$_2$CF$_3$ | OCH$_3$ |
| 3,4-Cl$_2$ | CF$_3$ | Q-1 | H | CF$_3$ |

TABLE 2-continued

| (X)$_m$ | R$^3$ | Q | R$^2$ | R$^1$ |
|---|---|---|---|---|
| 3,4-Cl$_2$ | CF$_3$ | Q-1 | H | C(O)NHCH$_2$CF$_3$ |
| 3,4-Cl$_2$ | CF$_3$ | Q-1 | H | D-22a |
| 3,4-Cl$_2$ | CF$_3$ | Q-1 | H | D-52a |
| 3,4-Cl$_2$ | CF$_3$ | Q-2 | H | OCH$_3$ |
| 3,4-Cl$_2$ | CF$_3$ | Q-2 | H | OEt |
| 3,4-Cl$_2$ | CF$_3$ | Q-2 | H | OCH$_2$CF$_3$ |
| 3,4-Cl$_2$ | CF$_3$ | Q-2 | H | OCH$_2$C≡CH |
| 3,4-Cl$_2$ | CF$_3$ | Q-2 | CH$_3$ | OCH$_3$ |
| 3,4-Cl$_2$ | CF$_3$ | Q-2 | CH$_3$ | OEt |
| 3,4-Cl$_2$ | CF$_3$ | Q-2 | Et | OCH$_3$ |
| 3,4-Cl$_2$ | CF$_3$ | Q-2 | Et | OEt |
| 3,4-Cl$_2$ | CF$_3$ | Q-2 | n-Pr | OCH$_3$ |
| 3,4-Cl$_2$ | CF$_3$ | Q-2 | i-Pr | OCH$_3$ |
| 3,4-Cl$_2$ | CF$_3$ | Q-2 | CH$_2$CF$_3$ | OCH$_3$ |
| 3,4-Cl$_2$ | CF$_3$ | Q-2 | CH$_2$C≡CH | OCH$_3$ |
| 3,4-Cl$_2$ | CF$_2$Cl | Q-1 | H | C(O)NHCH$_2$CF$_3$ |
| 3,4-Cl$_2$ | CF$_2$Cl | Q-1 | H | D-52a |
| 3,4-Cl$_2$ | CF$_2$Cl | Q-2 | H | OCH$_3$ |
| 3,4-Cl$_2$ | CF$_2$Cl | Q-2 | H | OEt |
| 3,4-Cl$_2$ | CF$_2$Cl | Q-2 | CH$_3$ | OCH$_3$ |
| 3,4-Cl$_2$ | CF$_2$Cl | Q-2 | CH$_3$ | OEt |
| 3,4-Cl$_2$ | CF$_2$Cl | Q-2 | Et | OCH$_3$ |
| 3,4-Cl$_2$ | CF$_2$Cl | Q-2 | CH$_2$CF$_3$ | OCH$_3$ |
| 3,5-Cl$_2$ | CHF$_2$ | Q-2 | H | OCH$_3$ |
| 3,5-Cl$_2$ | CHF$_2$ | Q-2 | H | OEt |
| 3,5-Cl$_2$ | CHF$_2$ | Q-2 | CH$_3$ | OCH$_3$ |
| 3,5-Cl$_2$ | CF$_3$ | Q-1 | H | c-Pr |
| 3,5-Cl$_2$ | CF$_3$ | Q-1 | H | CF$_3$ |
| 3,5-Cl$_2$ | CF$_3$ | Q-1 | H | C(O)NHCH$_2$CH$_2$Cl |
| 3,5-Cl$_2$ | CF$_3$ | Q-1 | H | C(O)NHCH$_2$CF$_3$ |
| 3,5-Cl$_2$ | CF$_3$ | Q-1 | H | D-22a |
| 3,5-Cl$_2$ | CF$_3$ | Q-1 | H | D-52a |
| 3,5-Cl$_2$ | CF$_3$ | Q-1 | CH$_2$OCH$_3$ | D-52a |
| 3,5-Cl$_2$ | CF$_3$ | Q-1 | CH$_2$CN | D-52a |
| 3,5-Cl$_2$ | CF$_3$ | Q-1 | C(O)CH$_3$ | D-52a |
| 3,5-Cl$_2$ | CF$_3$ | Q-1 | C(O)Et | D-52a |
| 3,5-Cl$_2$ | CF$_3$ | Q-1 | C(O)OCH$_3$ | D-52a |
| 3,5-Cl$_2$ | CF$_3$ | Q-1 | H | D-55a |
| 3,5-Cl$_2$ | CF$_3$ | Q-1 | H | D-58a |
| 3,5-Cl$_2$ | CF$_3$ | Q-2 | H | OCH$_3$ |
| 3,5-Cl$_2$ | CF$_3$ | Q-2 | H | OEt |
| 3,5-Cl$_2$ | CF$_3$ | Q-2 | H | OPr-n |
| 3,5-Cl$_2$ | CF$_3$ | Q-2 | H | OPr-i |
| 3,5-Cl$_2$ | CF$_3$ | Q-2 | H | OPr-c |
| 3,5-Cl$_2$ | CF$_3$ | Q-2 | H | OCH$_2$CHF$_2$ |
| 3,5-Cl$_2$ | CF$_3$ | Q-2 | H | OCH$_2$CF$_3$ |
| 3,5-Cl$_2$ | CF$_3$ | Q-2 | H | OCH$_2$CN |
| 3,5-Cl$_2$ | CF$_3$ | Q-2 | H | OCH$_2$C≡CH |
| 3,5-Cl$_2$ | CF$_3$ | Q-2 | H | SCH$_3$ |
| 3,5-Cl$_2$ | CF$_3$ | Q-2 | H | SEt |
| 3,5-Cl$_2$ | CF$_3$ | Q-2 | H | NHCN |
| 3,5-Cl$_2$ | CF$_3$ | Q-2 | H | NHOCH$_3$ |
| 3,5-Cl$_2$ | CF$_3$ | Q-2 | H | N(CH$_3$)OCH$_3$ |
| 3,5-Cl$_2$ | CF$_3$ | Q-2 | H | NHNO$_2$ |
| 3,5-Cl$_2$ | CF$_3$ | Q-2 | CH$_3$ | OCH$_3$ |
| 3,5-Cl$_2$ | CF$_3$ | Q-2 | CH$_3$ | OEt |
| 3,5-Cl$_2$ | CF$_3$ | Q-2 | CH$_3$ | SCH$_3$ |
| 3,5-Cl$_2$ | CF$_3$ | Q-2 | CH$_3$ | SEt |
| 3,5-Cl$_2$ | CF$_3$ | Q-2 | Et | OCH$_3$ |
| 3,5-Cl$_2$ | CF$_3$ | Q-2 | Et | OEt |
| 3,5-Cl$_2$ | CF$_3$ | Q-2 | n-Pr | OCH$_3$ |
| 3,5-Cl$_2$ | CF$_3$ | Q-2 | i-Pr | OCH$_3$ |
| 3,5-Cl$_2$ | CF$_3$ | Q-2 | c-Pr | OCH$_3$ |
| 3,5-Cl$_2$ | CF$_3$ | Q-2 | CH$_2$CHF$_2$ | OCH$_3$ |
| 3,5-Cl$_2$ | CF$_3$ | Q-2 | CH$_2$CF$_3$ | OCH$_3$ |
| 3,5-Cl$_2$ | CF$_3$ | Q-2 | CH$_2$CN | OCH$_3$ |
| 3,5-Cl$_2$ | CF$_3$ | Q-2 | CH$_2$C≡CH | OCH$_3$ |
| 3,5-Cl$_2$ | CF$_3$ | Q-2 | OCH$_3$ | OCH$_3$ |
| 3,5-Cl$_2$ | CF$_3$ | Q-2 | N(CH$_3$)$_2$ | OCH$_3$ |
| 3,5-Cl$_2$ | CF$_2$Cl | Q-1 | H | C(O)NHCH$_2$CF$_3$ |
| 3,5-Cl$_2$ | CF$_2$Cl | Q-1 | H | D-22a |
| 3,5-Cl$_2$ | CF$_2$Cl | Q-1 | H | D-52a |
| 3,5-Cl$_2$ | CF$_2$Cl | Q-2 | H | OCH$_3$ |
| 3,5-Cl$_2$ | CF$_2$Cl | Q-2 | H | OEt |
| 3,5-Cl$_2$ | CF$_2$Cl | Q-2 | CH$_3$ | OCH$_3$ |
| 3,5-Cl$_2$ | CF$_2$Cl | Q-2 | CH$_3$ | OEt |
| 3,5-Cl$_2$ | CF$_2$Cl | Q-2 | Et | OCH$_3$ |
| 3,5-Cl$_2$ | CF$_2$Cl | Q-2 | Et | OEt |

TABLE 2-continued

| (X)$_m$ | R$^3$ | Q | R$^2$ | R$^1$ |
|---|---|---|---|---|
| 3,5-Cl$_2$ | CF$_2$Cl | Q-2 | CH$_2$CF$_3$ | OCH$_3$ |
| 3,5-Cl$_2$ | CF$_2$Cl | Q-2 | CH$_2$C≡CH | OCH$_3$ |
| 3,5-Cl$_2$ | CF$_2$Br | Q-2 | H | OCH$_3$ |
| 3,5-Cl$_2$ | CF$_2$Br | Q-2 | H | OEt |
| 3,5-Cl$_2$ | CF$_2$Br | Q-2 | CH$_3$ | OCH$_3$ |
| 3,5-Cl$_2$ | CF$_2$CHF$_2$ | Q-2 | H | OCH$_3$ |
| 3,5-Cl$_2$ | CF$_2$CHF$_2$ | Q-2 | H | OEt |
| 3,5-Cl$_2$ | CF$_2$CHF$_2$ | Q-2 | CH$_3$ | OCH$_3$ |
| 3-Br-4-F | CF$_3$ | Q-1 | H | CF$_3$ |
| 3-Br-4-F | CF$_3$ | Q-1 | H | C(O)NHCH$_2$CF$_3$ |
| 3-Br-4-F | CF$_3$ | Q-1 | H | D-22a |
| 3-Br-4-F | CF$_3$ | Q-1 | H | D-52a |
| 3-Br-4-F | CF$_3$ | Q-2 | H | OCH$_3$ |
| 3-Br-4-F | CF$_3$ | Q-2 | H | OEt |
| 3-Br-4-F | CF$_3$ | Q-2 | H | OCH$_2$CF$_3$ |
| 3-Br-4-F | CF$_3$ | Q-2 | H | OCH$_2$C≡CH |
| 3-Br-4-F | CF$_3$ | Q-2 | CH$_3$ | OCH$_3$ |
| 3-Br-4-F | CF$_3$ | Q-2 | CH$_3$ | OEt |
| 3-Br-4-F | CF$_3$ | Q-2 | Et | OCH$_3$ |
| 3-Br-4-F | CF$_3$ | Q-2 | Et | OEt |
| 3-Br-4-F | CF$_3$ | Q-2 | n-Pr | OCH$_3$ |
| 3-Br-4-F | CF$_3$ | Q-2 | i-Pr | OCH$_3$ |
| 3-Br-4-F | CF$_3$ | Q-2 | CH$_2$CF$_3$ | OCH$_3$ |
| 3-Br-4-F | CF$_3$ | Q-2 | CH$_2$C≡CH | OCH$_3$ |
| 3-Br-4-F | CF$_2$Cl | Q-1 | H | C(O)NHCH$_2$CF$_3$ |
| 3-Br-4-F | CF$_2$Cl | Q-1 | H | D-52a |
| 3-Br-4-F | CF$_2$Cl | Q-2 | H | OCH$_3$ |
| 3-Br-4-F | CF$_2$Cl | Q-2 | H | OEt |
| 3-Br-4-F | CF$_2$Cl | Q-2 | CH$_3$ | OCH$_3$ |
| 3-Br-4-F | CF$_2$Cl | Q-2 | CH$_3$ | OEt |
| 3-Br-4-F | CF$_2$Cl | Q-2 | Et | OCH$_3$ |
| 3-Br-4-F | CF$_2$Cl | Q-2 | CH$_2$CF$_3$ | OCH$_3$ |
| 3-F-5-Br | CF$_3$ | Q-1 | H | CF$_3$ |
| 3-F-5-Br | CF$_3$ | Q-1 | H | C(O)NHCH$_2$CF$_3$ |
| 3-F-5-Br | CF$_3$ | Q-1 | H | D-22a |
| 3-F-5-Br | CF$_3$ | Q-1 | H | D-52a |
| 3-F-5-Br | CF$_3$ | Q-2 | H | OCH$_3$ |
| 3-F-5-Br | CF$_3$ | Q-2 | H | OEt |
| 3-F-5-Br | CF$_3$ | Q-2 | H | OCH$_2$CF$_3$ |
| 3-F-5-Br | CF$_3$ | Q-2 | H | OCH$_2$C≡CH |
| 3-F-5-Br | CF$_3$ | Q-2 | CH$_3$ | OCH$_3$ |
| 3-F-5-Br | CF$_3$ | Q-2 | CH$_3$ | OEt |
| 3-F-5-Br | CF$_3$ | Q-2 | Et | OCH$_3$ |
| 3-F-5-Br | CF$_3$ | Q-2 | Et | OEt |
| 3-F-5-Br | CF$_3$ | Q-2 | n-Pr | OCH$_3$ |
| 3-F-5-Br | CF$_3$ | Q-2 | i-Pr | OCH$_3$ |
| 3-F-5-Br | CF$_3$ | Q-2 | CH$_2$CF$_3$ | OCH$_3$ |
| 3-F-5-Br | CF$_3$ | Q-2 | CH$_2$C≡CH | OCH$_3$ |
| 3-F-5-Br | CF$_2$Cl | Q-1 | H | C(O)NHCH$_2$CF$_3$ |
| 3-F-5-Br | CF$_2$Cl | Q-1 | H | D-52a |
| 3-F-5-Br | CF$_2$Cl | Q-2 | H | OCH$_3$ |
| 3-F-5-Br | CF$_2$Cl | Q-2 | H | OEt |
| 3-F-5-Br | CF$_2$Cl | Q-2 | CH$_3$ | OCH$_3$ |
| 3-F-5-Br | CF$_2$Cl | Q-2 | CH$_3$ | OEt |
| 3-F-5-Br | CF$_2$Cl | Q-2 | Et | OCH$_3$ |
| 3-F-5-Br | CF$_2$Cl | Q-2 | CH$_2$CF$_3$ | OCH$_3$ |
| 3-Br-4-Cl | CF$_3$ | Q-1 | H | C(O)NHCH$_2$CF$_3$ |
| 3-Br-4-Cl | CF$_3$ | Q-1 | H | D-22a |
| 3-Br-4-Cl | CF$_3$ | Q-1 | H | D-52a |
| 3-Br-4-Cl | CF$_3$ | Q-2 | H | OCH$_3$ |
| 3-Br-4-Cl | CF$_3$ | Q-2 | H | OEt |
| 3-Br-4-Cl | CF$_3$ | Q-2 | CH$_3$ | OCH$_3$ |
| 3-Br-4-Cl | CF$_3$ | Q-2 | CH$_3$ | OEt |
| 3-Br-4-Cl | CF$_3$ | Q-2 | Et | OCH$_3$ |
| 3-Br-4-Cl | CF$_3$ | Q-2 | Et | OEt |
| 3-Br-4-Cl | CF$_3$ | Q-2 | CH$_2$CF$_3$ | OCH$_3$ |
| 3-Br-4-Cl | CF$_3$ | Q-2 | CH$_2$C≡CH | OCH$_3$ |
| 3-Br-4-Cl | CF$_2$Cl | Q-2 | H | OCH$_3$ |
| 3-Br-4-Cl | CF$_2$Cl | Q-2 | H | OEt |
| 3-Br-4-Cl | CF$_2$Cl | Q-2 | CH$_3$ | OCH$_3$ |
| 3-Cl-4-Br | CF$_3$ | Q-1 | H | C(O)NHCH$_2$CF$_3$ |
| 3-Cl-4-Br | CF$_3$ | Q-1 | H | D-22a |
| 3-Cl-4-Br | CF$_3$ | Q-1 | H | D-52a |
| 3-Cl-4-Br | CF$_3$ | Q-2 | H | OCH$_3$ |
| 3-Cl-4-Br | CF$_3$ | Q-2 | H | OEt |
| 3-Cl-4-Br | CF$_3$ | Q-2 | CH$_3$ | OCH$_3$ |
| 3-Cl-4-Br | CF$_3$ | Q-2 | CH$_3$ | OEt |
| 3-Cl-4-Br | CF$_3$ | Q-2 | Et | OCH$_3$ |

TABLE 2-continued

| (X)$_m$ | R$^3$ | Q | R$^2$ | R$^1$ |
| --- | --- | --- | --- | --- |
| 3-Cl-4-Br | CF$_3$ | Q-2 | Et | OEt |
| 3-Cl-4-Br | CF$_3$ | Q-2 | CH$_2$CF$_3$ | OCH$_3$ |
| 3-Cl-4-Br | CF$_3$ | Q-2 | CH$_2$C≡CH | OCH$_3$ |
| 3-Cl-4-Br | CF$_2$Cl | Q-2 | H | OCH$_3$ |
| 3-Cl-4-Br | CF$_2$Cl | Q-2 | H | OEt |
| 3-Cl-4-Br | CF$_2$Cl | Q-2 | CH$_3$ | OCH$_3$ |
| 3-Cl-5-Br | CHF$_2$ | Q-2 | H | OCH$_3$ |
| 3-Cl-5-Br | CHF$_2$ | Q-2 | H | OEt |
| 3-Cl-5-Br | CHF$_2$ | Q-2 | CH$_3$ | OCH$_3$ |
| 3-Cl-5-Br | CF$_3$ | Q-1 | H | c-Pr |
| 3-Cl-5-Br | CF$_3$ | Q-1 | H | CF$_3$ |
| 3-Cl-5-Br | CF$_3$ | Q-1 | H | C(O)NHCH$_2$CH$_2$Cl |
| 3-Cl-5-Br | CF$_3$ | Q-1 | H | C(O)NHCH$_2$CF$_3$ |
| 3-Cl-5-Br | CF$_3$ | Q-1 | H | D-22a |
| 3-Cl-5-Br | CF$_3$ | Q-1 | H | D-52a |
| 3-Cl-5-Br | CF$_3$ | Q-1 | CH$_2$OCH$_3$ | D-52a |
| 3-Cl-5-Br | CF$_3$ | Q-1 | CH$_2$CN | D-52a |
| 3-Cl-5-Br | CF$_3$ | Q-1 | C(O)CH$_3$ | D-52a |
| 3-Cl-5-Br | CF$_3$ | Q-1 | C(O)Et | D-52a |
| 3-Cl-5-Br | CF$_3$ | Q-1 | C(O)OCH$_3$ | D-52a |
| 3-Cl-5-Br | CF$_3$ | Q-1 | H | D-55a |
| 3-Cl-5-Br | CF$_3$ | Q-1 | H | D-58a |
| 3-Cl-5-Br | CF$_3$ | Q-2 | H | OCH$_3$ |
| 3-Cl-5-Br | CF$_3$ | Q-2 | H | OEt |
| 3-Cl-5-Br | CF$_3$ | Q-2 | H | OPr-n |
| 3-Cl-5-Br | CF$_3$ | Q-2 | H | OPr-i |
| 3-Cl-5-Br | CF$_3$ | Q-2 | H | OPr-c |
| 3-Cl-5-Br | CF$_3$ | Q-2 | H | OCH$_2$CHF$_2$ |
| 3-Cl-5-Br | CF$_3$ | Q-2 | H | OCH$_2$CF$_3$ |
| 3-Cl-5-Br | CF$_3$ | Q-2 | H | OCH$_2$CN |
| 3-Cl-5-Br | CF$_3$ | Q-2 | H | OCH$_2$C≡CH |
| 3-Cl-5-Br | CF$_3$ | Q-2 | H | SCH$_3$ |
| 3-Cl-5-Br | CF$_3$ | Q-2 | H | SEt |
| 3-Cl-5-Br | CF$_3$ | Q-2 | H | NHCN |
| 3-Cl-5-Br | CF$_3$ | Q-2 | H | NHOCH$_3$ |
| 3-Cl-5-Br | CF$_3$ | Q-2 | H | N(CH$_3$)OCH$_3$ |
| 3-Cl-5-Br | CF$_3$ | Q-2 | H | NHNO$_2$ |
| 3-Cl-5-Br | CF$_3$ | Q-2 | CH$_3$ | OCH$_3$ |
| 3-Cl-5-Br | CF$_3$ | Q-2 | CH$_3$ | OEt |
| 3-Cl-5-Br | CF$_3$ | Q-2 | CH$_3$ | SCH$_3$ |
| 3-Cl-5-Br | CF$_3$ | Q-2 | CH$_3$ | SEt |
| 3-Cl-5-Br | CF$_3$ | Q-2 | Et | OCH$_3$ |
| 3-Cl-5-Br | CF$_3$ | Q-2 | Et | OEt |
| 3-Cl-5-Br | CF$_3$ | Q-2 | n-Pr | OCH$_3$ |
| 3-Cl-5-Br | CF$_3$ | Q-2 | i-Pr | OCH$_3$ |
| 3-Cl-5-Br | CF$_3$ | Q-2 | c-Pr | OCH$_3$ |
| 3-Cl-5-Br | CF$_3$ | Q-2 | CH$_2$CHF$_2$ | OCH$_3$ |
| 3-Cl-5-Br | CF$_3$ | Q-2 | CH$_2$CF$_3$ | OCH$_3$ |
| 3-Cl-5-Br | CF$_3$ | Q-2 | CH$_2$CN | OCH$_3$ |
| 3-Cl-5-Br | CF$_3$ | Q-2 | CH$_2$C≡CH | OCH$_3$ |
| 3-Cl-5-Br | CF$_3$ | Q-2 | OCH$_3$ | OCH$_3$ |
| 3-Cl-5-Br | CF$_3$ | Q-2 | N(CH$_3$)$_2$ | OCH$_3$ |
| 3-Cl-5-Br | CF$_2$Cl | Q-1 | H | C(O)NHCH$_2$CF$_3$ |
| 3-Cl-5-Br | CF$_2$Cl | Q-1 | H | D-22a |
| 3-Cl-5-Br | CF$_2$Cl | Q-1 | H | D-52a |
| 3-Cl-5-Br | CF$_2$Cl | Q-2 | H | OCH$_3$ |
| 3-Cl-5-Br | CF$_2$Cl | Q-2 | H | OEt |
| 3-Cl-5-Br | CF$_2$Cl | Q-2 | CH$_3$ | OCH$_3$ |
| 3-Cl-5-Br | CF$_2$Cl | Q-2 | CH$_3$ | OEt |
| 3-Cl-5-Br | CF$_2$Cl | Q-2 | Et | OCH$_3$ |
| 3-Cl-5-Br | CF$_2$Cl | Q-2 | Et | OEt |
| 3-Cl-5-Br | CF$_2$Cl | Q-2 | CH$_2$CF$_3$ | OCH$_3$ |
| 3-Cl-5-Br | CF$_2$Cl | Q-2 | CH$_2$C≡CH | OCH$_3$ |
| 3-Cl-5-Br | CF$_2$Br | Q-2 | H | OCH$_3$ |
| 3-Cl-5-Br | CF$_2$Br | Q-2 | H | OEt |
| 3-Cl-5-Br | CF$_2$Br | Q-2 | CH$_3$ | OCH$_3$ |
| 3-Cl-5-Br | CF$_2$CHF$_2$ | Q-2 | H | OCH$_3$ |
| 3-Cl-5-Br | CF$_2$CHF$_2$ | Q-2 | H | OEt |
| 3-Cl-5-Br | CF$_2$CHF$_2$ | Q-2 | CH$_3$ | OCH$_3$ |
| 3,4-Br$_2$ | CF$_3$ | Q-1 | H | C(O)NHCH$_2$CF$_3$ |
| 3,4-Br$_2$ | CF$_3$ | Q-1 | H | D-22a |
| 3,4-Br$_2$ | CF$_3$ | Q-1 | H | D-52a |
| 3,4-Br$_2$ | CF$_3$ | Q-2 | H | OCH$_3$ |
| 3,4-Br$_2$ | CF$_3$ | Q-2 | H | OEt |
| 3,4-Br$_2$ | CF$_3$ | Q-2 | CH$_3$ | OCH$_3$ |
| 3,4-Br$_2$ | CF$_3$ | Q-2 | CH$_3$ | OEt |
| 3,4-Br$_2$ | CF$_3$ | Q-2 | Et | OCH$_3$ |
| 3,4-Br$_2$ | CF$_3$ | Q-2 | Et | OEt |

TABLE 2-continued

| (X)$_m$ | R$^3$ | Q | R$^2$ | R$^1$ |
|---|---|---|---|---|
| 3,4-Br$_2$ | CF$_3$ | Q-2 | CH$_2$CF$_3$ | OCH$_3$ |
| 3,4-Br$_2$ | CF$_3$ | Q-2 | CH$_2$C≡CH | OCH$_3$ |
| 3,4-Br$_2$ | CF$_2$Cl | Q-2 | H | OCH$_3$ |
| 3,4-Br$_2$ | CF$_2$Cl | Q-2 | H | OEt |
| 3,4-Br$_2$ | CF$_2$Cl | Q-2 | CH$_3$ | OCH$_3$ |
| 3,5-Br$_2$ | CHF$_2$ | Q-2 | H | OCH$_3$ |
| 3,5-Br$_2$ | CHF$_2$ | Q-2 | H | OEt |
| 3,5-Br$_2$ | CHF$_2$ | Q-2 | CH$_3$ | OCH$_3$ |
| 3,5-Br$_2$ | CF$_3$ | Q-1 | H | c-Pr |
| 3,5-Br$_2$ | CF$_3$ | Q-1 | H | CF$_3$ |
| 3,5-Br$_2$ | CF$_3$ | Q-1 | H | C(O)NHCH$_2$CH$_2$Cl |
| 3,5-Br$_2$ | CF$_3$ | Q-1 | H | C(O)NHCH$_2$CF$_3$ |
| 3,5-Br$_2$ | CF$_3$ | Q-1 | H | D-22a |
| 3,5-Br$_2$ | CF$_3$ | Q-1 | H | D-52a |
| 3,5-Br$_2$ | CF$_3$ | Q-1 | CH$_2$OCH$_3$ | D-52a |
| 3,5-Br$_2$ | CF$_3$ | Q-1 | CH$_2$CN | D-52a |
| 3,5-Br$_2$ | CF$_3$ | Q-1 | C(O)CH$_3$ | D-52a |
| 3,5-Br$_2$ | CF$_3$ | Q-1 | C(O)Et | D-52a |
| 3,5-Br$_2$ | CF$_3$ | Q-1 | C(O)OCH$_3$ | D-52a |
| 3,5-Br$_2$ | CF$_3$ | Q-1 | H | D-55a |
| 3,5-Br$_2$ | CF$_3$ | Q-1 | H | D-58a |
| 3,5-Br$_2$ | CF$_3$ | Q-2 | H | OCH$_3$ |
| 3,5-Br$_2$ | CF$_3$ | Q-2 | H | OEt |
| 3,5-Br$_2$ | CF$_3$ | Q-2 | H | OPr-n |
| 3,5-Br$_2$ | CF$_3$ | Q-2 | H | OPr-i |
| 3,5-Br$_2$ | CF$_3$ | Q-2 | H | OPr-c |
| 3,5-Br$_2$ | CF$_3$ | Q-2 | H | OCH$_2$CHF$_2$ |
| 3,5-Br$_2$ | CF$_3$ | Q-2 | H | OCH$_2$CF$_3$ |
| 3,5-Br$_2$ | CF$_3$ | Q-2 | H | OCH$_2$CN |
| 3,5-Br$_2$ | CF$_3$ | Q-2 | H | OCH$_2$C≡CH |
| 3,5-Br$_2$ | CF$_3$ | Q-2 | H | SCH$_3$ |
| 3,5-Br$_2$ | CF$_3$ | Q-2 | H | SEt |
| 3,5-Br$_2$ | CF$_3$ | Q-2 | H | NHCN |
| 3,5-Br$_2$ | CF$_3$ | Q-2 | H | NHOCH$_3$ |
| 3,5-Br$_2$ | CF$_3$ | Q-2 | H | N(CH$_3$)OCH$_3$ |
| 3,5-Br$_2$ | CF$_3$ | Q-2 | H | NHNO$_2$ |
| 3,5-Br$_2$ | CF$_3$ | Q-2 | CH$_3$ | OCH$_3$ |
| 3,5-Br$_2$ | CF$_3$ | Q-2 | CH$_3$ | OEt |
| 3,5-Br$_2$ | CF$_3$ | Q-2 | CH$_3$ | SCH$_3$ |
| 3,5-Br$_2$ | CF$_3$ | Q-2 | CH$_3$ | SEt |
| 3,5-Br$_2$ | CF$_3$ | Q-2 | Et | OCH$_3$ |
| 3,5-Br$_2$ | CF$_3$ | Q-2 | Et | OEt |
| 3,5-Br$_2$ | CF$_3$ | Q-2 | n-Pr | OCH$_3$ |
| 3,5-Br$_2$ | CF$_3$ | Q-2 | i-Pr | OCH$_3$ |
| 3,5-Br$_2$ | CF$_3$ | Q-2 | c-Pr | OCH$_3$ |
| 3,5-Br$_2$ | CF$_3$ | Q-2 | CH$_2$CHF$_2$ | OCH$_3$ |
| 3,5-Br$_2$ | CF$_3$ | Q-2 | CH$_2$CF$_3$ | OCH$_3$ |
| 3,5-Br$_2$ | CF$_3$ | Q-2 | CH$_2$CN | OCH$_3$ |
| 3,5-Br$_2$ | CF$_3$ | Q-2 | CH$_2$C≡CH | OCH$_3$ |
| 3,5-Br$_2$ | CF$_3$ | Q-2 | OCH$_3$ | OCH$_3$ |
| 3,5-Br$_2$ | CF$_3$ | Q-2 | N(CH$_3$)$_2$ | OCH$_3$ |
| 3,5-Br$_2$ | CF$_2$Cl | Q-1 | H | C(O)NHCH$_2$CF$_3$ |
| 3,5-Br$_2$ | CF$_2$Cl | Q-1 | H | D-22a |
| 3,5-Br$_2$ | CF$_2$Cl | Q-1 | H | D-52a |
| 3,5-Br$_2$ | CF$_2$Cl | Q-2 | H | OCH$_3$ |
| 3,5-Br$_2$ | CF$_2$Cl | Q-2 | H | OEt |
| 3,5-Br$_2$ | CF$_2$Cl | Q-2 | CH$_3$ | OCH$_3$ |
| 3,5-Br$_2$ | CF$_2$Cl | Q-2 | CH$_3$ | OEt |
| 3,5-Br$_2$ | CF$_2$Cl | Q-2 | Et | OCH$_3$ |
| 3,5-Br$_2$ | CF$_2$Cl | Q-2 | Et | OEt |
| 3,5-Br$_2$ | CF$_2$Cl | Q-2 | CH$_2$CF$_3$ | OCH$_3$ |
| 3,5-Br$_2$ | CF$_2$Cl | Q-2 | CH$_2$C≡CH | OCH$_3$ |
| 3,5-Br$_2$ | CF$_2$Br | Q-2 | H | OCH$_3$ |
| 3,5-Br$_2$ | CF$_2$Br | Q-2 | H | OEt |
| 3,5-Br$_2$ | CF$_2$Br | Q-2 | CH$_3$ | OCH$_3$ |
| 3,5-Br$_2$ | CF$_2$CHF$_2$ | Q-2 | H | OCH$_3$ |
| 3,5-Br$_2$ | CF$_2$CHF$_2$ | Q-2 | H | OEt |
| 3,5-Br$_2$ | CF$_2$CHF$_2$ | Q-2 | CH$_3$ | OCH$_3$ |
| 3-I-4-F | CF$_3$ | Q-1 | H | C(O)NHCH$_2$CF$_3$ |
| 3-I-4-F | CF$_3$ | Q-1 | H | D-22a |
| 3-I-4-F | CF$_3$ | Q-1 | H | D-52a |
| 3-I-4-F | CF$_3$ | Q-2 | H | OCH$_3$ |
| 3-I-4-F | CF$_3$ | Q-2 | H | OEt |
| 3-I-4-F | CF$_3$ | Q-2 | CH$_3$ | OCH$_3$ |
| 3-I-4-F | CF$_3$ | Q-2 | CH$_3$ | OEt |
| 3-I-4-F | CF$_3$ | Q-2 | Et | OCH$_3$ |
| 3-I-4-F | CF$_3$ | Q-2 | Et | OEt |
| 3-I-4-F | CF$_3$ | Q-2 | CH$_2$CF$_3$ | OCH$_3$ |

TABLE 2-continued

| (X)$_m$ | R$^3$ | Q | R$^2$ | R$^1$ |
|---|---|---|---|---|
| 3-I-4-F | CF$_3$ | Q-2 | CH$_2$C≡CH | OCH$_3$ |
| 3-I-4-F | CF$_2$Cl | Q-2 | H | OCH$_3$ |
| 3-I-4-F | CF$_2$Cl | Q-2 | H | OEt |
| 3-I-4-F | CF$_2$Cl | Q-2 | CH$_3$ | OCH$_3$ |
| 3-F-5-I | CF$_3$ | Q-1 | H | C(O)NHCH$_2$CF$_3$ |
| 3-F-5-I | CF$_3$ | Q-1 | H | D-22a |
| 3-F-5-I | CF$_3$ | Q-1 | H | D-52a |
| 3-F-5-I | CF$_3$ | Q-2 | H | OCH$_3$ |
| 3-F-5-I | CF$_3$ | Q-2 | H | OEt |
| 3-F-5-I | CF$_3$ | Q-2 | CH$_3$ | OCH$_3$ |
| 3-F-5-I | CF$_3$ | Q-2 | CH$_3$ | OEt |
| 3-F-5-I | CF$_3$ | Q-2 | Et | OCH$_3$ |
| 3-F-5-I | CF$_3$ | Q-2 | Et | OEt |
| 3-F-5-I | CF$_3$ | Q-2 | CH$_2$CF$_3$ | OCH$_3$ |
| 3-F-5-I | CF$_3$ | Q-2 | CH$_2$C≡CH | OCH$_3$ |
| 3-F-5-I | CF$_2$Cl | Q-2 | H | OCH$_3$ |
| 3-F-5-I | CF$_2$Cl | Q-2 | H | OEt |
| 3-F-5-I | CF$_2$Cl | Q-2 | CH$_3$ | OCH$_3$ |
| 3-Cl-5-I | CF$_3$ | Q-1 | H | CF$_3$ |
| 3-Cl-5-I | CF$_3$ | Q-1 | H | C(O)NHCH$_2$CF$_3$ |
| 3-Cl-5-I | CF$_3$ | Q-1 | H | D-22a |
| 3-Cl-5-I | CF$_3$ | Q-1 | H | D-52a |
| 3-Cl-5-I | CF$_3$ | Q-2 | H | OCH$_3$ |
| 3-Cl-5-I | CF$_3$ | Q-2 | H | OEt |
| 3-Cl-5-I | CF$_3$ | Q-2 | H | OCH$_2$CF$_3$ |
| 3-Cl-5-I | CF$_3$ | Q-2 | H | OCH$_2$C≡CH |
| 3-Cl-5-I | CF$_3$ | Q-2 | CH$_3$ | OCH$_3$ |
| 3-Cl-5-I | CF$_3$ | Q-2 | CH$_3$ | OEt |
| 3-Cl-5-I | CF$_3$ | Q-2 | Et | OCH$_3$ |
| 3-Cl-5-I | CF$_3$ | Q-2 | Et | OEt |
| 3-Cl-5-I | CF$_3$ | Q-2 | n-Pr | OCH$_3$ |
| 3-Cl-5-I | CF$_3$ | Q-2 | i-Pr | OCH$_3$ |
| 3-Cl-5-I | CF$_3$ | Q-2 | CH$_2$CF$_3$ | OCH$_3$ |
| 3-Cl-5-I | CF$_3$ | Q-2 | CH$_2$C≡CH | OCH$_3$ |
| 3-Cl-5-I | CF$_2$Cl | Q-1 | H | C(O)NHCH$_2$CF$_3$ |
| 3-Cl-5-I | CF$_2$Cl | Q-1 | H | D-52a |
| 3-Cl-5-I | CF$_2$Cl | Q-2 | H | OCH$_3$ |
| 3-Cl-5-I | CF$_2$Cl | Q-2 | H | OEt |
| 3-Cl-5-I | CF$_2$Cl | Q-2 | CH$_3$ | OCH$_3$ |
| 3-Cl-5-I | CF$_2$Cl | Q-2 | CH$_3$ | OEt |
| 3-Cl-5-I | CF$_2$Cl | Q-2 | Et | OCH$_3$ |
| 3-Cl-5-I | CF$_2$Cl | Q-2 | CH$_2$CF$_3$ | OCH$_3$ |
| 3,5-I$_2$ | CF$_3$ | Q-2 | H | OCH$_3$ |
| 3,5-I$_2$ | CF$_3$ | Q-2 | H | OEt |
| 3,5-I$_2$ | CF$_3$ | Q-2 | CH$_3$ | OCH$_3$ |
| 3-CH$_3$-4-F | CF$_3$ | Q-2 | H | OCH$_3$ |
| 3-CH$_3$-4-F | CF$_3$ | Q-2 | H | OEt |
| 3-CH$_3$-4-F | CF$_3$ | Q-2 | CH$_3$ | OCH$_3$ |
| 3-Cl-4-CH$_3$ | CF$_3$ | Q-2 | H | OCH$_3$ |
| 3-Cl-4-CH$_3$ | CF$_3$ | Q-2 | H | OEt |
| 3-Cl-4-CH$_3$ | CF$_3$ | Q-2 | CH$_3$ | OCH$_3$ |
| 3-Cl-5-CH$_3$ | CF$_3$ | Q-1 | H | C(O)NHCH$_2$CF$_3$ |
| 3-Cl-5-CH$_3$ | CF$_3$ | Q-1 | H | D-52a |
| 3-Cl-5-CH$_3$ | CF$_3$ | Q-2 | H | OCH$_3$ |
| 3-Cl-5-CH$_3$ | CF$_3$ | Q-2 | H | OEt |
| 3-Cl-5-CH$_3$ | CF$_3$ | Q-2 | CH$_3$ | OCH$_3$ |
| 3-Cl-5-CH$_3$ | CF$_3$ | Q-2 | CH$_3$ | OEt |
| 3-Cl-5-CH$_3$ | CF$_3$ | Q-2 | Et | OCH$_3$ |
| 3-Cl-5-CH$_3$ | CF$_3$ | Q-2 | CH$_2$CF$_3$ | OCH$_3$ |
| 3-Br-4-CH$_3$ | CF$_3$ | Q-2 | H | OCH$_3$ |
| 3-Br-4-CH$_3$ | CF$_3$ | Q-2 | H | OEt |
| 3-Br-4-CH$_3$ | CF$_3$ | Q-2 | CH$_3$ | OCH$_3$ |
| 3-Br-5-CH$_3$ | CF$_3$ | Q-1 | H | C(O)NHCH$_2$CF$_3$ |
| 3-Br-5-CH$_3$ | CF$_3$ | Q-1 | H | D-52a |
| 3-Br-5-CH$_3$ | CF$_3$ | Q-2 | H | OCH$_3$ |
| 3-Br-5-CH$_3$ | CF$_3$ | Q-2 | H | OEt |
| 3-Br-5-CH$_3$ | CF$_3$ | Q-2 | CH$_3$ | OCH$_3$ |
| 3-Br-5-CH$_3$ | CF$_3$ | Q-2 | CH$_3$ | OEt |
| 3-Br-5-CH$_3$ | CF$_3$ | Q-2 | Et | OCH$_3$ |
| 3-Br-5-CH$_3$ | CF$_3$ | Q-2 | CH$_2$CF$_3$ | OCH$_3$ |
| 3,5-(CH$_3$)$_2$ | CF$_3$ | Q-2 | H | OCH$_3$ |
| 3,5-(CH$_3$)$_2$ | CF$_3$ | Q-2 | H | OEt |
| 3,5-(CH$_3$)$_2$ | CF$_3$ | Q-2 | CH$_3$ | OCH$_3$ |
| 3-CF$_3$-4-F | CF$_3$ | Q-1 | H | CF$_3$ |
| 3-CF$_3$-4-F | CF$_3$ | Q-1 | H | C(O)NHCH$_2$CF$_3$ |
| 3-CF$_3$-4-F | CF$_3$ | Q-1 | H | D-22a |
| 3-CF$_3$-4-F | CF$_3$ | Q-1 | H | D-52a |
| 3-CF$_3$-4-F | CF$_3$ | Q-2 | H | OCH$_3$ |

TABLE 2-continued

| $(X)_m$ | $R^3$ | Q | $R^2$ | $R^1$ |
|---|---|---|---|---|
| 3-CF$_3$-4-F | CF$_3$ | Q-2 | H | OEt |
| 3-CF$_3$-4-F | CF$_3$ | Q-2 | H | OCH$_2$CF$_3$ |
| 3-CF$_3$-4-F | CF$_3$ | Q-2 | H | OCH$_2$C≡CH |
| 3-CF$_3$-4-F | CF$_3$ | Q-2 | CH$_3$ | OCH$_3$ |
| 3-CF$_3$-4-F | CF$_3$ | Q-2 | CH$_3$ | OEt |
| 3-CF$_3$-4-F | CF$_3$ | Q-2 | Et | OCH$_3$ |
| 3-CF$_3$-4-F | CF$_3$ | Q-2 | Et | OEt |
| 3-CF$_3$-4-F | CF$_3$ | Q-2 | n-Pr | OCH$_3$ |
| 3-CF$_3$-4-F | CF$_3$ | Q-2 | i-Pr | OCH$_3$ |
| 3-CF$_3$-4-F | CF$_3$ | Q-2 | CH$_2$CF$_3$ | OCH$_3$ |
| 3-CF$_3$-4-F | CF$_3$ | Q-2 | CH$_2$C≡CH | OCH$_3$ |
| 3-CF$_3$-4-F | CF$_2$Cl | Q-1 | H | C(O)NHCH$_2$CF$_3$ |
| 3-CF$_3$-4-F | CF$_2$Cl | Q-1 | H | D-52a |
| 3-CF$_3$-4-F | CF$_2$Cl | Q-2 | H | OCH$_3$ |
| 3-CF$_3$-4-F | CF$_2$Cl | Q-2 | H | OEt |
| 3-CF$_3$-4-F | CF$_2$Cl | Q-2 | CH$_3$ | OCH$_3$ |
| 3-CF$_3$-4-F | CF$_2$Cl | Q-2 | CH$_3$ | OEt |
| 3-CF$_3$-4-F | CF$_2$Cl | Q-2 | Et | OCH$_3$ |
| 3-CF$_3$-4-F | CF$_2$Cl | Q-2 | CH$_2$CF$_3$ | OCH$_3$ |
| 3-F-5-CF$_3$ | CF$_3$ | Q-1 | H | CF$_3$ |
| 3-F-5-CF$_3$ | CF$_3$ | Q-1 | H | C(O)NHCH$_2$CF$_3$ |
| 3-F-5-CF$_3$ | CF$_3$ | Q-1 | H | D-22a |
| 3-F-5-CF$_3$ | CF$_3$ | Q-1 | H | D-52a |
| 3-F-5-CF$_3$ | CF$_3$ | Q-2 | H | OCH$_3$ |
| 3-F-5-CF$_3$ | CF$_3$ | Q-2 | H | OEt |
| 3-F-5-CF$_3$ | CF$_3$ | Q-2 | H | OCH$_2$CF$_3$ |
| 3-F-5-CF$_3$ | CF$_3$ | Q-2 | H | OCH$_2$C≡CH |
| 3-F-5-CF$_3$ | CF$_3$ | Q-2 | CH$_3$ | OCH$_3$ |
| 3-F-5-CF$_3$ | CF$_3$ | Q-2 | CH$_3$ | OEt |
| 3-F-5-CF$_3$ | CF$_3$ | Q-2 | Et | OCH$_3$ |
| 3-F-5-CF$_3$ | CF$_3$ | Q-2 | Et | OEt |
| 3-F-5-CF$_3$ | CF$_3$ | Q-2 | n-Pr | OCH$_3$ |
| 3-F-5-CF$_3$ | CF$_3$ | Q-2 | i-Pr | OCH$_3$ |
| 3-F-5-CF$_3$ | CF$_3$ | Q-2 | CH$_2$CF$_3$ | OCH$_3$ |
| 3-F-5-CF$_3$ | CF$_3$ | Q-2 | CH$_2$C≡CH | OCH$_3$ |
| 3-F-5-CF$_3$ | CF$_2$Cl | Q-1 | H | C(O)NHCH$_2$CF$_3$ |
| 3-F-5-CF$_3$ | CF$_2$Cl | Q-1 | H | D-52a |
| 3-F-5-CF$_3$ | CF$_2$Cl | Q-2 | H | OCH$_3$ |
| 3-F-5-CF$_3$ | CF$_2$Cl | Q-2 | H | OEt |
| 3-F-5-CF$_3$ | CF$_2$Cl | Q-2 | CH$_3$ | OCH$_3$ |
| 3-F-5-CF$_3$ | CF$_2$Cl | Q-2 | CH$_3$ | OEt |
| 3-F-5-CF$_3$ | CF$_2$Cl | Q-2 | Et | OCH$_3$ |
| 3-F-5-CF$_3$ | CF$_2$Cl | Q-2 | CH$_2$CF$_3$ | OCH$_3$ |
| 3-CF$_3$-4-Cl | CF$_3$ | Q-1 | H | CF$_3$ |
| 3-CF$_3$-4-Cl | CF$_3$ | Q-1 | H | C(O)NHCH$_2$CF$_3$ |
| 3-CF$_3$-4-Cl | CF$_3$ | Q-1 | H | D-22a |
| 3-CF$_3$-4-Cl | CF$_3$ | Q-1 | H | D-52a |
| 3-CF$_3$-4-Cl | CF$_3$ | Q-2 | H | OCH$_3$ |
| 3-CF$_3$-4-Cl | CF$_3$ | Q-2 | H | OEt |
| 3-CF$_3$-4-Cl | CF$_3$ | Q-2 | H | OCH$_2$CF$_3$ |
| 3-CF$_3$-4-Cl | CF$_3$ | Q-2 | H | OCH$_2$C≡CH |
| 3-CF$_3$-4-Cl | CF$_3$ | Q-2 | CH$_3$ | OCH$_3$ |
| 3-CF$_3$-4-Cl | CF$_3$ | Q-2 | CH$_3$ | OEt |
| 3-CF$_3$-4-Cl | CF$_3$ | Q-2 | Et | OCH$_3$ |
| 3-CF$_3$-4-Cl | CF$_3$ | Q-2 | Et | OEt |
| 3-CF$_3$-4-Cl | CF$_3$ | Q-2 | n-Pr | OCH$_3$ |
| 3-CF$_3$-4-Cl | CF$_3$ | Q-2 | i-Pr | OCH$_3$ |
| 3-CF$_3$-4-Cl | CF$_3$ | Q-2 | CH$_2$CF$_3$ | OCH$_3$ |
| 3-CF$_3$-4-Cl | CF$_3$ | Q-2 | CH$_2$C≡CH | OCH$_3$ |
| 3-CF$_3$-4-Cl | CF$_2$Cl | Q-1 | H | C(O)NHCH$_2$CF$_3$ |
| 3-CF$_3$-4-Cl | CF$_2$Cl | Q-1 | H | D-52a |
| 3-CF$_3$-4-Cl | CF$_2$Cl | Q-2 | H | OCH$_3$ |
| 3-CF$_3$-4-Cl | CF$_2$Cl | Q-2 | H | OEt |
| 3-CF$_3$-4-Cl | CF$_2$Cl | Q-2 | CH$_3$ | OCH$_3$ |
| 3-CF$_3$-4-Cl | CF$_2$Cl | Q-2 | CH$_3$ | OEt |
| 3-CF$_3$-4-Cl | CF$_2$Cl | Q-2 | Et | OCH$_3$ |
| 3-CF$_3$-4-Cl | CF$_2$Cl | Q-2 | CH$_2$CF$_3$ | OCH$_3$ |
| 3-Cl-5-CF$_3$ | CHF$_2$ | Q-2 | H | OCH$_3$ |
| 3-Cl-5-CF$_3$ | CHF$_2$ | Q-2 | H | OEt |
| 3-Cl-5-CF$_3$ | CHF$_2$ | Q-2 | CH$_3$ | OCH$_3$ |
| 3-Cl-5-CF$_3$ | CF$_3$ | Q-1 | H | c-Pr |
| 3-Cl-5-CF$_3$ | CF$_3$ | Q-1 | H | CF$_3$ |
| 3-Cl-5-CF$_3$ | CF$_3$ | Q-1 | H | C(O)NHCH$_2$CH$_2$Cl |
| 3-Cl-5-CF$_3$ | CF$_3$ | Q-1 | H | C(O)NHCH$_2$CF$_3$ |
| 3-Cl-5-CF$_3$ | CF$_3$ | Q-1 | H | D-22a |
| 3-Cl-5-CF$_3$ | CF$_3$ | Q-1 | H | D-52a |
| 3-Cl-5-CF$_3$ | CF$_3$ | Q-1 | CH$_2$OCH$_3$ | D-52a |
| 3-Cl-5-CF$_3$ | CF$_3$ | Q-1 | CH$_2$CN | D-52a |

TABLE 2-continued

| (X)$_m$ | R$^3$ | Q | R$^2$ | R$^1$ |
|---|---|---|---|---|
| 3-Cl-5-CF$_3$ | CF$_3$ | Q-1 | C(O)CH$_3$ | D-52a |
| 3-Cl-5-CF$_3$ | CF$_3$ | Q-1 | C(O)Et | D-52a |
| 3-Cl-5-CF$_3$ | CF$_3$ | Q-1 | C(O)OCH$_3$ | D-52a |
| 3-Cl-5-CF$_3$ | CF$_3$ | Q-1 | H | D-55a |
| 3-Cl-5-CF$_3$ | CF$_3$ | Q-1 | H | D-58a |
| 3-Cl-5-CF$_3$ | CF$_3$ | Q-2 | H | OCH$_3$ |
| 3-Cl-5-CF$_3$ | CF$_3$ | Q-2 | H | OEt |
| 3-Cl-5-CF$_3$ | CF$_3$ | Q-2 | H | OPr-n |
| 3-Cl-5-CF$_3$ | CF$_3$ | Q-2 | H | OPr-i |
| 3-Cl-5-CF$_3$ | CF$_3$ | Q-2 | H | OPr-c |
| 3-Cl-5-CF$_3$ | CF$_3$ | Q-2 | H | OCH$_2$CHF$_2$ |
| 3-Cl-5-CF$_3$ | CF$_3$ | Q-2 | H | OCH$_2$CF$_3$ |
| 3-Cl-5-CF$_3$ | CF$_3$ | Q-2 | H | OCH$_2$CN |
| 3-Cl-5-CF$_3$ | CF$_3$ | Q-2 | H | OCH$_2$C≡CH |
| 3-Cl-5-CF$_3$ | CF$_3$ | Q-2 | H | SCH$_3$ |
| 3-Cl-5-CF$_3$ | CF$_3$ | Q-2 | H | SEt |
| 3-Cl-5-CF$_3$ | CF$_3$ | Q-2 | H | NHCN |
| 3-Cl-5-CF$_3$ | CF$_3$ | Q-2 | H | NHOCH$_3$ |
| 3-Cl-5-CF$_3$ | CF$_3$ | Q-2 | H | N(CH$_3$)OCH$_3$ |
| 3-Cl-5-CF$_3$ | CF$_3$ | Q-2 | H | NHNO$_2$ |
| 3-Cl-5-CF$_3$ | CF$_3$ | Q-2 | CH$_3$ | OCH$_3$ |
| 3-Cl-5-CF$_3$ | CF$_3$ | Q-2 | CH$_3$ | OEt |
| 3-Cl-5-CF$_3$ | CF$_3$ | Q-2 | CH$_3$ | SCH$_3$ |
| 3-Cl-5-CF$_3$ | CF$_3$ | Q-2 | CH$_3$ | SEt |
| 3-Cl-5-CF$_3$ | CF$_3$ | Q-2 | Et | OCH$_3$ |
| 3-Cl-5-CF$_3$ | CF$_3$ | Q-2 | Et | OEt |
| 3-Cl-5-CF$_3$ | CF$_3$ | Q-2 | n-Pr | OCH$_3$ |
| 3-Cl-5-CF$_3$ | CF$_3$ | Q-2 | i-Pr | OCH$_3$ |
| 3-Cl-5-CF$_3$ | CF$_3$ | Q-2 | c-Pr | OCH$_3$ |
| 3-Cl-5-CF$_3$ | CF$_3$ | Q-2 | CH$_2$CHF$_2$ | OCH$_3$ |
| 3-Cl-5-CF$_3$ | CF$_3$ | Q-2 | CH$_2$CF$_3$ | OCH$_3$ |
| 3-Cl-5-CF$_3$ | CF$_3$ | Q-2 | CH$_2$CN | OCH$_3$ |
| 3-Cl-5-CF$_3$ | CF$_3$ | Q-2 | CH$_2$C≡CH | OCH$_3$ |
| 3-Cl-5-CF$_3$ | CF$_3$ | Q-2 | OCH$_3$ | OCH$_3$ |
| 3-Cl-5-CF$_3$ | CF$_3$ | Q-2 | N(CH$_3$)$_2$ | OCH$_3$ |
| 3-Cl-5-CF$_3$ | CF$_2$Cl | Q-1 | H | C(O)NHCH$_2$CF$_3$ |
| 3-Cl-5-CF$_3$ | CF$_2$Cl | Q-1 | H | D-22a |
| 3-Cl-5-CF$_3$ | CF$_2$Cl | Q-1 | H | D-52a |
| 3-Cl-5-CF$_3$ | CF$_2$Cl | Q-2 | H | OCH$_3$ |
| 3-Cl-5-CF$_3$ | CF$_2$Cl | Q-2 | H | OEt |
| 3-Cl-5-CF$_3$ | CF$_2$Cl | Q-2 | CH$_3$ | OCH$_3$ |
| 3-Cl-5-CF$_3$ | CF$_2$Cl | Q-2 | CH$_3$ | OEt |
| 3-Cl-5-CF$_3$ | CF$_2$Cl | Q-2 | Et | OCH$_3$ |
| 3-Cl-5-CF$_3$ | CF$_2$Cl | Q-2 | Et | OEt |
| 3-Cl-5-CF$_3$ | CF$_2$Cl | Q-2 | CH$_2$CF$_3$ | OCH$_3$ |
| 3-Cl-5-CF$_3$ | CF$_2$Cl | Q-2 | CH$_2$C≡CH | OCH$_3$ |
| 3-Cl-5-CF$_3$ | CF$_2$Br | Q-2 | H | OCH$_3$ |
| 3-Cl-5-CF$_3$ | CF$_2$Br | Q-2 | H | OEt |
| 3-Cl-5-CF$_3$ | CF$_2$Br | Q-2 | CH$_3$ | OCH$_3$ |
| 3-Cl-5-CF$_3$ | CF$_2$CHF$_2$ | Q-2 | H | OCH$_3$ |
| 3-Cl-5-CF$_3$ | CF$_2$CHF$_2$ | Q-2 | H | OEt |
| 3-Cl-5-CF$_3$ | CF$_2$CHF$_2$ | Q-2 | CH$_3$ | OCH$_3$ |
| 3-Br-5-CF$_3$ | CHF$_2$ | Q-2 | H | OCH$_3$ |
| 3-Br-5-CF$_3$ | CHF$_2$ | Q-2 | H | OEt |
| 3-Br-5-CF$_3$ | CHF$_2$ | Q-2 | CH$_3$ | OCH$_3$ |
| 3-Br-5-CF$_3$ | CF$_3$ | Q-1 | H | c-Pr |
| 3-Br-5-CF$_3$ | CF$_3$ | Q-1 | H | CF$_3$ |
| 3-Br-5-CF$_3$ | CF$_3$ | Q-1 | H | C(O)NHCH$_2$CH$_2$Cl |
| 3-Br-5-CF$_3$ | CF$_3$ | Q-1 | H | C(O)NHCH$_2$CF$_3$ |
| 3-Br-5-CF$_3$ | CF$_3$ | Q-1 | H | D-22a |
| 3-Br-5-CF$_3$ | CF$_3$ | Q-1 | H | D-52a |
| 3-Br-5-CF$_3$ | CF$_3$ | Q-1 | CH$_2$OCH$_3$ | D-52a |
| 3-Br-5-CF$_3$ | CF$_3$ | Q-1 | CH$_2$CN | D-52a |
| 3-Br-5-CF$_3$ | CF$_3$ | Q-1 | C(O)CH$_3$ | D-52a |
| 3-Br-5-CF$_3$ | CF$_3$ | Q-1 | C(O)Et | D-52a |
| 3-Br-5-CF$_3$ | CF$_3$ | Q-1 | C(O)OCH$_3$ | D-52a |
| 3-Br-5-CF$_3$ | CF$_3$ | Q-1 | H | D-55a |
| 3-Br-5-CF$_3$ | CF$_3$ | Q1 | H | D-58a |
| 3-Br-5-CF$_3$ | CF$_3$ | Q-2 | H | OCH$_3$ |
| 3-Br-5-CF$_3$ | CF$_3$ | Q-2 | H | OEt |
| 3-Br-5-CF$_3$ | CF$_3$ | Q-2 | H | OPr-n |
| 3-Br-5-CF$_3$ | CF$_3$ | Q-2 | H | OPr-i |
| 3-Br-5-CF$_3$ | CF$_3$ | Q-2 | H | OPr-c |
| 3-Br-5-CF$_3$ | CF$_3$ | Q-2 | H | OCH$_2$CHF$_2$ |
| 3-Br-5-CF$_3$ | CF$_3$ | Q-2 | H | OCH$_2$CF$_3$ |
| 3-Br-5-CF$_3$ | CF$_3$ | Q-2 | H | OCH$_2$CN |
| 3-Br-5-CF$_3$ | CF$_3$ | Q-2 | H | OCH$_2$C≡CH |
| 3-Br-5-CF$_3$ | CF$_3$ | Q-2 | H | SCH$_3$ |

TABLE 2-continued

| (X)$_m$ | R$^3$ | Q | R$^2$ | R$^1$ |
|---|---|---|---|---|
| 3-Br-5-CF$_3$ | CF$_3$ | Q-2 | H | SEt |
| 3-Br-5-CF$_3$ | CF$_3$ | Q-2 | H | NHCN |
| 3-Br-5-CF$_3$ | CF$_3$ | Q-2 | H | NHOCH$_3$ |
| 3-Br-5-CF$_3$ | CF$_3$ | Q-2 | H | N(CH$_3$)OCH$_3$ |
| 3-Br-5-CF$_3$ | CF$_3$ | Q-2 | H | NHNO$_2$ |
| 3-Br-5-CF$_3$ | CF$_3$ | Q-2 | CH$_3$ | OCH$_3$ |
| 3-Br-5-CF$_3$ | CF$_3$ | Q-2 | CH$_3$ | OEt |
| 3-Br-5-CF$_3$ | CF$_3$ | Q-2 | CH$_3$ | SCH$_3$ |
| 3-Br-5-CF$_3$ | CF$_3$ | Q-2 | CH$_3$ | SEt |
| 3-Br-5-CF$_3$ | CF$_3$ | Q-2 | Et | OCH$_3$ |
| 3-Br-5-CF$_3$ | CF$_3$ | Q-2 | Et | OEt |
| 3-Br-5-CF$_3$ | CF$_3$ | Q-2 | n-Pr | OCH$_3$ |
| 3-Br-5-CF$_3$ | CF$_3$ | Q-2 | i-Pr | OCH$_3$ |
| 3-Br-5-CF$_3$ | CF$_3$ | Q-2 | c-Pr | OCH$_3$ |
| 3-Br-5-CF$_3$ | CF$_3$ | Q-2 | CH$_2$CHF$_2$ | OCH$_3$ |
| 3-Br-5-CF$_3$ | CF$_3$ | Q-2 | CH$_2$CF$_3$ | OCH$_3$ |
| 3-Br-5-CF$_3$ | CF$_3$ | Q-2 | CH$_2$CN | OCH$_3$ |
| 3-Br-5-CF$_3$ | CF$_3$ | Q-2 | CH$_2$C≡CH | OCH$_3$ |
| 3-Br-5-CF$_3$ | CF$_3$ | Q-2 | OCH$_3$ | OCH$_3$ |
| 3-Br-5-CF$_3$ | CF$_3$ | Q-2 | N(CH$_3$)$_2$ | OCH$_3$ |
| 3-Br-5-CF$_3$ | CF$_2$Cl | Q-1 | H | C(O)NHCH$_2$CF$_3$ |
| 3-Br-5-CF$_3$ | CF$_2$Cl | Q-1 | H | D-22a |
| 3-Br-5-CF$_3$ | CF$_2$Cl | Q-1 | H | D-52a |
| 3-Br-5-CF$_3$ | CF$_2$Cl | Q-2 | H | OCH$_3$ |
| 3-Br-5-CF$_3$ | CF$_2$Cl | Q-2 | H | OEt |
| 3-Br-5-CF$_3$ | CF$_2$Cl | Q-2 | CH$_3$ | OCH$_3$ |
| 3-Br-5-CF$_3$ | CF$_2$Cl | Q-2 | CH$_3$ | OEt |
| 3-Br-5-CF$_3$ | CF$_2$Cl | Q-2 | Et | OCH$_3$ |
| 3-Br-5-CF$_3$ | CF$_2$Cl | Q-2 | Et | OEt |
| 3-Br-5-CF$_3$ | CF$_2$Cl | Q-2 | CH$_2$CF$_3$ | OCH$_3$ |
| 3-Br-5-CF$_3$ | CF$_2$Cl | Q-2 | CH$_2$C≡CH | OCH$_3$ |
| 3-Br-5-CF$_3$ | CF$_2$Br | Q-2 | H | OCH$_3$ |
| 3-Br-5-CF$_3$ | CF$_2$Br | Q-2 | H | OEt |
| 3-Br-5-CF$_3$ | CF$_2$Br | Q-2 | CH$_3$ | OCH$_3$ |
| 3-Br-5-CF$_3$ | CF$_2$CHF$_2$ | Q-2 | H | OCH$_3$ |
| 3-Br-5-CF$_3$ | CF$_2$CHF$_2$ | Q-2 | H | OEt |
| 3-Br-5-CF$_3$ | CF$_2$CHF$_2$ | Q-2 | CH$_3$ | OCH$_3$ |
| 3-CH$_3$-5-CF$_3$ | CF$_3$ | Q-1 | H | C(O)NHCH$_2$CF$_3$ |
| 3-CH$_3$-5-CF$_3$ | CF$_3$ | Q-1 | H | D-52a |
| 3-CH$_3$-5-CF$_3$ | CF$_3$ | Q-2 | H | OCH$_3$ |
| 3-CH$_3$-5-CF$_3$ | CF$_3$ | Q-2 | H | OEt |
| 3-CH$_3$-5-CF$_3$ | CF$_3$ | Q-2 | CH$_3$ | OCH$_3$ |
| 3-CH$_3$-5-CF$_3$ | CF$_3$ | Q-2 | CH$_3$ | OEt |
| 3-CH$_3$-5-CF$_3$ | CF$_3$ | Q-2 | Et | OCH$_3$ |
| 3-CH$_3$-5-CF$_3$ | CF$_3$ | Q-2 | CH$_2$CF$_3$ | OCH$_3$ |
| 3,5-(CF$_3$)$_2$ | CHF$_2$ | Q-1 | H | C(O)NHCH$_2$CF$_3$ |
| 3,5-(CF$_3$)$_2$ | CHF$_2$ | Q-1 | H | D-52a |
| 3,5-(CF$_3$)$_2$ | CHF$_2$ | Q-2 | H | OCH$_3$ |
| 3,5-(CF$_3$)$_2$ | CHF$_2$ | Q-2 | H | OEt |
| 3,5-(CF$_3$)$_2$ | CHF$_2$ | Q-2 | CH$_3$ | OCH$_3$ |
| 3,5-(CF$_3$)$_2$ | CHF$_2$ | Q-2 | CH$_3$ | OEt |
| 3,5-(CF$_3$)$_2$ | CHF$_2$ | Q-2 | Et | OCH$_3$ |
| 3,5-(CF$_3$)$_2$ | CHF$_2$ | Q-2 | CH$_2$CF$_3$ | OCH$_3$ |
| 3,5-(CF$_3$)$_2$ | CHFCl | Q-2 | H | OCH$_3$ |
| 3,5-(CF$_3$)$_2$ | CHFCl | Q-2 | H | OEt |
| 3,5-(CF$_3$)$_2$ | CHFCl | Q-2 | CH$_3$ | OCH$_3$ |
| 3,5-(CF$_3$)$_2$ | CHCl$_2$ | Q-2 | H | OCH$_3$ |
| 3,5-(CF$_3$)$_2$ | CHCl$_2$ | Q-2 | H | OEt |
| 3,5-(CF$_3$)$_2$ | CHCl$_2$ | Q-2 | CH$_3$ | OCH$_3$ |
| 3,5-(CF$_3$)$_2$ | CHFBr | Q-2 | H | OCH$_3$ |
| 3,5-(CF$_3$)$_2$ | CHFBr | Q-2 | H | OEt |
| 3,5-(CF$_3$)$_2$ | CHFBr | Q-2 | CH$_3$ | OCH$_3$ |
| 3,5-(CF$_3$)$_2$ | CF$_3$ | Q-1 | H | c-Pr |
| 3,5-(CF$_3$)$_2$ | CF$_3$ | Q-1 | H | CF$_3$ |
| 3,5-(CF$_3$)$_2$ | CF$_3$ | Q-1 | C(O)CH$_3$ | CF$_3$ |
| 3,5-(CF$_3$)$_2$ | CF$_3$ | Q-1 | H | CH$_2$CF$_3$ |
| 3,5-(CF$_3$)$_2$ | CF$_3$ | Q-1 | H | CH$_2$OCH$_3$ |
| 3,5-(CF$_3$)$_2$ | CF$_3$ | Q-1 | H | E-6a |
| 3,5-(CF$_3$)$_2$ | CF$_3$ | Q-1 | H | E-7a |
| 3,5-(CF$_3$)$_2$ | CF$_3$ | Q-1 | H | E-12a |
| 3,5-(CF$_3$)$_2$ | CF$_3$ | Q-1 | H | E-25a |
| 3,5-(CF$_3$)$_2$ | CF$_3$ | Q-1 | H | CH=NOCH$_3$ |
| 3,5-(CF$_3$)$_2$ | CF$_3$ | Q-1 | H | C(O)NHCH$_3$ |
| 3,5-(CF$_3$)$_2$ | CF$_3$ | Q-1 | H | C(O)N(CH$_3$)$_2$ |
| 3,5-(CF$_3$)$_2$ | CF$_3$ | Q-1 | H | C(O)NHEt |
| 3,5-(CF$_3$)$_2$ | CF$_3$ | Q-1 | H | C(O)NHPr-i |
| 3,5-(CF$_3$)$_2$ | CF$_3$ | Q-1 | H | C(O)NHCH$_2$CH$_2$F |
| 3,5-(CF$_3$)$_2$ | CF$_3$ | Q-1 | H | C(O)NHCH$_2$CH$_2$Cl |

TABLE 2-continued

| (X)$_m$ | R$^3$ | Q | R$^2$ | R$^1$ |
|---|---|---|---|---|
| 3,5-(CF$_3$)$_2$ | CF$_3$ | Q-1 | H | C(O)NHCH$_2$CF$_3$ |
| 3,5-(CF$_3$)$_2$ | CF$_3$ | Q-1 | H | C(O)NHCH$_2$CH=CH$_2$ |
| 3,5-(CF$_3$)$_2$ | CF$_3$ | Q-1 | H | C(O)NHCH$_2$C≡CH |
| 3,5-(CF$_3$)$_2$ | CF$_3$ | Q-1 | H | CH=CH$_2$ |
| 3,5-(CF$_3$)$_2$ | CF$_3$ | Q-1 | H | Ph-4-F |
| 3,5-(CF$_3$)$_2$ | CF$_3$ | Q-1 | H | Ph-4-NO$_2$ |
| 3,5-(CF$_3$)$_2$ | CF$_3$ | Q-1 | H | Ph-4-CN |
| 3,5-(CF$_3$)$_2$ | CF$_3$ | Q-1 | H | D-1a |
| 3,5-(CF$_3$)$_2$ | CF$_3$ | Q-1 | H | (D-8b)CH$_3$ |
| 3,5-(CF$_3$)$_2$ | CF$_3$ | Q-1 | H | D-11a |
| 3,5-(CF$_3$)$_2$ | CF$_3$ | Q-1 | H | D-14a |
| 3,5-(CF$_3$)$_2$ | CF$_3$ | Q-1 | H | (D-15a)CH$_3$ |
| 3,5-(CF$_3$)$_2$ | CF$_3$ | Q-1 | H | (D-16b)Cl |
| 3,5-(CF$_3$)$_2$ | CF$_3$ | Q-1 | H | (D-17b)Cl |
| 3,5-(CF$_3$)$_2$ | CF$_3$ | Q-1 | H | D-21a |
| 3,5-(CF$_3$)$_2$ | CF$_3$ | Q-1 | H | D-22a |
| 3,5-(CF$_3$)$_2$ | CF$_3$ | Q-1 | C(O)CH$_3$ | D-22a |
| 3,5-(CF$_3$)$_2$ | CF$_3$ | Q-1 | C(O)Et | D-22a |
| 3,5-(CF$_3$)$_2$ | CF$_3$ | Q-1 | H | D-23a |
| 3,5-(CF$_3$)$_2$ | CF$_3$ | Q-1 | H | D-24a |
| 3,5-(CF$_3$)$_2$ | CF$_3$ | Q-1 | H | D-28a |
| 3,5-(CF$_3$)$_2$ | CF$_3$ | Q-1 | H | (D-29b)CH$_3$ |
| 3,5-(CF$_3$)$_2$ | CF$_3$ | Q-1 | H | D-34a |
| 3,5-(CF$_3$)$_2$ | CF$_3$ | Q-1 | H | D-35a |
| 3,5-(CF$_3$)$_2$ | CF$_3$ | Q-1 | H | D-41a |
| 3,5-(CF$_3$)$_2$ | CF$_3$ | Q-1 | H | D-52a |
| 3,5-(CF$_3$)$_2$ | CF$_3$ | Q-1 | Et | D-52a |
| 3,5-(CF$_3$)$_2$ | CF$_3$ | Q-1 | CH$_2$OCH$_3$ | D-52a |
| 3,5-(CF$_3$)$_2$ | CF$_3$ | Q-1 | CH$_2$OC(O)CH$_3$ | D-52a |
| 3,5-(CF$_3$)$_2$ | CF$_3$ | Q-1 | CH$_2$CN | D-52a |
| 3,5-(CF$_3$)$_2$ | CF$_3$ | Q-1 | CH$_2$C≡CH | D-52a |
| 3,5-(CF$_3$)$_2$ | CF$_3$ | Q-1 | C(O)CH$_3$ | D-52a |
| 3,5-(CF$_3$)$_2$ | CF$_3$ | Q-1 | C(O)Et | D-52a |
| 3,5-(CF$_3$)$_2$ | CF$_3$ | Q-1 | C(O)Pr-i | D-52a |
| 3,5-(CF$_3$)$_2$ | CF$_3$ | Q-1 | C(O)Pr-c | D-52a |
| 3,5-(CF$_3$)$_2$ | CF$_3$ | Q-1 | C(O)Bu-t | D-52a |
| 3,5-(CF$_3$)$_2$ | CF$_3$ | Q-1 | C(O)CH$_2$OCH$_3$ | D-52a |
| 3,5-(CF$_3$)$_2$ | CF$_3$ | Q-1 | C(O)CH=CH$_2$ | D-52a |
| 3,5-(CF$_3$)$_2$ | CF$_3$ | Q-1 | C(O)OCH$_3$ | D-52a |
| 3,5-(CF$_3$)$_2$ | CF$_3$ | Q-1 | H | D-53a |
| 3,5-(CF$_3$)$_2$ | CF$_3$ | Q-1 | H | D-54a |
| 3,5-(CF$_3$)$_2$ | CF$_3$ | Q-1 | H | D-55a |
| 3,5-(CF$_3$)$_2$ | CF$_3$ | Q-1 | H | D-56a |
| 3,5-(CF$_3$)$_2$ | CF$_3$ | Q-1 | H | D-58a |
| 3,5-(CF$_3$)$_2$ | CF$_3$ | Q-1 | H | D-59a |
| 3,5-(CF$_3$)$_2$ | CF$_3$ | Q-1 | H | OCH$_3$ |
| 3,5-(CF$_3$)$_2$ | CF$_3$ | Q-1 | H | OEt |
| 3,5-(CF$_3$)$_2$ | CF$_3$ | Q-1 | H | OCH$_2$CF$_3$ |
| 3,5-(CF$_3$)$_2$ | CF$_3$ | Q-2 | H | OCH$_3$ |
| 3,5-(CF$_3$)$_2$ | CF$_3$ | Q-2 | H | OEt |
| 3,5-(CF$_3$)$_2$ | CF$_3$ | Q-2 | H | OPr-n |
| 3,5-(CF$_3$)$_2$ | CF$_3$ | Q-2 | H | OPr-i |
| 3,5-(CF$_3$)$_2$ | CF$_3$ | Q-2 | H | OPr-c |
| 3,5-(CF$_3$)$_2$ | CF$_3$ | Q-2 | H | OCH$_2$F |
| 3,5-(CF$_3$)$_2$ | CF$_3$ | Q-2 | H | OCHF$_2$ |
| 3,5-(CF$_3$)$_2$ | CF$_3$ | Q-2 | H | OCH$_2$CH$_2$F |
| 3,5-(CF$_3$)$_2$ | CF$_3$ | Q-2 | H | OCHFCH$_3$ |
| 3,5-(CF$_3$)$_2$ | CF$_3$ | Q-2 | H | OCH$_2$CH$_2$Cl |
| 3,5-(CF$_3$)$_2$ | CF$_3$ | Q-2 | H | OCH$_2$CHF$_2$ |
| 3,5-(CF$_3$)$_2$ | CF$_3$ | Q-2 | H | OCH$_2$CF$_3$ |
| 3,5-(CF$_3$)$_2$ | CF$_3$ | Q-2 | H | OCH$_2$CF$_2$Cl |
| 3,5-(CF$_3$)$_2$ | CF$_3$ | Q-2 | H | OCH$_2$CH$_2$CH$_2$F |
| 3,5-(CF$_3$)$_2$ | CF$_3$ | Q-2 | H | OCH(CH$_3$)CH$_2$F |
| 3,5-(CF$_3$)$_2$ | CF$_3$ | Q-2 | H | OCH(CH$_2$F)$_2$ |
| 3,5-(CF$_3$)$_2$ | CF$_3$ | Q-2 | H | OCH$_2$CH$_2$CF$_3$ |
| 3,5-(CF$_3$)$_2$ | CF$_3$ | Q-2 | H | OCH(CH$_3$)CF$_3$ |
| 3,5-(CF$_3$)$_2$ | CF$_3$ | Q-2 | H | OCH$_2$CF$_2$CHF$_2$ |
| 3,5-(CF$_3$)$_2$ | CF$_3$ | Q-2 | H | OCH$_2$CF$_2$CF$_3$ |
| 3,5-(CF$_3$)$_2$ | CF$_3$ | Q-2 | H | OCF$_2$CHFCF$_3$ |
| 3,5-(CF$_3$)$_2$ | CF$_3$ | Q-2 | H | OCH(CF$_3$)$_2$ |
| 3,5-(CF$_3$)$_2$ | CF$_3$ | Q-2 | H | OCH$_2$CH$_2$OCH$_3$ |
| 3,5-(CF$_3$)$_2$ | CF$_3$ | Q-2 | H | OCH$_2$CH$_2$SCH$_3$ |
| 3,5-(CF$_3$)$_2$ | CF$_3$ | Q-2 | H | OCH$_2$CN |
| 3,5-(CF$_3$)$_2$ | CF$_3$ | Q-2 | H | OCH(CH$_3$)CN |
| 3,5-(CF$_3$)$_2$ | CF$_3$ | Q-2 | H | OCH$_2$CH$_2$CN |
| 3,5-(CF$_3$)$_2$ | CF$_3$ | Q-2 | H | OCH$_2$C(O)OCH$_3$ |
| 3,5-(CF$_3$)$_2$ | CF$_3$ | Q-2 | H | OCH(CH$_3$)C(O)OCH$_3$ |
| 3,5-(CF$_3$)$_2$ | CF$_3$ | Q-2 | H | OCH$_2$C(O)NH$_2$ |

TABLE 2-continued

| $(X)_m$ | $R^3$ | Q | $R^2$ | $R^1$ |
|---|---|---|---|---|
| 3,5-$(CF_3)_2$ | $CF_3$ | Q-2 | H | $OCH(CH_3)C(O)NH_2$ |
| 3,5-$(CF_3)_2$ | $CF_3$ | Q-2 | H | $OCH_2C(S)NH_2$ |
| 3,5-$(CF_3)_2$ | $CF_3$ | Q-2 | H | $OCH(CH_3)C(S)NH_2$ |
| 3,5-$(CF_3)_2$ | $CF_3$ | Q-2 | H | $OCH_2CH=CH_2$ |
| 3,5-$(CF_3)_2$ | $CF_3$ | Q-2 | H | $OCH_2CF=CH_2$ |
| 3,5-$(CF_3)_2$ | $CF_3$ | Q-2 | H | $OCH_2CCl=CH_2$ |
| 3,5-$(CF_3)_2$ | $CF_3$ | Q-2 | H | $OCH_2C\equiv CH$ |
| 3,5-$(CF_3)_2$ | $CF_3$ | Q-2 | H | $OCH_2Ph$ |
| 3,5-$(CF_3)_2$ | $CF_3$ | Q-2 | H | $SCH_3$ |
| 3,5-$(CF_3)_2$ | $CF_3$ | Q-2 | H | SEt |
| 3,5-$(CF_3)_2$ | $CF_3$ | Q-2 | H | SPr-n |
| 3,5-$(CF_3)_2$ | $CF_3$ | Q-2 | H | SPr-i |
| 3,5-$(CF_3)_2$ | $CF_3$ | Q-2 | H | $SCH_2CH_2F$ |
| 3,5-$(CF_3)_2$ | $CF_3$ | Q-2 | H | $SCH_2CHF_2$ |
| 3,5-$(CF_3)_2$ | $CF_3$ | Q-2 | H | $SCH_2CF_3$ |
| 3,5-$(CF_3)_2$ | $CF_3$ | Q-2 | H | $SCH_2CH_2OCH_3$ |
| 3,5-$(CF_3)_2$ | $CF_3$ | Q-2 | H | $SCH_2CH=CH_2$ |
| 3,5-$(CF_3)_2$ | $CF_3$ | Q-2 | H | $SCH_2C\equiv CH$ |
| 3,5-$(CF_3)_2$ | $CF_3$ | Q-2 | H | $NHCH_3$ |
| 3,5-$(CF_3)_2$ | $CF_3$ | Q-2 | H | $N(CH_3)_2$ |
| 3,5-$(CF_3)_2$ | $CF_3$ | Q-2 | H | NHEt |
| 3,5-$(CF_3)_2$ | $CF_3$ | Q-2 | H | $NHCH_2CH_2F$ |
| 3,5-$(CF_3)_2$ | $CF_3$ | Q-2 | H | $NHCH_2CHF_2$ |
| 3,5-$(CF_3)_2$ | $CF_3$ | Q-2 | H | $NHCH_2CF_3$ |
| 3,5-$(CF_3)_2$ | $CF_3$ | Q-2 | H | $NHCH_2CH_2OCH_3$ |
| 3,5-$(CF_3)_2$ | $CF_3$ | Q-2 | H | $NHCH_2CH=CH_2$ |
| 3,5-$(CF_3)_2$ | $CF_3$ | Q-2 | H | $NHCH_2C\equiv CH$ |
| 3,5-$(CF_3)_2$ | $CF_3$ | Q-2 | H | NHCN |
| 3,5-$(CF_3)_2$ | $CF_3$ | Q-2 | H | $NHOCH_3$ |
| 3,5-$(CF_3)_2$ | $CF_3$ | Q-2 | H | NHOEt |
| 3,5-$(CF_3)_2$ | $CF_3$ | Q-2 | H | $N(CH_3)OCH_3$ |
| 3,5-$(CF_3)_2$ | $CF_3$ | Q-2 | H | $NHNO_2$ |
| 3,5-$(CF_3)_2$ | $CF_3$ | Q-2 | $CH_3$ | $OCH_3$ |
| 3,5-$(CF_3)_2$ | $CF_3$ | Q-2 | $CH_3$ | OEt |
| 3,5-$(CF_3)_2$ | $CF_3$ | Q-2 | $CH_3$ | OPr-i |
| 3,5-$(CF_3)_2$ | $CF_3$ | Q-2 | $CH_3$ | OPr-c |
| 3,5-$(CF_3)_2$ | $CF_3$ | Q-2 | $CH_3$ | $SCH_3$ |
| 3,5-$(CF_3)_2$ | $CF_3$ | Q-2 | $CH_3$ | SEt |
| 3,5-$(CF_3)_2$ | $CF_3$ | Q-2 | Et | $OCH_3$ |
| 3,5-$(CF_3)_2$ | $CF_3$ | Q-2 | Et | OEt |
| 3,5-$(CF_3)_2$ | $CF_3$ | Q-2 | n-Pr | $OCH_3$ |
| 3,5-$(CF_3)_2$ | $CF_3$ | Q-2 | i-Pr | $OCH_3$ |
| 3,5-$(CF_3)_2$ | $CF_3$ | Q-2 | c-Pr | $OCH_3$ |
| 3,5-$(CF_3)_2$ | $CF_3$ | Q-2 | $CH_2CH_2F$ | $OCH_3$ |
| 3,5-$(CF_3)_2$ | $CF_3$ | Q-2 | $CH_2CHF_2$ | $OCH_3$ |
| 3,5-$(CF_3)_2$ | $CF_3$ | Q-2 | $CH_2CF_3$ | $OCH_3$ |
| 3,5-$(CF_3)_2$ | $CF_3$ | Q-2 | $CH_2CN$ | $OCH_3$ |
| 3,5-$(CF_3)_2$ | $CF_3$ | Q-2 | $CH_2CH=CH_2$ | $OCH_3$ |
| 3,5-$(CF_3)_2$ | $CF_3$ | Q-2 | $CH_2C\equiv CH$ | $OCH_3$ |
| 3,5-$(CF_3)_2$ | $CF_3$ | Q-2 | $OCH_3$ | $OCH_3$ |
| 3,5-$(CF_3)_2$ | $CF_3$ | Q-2 | OEt | $OCH_3$ |
| 3,5-$(CF_3)_2$ | $CF_3$ | Q-2 | $NHCH_3$ | $OCH_3$ |
| 3,5-$(CF_3)_2$ | $CF_3$ | Q-2 | $N(CH_3)_2$ | $OCH_3$ |
| 3,5-$(CF_3)_2$ | $CF_3$ | Q-2 | $NHC(O)OCH_3$ | $OCH_3$ |
| 3,5-$(CF_3)_2$ | $CF_3$ | Q-3 | $CH_3$ | $OCH_3$ |
| 3,5-$(CF_3)_2$ | $CF_3$ | Q-3 | $CH_3$ | OEt |
| 3,5-$(CF_3)_2$ | $CF_3$ | Q-3 | $CH_3$ | OPr-i |
| 3,5-$(CF_3)_2$ | $CF_3$ | Q-3 | $CH_3$ | OPr-c |
| 3,5-$(CF_3)_2$ | $CF_3$ | Q-3 | $CH_3$ | $SCH_3$ |
| 3,5-$(CF_3)_2$ | $CF_3$ | Q-3 | $CH_3$ | SEt |
| 3,5-$(CF_3)_2$ | $CF_3$ | Q-3 | Et | $OCH_3$ |
| 3,5-$(CF_3)_2$ | $CF_3$ | Q-3 | Et | OEt |
| 3,5-$(CF_3)_2$ | $CF_3$ | Q-3 | n-Pr | $OCH_3$ |
| 3,5-$(CF_3)_2$ | $CF_3$ | Q-3 | i-Pr | $OCH_3$ |
| 3,5-$(CF_3)_2$ | $CF_3$ | Q-3 | c-Pr | $OCH_3$ |
| 3,5-$(CF_3)_2$ | $CF_3$ | Q-3 | $CH_2CHF_2$ | $OCH_3$ |
| 3,5-$(CF_3)_2$ | $CF_3$ | Q-3 | $CH_2CF_3$ | $OCH_3$ |
| 3,5-$(CF_3)_2$ | $CF_3$ | Q-3 | $CH_2CN$ | $OCH_3$ |
| 3,5-$(CF_3)_2$ | $CF_3$ | Q-3 | $CH_2C\equiv CH$ | $OCH_3$ |
| 3,5-$(CF_3)_2$ | $CF_2Cl$ | Q-1 | H | $CF_3$ |
| 3,5-$(CF_3)_2$ | $CF_2Cl$ | Q-1 | H | $C(O)NHCH_2CF_3$ |
| 3,5-$(CF_3)_2$ | $CF_2Cl$ | Q-1 | H | D-22a |
| 3,5-$(CF_3)_2$ | $CF_2Cl$ | Q-1 | H | D-52a |
| 3,5-$(CF_3)_2$ | $CF_2Cl$ | Q-2 | H | $OCH_3$ |
| 3,5-$(CF_3)_2$ | $CF_2Cl$ | Q-2 | H | OEt |
| 3,5-$(CF_3)_2$ | $CF_2Cl$ | Q-2 | H | $OCH_2CF_3$ |
| 3,5-$(CF_3)_2$ | $CF_2Cl$ | Q-2 | H | $OCH_2C\equiv CH$ |
| 3,5-$(CF_3)_2$ | $CF_2Cl$ | Q-2 | $CH_3$ | $OCH_3$ |

TABLE 2-continued

| (X)$_m$ | R$^3$ | Q | R$^2$ | R$^1$ |
| --- | --- | --- | --- | --- |
| 3,5-(CF$_3$)$_2$ | CF$_2$Cl | Q-2 | CH$_3$ | OEt |
| 3,5-(CF$_3$)$_2$ | CF$_2$Cl | Q-2 | Et | OCH$_3$ |
| 3,5-(CF$_3$)$_2$ | CF$_2$Cl | Q-2 | Et | OEt |
| 3,5-(CF$_3$)$_2$ | CF$_2$Cl | Q-2 | n-Pr | OCH$_3$ |
| 3,5-(CF$_3$)$_2$ | CF$_2$Cl | Q-2 | i-Pr | OCH$_3$ |
| 3,5-(CF$_3$)$_2$ | CF$_2$Cl | Q-2 | CH$_2$CF$_3$ | OCH$_3$ |
| 3,5-(CF$_3$)$_2$ | CF$_2$Cl | Q-2 | CH$_2$C≡CH | OCH$_3$ |
| 3,5-(CF$_3$)$_2$ | CF$_2$Br | Q-1 | H | C(O)NHCH$_2$CF$_3$ |
| 3,5-(CF$_3$)$_2$ | CF$_2$Br | Q-1 | H | D-52a |
| 3,5-(CF$_3$)$_2$ | CF$_2$Br | Q-2 | H | OCH$_3$ |
| 3,5-(CF$_3$)$_2$ | CF$_2$Br | Q-2 | H | OEt |
| 3,5-(CF$_3$)$_2$ | CF$_2$Br | Q-2 | CH$_3$ | OCH$_3$ |
| 3,5-(CF$_3$)$_2$ | CF$_2$Br | Q-2 | CH$_3$ | OEt |
| 3,5-(CF$_3$)$_2$ | CF$_2$Br | Q-2 | Et | OCH$_3$ |
| 3,5-(CF$_3$)$_2$ | CF$_2$Br | Q-2 | CH$_2$CF$_3$ | OCH$_3$ |
| 3,5-(CF$_3$)$_2$ | CF$_2$CHF$_2$ | Q-1 | H | C(O)NHCH$_2$CF$_3$ |
| 3,5-(CF$_3$)$_2$ | CF$_2$CHF$_2$ | Q-1 | H | D-52a |
| 3,5-(CF$_3$)$_2$ | CF$_2$CHF$_2$ | Q-2 | H | OCH$_3$ |
| 3,5-(CF$_3$)$_2$ | CF$_2$CHF$_2$ | Q-2 | H | OEt |
| 3,5-(CF$_3$)$_2$ | CF$_2$CHF$_2$ | Q-2 | CH$_3$ | OCH$_3$ |
| 3,5-(CF$_3$)$_2$ | CF$_2$CHF$_2$ | Q-2 | CH$_3$ | OEt |
| 3,5-(CF$_3$)$_2$ | CF$_2$CHF$_2$ | Q-2 | Et | OCH$_3$ |
| 3,5-(CF$_3$)$_2$ | CF$_2$CHF$_2$ | Q-2 | CH$_2$CF$_3$ | OCH$_3$ |
| 3,5-(CF$_3$)$_2$ | CF$_2$CF$_3$ | Q-2 | H | OCH$_3$ |
| 3,5-(CF$_3$)$_2$ | CF$_2$CF$_3$ | Q-2 | H | OEt |
| 3,5-(CF$_3$)$_2$ | CF$_2$CF$_3$ | Q-2 | CH$_3$ | OCH$_3$ |
| 3,5-(CF$_3$)$_2$ | CF$_2$OCH$_3$ | Q-2 | H | OCH$_3$ |
| 3,5-(CF$_3$)$_2$ | CF$_2$OCH$_3$ | Q-2 | H | OEt |
| 3,5-(CF$_3$)$_2$ | CF$_2$OCH$_3$ | Q-2 | CH$_3$ | OCH$_3$ |
| 3,5-(CF$_3$)$_2$ | T-3 | Q-2 | H | OCH$_3$ |
| 3,5-(CF$_3$)$_2$ | T-3 | Q-2 | H | OEt |
| 3,5-(CF$_3$)$_2$ | T-3 | Q-2 | CH$_3$ | OCH$_3$ |
| 3-Cl-5-CF$_2$CF$_3$ | CF$_3$ | Q-2 | H | OCH$_3$ |
| 3-Cl-5-CF$_2$CF$_3$ | CF$_3$ | Q-2 | H | OEt |
| 3-Cl-5-CF$_2$CF$_3$ | CF$_3$ | Q-2 | CH$_3$ | OCH$_3$ |
| 3-Br-5-CF$_2$CF$_3$ | CF$_3$ | Q-2 | H | OCH$_3$ |
| 3-Br-5-CF$_2$CF$_3$ | CF$_3$ | Q-2 | H | OEt |
| 3-Br-5-CF$_2$CF$_3$ | CF$_3$ | Q-2 | CH$_3$ | OCH$_3$ |
| 3-CF$_3$-5-OCH$_3$ | CF$_3$ | Q-1 | H | C(O)NHCH$_2$CF$_3$ |
| 3-CF$_3$-5-OCH$_3$ | CF$_3$ | Q-1 | H | D-52a |
| 3-CF$_3$-5-OCH$_3$ | CF$_3$ | Q-2 | H | OCH$_3$ |
| 3-CF$_3$-5-OCH$_3$ | CF$_3$ | Q-2 | H | OEt |
| 3-CF$_3$-5-OCH$_3$ | CF$_3$ | Q-2 | CH$_3$ | OCH$_3$ |
| 3-CF$_3$-5-OCH$_3$ | CF$_3$ | Q-2 | CH$_3$ | OEt |
| 3-CF$_3$-5-OCH$_3$ | CF$_3$ | Q-2 | Et | OCH$_3$ |
| 3-CF$_3$-5-OCH$_3$ | CF$_3$ | Q-2 | CH$_2$CF$_3$ | OCH$_3$ |
| 3-Cl-5-OCHF$_2$ | CF$_3$ | Q-1 | H | CF$_3$ |
| 3-Cl-5-OCHF$_2$ | CF$_3$ | Q-1 | H | C(O)NHCH$_2$CF$_3$ |
| 3-Cl-5-OCHF$_2$ | CF$_3$ | Q-1 | H | D-22a |
| 3-Cl-5-OCHF$_2$ | CF$_3$ | Q-1 | H | D-52a |
| 3-Cl-5-OCHF$_2$ | CF$_3$ | Q-2 | H | OCH$_3$ |
| 3-Cl-5-OCHF$_2$ | CF$_3$ | Q-2 | H | OEt |
| 3-Cl-5-OCHF$_2$ | CF$_3$ | Q-2 | H | OCH$_2$CF$_3$ |
| 3-Cl-5-OCHF$_2$ | CF$_3$ | Q-2 | H | OCH$_2$C≡CH |
| 3-Cl-5-OCHF$_2$ | CF$_3$ | Q-2 | CH$_3$ | OCH$_3$ |
| 3-Cl-5-OCHF$_2$ | CF$_3$ | Q-2 | CH$_3$ | OEt |
| 3-Cl-5-OCHF$_2$ | CF$_3$ | Q-2 | Et | OCH$_3$ |
| 3-Cl-5-OCHF$_2$ | CF$_3$ | Q-2 | Et | OEt |
| 3-Cl-5-OCHF$_2$ | CF$_3$ | Q-2 | n-Pr | OCH$_3$ |
| 3-Cl-5-OCHF$_2$ | CF$_3$ | Q-2 | i-Pr | OCH$_3$ |
| 3-Cl-5-OCHF$_2$ | CF$_3$ | Q-2 | CH$_2$CF$_3$ | OCH$_3$ |
| 3-Cl-5-OCHF$_2$ | CF$_3$ | Q-2 | CH$_2$C≡CH | OCH$_3$ |
| 3-Cl-5-OCHF$_2$ | CF$_2$Cl | Q-1 | H | C(O)NHCH$_2$CF$_3$ |
| 3-Cl-5-OCHF$_2$ | CF$_2$Cl | Q-1 | H | D-52a |
| 3-Cl-5-OCHF$_2$ | CF$_2$Cl | Q-2 | H | OCH$_3$ |
| 3-Cl-5-OCHF$_2$ | CF$_2$Cl | Q-2 | H | OEt |
| 3-Cl-5-OCHF$_2$ | CF$_2$Cl | Q-2 | CH$_3$ | OCH$_3$ |
| 3-Cl-5-OCHF$_2$ | CF$_2$Cl | Q-2 | CH$_3$ | OEt |
| 3-Cl-5-OCHF$_2$ | CF$_2$Cl | Q-2 | Et | OCH$_3$ |
| 3-Cl-5-OCHF$_2$ | CF$_2$Cl | Q-2 | CH$_2$CF$_3$ | OCH$_3$ |
| 3-Br-5-OCHF$_2$ | CF$_3$ | Q-1 | H | C(O)NHCH$_2$CF$_3$ |
| 3-Br-5-OCHF$_2$ | CF$_3$ | Q-1 | H | D-22a |
| 3-Br-5-OCHF$_2$ | CF$_3$ | Q-1 | H | D-52a |
| 3-Br-5-OCHF$_2$ | CF$_3$ | Q-2 | H | OCH$_3$ |
| 3-Br-5-OCHF$_2$ | CF$_3$ | Q-2 | H | OEt |
| 3-Br-5-OCHF$_2$ | CF$_3$ | Q-2 | CH$_3$ | OCH$_3$ |
| 3-Br-5-OCHF$_2$ | CF$_3$ | Q-2 | CH$_3$ | OEt |
| 3-Br-5-OCHF$_2$ | CF$_3$ | Q-2 | Et | OCH$_3$ |

TABLE 2-continued

| (X)$_m$ | R$^3$ | Q | R$^2$ | R$^1$ |
|---|---|---|---|---|
| 3-Br-5-OCHF$_2$ | CF$_3$ | Q-2 | Et | OEt |
| 3-Br-5-OCHF$_2$ | CF$_3$ | Q-2 | CH$_2$CF$_3$ | OCH$_3$ |
| 3-Br-5-OCHF$_2$ | CF$_3$ | Q-2 | CH$_2$C≡CH | OCH$_3$ |
| 3-Br-5-OCHF$_2$ | CF$_2$Cl | Q-2 | H | OCH$_3$ |
| 3-Br-5-OCHF$_2$ | CF$_2$Cl | Q-2 | H | OEt |
| 3-Br-5-OCHF$_2$ | CF$_2$Cl | Q-2 | CH$_3$ | OCH$_3$ |
| 3-CF$_3$-5-OCHF$_2$ | CF$_3$ | Q-1 | H | C(O)NHCH$_2$CF$_3$ |
| 3-CF$_3$-5-OCHF$_2$ | CF$_3$ | Q-1 | H | D-22a |
| 3-CF$_3$-5-OCHF$_2$ | CF$_3$ | Q-1 | H | D-52a |
| 3-CF$_3$-5-OCHF$_2$ | CF$_3$ | Q-2 | H | OCH$_3$ |
| 3-CF$_3$-5-OCHF$_2$ | CF$_3$ | Q-2 | H | OEt |
| 3-CF$_3$-5-OCHF$_2$ | CF$_3$ | Q-2 | CH$_3$ | OCH$_3$ |
| 3-CF$_3$-5-OCHF$_2$ | CF$_3$ | Q-2 | CH$_3$ | OEt |
| 3-CF$_3$-5-OCHF$_2$ | CF$_3$ | Q-2 | Et | OCH$_3$ |
| 3-CF$_3$-5-OCHF$_2$ | CF$_3$ | Q-2 | Et | OEt |
| 3-CF$_3$-5-OCHF$_2$ | CF$_3$ | Q-2 | CH$_2$CF$_3$ | OCH$_3$ |
| 3-CF$_3$-5-OCHF$_2$ | CF$_3$ | Q-2 | CH$_2$C≡CH | OCH$_3$ |
| 3-CF$_3$-5-OCHF$_2$ | CF$_2$Cl | Q-2 | H | OCH$_3$ |
| 3-CF$_3$-5-OCHF$_2$ | CF$_2$Cl | Q-2 | H | OEt |
| 3-CF$_3$-5-OCHF$_2$ | CF$_2$Cl | Q-2 | CH$_3$ | OCH$_3$ |
| 3-Cl-5-OCF$_3$ | CF$_3$ | Q-1 | H | CF$_3$ |
| 3-Cl-5-OCF$_3$ | CF$_3$ | Q-1 | H | C(O)NHCH$_2$CF$_3$ |
| 3-Cl-5-OCF$_3$ | CF$_3$ | Q-1 | H | D-22a |
| 3-Cl-5-OCF$_3$ | CF$_3$ | Q-1 | H | D-52a |
| 3-Cl-5-OCF$_3$ | CF$_3$ | Q-2 | H | OCH$_3$ |
| 3-Cl-5-OCF$_3$ | CF$_3$ | Q-2 | H | OEt |
| 3-Cl-5-OCF$_3$ | CF$_3$ | Q-2 | H | OCH$_2$CF$_3$ |
| 3-Cl-5-OCF$_3$ | CF$_3$ | Q-2 | H | OCH$_2$C≡CH |
| 3-Cl-5-OCF$_3$ | CF$_3$ | Q-2 | CH$_3$ | OCH$_3$ |
| 3-Cl-5-OCF$_3$ | CF$_3$ | Q-2 | CH$_3$ | OEt |
| 3-Cl-5-OCF$_3$ | CF$_3$ | Q-2 | Et | OCH$_3$ |
| 3-Cl-5-OCF$_3$ | CF$_3$ | Q-2 | Et | OEt |
| 3-Cl-5-OCF$_3$ | CF$_3$ | Q-2 | n-Pr | OCH$_3$ |
| 3-Cl-5-OCF$_3$ | CF$_3$ | Q-2 | i-Pr | OCH$_3$ |
| 3-Cl-5-OCF$_3$ | CF$_3$ | Q-2 | CH$_2$CF$_3$ | OCH$_3$ |
| 3-Cl-5-OCF$_3$ | CF$_3$ | Q-2 | CH$_2$C≡CH | OCH$_3$ |
| 3-Cl-5-OCF$_3$ | CF$_2$Cl | Q-1 | H | C(O)NHCH$_2$CF$_3$ |
| 3-Cl-5-OCF$_3$ | CF$_2$Cl | Q-1 | H | D-52a |
| 3-Cl-5-OCF$_3$ | CF$_2$Cl | Q-2 | H | OCH$_3$ |
| 3-Cl-5-OCF$_3$ | CF$_2$Cl | Q-2 | H | OEt |
| 3-Cl-5-OCF$_3$ | CF$_2$Cl | Q-2 | CH$_3$ | OCH$_3$ |
| 3-Cl-5-OCF$_3$ | CF$_2$Cl | Q-2 | CH$_3$ | OEt |
| 3-Cl-5-OCF$_3$ | CF$_2$Cl | Q-2 | Et | OCH$_3$ |
| 3-Cl-5-OCF$_3$ | CF$_2$Cl | Q-2 | CH$_2$CF$_3$ | OCH$_3$ |
| 3-Br-5-OCF$_3$ | CF$_3$ | Q-1 | H | C(O)NHCH$_2$CF$_3$ |
| 3-Br-5-OCF$_3$ | CF$_3$ | Q-1 | H | D-22a |
| 3-Br-5-OCF$_3$ | CF$_3$ | Q-1 | H | D-52a |
| 3-Br-5-OCF$_3$ | CF$_3$ | Q-2 | H | OCH$_3$ |
| 3-Br-5-OCF$_3$ | CF$_3$ | Q-2 | H | OEt |
| 3-Br-5-OCF$_3$ | CF$_3$ | Q-2 | CH$_3$ | OCH$_3$ |
| 3-Br-5-OCF$_3$ | CF$_3$ | Q-2 | CH$_3$ | OEt |
| 3-Br-5-OCF$_3$ | CF$_3$ | Q-2 | Et | OCH$_3$ |
| 3-Br-5-OCF$_3$ | CF$_3$ | Q-2 | Et | OEt |
| 3-Br-5-OCF$_3$ | CF$_3$ | Q-2 | CH$_2$CF$_3$ | OCH$_3$ |
| 3-Br-5-OCF$_3$ | CF$_3$ | Q-2 | CH$_2$C≡CH | OCH$_3$ |
| 3-Br-5-OCF$_3$ | CF$_2$Cl | Q-2 | H | OCH$_3$ |
| 3-Br-5-OCF$_3$ | CF$_2$Cl | Q-2 | H | OEt |
| 3-Br-5-OCF$_3$ | CF$_2$Cl | Q-2 | CH$_3$ | OCH$_3$ |
| 3-CF$_3$-5-OCF$_3$ | CF$_3$ | Q-1 | H | C(O)NHCH$_2$CF$_3$ |
| 3-CF$_3$-5-OCF$_3$ | CF$_3$ | Q-1 | H | D-22a |
| 3-CF$_3$-5-OCF$_3$ | CF$_3$ | Q-1 | H | D-52a |
| 3-CF$_3$-5-OCF$_3$ | CF$_3$ | Q-2 | H | OCH$_3$ |
| 3-CF$_3$-5-OCF$_3$ | CF$_3$ | Q-2 | H | OEt |
| 3-CF$_3$-5-OCF$_3$ | CF$_3$ | Q-2 | CH$_3$ | OCH$_3$ |
| 3-CF$_3$-5-OCF$_3$ | CF$_3$ | Q-2 | CH$_3$ | OEt |
| 3-CF$_3$-5-OCF$_3$ | CF$_3$ | Q-2 | Et | OCH$_3$ |
| 3-CF$_3$-5-OCF$_3$ | CF$_3$ | Q-2 | Et | OEt |
| 3-CF$_3$-5-OCF$_3$ | CF$_3$ | Q-2 | CH$_2$CF$_3$ | OCH$_3$ |
| 3-CF$_3$-5-OCF$_3$ | CF$_3$ | Q-2 | CH$_2$C≡CH | OCH$_3$ |
| 3-CF$_3$-5-OCF$_3$ | CF$_2$Cl | Q-2 | H | OCH$_3$ |
| 3-CF$_3$-5-OCF$_3$ | CF$_2$Cl | Q-2 | H | OEt |
| 3-CF$_3$-5-OCF$_3$ | CF$_2$Cl | Q-2 | CH$_3$ | OCH$_3$ |
| 3-Cl-5-SCF$_3$ | CF$_3$ | Q-1 | H | CF$_3$ |
| 3-Cl-5-SCF$_3$ | CF$_3$ | Q-1 | H | C(O)NHCH$_2$CF$_3$ |
| 3-Cl-5-SCF$_3$ | CF$_3$ | Q-1 | H | D-22a |
| 3-Cl-5-SCF$_3$ | CF$_3$ | Q-1 | H | D-52a |
| 3-Cl-5-SCF$_3$ | CF$_3$ | Q-2 | H | OCH$_3$ |
| 3-Cl-5-SCF$_3$ | CF$_3$ | Q-2 | H | OEt |

TABLE 2-continued

| (X)$_m$ | R$^3$ | Q | R$^2$ | R$^1$ |
|---|---|---|---|---|
| 3-Cl-5-SCF$_3$ | CF$_3$ | Q-2 | H | OCH$_2$CF$_3$ |
| 3-Cl-5-SCF$_3$ | CF$_3$ | Q-2 | H | OCH$_2$C≡CH |
| 3-Cl-5-SCF$_3$ | CF$_3$ | Q-2 | CH$_3$ | OCH$_3$ |
| 3-Cl-5-SCF$_3$ | CF$_3$ | Q-2 | CH$_3$ | OEt |
| 3-Cl-5-SCF$_3$ | CF$_3$ | Q-2 | Et | OCH$_3$ |
| 3-Cl-5-SCF$_3$ | CF$_3$ | Q-2 | Et | OEt |
| 3-Cl-5-SCF$_3$ | CF$_3$ | Q-2 | n-Pr | OCH$_3$ |
| 3-Cl-5-SCF$_3$ | CF$_3$ | Q-2 | i-Pr | OCH$_3$ |
| 3-Cl-5-SCF$_3$ | CF$_3$ | Q-2 | CH$_2$CF$_3$ | OCH$_3$ |
| 3-Cl-5-SCF$_3$ | CF$_3$ | Q-2 | CH$_2$C≡CH | OCH$_3$ |
| 3-Cl-5-SCF$_3$ | CF$_2$Cl | Q-1 | H | C(O)NHCH$_2$CF$_3$ |
| 3-Cl-5-SCF$_3$ | CF$_2$Cl | Q-1 | H | D-52a |
| 3-Cl-5-SCF$_3$ | CF$_2$Cl | Q-2 | H | OCH$_3$ |
| 3-Cl-5-SCF$_3$ | CF$_2$Cl | Q-2 | H | OEt |
| 3-Cl-5-SCF$_3$ | CF$_2$Cl | Q-2 | CH$_3$ | OCH$_3$ |
| 3-Cl-5-SCF$_3$ | CF$_2$Cl | Q-2 | CH$_3$ | OEt |
| 3-Cl-5-SCF$_3$ | CF$_2$Cl | Q-2 | Et | OCH$_3$ |
| 3-Cl-5-SCF$_3$ | CF$_2$Cl | Q-2 | CH$_2$CF$_3$ | OCH$_3$ |
| 3-Cl-5-S(O)CF$_3$ | CF$_3$ | Q-2 | H | OCH$_3$ |
| 3-Cl-5-S(O)CF$_3$ | CF$_3$ | Q-2 | H | OEt |
| 3-Cl-5-S(O)CF$_3$ | CF$_3$ | Q-2 | CH$_3$ | OCH$_3$ |
| 3-Cl-5-SO$_2$CF$_3$ | CF$_3$ | Q-2 | H | OCH$_3$ |
| 3-Cl-5-SO$_2$CF$_3$ | CF$_3$ | Q-2 | H | OEt |
| 3-Cl-5-SO$_2$CF$_3$ | CF$_3$ | Q-2 | CH$_3$ | OCH$_3$ |
| 3-Br-5-SCF$_3$ | CF$_3$ | Q-1 | H | C(O)NHCH$_2$CF$_3$ |
| 3-Br-5-SCF$_3$ | CF$_3$ | Q-1 | H | D-22a |
| 3-Br-5-SCF$_3$ | CF$_3$ | Q-1 | H | D-52a |
| 3-Br-5-SCF$_3$ | CF$_3$ | Q-2 | H | OCH$_3$ |
| 3-Br-5-SCF$_3$ | CF$_3$ | Q-2 | H | OEt |
| 3-Br-5-SCF$_3$ | CF$_3$ | Q-2 | CH$_3$ | OCH$_3$ |
| 3-Br-5-SCF$_3$ | CF$_3$ | Q-2 | CH$_3$ | OEt |
| 3-Br-5-SCF$_3$ | CF$_3$ | Q-2 | Et | OCH$_3$ |
| 3-Br-5-SCF$_3$ | CF$_3$ | Q-2 | Et | OEt |
| 3-Br-5-SCF$_3$ | CF$_3$ | Q-2 | CH$_2$CF$_3$ | OCH$_3$ |
| 3-Br-5-SCF$_3$ | CF$_3$ | Q-2 | CH$_2$C≡CH | OCH$_3$ |
| 3-Br-5-SCF$_3$ | CF$_2$Cl | Q-2 | H | OCH$_3$ |
| 3-Br-5-SCF$_3$ | CF$_2$Cl | Q-2 | H | OEt |
| 3-Br-5-SCF$_3$ | CF$_2$Cl | Q-2 | CH$_3$ | OCH$_3$ |
| 3-Br-5-S(O)CF$_3$ | CF$_3$ | Q-2 | H | OCH$_3$ |
| 3-Br-5-S(O)CF$_3$ | CF$_3$ | Q-2 | H | OEt |
| 3-Br-5-S(O)CF$_3$ | CF$_3$ | Q-2 | CH$_3$ | OCH$_3$ |
| 3-Br-5-SO$_2$CF$_3$ | CF$_3$ | Q-2 | H | OCH$_3$ |
| 3-Br-5-SO$_2$CF$_3$ | CF$_3$ | Q-2 | H | OEt |
| 3-Br-5-SO$_2$CF$_3$ | CF$_3$ | Q-2 | CH$_3$ | OCH$_3$ |
| 3-Cl-5-SCF$_2$CHFCl | CF$_3$ | Q-2 | H | OCH$_3$ |
| 3-Cl-5-SCF$_2$CHFCl | CF$_3$ | Q-2 | H | OEt |
| 3-Cl-5-SCF$_2$CHFCl | CF$_3$ | Q-2 | CH$_3$ | OCH$_3$ |
| 3-Br-5-SCF$_2$CHFCl | CF$_3$ | Q-2 | H | OCH$_3$ |
| 3-Br-5-SCF$_2$CHFCl | CF$_3$ | Q-2 | H | OEt |
| 3-Br-5-SCF$_2$CHFCl | CF$_3$ | Q-2 | CH$_3$ | OCH$_3$ |
| 3-Cl-5-NO$_2$ | CF$_3$ | Q-2 | H | OCH$_3$ |
| 3-Cl-5-NO$_2$ | CF$_3$ | Q-2 | H | OEt |
| 3-Cl-5-NO$_2$ | CF$_3$ | Q-2 | CH$_3$ | OCH$_3$ |
| 3-Br-5-NO$_2$ | CF$_3$ | Q-2 | H | OCH$_3$ |
| 3-Br-5-NO$_2$ | CF$_3$ | Q-2 | H | OEt |
| 3-Br-5-NO$_2$ | CF$_3$ | Q-2 | CH$_3$ | OCH$_3$ |
| 3-CF$_3$-5-NO$_2$ | CF$_3$ | Q-1 | H | C(O)NHCH$_2$CF$_3$ |
| 3-CF$_3$-5-NO$_2$ | CF$_3$ | Q-1 | H | D-52a |
| 3-CF$_3$-5-NO$_2$ | CF$_3$ | Q-2 | H | OCH$_3$ |
| 3-CF$_3$-5-NO$_2$ | CF$_3$ | Q-2 | H | OEt |
| 3-CF$_3$-5-NO$_2$ | CF$_3$ | Q-2 | CH$_3$ | OCH$_3$ |
| 3-CF$_3$-5-NO$_2$ | CF$_3$ | Q-2 | CH$_3$ | OEt |
| 3-CF$_3$-5-NO$_2$ | CF$_3$ | Q-2 | Et | OCH$_3$ |
| 3-CF$_3$-5-NO$_2$ | CF$_3$ | Q-2 | CH$_2$CF$_3$ | OCH$_3$ |
| 3-Cl-5-CN | CF$_3$ | Q-1 | H | C(O)NHCH$_2$CF$_3$ |
| 3-Cl-5-CN | CF$_3$ | Q-1 | H | D-52a |
| 3-Cl-5-CN | CF$_3$ | Q-2 | H | OCH$_3$ |
| 3-Cl-5-CN | CF$_3$ | Q-2 | H | OEt |
| 3-Cl-5-CN | CF$_3$ | Q-2 | CH$_3$ | OCH$_3$ |
| 3-Cl-5-CN | CF$_3$ | Q-2 | CH$_3$ | OEt |
| 3-Cl-5-CN | CF$_3$ | Q-2 | Et | OCH$_3$ |
| 3-Cl-5-CN | CF$_3$ | Q-2 | CH$_2$CF$_3$ | OCH$_3$ |
| 3-Br-5-CN | CF$_3$ | Q-1 | H | C(O)NHCH$_2$CF$_3$ |
| 3-Br-5-CN | CF$_3$ | Q-1 | H | D-52a |
| 3-Br-5-CN | CF$_3$ | Q-2 | H | OCH$_3$ |
| 3-Br-5-CN | CF$_3$ | Q-2 | H | OEt |
| 3-Br-5-CN | CF$_3$ | Q-2 | CH$_3$ | OCH$_3$ |
| 3-Br-5-CN | CF$_3$ | Q-2 | CH$_3$ | OEt |

TABLE 2-continued

| (X)$_m$ | R$^3$ | Q | R$^2$ | R$^1$ |
|---|---|---|---|---|
| 3-Br-5-CN | CF$_3$ | Q-2 | Et | OCH$_3$ |
| 3-Br-5-CN | CF$_3$ | Q-2 | CH$_2$CF$_3$ | OCH$_3$ |
| 3-CF$_3$-5-CN | CF$_3$ | Q-1 | H | C(O)NHCH$_2$CF$_3$ |
| 3-CF$_3$-5-CN | CF$_3$ | Q-1 | H | D-22a |
| 3-CF$_3$-5-CN | CF$_3$ | Q-1 | H | D-52a |
| 3-CF$_3$-5-CN | CF$_3$ | Q-2 | H | OCH$_3$ |
| 3-CF$_3$-5-CN | CF$_3$ | Q-2 | H | OEt |
| 3-CF$_3$-5-CN | CF$_3$ | Q-2 | CH$_3$ | OCH$_3$ |
| 3-CF$_3$-5-CN | CF$_3$ | Q-2 | CH$_3$ | OEt |
| 3-CF$_3$-5-CN | CF$_3$ | Q-2 | Et | OCH$_3$ |
| 3-CF$_3$-5-CN | CF$_3$ | Q-2 | Et | OEt |
| 3-CF$_3$-5-CN | CF$_3$ | Q-2 | CH$_2$CF$_3$ | OCH$_3$ |
| 3-CF$_3$-5-CN | CF$_3$ | Q-2 | CH$_2$C≡CH | OCH$_3$ |
| 3-CF$_3$-5-CN | CF$_2$Cl | Q-2 | H | OCH$_3$ |
| 3-CF$_3$-5-CN | CF$_2$Cl | Q-2 | H | OEt |
| 3-CF$_3$-5-CN | CF$_2$Cl | Q-2 | CH$_3$ | OCH$_3$ |
| 3,4,5-F$_3$ | CF$_3$ | Q-1 | H | C(O)NHCH$_2$CF$_3$ |
| 3,4,5-F$_3$ | CF$_3$ | Q-1 | H | D-22a |
| 3,4,5-F$_3$ | CF$_3$ | Q-1 | H | D-52a |
| 3,4,5-F$_3$ | CF$_3$ | Q-2 | H | OCH$_3$ |
| 3,4,5-F$_3$ | CF$_3$ | Q-2 | H | OEt |
| 3,4,5-F$_3$ | CF$_3$ | Q-2 | CH$_3$ | OCH$_3$ |
| 3,4,5-F$_3$ | CF$_3$ | Q-2 | CH$_3$ | OEt |
| 3,4,5-F$_3$ | CF$_3$ | Q-2 | Et | OCH$_3$ |
| 3,4,5-F$_3$ | CF$_3$ | Q-2 | Et | OEt |
| 3,4,5-F$_3$ | CF$_3$ | Q-2 | CH$_2$CF$_3$ | OCH$_3$ |
| 3,4,5-F$_3$ | CF$_3$ | Q-2 | CH$_2$C≡CH | OCH$_3$ |
| 3,4,5-F$_3$ | CF$_2$Cl | Q-2 | H | OCH$_3$ |
| 3,4,5-F$_3$ | CF$_2$Cl | Q-2 | H | OEt |
| 3,4,5-F$_3$ | CF$_2$Cl | Q-2 | CH$_3$ | OCH$_3$ |
| 3,5-Cl$_2$-4-F | CHF$_2$ | Q-2 | H | OCH$_3$ |
| 3,5-Cl$_2$-4-F | CHF$_2$ | Q-2 | H | OEt |
| 3,5-Cl$_2$-4-F | CHF$_2$ | Q-2 | CH$_3$ | OCH$_3$ |
| 3,5-Cl$_2$-4-F | CF$_3$ | Q-1 | H | c-Pr |
| 3,5-Cl$_2$-4-F | CF$_3$ | Q-1 | H | CF$_3$ |
| 3,5-Cl$_2$-4-F | CF$_3$ | Q-1 | H | C(O)NHCH$_2$CH$_2$Cl |
| 3,5-Cl$_2$-4-F | CF$_3$ | Q-1 | H | C(O)NHCH$_2$CF$_3$ |
| 3,5-Cl$_2$-4-F | CF$_3$ | Q-1 | H | D-22a |
| 3,5-Cl$_2$-4-F | CF$_3$ | Q-1 | CH$_2$OCH$_3$ | D-52a |
| 3,5-Cl$_2$-4-F | CF$_3$ | Q-1 | CH$_2$CN | D-52a |
| 3,5-Cl$_2$-4-F | CF$_3$ | Q-1 | C(O)CH$_3$ | D-52a |
| 3,5-Cl$_2$-4-F | CF$_3$ | Q-1 | C(O)Et | D-52a |
| 3,5-Cl$_2$-4-F | CF$_3$ | Q-1 | C(O)OCH$_3$ | D-52a |
| 3,5-Cl$_2$-4-F | CF$_3$ | Q-1 | H | D-55a |
| 3,5-Cl$_2$-4-F | CF$_3$ | Q-1 | H | D-58a |
| 3,5-Cl$_2$-4-F | CF$_3$ | Q-2 | H | OCH$_3$ |
| 3,5-Cl$_2$-4-F | CF$_3$ | Q-2 | H | OEt |
| 3,5-Cl$_2$-4-F | CF$_3$ | Q-2 | H | OPr-n |
| 3,5-Cl$_2$-4-F | CF$_3$ | Q-2 | H | OPr-i |
| 3,5-Cl$_2$-4-F | CF$_3$ | Q-2 | H | OPr-c |
| 3,5-Cl$_2$-4-F | CF$_3$ | Q-2 | H | OCH$_2$CHF$_2$ |
| 3,5-Cl$_2$-4-F | CF$_3$ | Q-2 | H | OCH$_2$CF$_3$ |
| 3,5-Cl$_2$-4-F | CF$_3$ | Q-2 | H | OCH$_2$CN |
| 3,5-Cl$_2$-4-F | CF$_3$ | Q-2 | H | OCH$_2$C≡CH |
| 3,5-Cl$_2$-4-F | CF$_3$ | Q-2 | H | SCH$_3$ |
| 3,5-Cl$_2$-4-F | CF$_3$ | Q-2 | H | SEt |
| 3,5-Cl$_2$-4-F | CF$_3$ | Q-2 | H | NHCN |
| 3,5-Cl$_2$-4-F | CF$_3$ | Q-2 | H | NHOCH$_3$ |
| 3,5-Cl$_2$-4-F | CF$_3$ | Q-2 | H | N(CH$_3$)OCH$_3$ |
| 3,5-Cl$_2$-4-F | CF$_3$ | Q-2 | H | NHNO$_2$ |
| 3,5-Cl$_2$-4-F | CF$_3$ | Q-2 | CH$_3$ | OCH$_3$ |
| 3,5-Cl$_2$-4-F | CF$_3$ | Q-2 | CH$_3$ | OEt |
| 3,5-Cl$_2$-4-F | CF$_3$ | Q-2 | CH$_3$ | SCH$_3$ |
| 3,5-Cl$_2$-4-F | CF$_3$ | Q-2 | CH$_3$ | SEt |
| 3,5-Cl$_2$-4-F | CF$_3$ | Q-2 | Et | OCH$_3$ |
| 3,5-Cl$_2$-4-F | CF$_3$ | Q-2 | Et | OEt |
| 3,5-Cl$_2$-4-F | CF$_3$ | Q-2 | n-Pr | OCH$_3$ |
| 3,5-Cl$_2$-4-F | CF$_3$ | Q-2 | i-Pr | OCH$_3$ |
| 3,5-Cl$_2$-4-F | CF$_3$ | Q-2 | c-Pr | OCH$_3$ |
| 3,5-Cl$_2$-4-F | CF$_3$ | Q-2 | CH$_2$CHF$_2$ | OCH$_3$ |
| 3,5-Cl$_2$-4-F | CF$_3$ | Q-2 | CH$_2$CF$_3$ | OCH$_3$ |
| 3,5-Cl$_2$-4-F | CF$_3$ | Q-2 | CH$_2$CN | OCH$_3$ |
| 3,5-Cl$_2$-4-F | CF$_3$ | Q-2 | CH$_2$C≡CH | OCH$_3$ |
| 3,5-Cl$_2$-4-F | CF$_3$ | Q-2 | OCH$_3$ | OCH$_3$ |
| 3,5-Cl$_2$-4-F | CF$_3$ | Q-2 | N(CH$_3$)$_2$ | OCH$_3$ |
| 3,5-Cl$_2$-4-F | CF$_2$Cl | Q-1 | H | C(O)NHCH$_2$CF$_3$ |
| 3,5-Cl$_2$-4-F | CF$_2$Cl | Q-1 | H | D-22a |

TABLE 2-continued

| (X)$_m$ | R$^3$ | Q | R$^2$ | R$^1$ |
|---|---|---|---|---|
| 3,5-Cl$_2$-4-F | CF$_2$Cl | Q-1 | H | D-52a |
| 3,5-Cl$_2$-4-F | CF$_2$Cl | Q-2 | H | OCH$_3$ |
| 3,5-Cl$_2$-4-F | CF$_2$Cl | Q-2 | H | OEt |
| 3,5-Cl$_2$-4-F | CF$_2$Cl | Q-2 | CH$_3$ | OCH$_3$ |
| 3,5-Cl$_2$-4-F | CF$_2$Cl | Q-2 | CH$_3$ | OEt |
| 3,5-Cl$_2$-4-F | CF$_2$Cl | Q-2 | Et | OCH$_3$ |
| 3,5-Cl$_2$-4-F | CF$_2$Cl | Q-2 | Et | OEt |
| 3,5-Cl$_2$-4-F | CF$_2$Cl | Q-2 | CH$_2$CF$_3$ | OCH$_3$ |
| 3,5-Cl$_2$-4-F | CF$_2$Cl | Q-2 | CH$_2$C≡CH | OCH$_3$ |
| 3,5-Cl$_2$-4-F | CF$_2$Br | Q-2 | H | OCH$_3$ |
| 3,5-Cl$_2$-4-F | CF$_2$Br | Q-2 | H | OEt |
| 3,5-Cl$_2$-4-F | CF$_2$Br | Q-2 | CH$_3$ | OCH$_3$ |
| 3,5-Cl$_2$-4-F | CF$_2$CHF$_2$ | Q-2 | H | OCH$_3$ |
| 3,5-Cl$_2$-4-F | CF$_2$CHF$_2$ | Q-2 | H | OEt |
| 3,5-Cl$_2$-4-F | CF$_2$CHF$_2$ | Q-2 | CH$_3$ | OCH$_3$ |
| 3,4,5-Cl$_3$ | CHF$_2$ | Q-2 | H | OCH$_3$ |
| 3,4,5-Cl$_3$ | CHF$_2$ | Q-2 | H | OEt |
| 3,4,5-Cl$_3$ | CHF$_2$ | Q-2 | CH$_3$ | OCH$_3$ |
| 3,4,5-Cl$_3$ | CF$_3$ | Q-1 | H | c-Pr |
| 3,4,5-Cl$_3$ | CF$_3$ | Q-1 | H | CF$_3$ |
| 3,4,5-Cl$_3$ | CF$_3$ | Q-1 | H | C(O)NHCH$_2$CH$_2$Cl |
| 3,4,5-Cl$_3$ | CF$_3$ | Q-1 | H | C(O)NHCH$_2$CF$_3$ |
| 3,4,5-Cl$_3$ | CF$_3$ | Q-1 | H | D-22a |
| 3,4,5-Cl$_3$ | CF$_3$ | Q-1 | H | D-52a |
| 3,4,5-Cl$_3$ | CF$_3$ | Q-1 | CH$_2$OCH$_3$ | D-52a |
| 3,4,5-Cl$_3$ | CF$_3$ | Q-1 | CH$_2$CN | D-52a |
| 3,4,5-Cl$_3$ | CF$_3$ | Q-1 | C(O)CH$_3$ | D-52a |
| 3,4,5-Cl$_3$ | CF$_3$ | Q-1 | C(O)Et | D-52a |
| 3,4,5-Cl$_3$ | CF$_3$ | Q-1 | C(O)OCH$_3$ | D-52a |
| 3,4,5-Cl$_3$ | CF$_3$ | Q-1 | H | D-55a |
| 3,4,5-Cl$_3$ | CF$_3$ | Q-1 | H | D-58a |
| 3,4,5-Cl$_3$ | CF$_3$ | Q-2 | H | OCH$_3$ |
| 3,4,5-Cl$_3$ | CF$_3$ | Q-2 | H | OEt |
| 3,4,5-Cl$_3$ | CF$_3$ | Q-2 | H | OPr-n |
| 3,4,5-Cl$_3$ | CF$_3$ | Q-2 | H | OPr-i |
| 3,4,5-Cl$_3$ | CF$_3$ | Q-2 | H | OPr-c |
| 3,4,5-Cl$_3$ | CF$_3$ | Q-2 | H | OCH$_2$CHF$_2$ |
| 3,4,5-Cl$_3$ | CF$_3$ | Q-2 | H | OCH$_2$CF$_3$ |
| 3,4,5-Cl$_3$ | CF$_3$ | Q-2 | H | OCH$_2$CN |
| 3,4,5-Cl$_3$ | CF$_3$ | Q-2 | H | OCH$_2$C≡CH |
| 3,4,5-Cl$_3$ | CF$_3$ | Q-2 | H | SCH$_3$ |
| 3,4,5-Cl$_3$ | CF$_3$ | Q-2 | H | SEt |
| 3,4,5-Cl$_3$ | CF$_3$ | Q-2 | H | NHCN |
| 3,4,5-Cl$_3$ | CF$_3$ | Q-2 | H | NHOCH$_3$ |
| 3,4,5-Cl$_3$ | CF$_3$ | Q-2 | H | N(CH$_3$)OCH$_3$ |
| 3,4,5-Cl$_3$ | CF$_3$ | Q-2 | H | NHNO$_2$ |
| 3,4,5-Cl$_3$ | CF$_3$ | Q-2 | CH$_3$ | OCH$_3$ |
| 3,4,5-Cl$_3$ | CF$_3$ | Q-2 | CH$_3$ | OEt |
| 3,4,5-Cl$_3$ | CF$_3$ | Q-2 | CH$_3$ | SCH$_3$ |
| 3,4,5-Cl$_3$ | CF$_3$ | Q-2 | CH$_3$ | SEt |
| 3,4,5-Cl$_3$ | CF$_3$ | Q-2 | Et | OCH$_3$ |
| 3,4,5-Cl$_3$ | CF$_3$ | Q-2 | Et | OEt |
| 3,4,5-Cl$_3$ | CF$_3$ | Q-2 | n-Pr | OCH$_3$ |
| 3,4,5-Cl$_3$ | CF$_3$ | Q-2 | i-Pr | OCH$_3$ |
| 3,4,5-Cl$_3$ | CF$_3$ | Q-2 | c-Pr | OCH$_3$ |
| 3,4,5-Cl$_3$ | CF$_3$ | Q-2 | CH$_2$CHF$_2$ | OCH$_3$ |
| 3,4,5-Cl$_3$ | CF$_3$ | Q-2 | CH$_2$CF$_3$ | OCH$_3$ |
| 3,4,5-Cl$_3$ | CF$_3$ | Q-2 | CH$_2$CN | OCH$_3$ |
| 3,4,5-Cl$_3$ | CF$_3$ | Q-2 | CH$_2$C≡CH | OCH$_3$ |
| 3,4,5-Cl$_3$ | CF$_3$ | Q-2 | OCH$_3$ | OCH$_3$ |
| 3,4,5-Cl$_3$ | CF$_3$ | Q-2 | N(CH$_3$)$_2$ | OCH$_3$ |
| 3,4,5-Cl$_3$ | CF$_2$Cl | Q-1 | H | C(O)NHCH$_2$CF$_3$ |
| 3,4,5-Cl$_3$ | CF$_2$Cl | Q-1 | H | D-22a |
| 3,4,5-Cl$_3$ | CF$_2$Cl | Q-1 | H | D-52a |
| 3,4,5-Cl$_3$ | CF$_2$Cl | Q-2 | H | OCH$_3$ |
| 3,4,5-Cl$_3$ | CF$_2$Cl | Q-2 | H | OEt |
| 3,4,5-Cl$_3$ | CF$_2$Cl | Q-2 | CH$_3$ | OCH$_3$ |
| 3,4,5-Cl$_3$ | CF$_2$Cl | Q-2 | CH$_3$ | OEt |
| 3,4,5-Cl$_3$ | CF$_2$Cl | Q-2 | Et | OCH$_3$ |
| 3,4,5-Cl$_3$ | CF$_2$Cl | Q-2 | Et | OEt |
| 3,4,5-Cl$_3$ | CF$_2$Cl | Q-2 | CH$_2$CF$_3$ | OCH$_3$ |
| 3,4,5-Cl$_3$ | CF$_2$Cl | Q-2 | CH$_2$C≡CH | OCH$_3$ |
| 3,4,5-Cl$_3$ | CF$_2$Br | Q-2 | H | OCH$_3$ |
| 3,4,5-Cl$_3$ | CF$_2$Br | Q-2 | H | OEt |
| 3,4,5-Cl$_3$ | CF$_2$Br | Q-2 | CH$_3$ | OCH$_3$ |
| 3,4,5-Cl$_3$ | CF$_2$CHF$_2$ | Q-2 | H | OCH$_3$ |
| 3,4,5-Cl$_3$ | CF$_2$CHF$_2$ | Q-2 | H | OEt |
| 3,4,5-Cl$_3$ | CF$_2$CHF$_2$ | Q-2 | CH$_3$ | OCH$_3$ |

TABLE 2-continued

| (X)$_m$ | R$^3$ | Q | R$^2$ | R$^1$ |
|---|---|---|---|---|
| 3,5-Br$_2$-4-F | CHF$_2$ | Q-2 | H | OCH$_3$ |
| 3,5-Br$_2$-4-F | CHF$_2$ | Q-2 | H | OEt |
| 3,5-Br$_2$-4-F | CHF$_2$ | Q-2 | CH$_3$ | OCH$_3$ |
| 3,5-Br$_2$-4-F | CF$_3$ | Q-1 | H | c-Pr |
| 3,5-Br$_2$-4-F | CF$_3$ | Q-1 | H | CF$_3$ |
| 3,5-Br$_2$-4-F | CF$_3$ | Q-1 | H | C(O)NHCH$_2$CH$_2$Cl |
| 3,5-Br$_2$-4-F | CF$_3$ | Q-1 | H | C(O)NHCH$_2$CF$_3$ |
| 3,5-Br$_2$-4-F | CF$_3$ | Q-1 | H | D-22a |
| 3,5-Br$_2$-4-F | CF$_3$ | Q-1 | H | D-52a |
| 3,5-Br$_2$-4-F | CF$_3$ | Q-1 | CH$_2$OCH$_3$ | D-52a |
| 3,5-Br$_2$-4-F | CF$_3$ | Q-1 | CH$_2$CN | D-52a |
| 3,5-Br$_2$-4-F | CF$_3$ | Q-1 | C(O)CH$_3$ | D-52a |
| 3,5-Br$_2$-4-F | CF$_3$ | Q-1 | C(O)Et | D-52a |
| 3,5-Br$_2$-4-F | CF$_3$ | Q-1 | C(O)OCH$_3$ | D-52a |
| 3,5-Br$_2$-4-F | CF$_3$ | Q-1 | H | D-55a |
| 3,5-Br$_2$-4-F | CF$_3$ | Q-1 | H | D-58a |
| 3,5-Br$_2$-4-F | CF$_3$ | Q-2 | H | OCH$_3$ |
| 3,5-Br$_2$-4-F | CF$_3$ | Q-2 | H | OEt |
| 3,5-Br$_2$-4-F | CF$_3$ | Q-2 | H | OPr-n |
| 3,5-Br$_2$-4-F | CF$_3$ | Q-2 | H | OPr-i |
| 3,5-Br$_2$-4-F | CF$_3$ | Q-2 | H | OPr-c |
| 3,5-Br$_2$-4-F | CF$_3$ | Q-2 | H | OCH$_2$CHF$_2$ |
| 3,5-Br$_2$-4-F | CF$_3$ | Q-2 | H | OCH$_2$CF$_3$ |
| 3,5-Br$_2$-4-F | CF$_3$ | Q-2 | H | OCH$_2$CN |
| 3,5-Br$_2$-4-F | CF$_3$ | Q-2 | H | OCH$_2$C≡CH |
| 3,5-Br$_2$-4-F | CF$_3$ | Q-2 | H | SCH$_3$ |
| 3,5-Br$_2$-4-F | CF$_3$ | Q-2 | H | SEt |
| 3,5-Br$_2$-4-F | CF$_3$ | Q-2 | H | NHCN |
| 3,5-Br$_2$-4-F | CF$_3$ | Q-2 | H | NHOCH$_3$ |
| 3,5-Br$_2$-4-F | CF$_3$ | Q-2 | H | N(CH$_3$)OCH$_3$ |
| 3,5-Br$_2$-4-F | CF$_3$ | Q-2 | H | NHNO$_2$ |
| 3,5-Br$_2$-4-F | CF$_3$ | Q-2 | CH$_3$ | OCH$_3$ |
| 3,5-Br$_2$-4-F | CF$_3$ | Q-2 | CH$_3$ | OEt |
| 3,5-Br$_2$-4-F | CF$_3$ | Q-2 | CH$_3$ | SCH$_3$ |
| 3,5-Br$_2$-4-F | CF$_3$ | Q-2 | CH$_3$ | SEt |
| 3,5-Br$_2$-4-F | CF$_3$ | Q-2 | Et | OCH$_3$ |
| 3,5-Br$_2$-4-F | CF$_3$ | Q-2 | Et | OEt |
| 3,5-Br$_2$-4-F | CF$_3$ | Q-2 | n-Pr | OCH$_3$ |
| 3,5-Br$_2$-4-F | CF$_3$ | Q-2 | i-Pr | OCH$_3$ |
| 3,5-Br$_2$-4-F | CF$_3$ | Q-2 | c-Pr | OCH$_3$ |
| 3,5-Br$_2$-4-F | CF$_3$ | Q-2 | CH$_2$CHF$_2$ | OCH$_3$ |
| 3,5-Br$_2$-4-F | CF$_3$ | Q-2 | CH$_2$CF$_3$ | OCH$_3$ |
| 3,5-Br$_2$-4-F | CF$_3$ | Q-2 | CH$_2$CN | OCH$_3$ |
| 3,5-Br$_2$-4-F | CF$_3$ | Q-2 | CH$_2$C≡CH | OCH$_3$ |
| 3,5-Br$_2$-4-F | CF$_3$ | Q-2 | OCH$_3$ | OCH$_3$ |
| 3,5-Br$_2$-4-F | CF$_3$ | Q-2 | N(CH$_3$)$_2$ | OCH$_3$ |
| 3,5-Br$_2$-4-F | CF$_2$Cl | Q-1 | H | C(O)NHCH$_2$CF$_3$ |
| 3,5-Br$_2$-4-F | CF$_2$Cl | Q-1 | H | D-22a |
| 3,5-Br$_2$-4-F | CF$_2$Cl | Q-1 | H | D-52a |
| 3,5-Br$_2$-4-F | CF$_2$Cl | Q-2 | H | OCH$_3$ |
| 3,5-Br$_2$-4-F | CF$_2$Cl | Q-2 | H | OEt |
| 3,5-Br$_2$-4-F | CF$_2$Cl | Q-2 | CH$_3$ | OCH$_3$ |
| 3,5-Br$_2$-4-F | CF$_2$Cl | Q-2 | CH$_3$ | OEt |
| 3,5-Br$_2$-4-F | CF$_2$Cl | Q-2 | Et | OCH$_3$ |
| 3,5-Br$_2$-4-F | CF$_2$Cl | Q-2 | Et | OEt |
| 3,5-Br$_2$-4-F | CF$_2$Cl | Q-2 | CH$_2$CF$_3$ | OCH$_3$ |
| 3,5-Br$_2$-4-F | CF$_2$Cl | Q-2 | CH$_2$C≡CH | OCH$_3$ |
| 3,5-Br$_2$-4-F | CF$_2$Br | Q-2 | H | OCH$_3$ |
| 3,5-Br$_2$-4-F | CF$_2$Br | Q-2 | H | OEt |
| 3,5-Br$_2$-4-F | CF$_2$Br | Q-2 | CH$_3$ | OCH$_3$ |
| 3,5-Br$_2$-4-F | CF$_2$CHF$_2$ | Q-2 | H | OCH$_3$ |
| 3,5-Br$_2$-4-F | CF$_2$CHF$_2$ | Q-2 | H | OEt |
| 3,5-Br$_2$-4-F | CF$_2$CHF$_2$ | Q-2 | CH$_3$ | OCH$_3$ |
| 3,4,5-Br$_3$ | CF$_3$ | Q-1 | H | C(O)NHCH$_2$CF$_3$ |
| 3,4,5-Br$_3$ | CF$_3$ | Q-1 | H | D-22a |
| 3,4,5-Br$_3$ | CF$_3$ | Q-1 | H | D-52a |
| 3,4,5-Br$_3$ | CF$_3$ | Q-2 | H | OCH$_3$ |
| 3,4,5-Br$_3$ | CF$_3$ | Q-2 | H | OEt |
| 3,4,5-Br$_3$ | CF$_3$ | Q-2 | CH$_3$ | OCH$_3$ |
| 3,4,5-Br$_3$ | CF$_3$ | Q-2 | CH$_3$ | OEt |
| 3,4,5-Br$_3$ | CF$_3$ | Q-2 | Et | OCH$_3$ |
| 3,4,5-Br$_3$ | CF$_3$ | Q-2 | Et | OEt |
| 3,4,5-Br$_3$ | CF$_3$ | Q-2 | CH$_2$CF$_3$ | OCH$_3$ |
| 3,4,5-Br$_3$ | CF$_3$ | Q-2 | CH$_2$C≡CH | OCH$_3$ |
| 3,4,5-Br$_3$ | CF$_2$Cl | Q-2 | H | OCH$_3$ |
| 3,4,5-Br$_3$ | CF$_2$Cl | Q-2 | H | OEt |
| 3,4,5-Br$_3$ | CF$_2$Cl | Q-2 | CH$_3$ | OCH$_3$ |
| 3,4-Cl$_2$-5-CH$_3$ | CF$_3$ | Q-1 | H | C(O)NHCH$_2$CF$_3$ |

TABLE 2-continued

| (X)$_m$ | R$^3$ | Q | R$^2$ | R$^1$ |
|---|---|---|---|---|
| 3,4-Cl$_2$-5-CH$_3$ | CF$_3$ | Q-1 | H | D-52a |
| 3,4-Cl$_2$-5-CH$_3$ | CF$_3$ | Q-2 | H | OCH$_3$ |
| 3,4-Cl$_2$-5-CH$_3$ | CF$_3$ | Q-2 | H | OEt |
| 3,4-Cl$_2$-5-CH$_3$ | CF$_3$ | Q-2 | CH$_3$ | OCH$_3$ |
| 3,4-Cl$_2$-5-CH$_3$ | CF$_3$ | Q-2 | CH$_3$ | OEt |
| 3,4-Cl$_2$-5-CH$_3$ | CF$_3$ | Q-2 | Et | OCH$_3$ |
| 3,4-Cl$_2$-5-CH$_3$ | CF$_3$ | Q-2 | CH$_2$CF$_3$ | OCH$_3$ |
| 3,4-F$_2$-5-CF$_3$ | CHF$_2$ | Q-2 | H | OCH$_3$ |
| 3,4-F$_2$-5-CF$_3$ | CHF$_2$ | Q-2 | H | OEt |
| 3,4-F$_2$-5-CF$_3$ | CHF$_2$ | Q-2 | CH$_3$ | OCH$_3$ |
| 3,4-F$_2$-5-CF$_3$ | CF$_3$ | Q-1 | H | c-Pr |
| 3,4-F$_2$-5-CF$_3$ | CF$_3$ | Q-1 | H | CF$_3$ |
| 3,4-F$_2$-5-CF$_3$ | CF$_3$ | Q-1 | H | C(O)NHCH$_2$CH$_2$Cl |
| 3,4-F$_2$-5-CF$_3$ | CF$_3$ | Q-1 | H | C(O)NHCH$_2$CF$_3$ |
| 3,4-F$_2$-5-CF$_3$ | CF$_3$ | Q-1 | H | D-22a |
| 3,4-F$_2$-5-CF$_3$ | CF$_3$ | Q-1 | H | D-52a |
| 3,4-F$_2$-5-CF$_3$ | CF$_3$ | Q-1 | CH$_2$OCH$_3$ | D-52a |
| 3,4-F$_2$-5-CF$_3$ | CF$_3$ | Q-1 | CH$_2$CN | D-52a |
| 3,4-F$_2$-5-CF$_3$ | CF$_3$ | Q-1 | C(O)CH$_3$ | D-52a |
| 3,4-F$_2$-5-CF$_3$ | CF$_3$ | Q-1 | C(O)Et | D-52a |
| 3,4-F$_2$-5-CF$_3$ | CF$_3$ | Q-1 | C(O)OCH$_3$ | D-52a |
| 3,4-F$_2$-5-CF$_3$ | CF$_3$ | Q-1 | H | D-55a |
| 3,4-F$_2$-5-CF$_3$ | CF$_3$ | Q-1 | H | D-58a |
| 3,4-F$_2$-5-CF$_3$ | CF$_3$ | Q-2 | H | OCH$_3$ |
| 3,4-F$_2$-5-CF$_3$ | CF$_3$ | Q-2 | H | OEt |
| 3,4-F$_2$-5-CF$_3$ | CF$_3$ | Q-2 | H | OPr-n |
| 3,4-F$_2$-5-CF$_3$ | CF$_3$ | Q-2 | H | OPr-i |
| 3,4-F$_2$-5-CF$_3$ | CF$_3$ | Q-2 | H | OPr-c |
| 3,4-F$_2$-5-CF$_3$ | CF$_3$ | Q-2 | H | OCH$_2$CHF$_2$ |
| 3,4-F$_2$-5-CF$_3$ | CF$_3$ | Q-2 | H | OCH$_2$CF$_3$ |
| 3,4-F$_2$-5-CF$_3$ | CF$_3$ | Q-2 | H | OCH$_2$CN |
| 3,4-F$_2$-5-CF$_3$ | CF$_3$ | Q-2 | H | OCH$_2$C≡CH |
| 3,4-F$_2$-5-CF$_3$ | CF$_3$ | Q-2 | H | SCH$_3$ |
| 3,4-F$_2$-5-CF$_3$ | CF$_3$ | Q-2 | H | SEt |
| 3,4-F$_2$-5-CF$_3$ | CF$_3$ | Q-2 | H | NHCN |
| 3,4-F$_2$-5-CF$_3$ | CF$_3$ | Q-2 | H | NHOCH$_3$ |
| 3,4-F$_2$-5-CF$_3$ | CF$_3$ | Q-2 | H | N(CH$_3$)OCH$_3$ |
| 3,4-F$_2$-5-CF$_3$ | CF$_3$ | Q-2 | H | NHNO$_2$ |
| 3,4-F$_2$-5-CF$_3$ | CF$_3$ | Q-2 | CH$_3$ | OCH$_3$ |
| 3,4-F$_2$-5-CF$_3$ | CF$_3$ | Q-2 | CH$_3$ | OEt |
| 3,4-F$_2$-5-CF$_3$ | CF$_3$ | Q-2 | CH$_3$ | SCH$_3$ |
| 3,4-F$_2$-5-CF$_3$ | CF$_3$ | Q-2 | CH$_3$ | SEt |
| 3,4-F$_2$-5-CF$_3$ | CF$_3$ | Q-2 | Et | OCH$_3$ |
| 3,4-F$_2$-5-CF$_3$ | CF$_3$ | Q-2 | Et | OEt |
| 3,4-F$_2$-5-CF$_3$ | CF$_3$ | Q-2 | n-Pr | OCH$_3$ |
| 3,4-F$_2$-5-CF$_3$ | CF$_3$ | Q-2 | i-Pr | OCH$_3$ |
| 3,4-F$_2$-5-CF$_3$ | CF$_3$ | Q-2 | c-Pr | OCH$_3$ |
| 3,4-F$_2$-5-CF$_3$ | CF$_3$ | Q-2 | CH$_2$CHF$_2$ | OCH$_3$ |
| 3,4-F$_2$-5-CF$_3$ | CF$_3$ | Q-2 | CH$_2$CF$_3$ | OCH$_3$ |
| 3,4-F$_2$-5-CF$_3$ | CF$_3$ | Q-2 | CH$_2$CN | OCH$_3$ |
| 3,4-F$_2$-5-CF$_3$ | CF$_3$ | Q-2 | CH$_2$C≡CH | OCH$_3$ |
| 3,4-F$_2$-5-CF$_3$ | CF$_3$ | Q-2 | OCH$_3$ | OCH$_3$ |
| 3,4-F$_2$-5-CF$_3$ | CF$_3$ | Q-2 | N(CH$_3$)$_2$ | OCH$_3$ |
| 3,4-F$_2$-5-CF$_3$ | CF$_2$Cl | Q-1 | H | C(O)NHCH$_2$CF$_3$ |
| 3,4-F$_2$-5-CF$_3$ | CF$_2$Cl | Q-1 | H | D-22a |
| 3,4-F$_2$-5-CF$_3$ | CF$_2$Cl | Q-1 | H | D-52a |
| 3,4-F$_2$-5-CF$_3$ | CF$_2$Cl | Q-2 | H | OCH$_3$ |
| 3,4-F$_2$-5-CF$_3$ | CF$_2$Cl | Q-2 | H | OEt |
| 3,4-F$_2$-5-CF$_3$ | CF$_2$Cl | Q-2 | CH$_3$ | OCH$_3$ |
| 3,4-F$_2$-5-CF$_3$ | CF$_2$Cl | Q-2 | CH$_3$ | OEt |
| 3,4-F$_2$-5-CF$_3$ | CF$_2$Cl | Q-2 | Et | OCH$_3$ |
| 3,4-F$_2$-5-CF$_3$ | CF$_2$Cl | Q-2 | Et | OEt |
| 3,4-F$_2$-5-CF$_3$ | CF$_2$Cl | Q-2 | CH$_2$CF$_3$ | OCH$_3$ |
| 3,4-F$_2$-5-CF$_3$ | CF$_2$Cl | Q-2 | CH$_2$C≡CH | OCH$_3$ |
| 3,4-F$_2$-5-CF$_3$ | CF$_2$Br | Q-2 | H | OCH$_3$ |
| 3,4-F$_2$-5-CF$_3$ | CF$_2$Br | Q-2 | H | OEt |
| 3,4-F$_2$-5-CF$_3$ | CF$_2$Br | Q-2 | CH$_3$ | OCH$_3$ |
| 3,4-F$_2$-5-CF$_3$ | CF$_2$CHF$_2$ | Q-2 | H | OCH$_3$ |
| 3,4-F$_2$-5-CF$_3$ | CF$_2$CHF$_2$ | Q-2 | H | OEt |
| 3,4-F$_2$-5-CF$_3$ | CF$_2$CHF$_2$ | Q-2 | CH$_3$ | OCH$_3$ |
| 3-Cl-4-F-5-CF$_3$ | CHF$_2$ | Q-2 | H | OCH$_3$ |
| 3-Cl-4-F-5-CF$_3$ | CHF$_2$ | Q-2 | H | OEt |
| 3-Cl-4-F-5-CF$_3$ | CHF$_2$ | Q-2 | CH$_3$ | OCH$_3$ |
| 3-Cl-4-F-5-CF$_3$ | CF$_3$ | Q-1 | H | c-Pr |
| 3-Cl-4-F-5-CF$_3$ | CF$_3$ | Q-1 | H | CF$_3$ |
| 3-Cl-4-F-5-CF$_3$ | CF$_3$ | Q-1 | H | C(O)NHCH$_2$CH$_2$Cl |
| 3-Cl-4-F-5-CF$_3$ | CF$_3$ | Q-1 | H | C(O)NHCH$_2$CF$_3$ |
| 3-Cl-4-F-5-CF$_3$ | CF$_3$ | Q-1 | H | D-22a |

TABLE 2-continued

| (X)$_m$ | R$^3$ | Q | R$^2$ | R$^1$ |
|---|---|---|---|---|
| 3-Cl-4-F-5-CF$_3$ | CF$_3$ | Q-1 | H | D-52a |
| 3-Cl-4-F-5-CF$_3$ | CF$_3$ | Q-1 | CH$_2$OCH$_3$ | D-52a |
| 3-Cl-4-F-5-CF$_3$ | CF$_3$ | Q-1 | CH$_2$CN | D-52a |
| 3-Cl-4-F-5-CF$_3$ | CF$_3$ | Q-1 | C(O)CH$_3$ | D-52a |
| 3-Cl-4-F-5-CF$_3$ | CF$_3$ | Q-1 | C(O)Et | D-52a |
| 3-Cl-4-F-5-CF$_3$ | CF$_3$ | Q-1 | C(O)OCH$_3$ | D-52a |
| 3-Cl-4-F-5-CF$_3$ | CF$_3$ | Q-1 | H | D-55a |
| 3-Cl-4-F-5-CF$_3$ | CF$_3$ | Q-1 | H | D-58a |
| 3-Cl-4-F-5-CF$_3$ | CF$_3$ | Q-2 | H | OCH$_3$ |
| 3-Cl-4-F-5-CF$_3$ | CF$_3$ | Q-2 | H | OEt |
| 3-Cl-4-F-5-CF$_3$ | CF$_3$ | Q-2 | H | OPr-n |
| 3-Cl-4-F-5-CF$_3$ | CF$_3$ | Q-2 | H | OPr-i |
| 3-Cl-4-F-5-CF$_3$ | CF$_3$ | Q-2 | H | OPr-c |
| 3-Cl-4-F-5-CF$_3$ | CF$_3$ | Q-2 | H | OCH$_2$CHF$_2$ |
| 3-Cl-4-F-5-CF$_3$ | CF$_3$ | Q-2 | H | OCH$_2$CF$_3$ |
| 3-Cl-4-F-5-CF$_3$ | CF$_3$ | Q-2 | H | OCH$_2$CN |
| 3-Cl-4-F-5-CF$_3$ | CF$_3$ | Q-2 | H | OCH$_2$C≡CH |
| 3-Cl-4-F-5-CF$_3$ | CF$_3$ | Q-2 | H | SCH$_3$ |
| 3-Cl-4-F-5-CF$_3$ | CF$_3$ | Q-2 | H | SEt |
| 3-Cl-4-F-5-CF$_3$ | CF$_3$ | Q-2 | H | NHCN |
| 3-Cl-4-F-5-CF$_3$ | CF$_3$ | Q-2 | H | NHOCH$_3$ |
| 3-Cl-4-F-5-CF$_3$ | CF$_3$ | Q-2 | H | N(CH$_3$)OCH$_3$ |
| 3-Cl-4-F-5-CF$_3$ | CF$_3$ | Q-2 | H | NHNO$_2$ |
| 3-Cl-4-F-5-CF$_3$ | CF$_3$ | Q-2 | CH$_3$ | OCH$_3$ |
| 3-Cl-4-F-5-CF$_3$ | CF$_3$ | Q-2 | CH$_3$ | OEt |
| 3-Cl-4-F-5-CF$_3$ | CF$_3$ | Q-2 | CH$_3$ | SCH$_3$ |
| 3-Cl-4-F-5-CF$_3$ | CF$_3$ | Q-2 | CH$_3$ | SEt |
| 3-Cl-4-F-5-CF$_3$ | CF$_3$ | Q-2 | Et | OCH$_3$ |
| 3-Cl-4-F-5-CF$_3$ | CF$_3$ | Q-2 | Et | OEt |
| 3-Cl-4-F-5-CF$_3$ | CF$_3$ | Q-2 | n-Pr | OCH$_3$ |
| 3-Cl-4-F-5-CF$_3$ | CF$_3$ | Q-2 | i-Pr | OCH$_3$ |
| 3-Cl-4-F-5-CF$_3$ | CF$_3$ | Q-2 | c-Pr | OCH$_3$ |
| 3-Cl-4-F-5-CF$_3$ | CF$_3$ | Q-2 | CH$_2$CHF$_2$ | OCH$_3$ |
| 3-Cl-4-F-5-CF$_3$ | CF$_3$ | Q-2 | CH$_2$CF$_3$ | OCH$_3$ |
| 3-Cl-4-F-5-CF$_3$ | CF$_3$ | Q-2 | CH$_2$CN | OCH$_3$ |
| 3-Cl-4-F-5-CF$_3$ | CF$_3$ | Q-2 | CH$_2$C≡CH | OCH$_3$ |
| 3-Cl-4-F-5-CF$_3$ | CF$_3$ | Q-2 | OCH$_3$ | OCH$_3$ |
| 3-Cl-4-F-5-CF$_3$ | CF$_3$ | Q-2 | N(CH$_3$)$_2$ | OCH$_3$ |
| 3-Cl-4-F-5-CF$_3$ | CF$_2$Cl | Q-1 | H | C(O)NHCH$_2$CF$_3$ |
| 3-Cl-4-F-5-CF$_3$ | CF$_2$Cl | Q-1 | H | D-22a |
| 3-Cl-4-F-5-CF$_3$ | CF$_2$Cl | Q-1 | H | D-52a |
| 3-Cl-4-F-5-CF$_3$ | CF$_2$Cl | Q-2 | H | OCH$_3$ |
| 3-Cl-4-F-5-CF$_3$ | CF$_2$Cl | Q-2 | H | OEt |
| 3-Cl-4-F-5-CF$_3$ | CF$_2$Cl | Q-2 | CH$_3$ | OCH$_3$ |
| 3-Cl-4-F-5-CF$_3$ | CF$_2$Cl | Q-2 | CH$_3$ | OEt |
| 3-Cl-4-F-5-CF$_3$ | CF$_2$Cl | Q-2 | Et | OCH$_3$ |
| 3-Cl-4-F-5-CF$_3$ | CF$_2$Cl | Q-2 | Et | OEt |
| 3-Cl-4-F-5-CF$_3$ | CF$_2$Cl | Q-2 | CH$_2$CF$_3$ | OCH$_3$ |
| 3-Cl-4-F-5-CF$_3$ | CF$_2$Cl | Q-2 | CH$_2$C≡CH | OCH$_3$ |
| 3-Cl-4-F-5-CF$_3$ | CF$_2$Br | Q-2 | H | OCH$_3$ |
| 3-Cl-4-F-5-CF$_3$ | CF$_2$Br | Q-2 | H | OEt |
| 3-Cl-4-F-5-CF$_3$ | CF$_2$Br | Q-2 | CH$_3$ | OCH$_3$ |
| 3-Cl-4-F-5-CF$_3$ | CF$_2$CHF$_2$ | Q-2 | H | OCH$_3$ |
| 3-Cl-4-F-5-CF$_3$ | CF$_2$CHF$_2$ | Q-2 | H | OEt |
| 3-Cl-4-F-5-CF$_3$ | CF$_2$CHF$_2$ | Q-2 | CH$_3$ | OCH$_3$ |
| 3,4-Cl$_2$-5-CF$_3$ | CHF$_2$ | Q-2 | H | OCH$_3$ |
| 3,4-Cl$_2$-5-CF$_3$ | CHF$_2$ | Q-2 | H | OEt |
| 3,4-Cl$_2$-5-CF$_3$ | CHF$_2$ | Q-2 | CH$_3$ | OCH$_3$ |
| 3,4-Cl$_2$-5-CF$_3$ | CF$_3$ | Q-1 | H | c-Pr |
| 3,4-Cl$_2$-5-CF$_3$ | CF$_3$ | Q-1 | H | CF$_3$ |
| 3,4-Cl$_2$-5-CF$_3$ | CF$_3$ | Q-1 | H | C(O)NHCH$_2$CH$_2$Cl |
| 3,4-Cl$_2$-5-CF$_3$ | CF$_3$ | Q-1 | H | C(O)NHCH$_2$CF$_3$ |
| 3,4-Cl$_2$-5-CF$_3$ | CF$_3$ | Q-1 | H | D-22a |
| 3,4-Cl$_2$-5-CF$_3$ | CF$_3$ | Q-1 | H | D-52a |
| 3,4-Cl$_2$-5-CF$_3$ | CF$_3$ | Q-1 | CH$_2$OCH$_3$ | D-52a |
| 3,4-Cl$_2$-5-CF$_3$ | CF$_3$ | Q-1 | CH$_2$CN | D-52a |
| 3,4-Cl$_2$-5-CF$_3$ | CF$_3$ | Q-1 | C(O)CH$_3$ | D-52a |
| 3,4-Cl$_2$-5-CF$_3$ | CF$_3$ | Q-1 | C(O)Et | D-52a |
| 3,4-Cl$_2$-5-CF$_3$ | CF$_3$ | Q-1 | C(O)OCH$_3$ | D-52a |
| 3,4-Cl$_2$-5-CF$_3$ | CF$_3$ | Q-1 | H | D-55a |
| 3,4-Cl$_2$-5-CF$_3$ | CF$_3$ | Q-1 | H | D-58a |
| 3,4-Cl$_2$-5-CF$_3$ | CF$_3$ | Q-2 | H | OCH$_3$ |
| 3,4-Cl$_2$-5-CF$_3$ | CF$_3$ | Q-2 | H | OEt |
| 3,4-Cl$_2$-5-CF$_3$ | CF$_3$ | Q-2 | H | OPr-n |
| 3,4-Cl$_2$-5-CF$_3$ | CF$_3$ | Q-2 | H | OPr-i |
| 3,4-Cl$_2$-5-CF$_3$ | CF$_3$ | Q-2 | H | OPr-c |
| 3,4-Cl$_2$-5-CF$_3$ | CF$_3$ | Q-2 | H | OCH$_2$CHF$_2$ |
| 3,4-Cl$_2$-5-CF$_3$ | CF$_3$ | Q-2 | H | OCH$_2$CF$_3$ |

TABLE 2-continued

| (X)$_m$ | R$^3$ | Q | R$^2$ | R$^1$ |
|---|---|---|---|---|
| 3,4-Cl$_2$-5-CF$_3$ | CF$_3$ | Q-2 | H | OCH$_2$CN |
| 3,4-Cl$_2$-5-CF$_3$ | CF$_3$ | Q-2 | H | OCH$_2$C≡CH |
| 3,4-Cl$_2$-5-CF$_3$ | CF$_3$ | Q-2 | H | SCH$_3$ |
| 3,4-Cl$_2$-5-CF$_3$ | CF$_3$ | Q-2 | H | SEt |
| 3,4-Cl$_2$-5-CF$_3$ | CF$_3$ | Q-2 | H | NHCN |
| 3,4-Cl$_2$-5-CF$_3$ | CF$_3$ | Q-2 | H | NHOCH$_3$ |
| 3,4-Cl$_2$-5-CF$_3$ | CF$_3$ | Q-2 | H | N(CH$_3$)OCH$_3$ |
| 3,4-Cl$_2$-5-CF$_3$ | CF$_3$ | Q-2 | H | NHNO$_2$ |
| 3,4-Cl$_2$-5-CF$_3$ | CF$_3$ | Q-2 | CH$_3$ | OCH$_3$ |
| 3,4-Cl$_2$-5-CF$_3$ | CF$_3$ | Q-2 | CH$_3$ | OEt |
| 3,4-Cl$_2$-5-CF$_3$ | CF$_3$ | Q-2 | CH$_3$ | SCH$_3$ |
| 3,4-Cl$_2$-5-CF$_3$ | CF$_3$ | Q-2 | CH$_3$ | SEt |
| 3,4-Cl$_2$-5-CF$_3$ | CF$_3$ | Q-2 | Et | OCH$_3$ |
| 3,4-Cl$_2$-5-CF$_3$ | CF$_3$ | Q-2 | Et | OEt |
| 3,4-Cl$_2$-5-CF$_3$ | CF$_3$ | Q-2 | n-Pr | OCH$_3$ |
| 3,4-Cl$_2$-5-CF$_3$ | CF$_3$ | Q-2 | i-Pr | OCH$_3$ |
| 3,4-Cl$_2$-5-CF$_3$ | CF$_3$ | Q-2 | c-Pr | OCH$_3$ |
| 3,4-Cl$_2$-5-CF$_3$ | CF$_3$ | Q-2 | CH$_2$CHF$_2$ | OCH$_3$ |
| 3,4-Cl$_2$-5-CF$_3$ | CF$_3$ | Q-2 | CH$_2$CF$_3$ | OCH$_3$ |
| 3,4-Cl$_2$-5-CF$_3$ | CF$_3$ | Q-2 | CH$_2$CN | OCH$_3$ |
| 3,4-Cl$_2$-5-CF$_3$ | CF$_3$ | Q-2 | CH$_2$C≡CH | OCH$_3$ |
| 3,4-Cl$_2$-5-CF$_3$ | CF$_3$ | Q-2 | OCH$_3$ | OCH$_3$ |
| 3,4-Cl$_2$-5-CF$_3$ | CF$_3$ | Q-2 | N(CH$_3$)$_2$ | OCH$_3$ |
| 3,4-Cl$_2$-5-CF$_3$ | CF$_2$Cl | Q-1 | H | C(O)NHCH$_2$CF$_3$ |
| 3,4-Cl$_2$-5-CF$_3$ | CF$_2$Cl | Q-1 | H | D-22a |
| 3,4-Cl$_2$-5-CF$_3$ | CF$_2$Cl | Q-1 | H | D-52a |
| 3,4-Cl$_2$-5-CF$_3$ | CF$_2$Cl | Q-2 | H | OCH$_3$ |
| 3,4-Cl$_2$-5-CF$_3$ | CF$_2$Cl | Q-2 | H | OEt |
| 3,4-Cl$_2$-5-CF$_3$ | CF$_2$Cl | Q-2 | CH$_3$ | OCH$_3$ |
| 3,4-Cl$_2$-5-CF$_3$ | CF$_2$Cl | Q-2 | CH$_3$ | OEt |
| 3,4-Cl$_2$-5-CF$_3$ | CF$_2$Cl | Q-2 | Et | OCH$_3$ |
| 3,4-Cl$_2$-5-CF$_3$ | CF$_2$Cl | Q-2 | Et | OEt |
| 3,4-Cl$_2$-5-CF$_3$ | CF$_2$Cl | Q-2 | CH$_2$CF$_3$ | OCH$_3$ |
| 3,4-Cl$_2$-5-CF$_3$ | CF$_2$Cl | Q-2 | CH$_2$C≡CH | OCH$_3$ |
| 3,4-Cl$_2$-5-CF$_3$ | CF$_2$Br | Q-2 | H | OCH$_3$ |
| 3,4-Cl$_2$-5-CF$_3$ | CF$_2$Br | Q-2 | H | OEt |
| 3,4-Cl$_2$-5-CF$_3$ | CF$_2$Br | Q-2 | CH$_3$ | OCH$_3$ |
| 3,4-Cl$_2$-5-CF$_3$ | CF$_2$CHF$_2$ | Q-2 | H | OCH$_3$ |
| 3,4-Cl$_2$-5-CF$_3$ | CF$_2$CHF$_2$ | Q-2 | H | OEt |
| 3,4-Cl$_2$-5-CF$_3$ | CF$_2$CHF$_2$ | Q-2 | CH$_3$ | OCH$_3$ |
| 3,5-(CF$_3$)$_2$-4-Cl | CHF$_2$ | Q-2 | H | OCH$_3$ |
| 3,5-(CF$_3$)$_2$-4-Cl | CHF$_2$ | Q-2 | H | OEt |
| 3,5-(CF$_3$)$_2$-4-Cl | CHF$_2$ | Q-2 | CH$_3$ | OCH$_3$ |
| 3,5-(CF$_3$)$_2$-4-Cl | CF$_3$ | Q-1 | H | c-Pr |
| 3,5-(CF$_3$)$_2$-4-Cl | CF$_3$ | Q-1 | H | CF$_3$ |
| 3,5-(CF$_3$)$_2$-4-Cl | CF$_3$ | Q-1 | H | C(O)NHCH$_2$CH$_2$Cl |
| 3,5-(CF$_3$)$_2$-4-Cl | CF$_3$ | Q-1 | H | C(O)NHCH$_2$CF$_3$ |
| 3,5-(CF$_3$)$_2$-4-Cl | CF$_3$ | Q-1 | H | D-22a |
| 3,5-(CF$_3$)$_2$-4-Cl | CF$_3$ | Q-1 | H | D-52a |
| 3,5-(CF$_3$)$_2$-4-Cl | CF$_3$ | Q-1 | CH$_2$OCH$_3$ | D-52a |
| 3,5-(CF$_3$)$_2$-4-Cl | CF$_3$ | Q-1 | CH$_2$CN | D-52a |
| 3,5-(CF$_3$)$_2$-4-Cl | CF$_3$ | Q-1 | C(O)CH$_3$ | D-52a |
| 3,5-(CF$_3$)$_2$-4-Cl | CF$_3$ | Q-1 | C(O)Et | D-52a |
| 3,5-(CF$_3$)$_2$-4-Cl | CF$_3$ | Q-1 | C(O)OCH$_3$ | D-52a |
| 3,5-(CF$_3$)$_2$-4-Cl | CF$_3$ | Q-1 | H | D-55a |
| 3,5-(CF$_3$)$_2$-4-Cl | CF$_3$ | Q-1 | H | D-58a |
| 3,5-(CF$_3$)$_2$-4-Cl | CF$_3$ | Q-2 | H | OCH$_3$ |
| 3,5-(CF$_3$)$_2$-4-Cl | CF$_3$ | Q-2 | H | OEt |
| 3,5-(CF$_3$)$_2$-4-Cl | CF$_3$ | Q-2 | H | OPr-n |
| 3,5-(CF$_3$)$_2$-4-Cl | CF$_3$ | Q-2 | H | OPr-i |
| 3,5-(CF$_3$)$_2$-4-Cl | CF$_3$ | Q-2 | H | OPr-c |
| 3,5-(CF$_3$)$_2$-4-Cl | CF$_3$ | Q-2 | H | OCH$_2$CHF$_2$ |
| 3,5-(CF$_3$)$_2$-4-Cl | CF$_3$ | Q-2 | H | OCH$_2$CF$_3$ |
| 3,5-(CF$_3$)$_2$-4-Cl | CF$_3$ | Q-2 | H | OCH$_2$CN |
| 3,5-(CF$_3$)$_2$-4-Cl | CF$_3$ | Q-2 | H | OCH$_2$C≡CH |
| 3,5-(CF$_3$)$_2$-4-Cl | CF$_3$ | Q-2 | H | SCH$_3$ |
| 3,5-(CF$_3$)$_2$-4-Cl | CF$_3$ | Q-2 | H | SEt |
| 3,5-(CF$_3$)$_2$-4-Cl | CF$_3$ | Q-2 | H | NHCN |
| 3,5-(CF$_3$)$_2$-4-Cl | CF$_3$ | Q-2 | H | NHOCH$_3$ |
| 3,5-(CF$_3$)$_2$-4-Cl | CF$_3$ | Q-2 | H | N(CH$_3$)OCH$_3$ |
| 3,5-(CF$_3$)$_2$-4-Cl | CF$_3$ | Q-2 | H | NHNO$_2$ |
| 3,5-(CF$_3$)$_2$-4-Cl | CF$_3$ | Q-2 | CH$_3$ | OCH$_3$ |
| 3,5-(CF$_3$)$_2$-4-Cl | CF$_3$ | Q-2 | CH$_3$ | OEt |
| 3,5-(CF$_3$)$_2$-4-Cl | CF$_3$ | Q-2 | CH$_3$ | SCH$_3$ |
| 3,5-(CF$_3$)$_2$-4-Cl | CF$_3$ | Q-2 | CH$_3$ | SEt |
| 3,5-(CF$_3$)$_2$-4-Cl | CF$_3$ | Q-2 | Et | OCH$_3$ |
| 3,5-(CF$_3$)$_2$-4-Cl | CF$_3$ | Q-2 | Et | OEt |
| 3,5-(CF$_3$)$_2$-4-Cl | CF$_3$ | Q-2 | n-Pr | OCH$_3$ |

TABLE 2-continued

| (X)$_m$ | R$^3$ | Q | R$^2$ | R$^1$ |
|---|---|---|---|---|
| 3,5-(CF$_3$)$_2$-4-Cl | CF$_3$ | Q-2 | i-Pr | OCH$_3$ |
| 3,5-(CF$_3$)$_2$-4-Cl | CF$_3$ | Q-2 | c-Pr | OCH$_3$ |
| 3,5-(CF$_3$)$_2$-4-Cl | CF$_3$ | Q-2 | CH$_2$CHF$_2$ | OCH$_3$ |
| 3,5-(CF$_3$)$_2$-4-Cl | CF$_3$ | Q-2 | CH$_2$CF$_3$ | OCH$_3$ |
| 3,5-(CF$_3$)$_2$-4-Cl | CF$_3$ | Q-2 | CH$_2$CN | OCH$_3$ |
| 3,5-(CF$_3$)$_2$-4-Cl | CF$_3$ | Q-2 | CH$_2$C≡CH | OCH$_3$ |
| 3,5-(CF$_3$)$_2$-4-Cl | CF$_3$ | Q-2 | OCH$_3$ | OCH$_3$ |
| 3,5-(CF$_3$)$_2$-4-Cl | CF$_3$ | Q-2 | N(CH$_3$)$_2$ | OCH$_3$ |
| 3,5-(CF$_3$)$_2$-4-Cl | CF$_2$Cl | Q-1 | H | C(O)NHCH$_2$CF$_3$ |
| 3,5-(CF$_3$)$_2$-4-Cl | CF$_2$Cl | Q-1 | H | D-22a |
| 3,5-(CF$_3$)$_2$-4-Cl | CF$_2$Cl | Q-1 | H | D-52a |
| 3,5-(CF$_3$)$_2$-4-Cl | CF$_2$Cl | Q-2 | H | OCH$_3$ |
| 3,5-(CF$_3$)$_2$-4-Cl | CF$_2$Cl | Q-2 | H | OEt |
| 3,5-(CF$_3$)$_2$-4-Cl | CF$_2$Cl | Q-2 | CH$_3$ | OCH$_3$ |
| 3,5-(CF$_3$)$_2$-4-Cl | CF$_2$Cl | Q-2 | CH$_3$ | OEt |
| 3,5-(CF$_3$)$_2$-4-Cl | CF$_2$Cl | Q-2 | Et | OCH$_3$ |
| 3,5-(CF$_3$)$_2$-4-Cl | CF$_2$Cl | Q-2 | Et | OEt |
| 3,5-(CF$_3$)$_2$-4-Cl | CF$_2$Cl | Q-2 | CH$_2$CF$_3$ | OCH$_3$ |
| 3,5-(CF$_3$)$_2$-4-Cl | CF$_2$Cl | Q-2 | CH$_2$C≡CH | OCH$_3$ |
| 3,5-(CF$_3$)$_2$-4-Cl | CF$_2$Br | Q-2 | H | OCH$_3$ |
| 3,5-(CF$_3$)$_2$-4-Cl | CF$_2$Br | Q-2 | H | OEt |
| 3,5-(CF$_3$)$_2$-4-Cl | CF$_2$Br | Q-2 | CH$_3$ | OCH$_3$ |
| 3,5-(CF$_3$)$_2$-4-Cl | CF$_2$CHF$_2$ | Q-2 | H | OCH$_3$ |
| 3,5-(CF$_3$)$_2$-4-Cl | CF$_2$CHF$_2$ | Q-2 | H | OEt |
| 3,5-(CF$_3$)$_2$-4-Cl | CF$_2$CHF$_2$ | Q-2 | CH$_3$ | OCH$_3$ |
| 3,5-Cl$_2$-4-OCHF$_2$ | CF$_3$ | Q-1 | H | C(O)NHCH$_2$CF$_3$ |
| 3,5-Cl$_2$-4-OCHF$_2$ | CF$_3$ | Q-1 | H | D-22a |
| 3,5-Cl$_2$-4-OCHF$_2$ | CF$_3$ | Q-1 | H | D-52a |
| 3,5-Cl$_2$-4-OCHF$_2$ | CF$_3$ | Q-2 | H | OCH$_3$ |
| 3,5-Cl$_2$-4-OCHF$_2$ | CF$_3$ | Q-2 | H | OEt |
| 3,5-Cl$_2$-4-OCHF$_2$ | CF$_3$ | Q-2 | CH$_3$ | OCH$_3$ |
| 3,5-Cl$_2$-4-OCHF$_2$ | CF$_3$ | Q-2 | CH$_3$ | OEt |
| 3,5-Cl$_2$-4-OCHF$_2$ | CF$_3$ | Q-2 | Et | OCH$_3$ |
| 3,5-Cl$_2$-4-OCHF$_2$ | CF$_3$ | Q-2 | Et | OEt |
| 3,5-Cl$_2$-4-OCHF$_2$ | CF$_3$ | Q-2 | CH$_2$CF$_3$ | OCH$_3$ |
| 3,5-Cl$_2$-4-OCHF$_2$ | CF$_3$ | Q-2 | CH$_2$C≡CH | OCH$_3$ |
| 3,5-Cl$_2$-4-OCHF$_2$ | CF$_2$Cl | Q-2 | H | OCH$_3$ |
| 3,5-Cl$_2$-4-OCHF$_2$ | CF$_2$Cl | Q-2 | H | OEt |
| 3,5-Cl$_2$-4-OCHF$_2$ | CF$_2$Cl | Q-2 | CH$_3$ | OCH$_3$ |
| 3,5-Br$_2$-4-OCHF$_2$ | CF$_3$ | Q-1 | H | C(O)NHCH$_2$CF$_3$ |
| 3,5-Br$_2$-4-OCHF$_2$ | CF$_3$ | Q-1 | H | D-22a |
| 3,5-Br$_2$-4-OCHF$_2$ | CF$_3$ | Q-1 | H | D-52a |
| 3,5-Br$_2$-4-OCHF$_2$ | CF$_3$ | Q-2 | H | OCH$_3$ |
| 3,5-Br$_2$-4-OCHF$_2$ | CF$_3$ | Q-2 | H | OEt |
| 3,5-Br$_2$-4-OCHF$_2$ | CF$_3$ | Q-2 | CH$_3$ | OCH$_3$ |
| 3,5-Br$_2$-4-OCHF$_2$ | CF$_3$ | Q-2 | CH$_3$ | OEt |
| 3,5-Br$_2$-4-OCHF$_2$ | CF$_3$ | Q-2 | Et | OCH$_3$ |
| 3,5-Br$_2$-4-OCHF$_2$ | CF$_3$ | Q-2 | Et | OEt |
| 3,5-Br$_2$-4-OCHF$_2$ | CF$_3$ | Q-2 | CH$_2$CF$_3$ | OCH$_3$ |
| 3,5-Br$_2$-4-OCHF$_2$ | CF$_3$ | Q-2 | CH$_2$C≡CH | OCH$_3$ |
| 3,5-Br$_2$-4-OCHF$_2$ | CF$_2$Cl | Q-2 | H | OCH$_3$ |
| 3,5-Br$_2$-4-OCHF$_2$ | CF$_2$Cl | Q-2 | H | OEt |
| 3,5-Br$_2$-4-OCHF$_2$ | CF$_2$Cl | Q-2 | CH$_3$ | OCH$_3$ |

The compound of the present invention can effectively control with a low concentration thereof, any pests such as insects including so-called agricultural insect pests damaging agricultural or horticultural crops and trees, so-called domestic animal insect pests being parasitic in domestic animals/fowls, so-called insanitary insects adversely affecting in various manners, the living environment of the human such as the house and so-called stored grain insect pests damaging grains stored in a warehouse; and mites, Crustacea, Mollusc and Nematoda which are generated and cause damages in a situation similar to that in the case of the insects.

Specific examples of the insects, the mites, the Crustacea, the Mollusc and the Nematoda capable of being controlled using the compound of the present invention include:

Lepidopteran insects such as *Adoxophyes honmai, Adoxophyes orana faciata, Arcihps breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aene-* scens, *Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata* and *Manduca sexta*;

Thysanopteran insects such as *Frankliniella intonsa, Frankliniella occidentalis, Heliothrips haemorrhoidalis, Scirtothrips dorsalis, Thrips palmi, Thrips tabaci* and *Ponticulothrips diospyrosi*;

Hemipteran insects such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis* and *Cimex lectularius*;

Coleopteran insects such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus* and *Paederus fuscipes*;

Dipterous insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis (Glossina morsitans), Prosimulium yezoensis, Tabanus trigonus, Telmatoscopus albipunctatus, Leptoconops nipponensis, Culex pipiens pallens, Aedes aegypti, Aedes albopicutus* and *Anopheles hyracanus sinesis*;

Hymenopteran insects such as *Apethymus kuri, Athalia rosae, Arge pagana, Neodiprion sertifer, Dryocosmus kuriphilus, Eciton burchelli (Eciton schmitti), Camponotus japonicus, Vespa mandarina, Myrmecia* spp., *Solenopsis* spp. and *Monomorium pharaonis*;

Orthopteran insects such as *Teleogryllus emma, Gryllotalpa orientalis, Locusta migratoria, Oxya yezoensis* and *Schistocerca gregaria*;

Collembolan insects such as *Onychiurus folsomi, Onychiurus sibiricus* and *Bourletiella hortensis*;

Dictyopteran insects such as *Periplaneta fuliginosa, Periplaneta japonica* and *Blattella germanica*;

Isopterous insects such as *Coptotermes formosanus, Reticulitermes speratus* and *Odontotermes formosanus*;

Isopterous insects such as *Ctenocephalidae felis, Ctenocephalides canis, Echidnophaga gallinacea, Pulex irritans* and *Xenopsylla cheopis*;

Mallophaga insects such as *Menacanthus stramineus* and *Bovicola bovis*;

Anoplura insects such as *Haematopinus eurysternus, Haematopinus suis, Linognathus vituli* and *Solenopotes capillatus*;

Tarsonemidae such as *Phytonemus pallidus, Polyphagotarsonemus latus* and *Tarsonemus bilobatus*;

Eupodidae such as *Penthaleus erythrocephalus* and *Penthaleus major*;

Tetranychidae such as *Oligonychus shinkajii, Panonychus citri, Panonychus mori, Panonychus ulmi, Tetranychus kanzawai* and *Tetranychus urticae*;

Eriophydae such as *Acaphylla theavagrans, Aceria tulipae, Aculops lycopersici, Aculops pelekassi, Aculus schlechtendali, Eriophyes chibaensis* and *Phyllocoptruta oleivora*;

Acaridae such as *Rhizoglyphus robini, Tyrophagus putrescentiae* and *Tyrophagus similis*;

Varroa destructors such as *Varroa jacobsoni*;

Ixodidae such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp. and *Dermacentor* spp.

Cheyletidae such as *Cheyletiella yasguri* and *Cheyletiella blakei*;

Demodicidae such as *Demodex canis* and *Demodex cati*;

Psoroptidae such as *Psoroptes ovis*;

Sarcoptidae such as *Sarcoptes scabiei, Notoedres cati* and *Knemidocoptes* spp.;

Crustacea such as *Armadillidium vulgare*;

Gastropoda such as *Pomacea canaliculata, Achatina fulica, Meghimatium bilineatum, Limax Valentiana, Acusta despecta sieboldiana* and *Euhadra peliomphala*; and Nematoda such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi* and *Bursaphelenchus xylophilus*, which should not be construed as limiting the scope of the present invention.

In addition, specific examples of the internal parasites of domestic animals, fowls, pet animals or the like capable of being controlled using the compound of the present invention include:

Nematoda such as *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris* and *Parascaris*;

Nematoda Filariidae such as *Wuchereria, Brugia, Onchoceca, Dirofilaria* and *Loa*;

Nematoda Dracunculidae such as *Deacunculus*;

Cestoda such as *Dipylidium caninum, Taenia taeniaeformis, Taenia solium, Taenia saginata, Hymenolepis diminuta,*

*Moniezia benedeni, Diphyllobothrium latum, Diphyllobothrium erinacei, Echinococcus granulosus* and *Echinococcus multilocularis*;

Trematoda such as *Fasciola hepatica* and *F. gigantica, Paragonimus westermanii, Fasciolopsic bruski, Eurytrema pancreaticum* and *E. coelomaticum, Clonorchis sinensis, Schistosoma japonicum, Schistosoma haematobium* and *Schistosoma mansoni*;

*Eimeria* spp. such as *Eimeria tenella, Eimeria acervulina, Eimeria brunetti, Eimeria maxima, Eimeria necatrix, Eimeria bovis* and *Eimeria ovinoidalis*;

*Trypanosomsa cruzi; Leishmania* spp.; *Plasmodium* spp.; *Babesis* spp.; *Trichomonadidae* spp.; *Histomanas* spp.; *Giardia* spp.; *Toxoplasma* spp.; *Entamoeba histolytica* and *Theileria* spp, which should not be construed as limiting the scope of the present invention.

Furthermore, the compound of the present invention is effective against pests which have developed the resistance to the related art insecticides such as organic phosphorus-based compounds, carbamate-based compounds and pyrethroid-based compounds.

That is, the compound of the present invention can effectively control pests belonging to insects such as Collembola (Collembola), Blattaria (Blattidae), Orthoptera (Caelifera), Isoptera, Thysanoptera (Thripidae), Hemiptera (Pentatomidae and Deltcephalidae), Lepidoptera (Lepidoptera), Coleoptera (Leiodidae), Hymenoptera (Hymenoptera), Diptera (Diptera), Isoptera (Siphonaptera) and Phthiraptera; mites; Gastropoda; and Nematoda with a low concentration. On the other hand, the compound of the present invention has an extremely useful characteristic of having substantially no adverse effect on the mammal, the fish, the Crustacea and beneficial insects (useful insects such as Apidae and Bombus, and natural enemies such as Aphelimidae, Aphidiidae, Tachimidae, *Orius* and *Amblyseius*).

For using the compound of the present invention, the compound can be put to practical use as a preparation in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet and an emulsifiable gel, typically by mixing the compound with an appropriate solid carrier or liquid carrier, further if desired by adding to the resultant mixture, a surfactant, a penetrant, a spreader, a thickener, an antifreezing agent, a binder, an anticaking agent, a disintegrant, an antifoamer, an antiseptic or a stabilizer. In addition, from the viewpoint of laborsaving and safety-enhancing, the compound can be put to use by encapsulating the above preparation in any dosage form in a water soluble packaging material such as a water soluble capsule and a bag of water soluble film.

Examples of the solid carrier include: natural mineral matters such as quartz, calcite, sepiolite, dolomite, chalk, kaolinite, pyrophyllite, sericite, halloysite, methahalloysite, kibushi clay, gairome clay, pottery stone, zeeklite, allophane, Shirasu, mica, talc, bentonite, activated clay, acid clay, pumice, attapulgite, zeolite and diatom earth; burned products of natural mineral matters such as burned clay, perlite, Shirasu balloon, vermiculite, attapulgous clay and burned diatom earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride; saccharides such as glucose, fructose, sucrose and lactose; polysaccharides such as starch, powdered cellulose and dextrin; organic substances such as urea, urea derivatives, benzoic acid and salts of benzoic acid; plants such as wood flour, cork flour, corncob, walnut shell and tobacco stem; fly ash; white carbon (such as hydrous synthetic silica, anhydrous synthetic silica and hydrous synthetic silicate); and fertilizers.

Examples of the liquid carrier include: aromatic hydrocarbons such as xylene, alkyl ($C_9$, $C_{10}$, or the like) benzene, phenylxylylethane and alkyl ($C_1$, $C_3$, or the like) naphthalene; aliphatic hydrocarbons such as machine oil, n-paraffin, iso-paraffin and naphthene; a mixture of aromatic hydrocarbons and aliphatic hydrocarbons such as kerosene; alcohols such as ethanol, isopropanol, cyclohexanol, phenoxyethanol and benzyl alcohol; polyalcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyrolactone; esters such as aliphatic acid methyl esters, dialkyl succinate esters, dialkyl glutamate esters, dialkyl adipate esters, and dialkyl phthalate esters; acid amides such as N-alkyl ($C_1$, $C_8$, $C_{12}$, or the like) pyrrolidone; oils and fats such as soybean oil, linseed oil, rapeseed oil, coconut oil, cottonseed oil and castor oil; dimethyl sulfoxide; and water.

These solid or liquid carriers may be used individually or in combination of two or more types thereof Examples of the surfactant include: nonionic surfactants such as polyoxyethylene alkyl ethers, polyoxyethylene alkyl (mono- or di-)phenyl ethers, polyoxyethylene (mono-, di- or tri-)stylylphenyl ethers, polyoxyethylene-polyoxypropylene block copolymers, polyoxyethylene aliphatic acid (mono- or di-) esters, sorbitan aliphatic acid esters, polyoxyethylene sorbitan aliphatic acid esters, castor oil ethylene-oxide adducts, acetylene glycol, acetylene alcohols, acetylene glycol ethylene-oxide adducts, acetylene alcohol ethylene-oxide adducts and alkylglucosides; anionic surfactants such as alkyl sulfate ester salts, alkylbenzene sulfonates, lignin sulfonates, alkyl sulfosuccinates, naphthalene sulfonates, alkylnaphthalene sulfonates, salts of naphthalene sulfonate formalin condensate, salts of alkylnaphthalene sulfonate formalin condensate, polyoxyethylenealkylether sulfate or phosphate esters, polyoxyethylene (mono- or di-)alkylphenyl ether sulfate or phosphate esters, polyoxyethylene (mono-, di- or tri-)stylylphenyl ether sulfate or phosphate esters, polycarboxylic acid salts (such as polyacrylic acid salts, polymaleic acid salts and maleic acid-olefin copolymer) and polystylene sulfonates; cationic surfactants such as alkylamine salts and alkyl quaternary ammonium salts; amphoteric surfactants such as amino acid-type surfactants and betaine-type surfactants; silicone-based surfactants; and fluorinated surfactants.

Though the content of these surfactants is not particularly limited, it is desirably in a range of usually 0.05 to 20 parts by weight, relative to 100 parts by weight of the preparation of the present invention. In addition, these surfactants may be used individually or in combination of two or more types thereof.

Though the application dosage of the compound of the present invention varies depending on the application situation, the application period, the application method, the cultivated crop or the like, it is generally appropriate to be around 0.005 to 50 kg per hectare as an active ingredient amount.

On the other hand, in using the compound of the present invention for controlling external or internal parasites of the mammal and the bird as domestic animals and pet animals, an effective amount of the compound of the present invention can be administered together with additives for the preparation by: oral administration and parenteral administration such as injections (intramuscular-, subcutaneous, intravenous- and intraperitoneal-injection); a percutaneous administration such as immersing, spraying, bathing, cleaning, pouring-on and spotting-on, and dusting; and transnasal administration. The compound of the present invention can be administered also as a molded product using a strip, a plate, a band, a collar, an ear mark, a limb band and an indicator. For the administration of the compound of the present invention, the compound of the present invention can be prepared in any dosage form suitable for an administration route.

Examples of the prepared formulation in any form include solid preparations such as dustable powders, granules, wettable powders, pellets, tablets, boluses, capsules and molded products containing activated compounds; soluble concentrates for injection, soluble concentrates for oral administration and soluble concentrates used on the skin or in the body cavity; solution preparations such as pour-on drugs, spot-on drugs, flowable drugs and emulsifiable concentrates; and semisolid preparations such as ointments and gels.

The solid preparation can be mainly used for oral administration, percutaneous administration of the preparation diluted with water, or an environmental treatment. The solid preparation can be prepared by mixing an activated compound with an appropriate excipient, if necessary together with an adjuvant, and converting the resultant mixture into a desired form.

Examples of the appropriate excipient include: inorganic substances such as carbonate salts, hydrogen carbonate salts, phosphate salts, aluminum oxide, silica and clay; and organic substances such as saccharides, celluloses, ground grains and starch.

The soluble concentrate for injection can be prepared by dissolving an activated compound capable of being administered intravenously, intramuscularly or subcutaneously in an appropriate solvent, and if necessary by adding to the resultant solution, additives such as solubilizers, acids, bases, buffering salts, antioxidants and protectives. Examples of the appropriate solvent include water, ethanol, butanol, benzyl alcohol, glycerin, propylene glycol, polyethylene glycol, N-methylpyrrolidone, mixtures thereof, physiologically acceptable vegetable oils and synthetic oils suitable for injection. Examples of the solubilizer include polyvinylpyrrolidone, polyoxyethylated castor oil and polyoxyethylated sorbitan esters. Examples of the protective include benzyl alcohol, trichlorobutanol, p-hydroxybenzoate esters and n-butanol.

The soluble concentrate for oral administration can be administered directly or after dilution and can be prepared in substantially the same manner as in the case of the soluble concentrate for injection.

The flowable drug, the emulsifiable concentrate and the like can be administered percutaneously directly or after dilution, or through an environmental treatment.

The soluble concentrate used on the skin can be administrated by dropping, spreading, rubbing, spraying, dusting or immersing (immersing, bathing or cleaning) to apply the drug on the skin. These soluble concentrates can be prepared in substantially the same manner as in the case of the soluble concentrate for injection.

The pour-on drug and the spot-on drug are dropped or sprayed on a limited range of the skin, so that these drugs can immerse an activated compound thereof into the skin to obtain a systemic effect thereof. The pour-on drug and the spot-on drug can be prepared by dissolving, suspending or emulsifying an active ingredient in an appropriate skin-adaptable solvent or solvent mixture. If necessary, in these drugs, an adjuvant such as a surfactant, a colorant, an absorption-accelerating substance, an antioxidant, a light stabilizer and an adhesive can be incorporated.

Examples of the appropriate solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetoamide, N-methylpyrrolidone or 2,2-dimethyl-4-oxy-methylene-1,3-dioxolane. Examples of the absorption accelerating substance include DMSO, isopropyl myristate, dipropylene glycol pelargonate, silicone oil, aliphatic esters, triglycerides and aliphatic alcohols. Examples of the antioxidant include sulfite salts, metabisulfite salts, ascorbic acid, butylhydroxytoluene, butylated hydroxyanisole and tocopherol.

The emulsifiable concentrate can be administered by an oral administration, a percutaneous administration or an injection. The emulsifiable concentrate can be prepared by dissolving an active ingredient in a hydrophobic phase or a hydrophilic phase and homogenizing the resultant solution with a solvent of another type of phase using an appropriate emulsifier, if necessary further together with an adjuvant such as a colorant, an absorption accelerating substance, a protective, an antioxidant, a sunscreen and a thickener.

Examples of the hydrophobic phase (oil) include paraffin oil, silicone oil, sesame oil, almond oil, castor oil, synthetic triglyceride, ethyl stearate, di-n-butylyl adipate, hexyl laurate, dipropylene glycol pelargonate, an ester of a branched aliphatic acid having a short chain length with a saturated aliphatic acid having a chain length of C16 to C18, isopropyl myristate, isopropyl palmitate, caprylate/caprate esters of a saturated aliphatic alcohol having a chain length of C12 to C18, isopropyl stearate, oleyl oleate, decyl oleate, ethyl oleate, ethyl lactate, a wax-like aliphatic acid ester, dibutyl phthalate, diisopropyl adipate, isotridecyl alcohol, 2-octyl dodecanol, cetylstearyl alcohol and oleyl alcohol.

Examples of the hydrophilic phase include water, propylene glycol, glycerin and sorbitor.

Examples of the emulsifier include: nonionic surfactants such as polyoxyethylated castor oil, polyoxyethylated monoolefin acid sorbitan, sorbitan monostearate, glycerin monostearate, polyoxyethyl stearate and alkylphenol polyglycol ether; amphoteric surfactants such as di-sodium N-lauryl-β-iminodipropionate and lecithin; anionic surfactants such as sodium laurylsulfate, aliphatic alcohol sulfate ether and mono-/di-alkyl polyglycol orth-phosphate ester monoethanolamine salt; and cationic surfactants such as cetyltrimethylammonium chloride.

Examples of the other adjuvants include carboxymethyl cellulose, methyl cellulose, polyacrylate, alginate, gelatin, gum Arabic, polyvinylpyrrolidone, polyvinyl alcohol, methyl vinyl ether, copolymers of maleic anhydride, polyethylene glycol, wax and colloidal silica.

The semisolid preparation can be administered by applying or spreading the preparation on the skin or by introducing the preparation into a body cavity. The gel can be prepared by adding to a solution prepared as described above with respect to the soluble concentrate for injection, a thickener in an amount sufficient for generating an ointment-like transparent substance having viscosity.

Next, examples of the formulation of the preparation in the case of using the compound of the present invention are described, with proviso that the formulation examples of the present invention are not limited to these examples. Here, in the following formulation examples, "part" represents a part by weight.

(Wettable Powder)

| | |
|---|---|
| Compound of the present invention | 0.1 to 80 parts |
| Solid carrier | 5 to 98.9 parts |
| Surfactant | 1 to 10 part(s) |
| Others | 0 to 5 parts |

Examples of the others include an anticaking agent and a stabilizer.

(Emulsifiable Concentrate)

| | |
|---|---|
| Compound of the present invention | 0.1 to 30 parts |
| Liquid carrier | 45 to 95 parts |
| Surfactant | 4.9 to 15 parts |
| Others | 0 to 10 parts |

Examples of the others include a spreader and a stabilizer.

(Suspension Concentrate)

| | |
|---|---|
| Compound of the present invention | 0.1 to 70 parts |
| Liquid carrier | 15 to 98.89 parts |
| Surfactant | 1 to 12 part(s) |
| Others | 0.01 to 30 parts |

Examples of the others include an antifreezing agent and a thickener.

(Water Dispersible Granule)

| | |
|---|---|
| Compound of the present invention | 0.1 to 90 parts |
| Solid carrier | 0 to 98.9 parts |
| Surfactant | 1 to 20 part(s) |
| Others | 0 to 10 parts |

Examples of the others include a binder and a stabilizer.

(Soluble Concentrate)

| | |
|---|---|
| Compound of the present invention | 0.01 to 70 parts |
| Liquid carrier | 20 to 99.99 parts |
| Others | 0 to 10 parts |

Examples of the others include an antifreezing agent and a spreader.

(Granule)

| | |
|---|---|
| Compound of the present invention | 0.01 to 80 parts |
| Solid carrier | 10 to 99.99 parts |
| Others | 0 to 10 parts |

Examples of the others include a binder and a stabilizer.

(Dustable Powder)

| | |
|---|---|
| Compound of the present invention | 0.01 to 30 parts |
| Solid carrier | 65 to 99.99 parts |
| Others | 0 to 5 parts |

Examples of the others include an antidrift agent and a stabilizer.

Next, examples of the preparation containing the compound of the present invention as an active ingredient are more specifically described, however the examples should not be construed as limiting the scope of the present invention.

Here, in the following formulation examples, "parts" represents parts by weight.

Formulation Example 1

Wettable Powder prepared by homogeneously mixing and grinding a composition containing:

| | |
|---|---|
| compound of the present invention No. 2-004 | 20 parts; |
| pyrophyllite | 74 parts; |
| SORPOL 5039 | 4 parts |
| (trade name; manufactured by TOHO Chemical Industry Co., Ltd.; mixture of nonionic surfactant and anionic surfactant); and | |
| CARPLEX #80D | 2 parts |
| (trade name; manufactured by Shionogi & Co., Ltd.; synthetic hydrous silicic acid). | |

Formulation Example 2

Emulsifiable Concentrate prepared by homogeneously mixing a composition containing:

| | |
|---|---|
| compound of the present invention No. 2-004 | 5 parts; |
| xylene | 75 parts; |
| N-methylpyrrolidone | 15 parts; and |
| SORPOL 2680 | 5 parts |
| (trade name; manufactured by TOHO Chemical Industry Co., Ltd.; mixture of nonionic surfactant and anionic surfactant). | |

Formulation Example 3

Suspension Concentrate prepared by homogeneously mixing a composition containing:

| | |
|---|---|
| compound of the present invention No. 2-004 | 25 parts; |
| AGRISOL S-710 | 10 parts |
| (trade name; manufactured by Kao Corporation; nonionic surfactant); | |
| LUNOX 1000C | 0.5 parts |
| (trade name; manufactured by TOHO Chemical Industry Co., Ltd.; anionic surfactant); | |

-continued

| | |
|---|---|
| xanthan gum | 0.2 parts; and |
| water | 64.3 parts, |
| and wet-grinding the resultant mixture. | |

Formulation Example 4

Water Dispersible Granule prepared by homogeneously mixing and grinding a composition containing:

| | |
|---|---|
| compound of the present invention No. 2-004 | 75 parts; |
| HITENOL NE-15 | 5 parts; |
| (trade name; manufactured by Dai-ichi Kogyo Seiyaku Co., Ltd.; anionic surfactant); | |
| VANILLEX N | 10 parts |
| (trade name; manufactured by Nippon Paper Industries Co., Ltd..; anionic surfactant); and | |
| CARPLEX #80D | 10 parts |
| (trade name; manufactured by Shionogi & Co., Ltd.; synthetic hydrous silicic acid), adding a small amount of water to the resultant mixture to stir and mix the mixture, granulating the mixture with an extrusion granulator, and drying the resultant granule. | |

Formulation Example 5

Granule prepared by homogeneously mixing and grinding a composition containing:

| | |
|---|---|
| compound of the present invention No. 2-004 | 5 parts; |
| bentonite | 50 parts; and |
| talc | 45 parts, |
| adding a small amount of water to the resultant mixture to stir and mix the mixture, granulating the mixture with an extrusion granulator, and drying the resultant granule. | |

Formulation Example 6

Dustable Powder prepared by homogeneously mixing and grinding a composition containing:

| | |
|---|---|
| compound of the present invention No. 2-004 | 3 parts; |
| CARPLEX #80D | 0.5 parts |
| (trade name; manufactured by Shionogi & Co., Ltd.; synthetic hydrous silicic acid); | |
| kaolinite | 95 parts; and |
| diisopropyl phosphate | 1.5 parts. |

For using the preparation, the preparation is directly dusted after dilution with water by 1 to 10,000 time(s) or without dilution.

Formulation Example 7

Wettable Powder Preparation

| | |
|---|---|
| compound of the present invention No. 2-004 | 25 parts |
| sodium diisobutylnaphthalenesulfonate | 1 part |
| calcium n-dodecylbenzenesulfonate | 10 parts |
| alkylaryl polyglycol ether | 12 parts |
| sodium salt of naphthalenesulfonic acid formalin condensate | 3 parts |
| emulsion-type silicone | 1 part |
| silicon dioxide | 3 parts |
| kaolin | 45 parts |

Formulation Example 8

Water Soluble Thickener Preparation

| | |
|---|---|
| compound of the present invention No. 2-004 | 20 parts |
| polyoxyethylene lauryl ether | 3 parts |
| sodium dioctylsulfosuccinate | 3.5 parts |
| dimethylsulfoxide | 37 parts |
| 2-propanol | 36.5 parts |

Formulation Example 9

Soluble Concentrate for Spraying

| | |
|---|---|
| compound of the present invention No. 2-004 | 2 parts |
| dimethylsulfoxide | 10 parts |
| 2-propanol | 35 parts |
| acetone | 53 parts |

Formulation Example 10

Soluble Concentrate for Percutaneous Administration

| | |
|---|---|
| compound of the present invention No. 2-004 | 5 parts |
| hexylene glycol | 50 parts |
| isopropanol | 45 parts |

Formulation Example 11

Soluble Concentrate for Percutaneous Administration

| | |
|---|---|
| compound of the present invention No. 2-004 | 5 parts |
| propylene glycol monomethyl ether | 50 parts |
| dipropylene glycol | 45 parts |

Formulation Example 12

Soluble Concentrate for Percutaneous Administration (Pouring-on)

| | |
|---|---|
| compound of the present invention No. 2-004 | 2 parts |
| light liquid paraffin | 98 parts |

Formulation Example 13

Soluble Concentrate for Percutaneous Administration (Pouring-on)

| | |
|---|---|
| compound of the present invention No. 2-004 | 2 parts |
| light liquid paraffin | 58 parts |
| olive oil | 30 parts |
| ODO-H | 9 parts |
| Shin-Etsu silicone | 1 part |

In addition, when the compound of the present invention is used as an agricultural chemical, if necessary the compound may be mixed with another type of herbicide, various insecticides, a miticide, a nematicide, a fungicide, a plant growth regulator, a synergist, a fertilizer or a soil conditioner to be applied during the preparation or the dusting.

Particularly, by mixing the compound with other agricultural chemicals or phytohormones to be applied, a cost reduction by reducing the application dose, an enlargement of the insecticidal spectrum by a synergism of a mixed drug and a higher pest control effect can be expected. At this time, it is possible to combine simultaneously the compound of the present invention and a plurality of publicly-known agricultural chemicals. Examples of types of agricultural chemicals to be mixed with the compound of the present invention to be used include compounds described in "The Pesticide Manual, Vol. 14 (2006)". Specific examples of the general names thereof include the following names, to which the examples are not limited.

Fungicides: acibenzolar-S-methyl, acylaminobenzamide, acypetacs, aldimorph, amisulbrom, amobam, ampropylos, anilazine, azaconazole, azithiram, azoxystrobin, barium polysulfide, benalaxyl, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulphide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chloroquinox, chlozolinate, climbazole, clotrimazole, copper acetate, copper carbonate basic, copper hydroxide, copper naphthenate, copper oleate, copper oxychloride, copper sulfate, copper sulfate basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, dichlobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, fluconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, mandipropamid, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, Chinese mushroom mycelia extract, and the like.

Bactericides: benzalkonium chloride, bethionol, bronopol, cresol, formaldehyde, nitrapyrin, oxolinic acid, oxyterracycline, streptomycin, tecloftalam, and the like.

Nematicides: aldoxycarb, cadusafos, DBCP, dichlofenthion, DSP, ethoprophos, fenamiphos, fensulfothion, fosthiazate, fosthietan, imicyafos, isamidofos, isazofos, oxamyl, thionazin, and the like.

Miticides: acequinocyl, acrinathrin, amitraz, BCI-033 (test name), bifenazate, bromopropylate, chinomethionat, chlorobenzilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen, S-1870 (test name), spirodiclofen, spyromesifen, tebufenpyrad, and the like.

Insecticides: abamectin, acephate, acetamipirid, alanycarb, aldicarb, allethrin, azinphos-methyl, *bacillus thuringiensis*, bendiocarb, benfuracarb, bensultap, bifenthrin, buprofezin, butocarboxim, carbaryl, carbofuran, carbosulfan, cartap, chlorantraniliprole, chiorfenapyr, chlorfenvinphos, chlorfluazuron, chlorpyrifos, chlorpyrifos-methyl, chlromafenozide, clothianidin, cycloprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, novaluron, omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyrifluquinazon, pyriproxyfen, rotenone, SI-0405 (test name), sulprofos, silafluofen, spinetoram, spinosad, spirotetramat, sulfotep, SYJ-159 (test name), tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron, vamidothion, and the like.

EXAMPLES

Hereinafter, the present invention is described more in detail referring specifically to Synthetic Examples and Test Examples of the compound of the present invention as Examples, which should not be construed as limiting the scope of the present invention.

Synthetic Examples

Synthetic Example 1

4-[5-(3,5-Dichlorophenyl)-5-trifluoromethyl-4,5-dihydroisoxazole-3-yl]-2-methyl-N-[1-(2-pyridyl)cyclopropyl]benzamide (compound of the present invention No. 1-007)

Process 1; Production of 3,5-dichloro-1-(1-trifluoromethylethenyl)benzene

To a solution of 25.0 g of 3,5-dichlorophenylboric acid in 200 mL of tetrahydrofuran and 100 mL of water, 27.5 g of 2-bromo-3,3,3-trifluoropropene, 38.0 g of potassium carbonate and 1.84 g of dichloro-bis(triphenylphosphine) palladium (II) were added and the resultant mixture was stirred while heating the mixture to reflux for 3 hours. After the completion of the reaction, the reaction mixture was left to be cooled to room temperature and 500 mL of ice water was added to the mixture, followed by extracting the mixture with ethyl acetate (500 mL×1). The organic phase was cleaned with water and then dried over anhydrous sodium sulfate, and the solvent was distilled off from the organic phase under reduced pressure, followed by purifying the resultant residue by silica gel column chromatography eluting with hexane to obtain 25.7 g of the objective substance as a colorless oily substance.

$^1$H NMR (CDCl$_3$, Me$_4$Si, 300 MHz) δ 7.41 (t, J=2.0 Hz, 1H), 7.3-7.35 (m, 2H), 6.05 (q, J=3.2 Hz, 1H), 5.82 (q, J=3.2 Hz, 1H)

Process 2; Production of 4-bromo-α-chloro-3-methylbenzaldoxim

Into a solution of 82.0 g of 4-bromo-3-methylbenzaldoxim in 450 mL of tetrahydrofuran, 120.0 g of concentrated hydrochloric acid was dropped while stirring and ice-cooling the mixture over 45 minutes. Next, into the reaction mixture, 220 mL of 8% sodium hypochlorite aqueous solution was carefully dropped over 75 minutes so that the temperature of the reaction mixture does not exceed 5° C. After the completion of the dropping, the reaction mixture was stirred at 10° C. or less continuously for another 90 minutes. After the completion of the reaction, a nitrogen gas was blown into the reaction mixture for 45 minutes and the deposited insoluble matter was filtered off, followed by distilling off tetrahydrofuran under reduced pressure. The residual aqueous solution was extracted with 240.0 g of ethyl acetate and the organic phase was cleaned with water (240 mL×2). Subsequently, the insoluble matter was filtered off and the solvent was distilled off under reduced pressure to obtain 93.5 g of the objective substance as a light yellow crystal.

Melting point: 77.0 to 78.0° C.

$^1$H NMR (CDCl$_3$, Me$_4$Si, 400 MHz) δ 8.00 (bs, 1H), 7.71 (d, J=2.2 Hz, 1H), 7.57 (d, J=8.4 Hz, 1H), 7.51 (dd, J=8.4, 2.2 Hz, 1H), 2.44 (s, 3H)

Process 3; Production of 3-(4-bromo-3-methylphenyl)-5-(3,5-dichlorophenyl)-5-trifluoromethyl-4,5-dihydroisoxazole To a solution of 22.7 g of 3,5-dichloro-1-(1-trifluoromethylethenyl)benzene produced in Process 1 and 26.0 g of 4-bromo-α-chloro-3-methylbenzaldoxim in 120 mL of tetrahydrofuran, 15.7 g of potassium hydrogen carbonate was added, and the resultant mixture was stirred while heating the mixture to reflux for 5 hours. After the completion of the reaction, the reaction mixture was left to be cooled to room temperature and the insoluble matter was filtered off, followed by distilling off the solvent under reduced pressure. To the resultant residual matter, 150 mL of water was added and the resultant mixture was stirred at room temperature for 18 hours, followed by filtering off and drying the deposited crystal to obtain 38.6 g of the objective substance as a white crystal.

Melting point: 105.0 to 108.0° C.

$^1$H NMR (CDCl$_3$, Me$_4$Si, 300 MHz) δ 7.59 (d, J=8.4 Hz, 1 Hz), 7.45 to 7.55 (m, 3H), 7.42 (t, J=1.8 Hz, 1H), 7.33 (dd, J=8.4, 2.1 Hz, 1H), 4.07 (d, J=17.1 Hz, 1H), 3.68 (d, J=17.1 Hz, 1H), 2.43 (s, 3H).

Process 4; Production of 4-[5-(3,5-dichlorophenyl)-5-trifluoromethyl-4,5-dihydroisoxazole-3-yl]-2-methylbenzoyl chloride To a solution of 18.1 g of 3-(4-bromo-3-methylphenyl)-5-(3,5-dichlorophenyl)-5-trifluoromethyl-4,5-dihydroisoxazole and 3.94 g of sodium acetate in 42 mL of 1,2-dimethoxyethane and 42 mL of water in an autoclave, 0.42 g of triphenylphosphine and 0.09 g of palladium (II) acetate were added and the resultant mixture was stirred in an atmosphere of 1.5 MPa carbon monoxide at 110° C. for 7 hours. After the completion of the reaction, the reaction mixture was left to be cooled to room temperature and the solid matter was filtered off, followed by charging the reaction mixture into 100 mL of ethyl acetate. The organic phase was cleaned with a 1% sodium hydrogen carbonate aqueous solution (70 mL×2) and then with 1N hydrochloric acid (55 mL×1), and was dried with saturated brine, followed by exchanging the solvent to toluene. To this toluene solution, 2 drops of N,N-dimethylformamide were added and into the resultant mixture, 6.0 g of thionyl chloride was dropped at 80° C. with stirring, followed by continuing the stirring at the same temperature for another 1.5 hours. After the completion of the reaction, the insoluble matter was filtered off and the solvent was distilled off under reduced pressure until the total volume of the reaction mixture was reduced to about ⅓. Next, into the reaction mixture, 50 mL of hexane was gradually dropped with stirring at 60° C. and after the completion of the dropping, the reaction mixture was left to be cooled to room temperature with stirring, followed by continuing the stirring at room temperature for another 1 hour. The deposited crystal was filtered off and dried to obtain 13.4 g of the objective substance as a white crystal.

Melting point: 140.5 to 143.0° C.

$^1$H NMR (CDCl$_3$, Me$_4$Si, 300 MHz) δ 8.25 (d, J=8.7 Hz, 1H), 7.64 (d, J=8.7 Hz, 1H), 7.59 (s, 1H), 7.51 (s, 2H), 7.43 (s, 1H), 4.11 (d, J=17.4 Hz, 1H), 3.73 (d, J=17.4 Hz, 1H), 2.60 (s, 3H).

Process 5; Production of 4-[5-(3,5-dichlorophenyl)-5-trifluoromethyl-4,5-dihydroisoxazole-3-yl]-2-methyl-N-[1-(2-pyridyl)cyclopropyl]benzamide Into a solution of 0.50 g of 4-[5-(3,5-dichlorophenyl)-5-trifluoromethyl-4,5-dihydroisoxazole-3-yl]-2-methylbenzoyl chloride in 10 mL of dichloromethane, 0.20 g of 1-(2-pyridyl)cyclopropylamine was dropped while stirring and ice-cooling the solution and after the completion of the dropping, the stirring was continued at room temperature for 2 hours. After the completion of the reaction, the reaction mixture was poured into 20 mL of water and extracted with ethyl acetate (20 mL×2). The organic phase was cleaned with water (10 mL×1) and then was dehydrated and dried with saturated brine and over anhydrous sodium sulfate, respectively, in this order, and the solvent was distilled off under reduced pressure. The resultant residue was purified by silica gel column chromatography eluting with ethyl acetate-hexane (1:1) to obtain 0.16 g of the objective substance as a yellow resin-state substance.

$^1$H NMR (CDCl$_3$, Me$_4$Si, 300 MHz) δ 8.50 (d, J=4.8 Hz, 1H), 7.35-7.65 (m, 8H), 7.05-7.1 (m, 1H), 6.65 (s, 1H), 4.10 (d, J=17.4 Hz, 1H), 3.70 (d, J=17.4 Hz, 1H), 2.50 (s, 3H), 1.7-1.75 (m, 2H), 1.4-1.45 (m, 2H)

Synthetic Example 2

N-[Amino(methoxy)methylidene]-4-[5-(3,5-dichlorophenyl)-5-trifluoromethyl-4,5-dihydroisoxazole-3-yl]-2-methyl benzoic acid amide (Compound of the Present Invention No. 2-003)

To a solution of 1.00 g of 4-[5-(3,5-dichlorophenyl)-5-trifluoromethyl-4,5-dihydroisoxazole-3-yl]-2-methylbenzoyl-chloride synthesized in Process 4 of Synthetic Example 1 in 20 mL of acetonitrile, 0.85 g of O-methylisourea sulfate and 1.26 g of potassium carbonate were added and the resultant mixture was stirred at room temperature for 1.5 hours. After the completion of the reaction, the insoluble substance was filtered off and the solvent was distilled off under reduced pressure. The resultant residue was purified by silica gel column chromatography eluting with ethyl acetate-hexane (1:1) to obtain 0.40 g of the objective substance as a yellow resin-state substance.

$^1$H NMR (CDCl$_3$, Me$_4$Si, 300 MHz) δ 9.20 (bs, 1H), 8.09 (d, J=8.4 Hz, 1H), 7.4-7.6 (m, 5H), 5.58 (bs, 1H), 4.10 (d, J=17.4 Hz, 1H), 3.93 (s, 3H), 3.71 (d, J=17.4 Hz, 1H), 2.65 (s, 3H).

Synthetic Example 3

N-(Amino(methylthio) methylidene)-4-(5-(3,5-dichlorophenyl)-5-trifluoromethyl-4,5-dihydroisoxazole-3-yl)-2-methyl benzoic acid amide (Compound of the Present Invention No. 2-010)

Process 1; Production of N-thiocarbamoyl-4-[5-(3,5-dichlorophenyl)-5-trifluoromethyl-4,5-dihydroisoxazole-3-yl]-2-methyl benzoic acid amide To a solution of 1.0 g of 4-(5-(3,5-dichlorophenyl)-5-trifluoromethyl-4,5-dihydroisoxazole-3-yl)-2-methylbenzoyl chloride synthesized in Process 4 of Synthetic Example 1 in 20 mL of tetrahydrofuran, 245 mg of potassium thiocyanate was added and the resultant mixture was stirred at 40° C. for 1 hour. Next, the reaction mixture was left to be cooled to room temperature and 5 mL of concentrated ammonia water was added to the reaction mixture, followed by continuing the stirring of the mixture for another 30 minutes. After the completion of the reaction, 20 mL of water was added to the reaction mixture to dilute the mixture and the diluted reaction mixture was extracted with 40 mL of ethyl acetate, followed by distilling off the solvent under reduced pressure. The resultant residue was purified by silica gel column chromatography eluting with ethyl acetate-hexane (1:1) to obtain 0.9 g of the objective substance as a colorless resin-state substance.

$^1$H NMR (CDCl$_3$, Me$_4$Si, 400 MHz) δ 9.94 (s, 1H), 9.35 (s, 1H), 7.4-7.6 (m, 6H), 4.12 (d, J=17.4 Hz, 1H), 3.72 (d, J=17.4 Hz, 1H), 2.50 (s, 3H).

Process 2; Production of N-[amino(methylthio)methylidene]-4-[5-(3,5-dichlorophenyl)-5-trifluoromethyl-4,5-dihydroisoxazole-3-yl]-2-methyl benzoic acid amide To a solution of 0.30 g of N-thiocarbamoyl-4-[5-(3,5-dichlorophenyl)-5-trifluoromethyl-4,5-dihydroisoxazole-3-yl]-2-methyl benzoic acid amide and 0.26 g of potassium carbonate in 10 mL of N,N-dimethylformamide, 0.107 g of methyl iodide was added and the resultant mixture was stirred at room temperature for 15 hours. After the completion of the reaction, the reaction mixture was diluted with 20 mL of water and the diluted reaction mixture was extracted with ethyl acetate (30 mL×1). The organic phase was dehydrated and dried with saturated brine and over anhydrous sodium sulfate, respectively, in this order, and the solvent was distilled off under reduced pressure. The resultant residue was purified by silica gel column chromatography eluting with ethyl acetate-hexane (1:3) to obtain 0.28 g of the objective substance as a colorless resin-state substance.

$^1$H NMR (CDCl$_3$, Me$_4$Si, 300 MHz) δ 8.14 (d, J=8.1 Hz, 1H), 7.4-7.55 (m, 5H), 4.10 (d, J=17.4 Hz, 1H), 3.71 (d, J=17.4 Hz, 1H), 2.64 (s, 3H), 2.55 (s, 3H).

Synthetic Example 4

N-[Amino(methylamino) methylidene]-4-[5-(3,5-dichlorophenyl)-5-trifluoromethyl-4,5-dihydroisoxazole-3-yl]-2-methyl benzoic acid amide (Compound of the Present Invention No. 2-012)

0.13 g of N-[amino(methylthio) methylidene]-4-[5-(3,5-dichlorophenyl)-5-trifluoromethyl-4,5-dihydroisoxazole-3-yl]-2-methyl benzoic acid amide (compound of the present invention No. 2-010) was added to 10 mL of a 40% methylaminemethanol solution and the resultant mixture was stirred at room temperature for 3 hours. After the completion of the reaction, the solvent was distilled off under reduced pressure and the resultant residue was purified by silica gel column chromatography eluting with ethyl acetate-hexane (1:1) to obtain 0.09 g of the objective substance as a colorless resin-state substance.

$^1$H NMR (CDCl$_3$, Me$_4$Si, 300 MHz) δ 9.00 (bs, 1H), 7.68 (bs, 1H), 7.3-7.6 (m, 5H), 6.50 (bs, 1H), 5.51 (bs, 1H), 4.09 (d, J=17.4 Hz, 1H), 3.70 (d, J=17.4 Hz, 1H), 2.60 (bs, 3H), 2.55 (s, 3H).

Synthetic Example 5

N-[Methoxy(methylamino)methylidene]-4-[5-(3,5-dichlorophenyl)-5-trifluoromethyl-4,5-dihydroisoxazole-3-yl]-2-methyl benzoic acid amide (Compound of the Present Invention No. 3-001)

Process 1; Production of O-methyl N-[4-[5-(3,5-dichlorophenyl)-5-trifluoromethyl-4,5-dihydroisoxazole-3-yl]-2-methylbenzoyl]thiocarbamic acid ester To a solution of 0.70 g of 4-[5-(3,5-dichlorophenyl)-5-trifluoromethyl-4,5-dihydroisoxazole-3-yl]-2-methylbenzoyl chloride synthesized in Process 4 of Synthetic Example 1 in 7.0 mL of tetrahydrofuran, 0.17 g of potassium thiocyanate was added and the resultant mixture was stirred at 40° C. for 1 hour. After the completion of the reaction, the reaction mixture was left to be cooled to room temperature and the insoluble substance was filtered off. The filtrate was added to a solution of 0.15 g of methanol in 6.0 ml of tetrahydrofuran and the stirring of the resultant mixture was continued at room temperature for another 18 hours. After the completion of the reaction, the solvent was distilled off under reduced pressure and the resultant residue was purified by silica gel column chromatography silica gel column chromatography eluting with ethyl acetate-hexane (1:4 to 1:1) to obtain 0.54 g of the objective substance as a yellow resin-state substance.

$^1$H NMR (CDCl$_3$, Me$_4$Si, 400 MHz) δ 8.91 (s, 1H), 7.45-7.6 (m, 5H), 7.44 (t, J=1.8 Hz, 1H), 4.15 (s, 3H), 4.09 (d, J=17.2 Hz, 1H), 3.71 (d, J=17.2 Hz, 1H), 2.50 (s, 3H).

Process 2; Production of O,S-dimethyl-4-[5-(3,5-dichlorophenyl)-5-trifluoromethyl-4,5-dihydroisoxazole-3-yl]-2-methylbenzoyliminothiocarbonate To a solution of 0.30 g of O-methyl N-[4-[5-(3,5-dichlorophenyl)-5-trifluoromethyl-4,5-dihydroisoxazole-3-yl]-2-methylbenzoyl]thiocarbamic acid ester and 0.12 g of potassium carbonate in 4.0 mL of N,N-dimethylformamide, 0.13 g of methyl iodide was added and the resultant mixture was stirred at room temperature for 14 hours. After the completion of the reaction, the reaction mixture was poured into 50 mL of ice water and the resultant reaction mixture was extracted with ethyl acetate (50 mL×1). The organic phase was dehydrated and dried with saturated brine and over anhydrous sodium sulfate, respectively, in this order, and the solvent was distilled off under reduced pressure. The resultant residue was purified by silica gel column chromatography eluting with ethyl acetate-hexane (1:4 to 1:1 gradient) to obtain 0.20 g of the objective substance as a yellow resin-state substance.

$^1$H NMR (CDCl$_3$, Me$_4$Si, 400 MHz) δ 8.09 (d, J=8.2 Hz, 1H), 7.45-7.6 (m, 4H), 7.42 (t, J=1.8 Hz, 1H), 4.10 (d, J=17.2 Hz, 1H), 4.08 (s, 3H), 3.73 (d, J=17.2 Hz, 1H), 2.67 (s, 3H), 2.41 (s, 3H).

Process 3; Production of N-[methoxy(methylamino)methylidene]-4-[5-(3,5-dichlorophenyl)-5-trifluoromethyl-4,5-dihydroisoxazole-3-yl]-2-methyl benzoic acid amide To a solution of 0.3 g of O,S-dimethyl-4-[5-(3,5-dichlorophenyl)-5-trifluoromethyl-4,5-dihydroisoxazole-3-yl]-2-methylbenzoyliminothiocarbonate in 20 mL of acetonitrile, 1.0 mL of a 40% methylaminemethanol solution was added and the resultant mixture was stirred at room temperature for 30 minutes. After the completion of the reaction, the solvent was distilled off under reduced pressure and the resultant residue was purified by silica gel column chromatography eluting with ethyl acetate-hexane (1:1) to obtain 0.3 g of the objective substance as a light yellow resin-state substance.

$^1$H NMR (CDCl$_3$, Me$_4$Si, 300 MHz) δ 9.86 (bs, 1H), 8.05 (d, J=7.8 Hz, 1H), 7.4-7.55 (m, 5H), 4.09 (d, J=17.4 Hz, 1H), 3.97 (s, 3H), 3.71 (d, J=17.4 Hz, 1H), 2.95 (d, J=5.0 Hz, 3H), 2.64 (s, 3H).

Reference Example 1

1-(2-Pyridyl)cyclopropylamine

In a nitrogen-atmosphere, to a solution of 1.0 g of 2-cyanopyridine and 3.0 g of titanium tetraisopropoxide in 14 mL of diethyl ether, 20 mL of ethyl magnesium bromide (in a 0.96 M tetrahydrofuran solution) was dropped while stirring the solution at −78° C. After the completion of the dropping, the resultant mixture was stirred at room temperature for 1 hour. Next, to the reaction mixture, 2.7 g of a trifluoroboron diethyl ether complex was added and the stirring of the reaction mixture was continued for another 18 hours in a nitrogen-atmosphere at room temperature. After the completion of the reaction, to the reaction mixture, 20 mL of a 1N hydrochloric acid aqueous solution was added and the resultant mixture was stirred for 10 minutes. Next, 30 mL of a 1N sodium hydroxide aqueous solution was added to the reaction mixture while ice-cooling the mixture to convert the mixture to basic and thereafter, the reaction mixture was extracted with diethyl ether (50 mL×2). The organic phase was dehydrated and dried with saturated brine and over anhydrous sodium sulfate, respectively, in this order, and the solvent was distilled off under reduced pressure to obtain 1.0 g of crude 1-(2-pyridyl)cyclopropylamine as a yellow oily substance. This substance was used in the reaction as it is without further purification.

The compound of the present invention can be produced according to the above Production Methods and Examples. Examples of the compound of the present invention produced in substantially the same manner as in Synthetic Example 1 to Synthetic Example 5 are individually shown in Table 3 to Table 6, however, the examples should not be construed as limiting the scope of the present invention.

Here, a description "Et" in Tables represents an ethyl group and in the same manner, "n-Pr" or "Pr-n" represents an n-propyl group, "i-Pr" or "Pr-i" represents an isopropyl group, "c-Pr" or "Pr-c" represents a cyclopropyl group and "n-Bu" or "Bu-n" represents an n-butyl group.

An aromatic heterocycle represented by D-52a in Table represents the following structure:

[Chemical Formula 30]

D-52a:

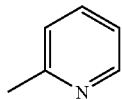

In addition, in Tables, the numbers representing substituted positions of substituents $(X)_m$ and $(Y)_n$ correspond to the positions of numbers attached to each structural formula in Tables 3 to 6, and an expression "-" represents "non-substituted".

Furthermore, "*1" in Tables means "resin-state".

TABLE 3

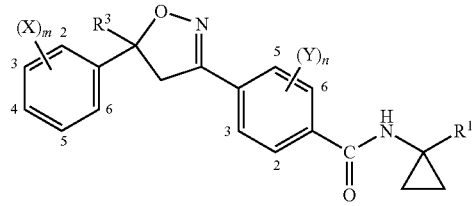

| No. | $(X)_m$ | $R^3$ | $(Y)_n$ | $R^1$ | m.p. (° C.) |
|---|---|---|---|---|---|
| 1-001 | 3,5-Cl$_2$ | CF$_3$ | 2-CH$_3$ | CH$_3$ | 183.0-185.0 |
| 1-002 | 3,5-Cl$_2$ | CF$_3$ | 2-CH$_3$ | c-Pr | *1 |
| 1-003 | 3,5-Cl$_2$ | CF$_3$ | 2-CH$_3$ | CN | 234.0-236.0 |
| 1-004 | 3,5-Cl$_2$ | CF$_3$ | 2-CH$_3$ | C(O)OH | *1 |
| 1-005 | 3,5-Cl$_2$ | CF$_3$ | 2-CH$_3$ | C(O)OCH$_3$ | *1 |
| 1-006 | 3,5-Cl$_2$ | CF$_3$ | 2-CH$_3$ | C(O)NHCH$_2$CF$_3$ | *1 |
| 1-007 | 3,5-Cl$_2$ | CF$_3$ | 2-CH$_3$ | D-52a | *1 |

TABLE 4

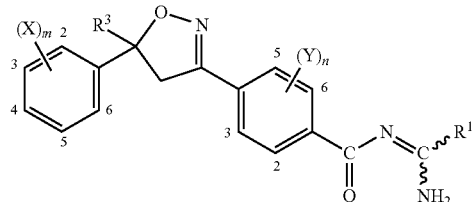

| No. | $(X)_m$ | $R^3$ | $(Y)_n$ | $R^1$ | m.p. (° C.) |
|---|---|---|---|---|---|
| 2-001 | 3,5-Cl$_2$ | CF$_3$ | 2-I | OCH$_3$ | *1 |
| 2-002 | 3,5-Cl$_2$ | CF$_3$ | 2-I | OEt | *1 |
| 2-003 | 3,5-Cl$_2$ | CF$_3$ | 2-CH$_3$ | OCH$_3$ | *1 |

TABLE 4-continued

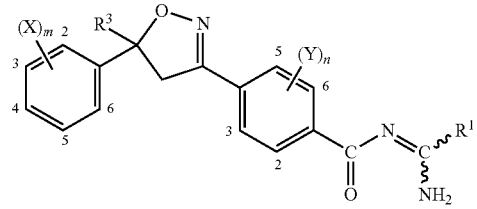

| No. | $(X)_m$ | $R^3$ | $(Y)_n$ | $R^1$ | m.p. (° C.) |
|---|---|---|---|---|---|
| 2-004 | 3,5-Cl$_2$ | CF$_3$ | 2-CH$_3$ | OEt | *1 |
| 2-005 | 3,5-Cl$_2$ | CF$_3$ | 2-CH$_3$ | OPr-n | *1 |
| 2-006 | 3,5-Cl$_2$ | CF$_3$ | 2-CH$_3$ | OPr-i | *1 |
| 2-007 | 3,5-Cl$_2$ | CF$_3$ | 2-CH$_3$ | OBu-n | *1 |
| 2-008 | 3,5-Cl$_2$ | CF$_3$ | 2-CH$_3$ | OCH$_2$CF$_3$ | *1 |
| 2-009 | 3,5-Cl$_2$ | CF$_3$ | 2-CH$_3$ | OCH$_2$C≡CH | *1 |
| 2-010 | 3,5-Cl$_2$ | CF$_3$ | 2-CH$_3$ | SCH$_3$ | *1 |
| 2-011 | 3,5-Cl$_2$ | CF$_3$ | 2-CH$_3$ | SEt | *1 |
| 2-012 | 3,5-Cl$_2$ | CF$_3$ | 2-CH$_3$ | NHCH$_3$ | *1 |
| 2-013 | 3,5-Cl$_2$ | CF$_3$ | 2-CH$_3$ | NHCN | *1 |
| 2-014 | 3,5-Cl$_2$ | CF$_3$ | 2-CH$_3$ | NHOCH$_3$ | *1 |
| 2-015 | 3,5-Cl$_2$ | CF$_3$ | 2-CH$_3$ | N(CH$_3$)OCH$_3$ | *1 |
| 2-016 | 3,5-Cl$_2$ | CF$_3$ | 2-CH$_3$ | NHOEt | *1 |
| 2-017 | 3,5-Cl$_2$ | CF$_3$ | 2-CH$_3$ | NHNO$_2$ | 205.0-207.0 |
| 2-018 | 3,5-Cl$_2$ | CF$_2$Cl | 2-CH$_3$ | OEt | *1 |
| 2-019 | 3,5-Br$_2$ | CF$_3$ | 2-CH$_3$ | OEt | *1 |
| 2-020 | 3,5-(CF$_3$)$_2$ | CF$_3$ | — | OCH$_3$ | 129.0-130.0 |
| 2-021 | 3,4,5-Cl$_3$ | CF$_3$ | — | OCH$_3$ | 141.0-143.0 |
| 2-022 | 3,5-Cl$_2$ | CF$_3$ | 2-CN | OEt | 95.0-100.0 |

TABLE 5

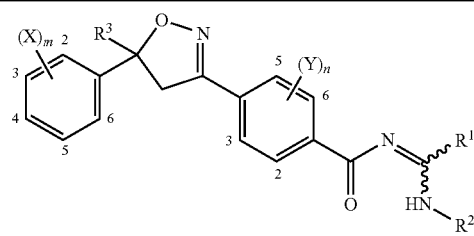

| No. | $(X)_m$ | $R^3$ | $(Y)_n$ | $R^1$ | $R^2$ | m.p. (° C.) |
|---|---|---|---|---|---|---|
| 3-001 | 3,5-Cl$_2$ | CF$_3$ | 2-CH$_3$ | OCH$_3$ | CH$_3$ | *1 |
| 3-002 | 3,5-Cl$_2$ | CF$_3$ | 2-CH$_3$ | OCH$_3$ | Et | *1 |
| 3-003 | 3,5-Cl$_2$ | CF$_3$ | 2-CH$_3$ | OCH$_3$ | n-Pr | *1 |
| 3-004 | 3,5-Cl$_2$ | CF$_3$ | 2-CH$_3$ | OCH$_3$ | —Pr | *1 |
| 3-005 | 3,5-Cl$_2$ | CF$_3$ | 2-CH$_3$ | OCH$_3$ | CH$_2$CF$_3$ | *1 |
| 3-006 | 3,5-Cl$_2$ | CF$_3$ | 2-CH$_3$ | OCH$_3$ | OCH$_3$ | *1 |
| 3-007 | 3,5-Cl$_2$ | CF$_3$ | 2-CH$_3$ | OCH$_3$ | N(CH$_3$)$_2$ | *1 |
| 3-008 | 3,5-Cl$_2$ | CF$_3$ | 2-CH$_3$ | OCH$_3$ | NHCHO | *1 |
| 3-009 | 3,5-Cl$_2$ | CF$_3$ | 2-CH$_3$ | OCH$_3$ | NHC(O)CH$_3$ | *1 |
| 3-010 | 3,5-Cl$_2$ | CF$_3$ | 2-CH$_3$ | OCH$_3$ | NHC(O)OCH$_3$ | *1 |
| 3-011 | 3,5-Cl$_2$ | CF$_3$ | 2-CH$_3$ | OEt | CH$_3$ | *1 |
| 3-012 | 3,5-Cl$_2$ | CF$_3$ | 2-CH$_3$ | OBu-n | CH$_3$ | *1 |
| 3-013 | 3,5-Cl$_2$ | CF$_3$ | 2-CH$_3$ | SCH$_3$ | CH$_3$ | *1 |

TABLE 6

| No. | (X)$_m$ | (Y)$_n$ | R$^2$ | R$^1$ | m.p. (° C.) |
|---|---|---|---|---|---|
| 4-001 | 3,5-Cl$_2$ | 2-CH$_3$ | CH$_3$ | SCH$_3$ | *1 |

$^1$H NMR data of the compound of the present invention of which melting point is not described in Table 3 to Table 6 is shown in Table 7.

Here, the description (A) in Table represents conditions (CDCl$_3$, Me$_4$Si, 300 MHz) under which the measurement was performed in a solvent of deuterated chloroform using tetramethylsilane as the standard substance at 300 MHz and the description (B) represents measurement conditions (CDCl$_3$, Me$_4$Si, 700 MHz).

TABLE 7

| No. | $^1$H NMR |
|---|---|
| 1-002 | (A) δ7.3-7.55 (m, 6H), 6.10 (s, 1H), 4.10 (d, J = 17.4 Hz, 1H), 3.70 (d, J = 17.4 Hz, 1H), 2.45 (s, 3H), 1.55-1.6 (m, 1H), 0.7-0.85 (m, 4H), 0.45-0.55 (m, 2H), 0.2-0.25 (m, 2H) |
| 1-004 | (A) δ7.45-8.0 (m, 6H), 4.10 (d, J = 17.1 Hz, 1H), 3.70 (d, J = 17.1 Hz, 1H), 2.65 (s, 3H), 1.75-2.0 (m, 4H) |
| 1-005 | (A) δ7.4-7.55 (m, 6H), 6.30 (s, 1H), 4.10 (d, J = 17.1 Hz, 1H), 3.75 (s, 3H), 3.70 (d, J = 17.1 Hz, 1H), 2.50 (s, 3H), 1.65-1.7 (m, 2H), 1.25-1.35 (m, 2H) |
| 1-006 | (A) δ7.3-7.55 (m, 6H), 7.1-7.2 (m, 1H), 6.70 (s, 1H), 4.10 (d, J = 17.1 Hz, 1H), 3.85-4.0 (m, 2H), 3.70 (d, J = 17.1 Hz, 1H), 2.45 (s, 3H), 1.55-1.65 (m, 2H), 1.1-1.15 (m, 2H) |
| 2-001 | (A) δ9.16 (bs, 1H), 8.16 (bs, 1H), 7.98 (d, J = 8.1 Hz, 1H), 7.73 (d, J = 8.1 Hz, 1H), 7.51 (bs, 2H), 7.44 (bs, 1H), 5.66 (bs, 1H), 4.07 (d, J = 17.4 Hz, 1H), 3.95 (s, 3H), 3.69 (d, J = 17.4 Hz, 1H) |
| 2-002 | (A) δ9.17 (bs, 1H), 8.16 (bs, 1H), 7.93 (d, J = 8.1 Hz, 1H), 7.7-7.8 (m, 1H), 7.51 (s, 2H), 7.43 (bs, 1H), 5.70 (bs, 1H), 4.41 (q, J = 7.2 Hz, 2H), 4.07 (d, J = 17.4 Hz, 1H), 3.69 (d, J = 17.4 Hz, 1H), 1.34 (t, J = 7.2 Hz, 3H) |
| 2-004 | (B) δ9.30 (bs, 1H), 8.08 (d, J = 8.4 Hz, 1H), 7.5-7.6 (m, 3H), 7.49 (s, 1H), 7.42 (s, 1H), 5.60 (bs, 1H), 4.42 (q, J = 7.2 Hz, 2H), 4.13 (d, J = 17.4 Hz, 1H), 3.74 (d, J = 17.4 Hz, 1H), 2.64 (s, 3H), 1.35 (t, J = 7.2 Hz, 3H) |
| 2-005 | (A) δ9.25 (bs, 1H), 8.07 (d, J = 8.1 Hz, 1H), 7.4-7.55 (m, 5H), 5.51 (bs, 1H), 4.32 (t, J = 6.6 Hz, 2H), 4.10 (d, J = 17.4 Hz, 1H), 3.71 (d, J = 17.4 Hz, 1H), 2.65 (s, 3H), 1.65-1.75 (m, 2H), 0.99 (t, J = 7.5 Hz, 3H) |
| 2-006 | (A) δ9.25 (bs, 1H), 8.05 (d, J = 8.1 Hz, 1H), 7.4-7.55 (m, 5H), 5.35-5.45 (m, 2H), 4.10 (d, J = 17.4 Hz, 1H), 3.71 (d, J = 17.4 Hz, 1H), 2.64 (s, 3H), 1.33 (d, J = 6.0 Hz, 6H) |
| 2-007 | (A) δ9.29 (bs, 1H), 8.07 (d, J = 8.1 Hz, 1H), 7.4-7.55 (m, 5H), 5.58 (bs, 1H), 4.36 (t, J = 6.9 Hz, 2H), 4.10 (d, J = 17.4 Hz, 1H), 3.71 (d, J = 17.4 Hz, 1H), 2.64 (s, 3H), 1.65-1.75 (m, 2H), 1.35-1.5 (m, 2H), 0.96 (t, J = 7.5 Hz, 3H) |
| 2-008 | (A) δ9.28 (bs, 1H), 8.06 (d, J = 8.1 Hz, 1H), 7.4-7.55 (m, 5H), 5.72 (bs, 1H), 4.77 (q, J = 8.7 Hz, 2H), 4.10 (d, J = 17.4 Hz, 1H), 3.71 (d, J = 17.4 Hz, 1H), 2.63 (s, 3H) |
| 2-009 | (A) δ9.25 (bs, 1H), 8.13 (d, J = 8.1 Hz, 1H), 7.4-7.55 (m, 5H), 5.74 (bs, 1H), 4.98 (s, 2H), 4.09 (d, J = 17.4 Hz, 1H), 3.71 (d, J = 17.4 Hz, 1H), 2.65 (s, 3H), 2.54 (t, J = 2.4 Hz, 1H) |
| 2-011 | (A) δ8.15 (d, J = 8.1 Hz, 1H), 7.4-7.55 (m, 5H), 4.13 (d, J = 17.4 Hz, 1H), 3.74 (d, J = 17.4 Hz, 1H), 3.19 (q, J = 7.5 Hz, 2H), 2.67 (s, 3H), 1.42 (t, J = 7.5 Hz, 3H) |
| 2-013 | (A) δ9.21 (bs, 1H), 8.81 (bs, 1H), 7.4-7.55 (m, 6H), 6.75 (bs, 1H), 4.10 (d, J = 17.4 Hz, 1H), 3.71 (d, J = 17.4 Hz, 1H), 2.53 (s, 3H) |
| 2-014 | (A) δ8.04 (bs, 1H), 7.4-7.65 (m, 6H), 6.24 (bs, 2H), 4.10 (d, J = 17.4 Hz, 1H), 3.6-3.8 (m, 4H), 2.51 (s, 3H) |
| 2-015 | (A) δ9.90 (bs, 1H), 7.95 (d, J = 8.1 Hz, 1H), 7.4-7.55 (m, 5H), 6.25 (bs, 1H), 4.09 (d, J = 17.4 Hz, 1H), 3.77 (s, 3H), 3.70 (d, J = 17.4 Hz, 1H), 3.37 (s, 3H), 2.62 (s, 3H) |
| 2-016 | (A) δ7.4-7.6 (m, 6H), 6.20 (bs, 1H), 4.09 (d, J = 17.4 Hz, 1H), 3.87 (q, J = 7.2 Hz, 2H), 3.70 (d, J = 17.4 Hz, 1H), 2.51 (s, 3H), 1.24 (t, J = 7.2 Hz, 3H) |
| 2-018 | (A) δ9.27 (bs, 1H), 8.07 (d, J = 8.2 Hz, 1H), 7.45-7.55 (m, 4H), 7.42 (t, J = 1.8 Hz, 1H), 5.58 (bs, 1H), 4.42 (q, J = 7.2 Hz, 2H), 4.15 (d, J = 17.4 Hz, 1H), 3.73 (d, J = 17.4 Hz, 1H), 2.64 (s, 3H), 1.35 (t, J = 7.2 Hz, 3H) |
| 2-019 | (A) δ9.25 (bs, 1H), 8.07 (d, J = 8.2 Hz, 1H), 7.7-7.75 (m, 3H), 7.45-7.55 (m, 2H), 5.54 (bs, 1H), 4.42 (q, J = 7.2 Hz, 2H), 4.09 (d, J = 17.4 Hz, 1H), 3.70 (d, J = 17.4 Hz, 1H), 2.64 (s, 3H), 1.35 (t, J = 7.2 Hz, 3H) |
| 3-002 | (A) δ9.87 (bs, 1H), 8.06 (d, J = 8.1 Hz, 1H), 7.4-7.55 (m, 5H), 4.10 (d, J = 17.4 Hz, 1H), 3.96 (s, 3H), 3.70 (d, J = 17.4 Hz, 1H), 3.3-3.45 (m, 2H), 2.64 (s, 3H), 1.2-1.3 (m, 3H) |
| 3-003 | (A) δ9.96 (bs, 1H), 8.06 (d, J = 8.1 Hz, 1H), 7.4-7.55 (m, 5H), 4.10 (d, J = 17.4 Hz, 1H), 3.95 (s, 3H), 3.71 (d, J = 17.4 Hz, 1H), 3.30 (q, J = 6.9 Hz, 2H), 2.64 (s, 3H), 1.55-1.7 (m, 2H), 0.98 (t, J = 8.1 Hz, 3H) |
| 3-004 | (A) δ9.82 (d, J = 7.5 Hz, 1H), 8.06 (d, J = 8.1 Hz, 1H), 7.4-7.55 (m, 5H), 4.10 (d, J = 17.4 Hz, 1H), 3.85-4.1 (m, 1H), 3.96 (s, 3H), 3.71 (d, J = 17.4 Hz, 1H), 2.65 (s, 3H), 1.26 (d, J = 6.6 Hz, 6H) |
| 3-005 | (A) δ10.27 (t, J = 6.9 Hz, 1H), 8.14 (d, J = 8.1 Hz, 1H), 7.4-7.6 (m, 5H), 4.10 (d, J = 17.4 Hz, 1H), 3.9-4.1 (m, 2H), 4.01 (s, 3H), 3.71 (d, J = 17.4 Hz, 1H), 2.66 (s, 3H) |
| 3-006 | (A) δ8.13 (s, 1H), 7.4-7.55 (m, 6H), 4.09 (d, J = 17.4 Hz, 1H), 3.81 (s, 3H), 3.77 (s, 3H), 3.70 (d, J = 17.4 Hz, 1H), 2.51 (s, 3H) |
| 3-007 | (A) δ10.56 (bs, 1H), 8.10 (d, J = 8.1 Hz, 1H), 7.4-7.55 (m, 5H), 4.10 (d, J = 17.4 Hz, 1H), 4.03 (s, 3H), 3.71 (d, J = 17.4 Hz, 1H), 2.68 (s, 6H), 2.63 (s, 3H) |
| 3-008 | (A) δ9.60 (bs, 1H), 7.7-8.0 (m, 2H), 7.4-7.55 (m, 5H), 6.51 (bs, 1H), 3.8-4.15 (m, 4H), 3.67 (d, J = 17.4 Hz, 1H), 2.39 (s, 3H) |
| 3-009 | (A) δ9.36 (bs, 1H), 7.85 (d, J = 8.1 Hz, 1H), 7.4-7.55 (m, 6H), 4.06 (d, J = 17.4 Hz, 1H), 3.93 (s, 3H), 3.67 (d, J = 17.4 Hz, 1H), 2.48 (s, 3H), 2.05 (bs, 3H) |
| 3-010 | (A) δ10.77 (bs, 1H), 8.14 (d, J = 8.1 Hz, 1H), 7.4-7.55 (m, 5H), 6.51 (bs, 1H), 4.10 (d, J = 17.4 Hz, 1H), 3.99 (s, 3H), 3.80 (s, 3H), 3.71 (d, J = 17.4 Hz, 1H), 2.65 (s, 3H) |
| 3-011 | (A) δ9.89 (bs, 1H), 8.01 (d, J = 8.1 Hz, 1H), 7.4-7.55 (m, 5H), 4.44 (q, J = 7.2 Hz, 2H), 4.09 (d, J = 17.4 Hz, 1H), 3.70 (d, J = 17.4 Hz, 1H), 2.95 (d, J = 5.1 Hz, 3H), 2.63 (s, 3H), 1.37 (t, J = 7.2 Hz, 3H) |
| 3-012 | (A) δ9.89 (bs, 1H), 8.01 (d, J = 8.1 Hz, 1H), 7.4-7.55 (m, 5H), 4.39 (t, J = 6.9 Hz, 2H), 4.09 (d, J = 17.4 Hz, 1H), 3.70 (d, J = 17.4 Hz, 1H), 2.95 (d, J = 5.4 Hz, 3H), 2.63 (s, 3H), 1.65-1.8 (m, 2H), 1.35-1.5 (m, 2H), 0.97 (t, J = 7.5 Hz, 3H) |
| 3-013 | (A) δ11.13 (bs, 1H), 8.07 (d, J = 8.1 Hz, 1H), 7.4-7.55 (m, 5H), 4.09 (d, J = 17.4 Hz, 1H), 3.70 (d, J = 17.4 Hz, 1H), 3.0-3.1 (m, 3H), 2.63 (s, 3H), 2.55 (s, 3H) |
| 4-001 | (B) δ8.69 (bs, 1H), 8.07 (d, J = 8.1 Hz, 1H), 7.4-7.55 (m, 4H), 7.31 (d, J = 7.7 Hz, 1H), 4.08 (d, J = 17.5 Hz, 1H), 3.70 (d, J = 17.5 Hz, 1H), 3.34 (s, 3H), 2.41 (s, 3H), 2.23 (s, 3H) |

TEST EXAMPLES

Next, the usefulness of the compound of the present invention as a pest control agent is more specifically described in the following Test Examples, which should not be construed as limiting the scope of the present invention.

Test Example 1

Mortality Test for *Plutella xylostella*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of canarium album was immersed for about 10 seconds and was air-dried and then put into a petri dish. In the petri dish, five 2 instar larvae of *Plutella xylostella* per petri dish were released and the petri dish was capped and stored in a thermostat room of 25° C. The number of killed larvae after 6 days was measured and the mortality was calculated from the following calculation formula:

Mortality (%)=(number of killed larvae/number of released larvae)×100.

Here, the test was carried out with two replications.

As the results of the test, among the compounds subjected to the test, the following compounds have exhibited the mortality of 80% or more. The compounds of the present invention: No. 1-001 to 1-003, 1-006, 1-007, 2-001, 2-003 to 2-011, 2-012*, 2-013 to 2-017, 2-018*, 2-019*, 2-020*, 2-021, 3-001 to 3-007, 3-008, 3-009, 3-010*, 3-011 to 3-013, and 4-001*.

Here, the above mark "*" indicates that the mortality test was performed using a drug solution of 100 ppm concentration and the mark "**" indicates that the mortality test was performed using a drug solution of 500 ppm concentration.

Test Example 2

Mortality Test for *Spodoptera litura*

A 10% emulsifiable concentrate of the compound of the present invention (depending on the type of the compound, a 10% wettable powder was subjected to the test) was diluted with water containing a spreader to prepare a drug solution in a concentration of 10 ppm. In this drug solution, a leaf of canarium album was immersed for about 10 seconds and was air-dried and then put into a petri dish. In the petri dish, five 2 instar larvae of *Spodoptera litura* per petri dish were released and the petri dish was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-003, 1-006, 1-007, 2-001, 2-003 to 2-006, 2-008 to 2-011, 2-012*, 2-013 to 2-017, 2-018*, 2-019*, 2-020*, 2-021, 3-001 to 3-007, 3-008, 3-009, 3-010*, 3-011, 3-013, and 4-001*.

Here, the above mark "*" indicates that the mortality test was performed using a drug solution of 100 ppm concentration and the mark "**" indicates that the mortality test was performed using a drug solution of 500 ppm concentration.

Test Example 3

Mortality Test for *Homona magnanima*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of canarium album was immersed for about 10 seconds and was air-dried and then put into a petri dish. In the petri dish, five 2 instar larvae of *Homona magnanima* per petri dish were released and the petri dish was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-006, 1-007, 2-001, 2-003, 2-004, 2-006, 2-009, 2-010, 2-013 to 2-017, 3-001, and 3-006.

Test Example 4

Mortality Test for *Helicoverpa armigera*

A 10% emulsifiable concentrate of the compound of the present invention (depending on the type of the compound, a 10% wettable powder was subjected to the test) was diluted with water containing a spreader to prepare a drug solution in a concentration of 100 ppm. In this drug solution, a leaf of canarium album was immersed for about 10 seconds and was air-dried and then put into a petri dish. In the petri dish, one 2 instar larva of *Helicoverpa armigera* per petri dish was released and the petri dish was capped and stored in a thermostat room of 25° C. The number of killed larvae after 6 days was measured and the mortality was calculated from the same calculation formula as that in Test Example 1. Here, the test was carried out with 2 replications.

As the results of the test, among the compounds subjected to the test, the following compounds have exhibited the mortality of 80% or more. The compounds of the present invention: No. 1-002, 1-006, 1-007, 2-001, 2-003 to 2-019, 2-021, 3-001 to 3-007, 3-010, 3-011.

Test Example 5

Mortality Test for *Frankliniella occidentalis*

In a styrol cup having an inner diameter of 7 cm, a wet filtration paper was laid, and on the paper, a leaf of kidney bean cut out so as to have the same diameter as the inner diameter of the cup was laid, followed by inoculating ten 1 instar larvae of *Frankliniella occidentalis* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostat room of 25° C. The number of killed larvae after 2 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-001, 1-002, 1-006, 1-007, 2-001, 2-003 to 2-019, 3-001 to 3-013, and 4-001.

Test Example 6

Mortality Test for *Thrips palmi*

In a styrol cup having an inner diameter of 7 cm, a wet filtration paper was laid, and on the paper, a leaf of kidney bean cut out so as to have the same diameter as the inner diameter of the cup was laid, followed by inoculating 10 imagines of *Thrips palmi* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 100 ppm. The drug solution was dusted using a rotary dusting tower in an amount of 2.5 mL per one styrol cup and the cup was capped and stored in a thermostat room of 25° C. The number of killed imagines after 2 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-001, 1-002, 1-006, 1-007, 2-001, 2-003 to 2-019, 2-021, 3-001 to 3-013, and 4-001.

Test Example 7

Mortality Test for *Eysarcoris lewisi*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of *Oryza sativa* was immersed for about 10 seconds and was air-dried and then put into a test tube. In the test tube, five 1 instar larvae of *Eysarcoris lewisi* per one test tube were released and the test tube was capped with a sponge and stored in a thermostat room of 25° C. The number of killed larvae after 2 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-001, 2-003 to 2-006, 2-008 to 2-011, 2-013, 2-014, 3-001 to 3-003, 3-006, and 3-007.

Test Example 8

Mortality Test for *Nilaparvata lugens*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf sheath of *Oryza sativa* was immersed for about 10 seconds and was air-dried and then put into a test tube. In the test tube, five 2 instar larvae of *Nilaparvata lugens* per test tube were released and the test tube was capped with a sponge and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-001, 2-003 to 2-007, 2-009 to 2-011, 2-013 to 2-019, 3-001 to 3-003, 3-005 to 3-007, and 3-009 to 3-011.

Test Example 9

Mortality Test for *Bemisia argentifolii*

In a styrol cup having an inner diameter of 7 cm, a wet filtration paper was laid, and on the paper, a cut-out leaf of tomato on which *Bemisia argentifolii* laid eggs (10 eggs/leaf) was laid. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-001, 2-003 to 2-011, 2-013, 2-014, 2-016 to 2-019, 3-001, 3-006, and 3-011.

Test Example 10

Mortality Test for *Myzus persicae*

In a glass petri dish having an inner diameter of 3 cm, a wet absorbent cotton was laid, and on the cotton, a leaf of canarium album cut out so as to have the same diameter as the inner diameter of the petri dish was laid, followed by releasing 4 apterous imagines of *Myzus persicae* on the leaf. After one day, 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower (2.5 mg/cm$^2$) and the petri dish was capped and stored in a thermostat room of 25° C. The number of killed imagines after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-001, 2-003 to 2-010, 2-013, 2-015 to 2-019, 3-001, 3-006, 3-007, and 3-010 to 3-013.

Test Example 11

Mortality Test for *Planococcus kraunhiae*

In a styrol cup having an inner diameter of 7 cm, a wet filtration paper was laid, and on the paper, a leaf of kidney bean cut out so as to have the same diameter as the inner diameter of the cup was laid, followed by inoculating ten 1 instar larvae of *Planococcus kraunhiae* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 2-003 to 2-010, 2, 013, 2-016, 2-017, 3-001, 3-002, 3-006, 3-007, and 4-001.

Test Example 12

Mortality Test for *Aulacophora femoralis*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of cucumber was immersed for about 10 seconds and was air-dried and then put into a petri dish. In the petri dish, five 2 instar larvae of *Aulacophora femoralis* per petri dish were released and the petri dish was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-001, 1-002, 1-006, 1-007, 2-001, 2-003 to 2-017, 3-001 to 3-013, and 4-001.

Test Example 13

Mortality Test for *Liriomyza trifolii*

A 10% emulsifiable concentrate of the compound of the present invention (depending on the type of the compound, a 10% wettable powder was subjected to the test) was diluted with water containing a spreader to prepare a drug solution in a concentration of 500 ppm. In this drug solution, a leaf of kidney bean on which *Liriomyza trifolii* laid eggs (10 eggs/leaf) and which was cut out to a diameter of 7 cm was immersed for about 10 seconds and was air-dried and then laid on a wet filtration paper laid in a styrol cup having an inner diameter of 7 cm. The styrol cup was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-003 to 2-004, 2-010, and 2-017 to 2-019.

Test Example 14

Mortality Test for *Tetranychus urticae*

In a styrol cup having an inner diameter of 7 cm, a wet filtration paper was laid, and on the paper, a leaf of kidney bean cut out so as to have the same diameter as the inner diameter of the cup was laid, followed by inoculating 10 larvae of *Tetranychus urticae* per leaf to the leaf. A 10% emulsifiable concentrate of the compound of the present invention (depending on the type of the compound, a 10% wettable powder was subjected to the test) was diluted with water containing a spreader to prepare a drug solution in a concentration of 500 ppm. The drug solution was dusted using a rotary dusting tower in an amount of 2.5 mL per styrol cup and the cup was capped and stored in a thermostat room of 25° C. The number of killed larvae after 6 days was measured and the mortality was calculated from the same calculation formula as that in Test Example 1. Here, the test was carried out with two replications.

As the results of the test, among the compounds subjected to the test, the following compounds have exhibited the mortality of 80% or more. The compounds of the present invention: No. 1-002, 1-006, 1-007, 2-001, 2-003 to 2-010, 2-013 to 2-019, 3-001 to 3-04, 3-007, and 3-010 to 3-012.

Test Example 15

Mortality Test for Cat Flea

To the bottom surface and the side surface of a petri dish having an inner diameter of 5.3 cm, 400 µL of an acetone solution in which 40 mg of the compound of the present invention was dissolved in 40 mL of acetone (concentration: 1,000 ppm) was applied and the acetone was volatilized to form a thin film of the compound of the present invention on the inner wall of the petri dish. The inner wall of the used petri dish has an area of 40 cm$^2$, so that the amount of the applied drug is 1 µg/cm$^2$. In the petri dish, 10 *Ctenocephalides felis* imagines (male and female were mixed) were released and the petri dish was capped and stored in a thermostat room of 25° C. The number of killed larvae after 4 days was measured and the mortality was calculated from the same calculation formula as that in Test Example 1. Here, the test was carried out on the single sample.

As the results of the test, among the compounds subjected to the test, the following compounds have exhibited the mortality of 80% or more. The compounds of the present invention: No. 1-002, 1-007, 2-001, 2-003 to 2-007, 2-009 to 2-011, 2-014, 2-016, 2-017, 3-001 to 3-004, 3-006, and 3-011.

Test Example 16

Mortality Test for American Dog Tick

To the bottom surfaces and the side surfaces of two petri dishes having an inner diameter of 5.3 cm, 400 µL of an acetone solution in which 4 mg of a compound of the present invention was dissolved in 40 mL of acetone (concentration: 100 ppm) was applied and the acetone was volatilized to form a thin film of the compound of the present invention on the inner walls of the petri dishes. The inner wall of the used petri dish has an area of 40 cm$^2$, so that the amount of the applied drug is 0.1 µg/cm$^2$. In one petri dish, 10 American dog ticks (*Dermacentor variabilis*) protonymphs (male and female were mixed) were released and the petri dish was capped with the other petri dish. The seam part of the two petri dishes was sealed with a tape so that the protonymphs could not flee and the two petri dishes were stored in a thermostat room of 25° C. The number of killed protonymphes after 4 days was measured and the mortality was calculated from the same calculation formula as that in Test Example 1. Here, the test was carried out on the single sample.

As the results of the test, among the compounds subjected to the test, the following compounds have exhibited the mortality of 80% or more. The compounds of the present invention: No. 1-002, 1-007, 2-001, 2-003 to 2-007, 2-009 to 2-012, 2-014, 2-016, 2-017, 2-021, 3-001 to 3-008, 3-010, and 3-011, 3-013.

Test Example 17

Mortality Test for *Helicoverpa armigera*
(Comparative Test 1)

10% emulsifiable concentrates of the compound of the present invention and a comparative compound were diluted with water containing a spreader to prepare drug solutions in a predetermined concentration. In these drug solutions, a leaf of Canarium album was immersed for about 10 seconds and was air-dried and then put into a petri dish. In the petri dish, seven 3-instar larvae of *Helicoverpa armigera* per petri dish were released and the petri dish was capped with a lid having pores and stored in a thermostat room of 25° C. After 2 days of the treatment, an artificial feed (1 cm$^3$) was added into the petri dish. The number of killed larvae after 6 days was measured and the mortality was calculated from the following calculation formula:

Mortality (%)=(number of killed larvae/number of released larvae)×100.

Here, the test was carried out with two replications.

The mortality of each compound subjected to the test at predetermined concentrations is shown in Table 8.

TABLE 8

| Compound subjected | Concentrations (ppm) | | | | | | |
|---|---|---|---|---|---|---|---|
| to test | 100 | 33 | 10 | 3.3 | 1 | 0.3 | 0.1 |
| Compound of present invention No. 2-003 | | | 100 | 100 | 100 | 85.7 | 57.1 |
| Comparative compound A | 100 | 100 | 92.9 | 21.4 | | | |
| Compound of present invention No. 3-001 | | | 100 | 100 | 71.4 | 21.4 | 0 |
| Comparative compound B | 100 | 85.7 | 71.4 | 35.7 | | | |

Comparative compound A: US Patent No. 2007/0066617 specification, Compound No. 5-574

[Chemical Formula 31]

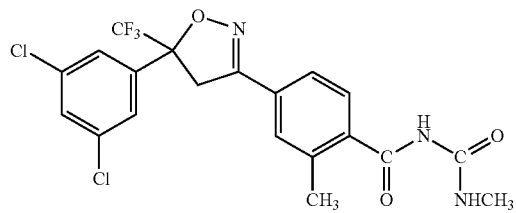

Comparative compound B: International Patent Application Publication No. 2007/026965 specification, Compound No. 8-001

[Chemical Formula 32]

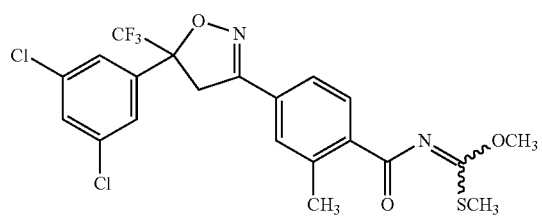

Test Example 18

Mortality Test for *Frankliniella occidentalis*
(Comparative Test 2)

In a styrol cup having an inner diameter of 7 cm, a wet filtration paper was laid, and on the paper, a leaf of kidney bean cut out so as to have the same diameter as the inner diameter of the cup was laid, followed by inoculating ten 1 instar larvae of *Frankliniella occidentalis* per leaf to the leaf. 10% emulsifiable concentrates of the compound of the present invention and a comparative compound were diluted with water containing a spreader to prepare drug solutions in a predetermined concentration. The drug solutions were dusted using a rotary dusting tower in an amount of 2.5 mL per styrol cup, and the cup was capped and stored in a thermostat room of 25° C. The number of killed larvae after 2 days was measured and the mortality was calculated from the following calculation formula:

Mortality (%)=(number of killed larvae/number of released larvae)×100.

Here, the test was carried out with two replications.

The mortality of each compound subjected to the test at predetermined concentrations is shown in Table 9.

TABLE 9

| Compound subjected | Concentrations (ppm) | | | | | | |
|---|---|---|---|---|---|---|---|
| to test | 100 | 33 | 10 | 3.3 | 1 | 0.3 | 0.1 |
| Compound of present invention No. 1-007 | | | 100 | 96.3 | 38.1 | 0 | 0 |
| Comparative compound C | 0 | 0 | 0 | 0 | | | |
| Compound of present invention No. 2-004 | | | 100 | 100 | 100 | 17.5 | 0 |
| Comparative compound D | 100 | 100 | 45.7 | 0 | | | |

Comparative compound C: International Patent Application Publication No. 2005/085216 specification, Compound No. 1-146

[Chemical Formula 33]

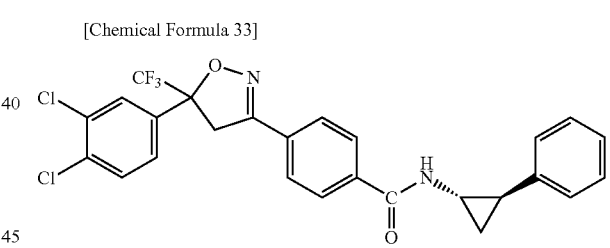

Comparative compound D: US Patent No. 2007/0066617 specification, Compound No. 5-576

[Chemical Formula 34]

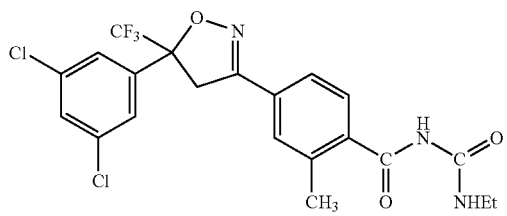

INDUSTRIAL APPLICABILITY

The isoxazoline-substituted benzamide compound according to the present invention is an extremely useful compound exhibiting excellent pest control activity, particularly excellent insecticidal/miticidal activity and having substantially no adverse effect on non-target organisms such as the mammal, the fish and beneficial insects.

The invention claimed is:

1. An isoxazoline-substituted benzamide compound represented by General Formula (1):

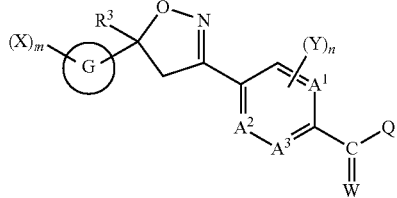

where:
A$^1$ represents a carbon atom or a nitrogen atom;
each of A$^2$ and A$^3$ represents a carbon atom;
G represents a benzene ring;
W represents an oxygen atom or a sulfur atom;
Q is a structure represented by Q-1:

Q-1:

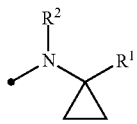

R$^1$ represents a C$_1$ to C$_4$ haloalkyl, a C$_1$ to C$_2$ alkoxy(C$_1$ to C$_2$) alkyl, a C$_3$ to C$_4$ cycloalkyl, a C$_2$ to C$_4$ alkenyl, —C(O)N(R$^{13}$)R$^{12}$, a phenyl substituted with (Z)$_{p1}$, D-22, D-52 or D-55, wherein
R$^{12}$ represents a C$_1$ to C$_4$ alkyl, a C$_1$ to C$_4$ haloalkyl, a C$_3$ to C$_4$ alkenyl or a C$_3$ to C$_4$ alkynyl,
R$^{13}$ represents a hydrogen atom or a methyl,
Z represents a cyano or a nitro,
p1 represents 1, and
D-22, D-52 or D-55 individually represent an aromatic heterocycle represented by Structural Formulae:

D-22

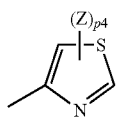

D-52

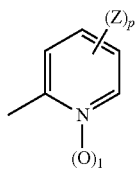

D-55

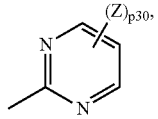

wherein
Z represents a cyano or a nitro,
p2 represents an integer of 0 or 1,
p3 and p4 represent an integer of 0 or 1, and
t represents 0, and
R$^2$ represents a hydrogen atom, a C$_1$ to C$_2$ alkyl, a cyanomethyl, a C$_1$ to C$_2$ alkoxymethyl, a propargyl, —C(O)R$^{15}$ or —C(O)OR$^{16}$, wherein
R$^{15}$ represents a C$_1$ to C$_2$ alkyl, a C$_1$ to C$_2$ alkoxymethyl, a cyclopropyl or a vinyl, and
R$^{16}$ represents a C$_1$ to C$_2$ alkyl;
each X independently represents a halogen atom, a cyano, —SF$_5$, a C$_1$ to C$_2$ haloalkyl, a C$_1$ to C$_2$ haloalkoxy or a C$_1$ to C$_2$ haloalkylthio,
Y represents a halogen atom, a cyano, a nitro, a C$_1$ to C$_2$ alkyl, a C$_1$ to C$_2$ haloalkyl, a C$_1$ to C$_2$ alkoxymethyl, a C$_2$ to C$_3$ alkenyl, a C$_2$ to C$_3$ alkynyl, a C$_1$ to C$_2$ haloalkoxy, a C$_1$ to C$_2$ haloalkylthio, —N(R$^7$)R$^6$ or —C(S)NH$_2$, wherein
R$^6$ represents a hydrogen atom, a C$_1$ to C$_2$ alkyl or a C$_1$ to C$_2$ alkylcarbonyl, and
R$^7$ represents a hydrogen atom or a C$_1$ to C$_2$ alkyl;
R$^3$ represents a C$_1$ to C$_2$ haloalkyl;
m represents an integer of 1 to 3;
n represents an integer of 0 or 1;
or a salt thereof.

2. The isoxazoline-substituted benzamide compound according to claim 1, wherein
A$^1$ represents a carbon atom,
W represents an oxygen atom,
Q represents Q-1,
each X independently represents a halogen atom or a trifluoromethyl,
Y represents a halogen atom, a methyl, an ethyl or a trifluoromethyl,
R$^1$ represents a C$_1$ to C$_2$ haloalkyl, —C(O)NHR$^{12}$, D-22 or D-52,
R$^2$ represents a hydrogen atom,
R$^3$ represents a trifluoromethyl or a chlorodifluoromethyl,
R$^{12}$ represents a C$_1$ to C$_2$ haloalkyl, and
p2 and p4 represent 0, or
a salt thereof.

3. A control agent against internal or external parasites of the mammal or the bird comprising:
a solid or liquid carrier; and
one or more of the isoxazoline-substituted benzamide compounds of claim 1, or a salt thereof, as an active ingredient.

4. An insecticide or a miticide comprising:
a surfactant;
a solid or liquid carrier; and
one or more of the isoxazoline-substituted benzamide compounds of claim 1, or a salt thereof, as an active ingredient.

* * * * *